US009937196B2

(12) United States Patent
Samal et al.

(10) Patent No.: US 9,937,196 B2
(45) Date of Patent: Apr. 10, 2018

(54) GENOMIC SEQUENCE OF AVIAN PARAMYXOVIRUS TYPE 2 AND USES THEREOF

(75) Inventors: Siba K. Samal, College Park, MD (US); Peter L. Collins, Silver Spring, MD (US)

(73) Assignees: University of Maryland, College Park, College Park, MD (US); The United States of America, as represented by the Secretary, Department of Health and Human Services, Washington, DC (US)

( * ) Notice: Subject to any disclaimer, the term of this patent is extended or adjusted under 35 U.S.C. 154(b) by 526 days.

(21) Appl. No.: 12/803,165

(22) Filed: Jun. 21, 2010

(65) Prior Publication Data

US 2011/0217266 A1 Sep. 8, 2011

Related U.S. Application Data

(60) Provisional application No. 61/218,851, filed on Jun. 19, 2009.

(51) Int. Cl.

| | |
|---|---|
| ***A61K 31/7088*** | (2006.01) |
| ***A61K 35/76*** | (2015.01) |
| ***C07H 21/04*** | (2006.01) |
| ***C12N 5/10*** | (2006.01) |

(52) U.S. Cl.

CPC .......... *A61K 31/7088* (2013.01); *A61K 35/76* (2013.01); *C07H 21/04* (2013.01); *C12N 5/10* (2013.01)

(58) Field of Classification Search

CPC ............ C12N 7/00; C12N 7/02; C12N 7/025; C12N 15/01; C12N 2760/18011; C12N 2760/18021; C12N 2760/18051; C12N 2760/18052

USPC ........... 536/23.1, 23.72; 435/235.1, 239, 455

See application file for complete search history.

(56) References Cited

U.S. PATENT DOCUMENTS

2010/0092430 A1* 4/2010 Beier et al. .................. 424/93.6

OTHER PUBLICATIONS

NCBI database accession No. AF515835 (2002), submitted by Yang et al.*
Alignment of AF515835 and SEQ ID No. 1.*
NCBI database accession No. AF515838 (2006), submitted by Zhang et al.*
Alignment of AF515838 and SEQ ID No. 1.*
Zhang et al. (2006) Avian Dis., vol. 50(3), 386-390.*
Subbiah et al. (Sep. 2008) Virus Research, vol. 137(1), 40-48.*
Chang et al. (2001) J. Gen. Virol., vol. 82, 2157-2168.*
Huang et al. (2003) Poultry Science, vol. 82, 899-906.*

* cited by examiner

*Primary Examiner* — Anne Marie S Wehbe
(74) *Attorney, Agent, or Firm* — Hodgson Russ LLP

(57) ABSTRACT

In this application is described the complete genomic sequence of avian parmyxovirus type 2, strains Yucaipa, England, Kenya and Bangor. The sequences are useful for production of recombinant infective virus, a virus vector, for vaccine development and for therapeutic compositions.

14 Claims, 4 Drawing Sheets

Figure 1. Phylogenetic tree of representative members of the family *Paramyxoviridae.*
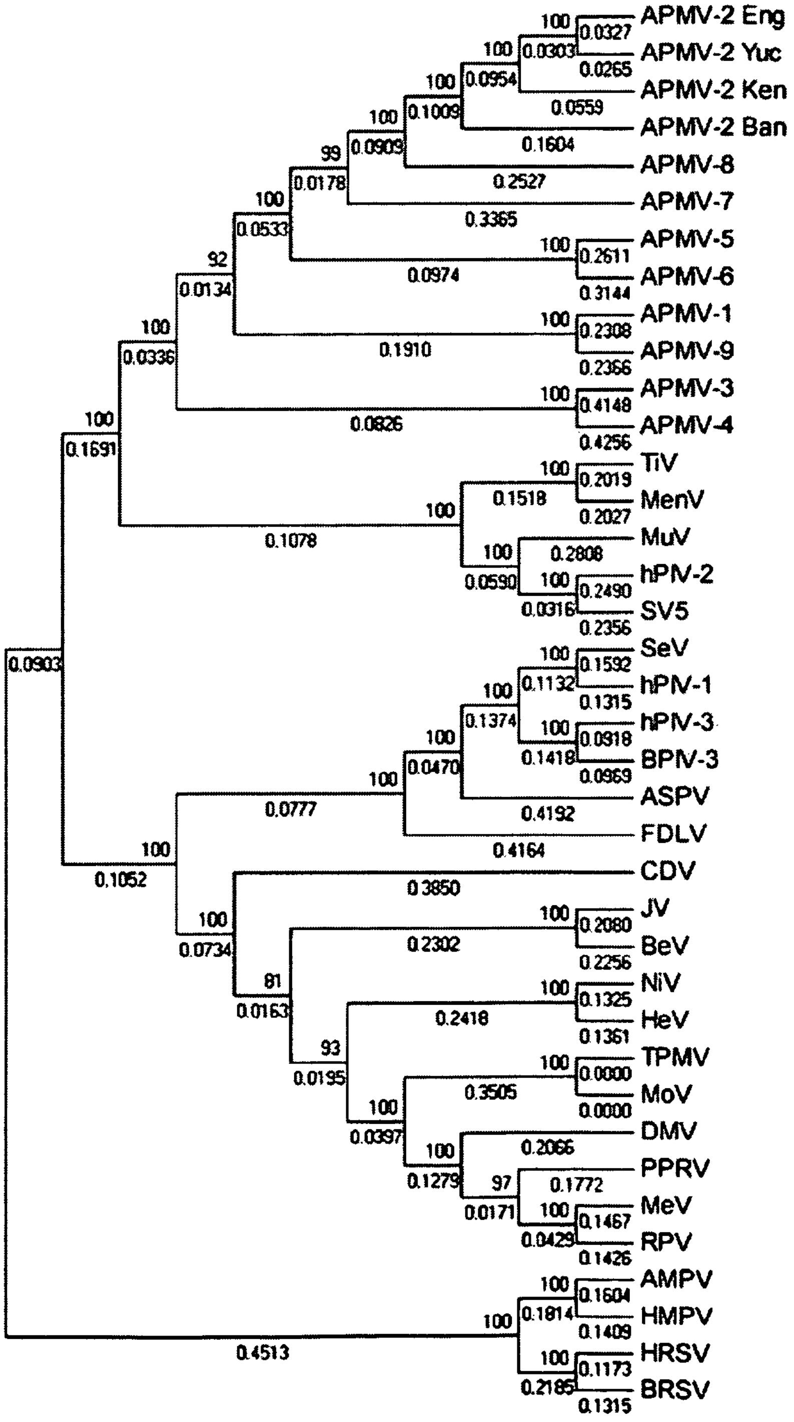

Figure 2. Generation of full length cDNA clone of APMV-2/Yuc.
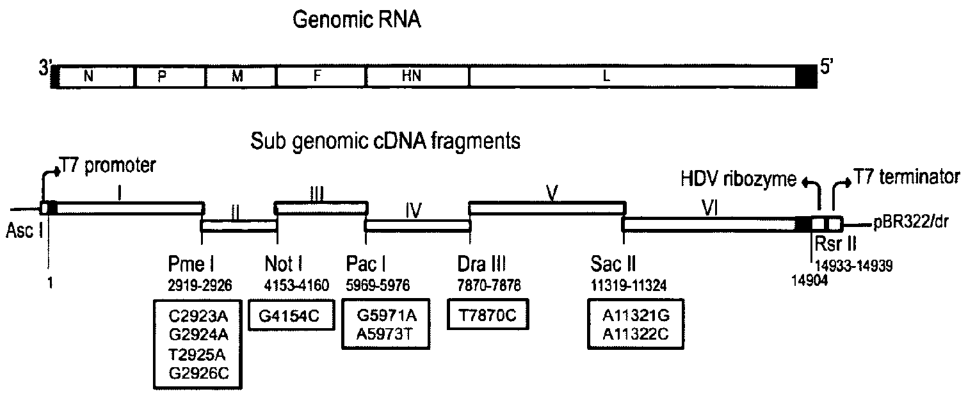

A
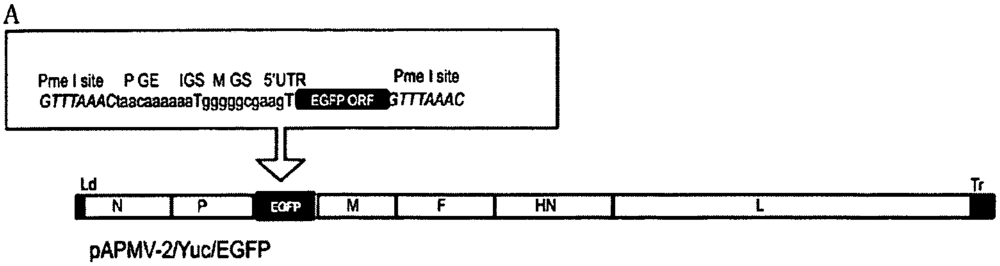
B
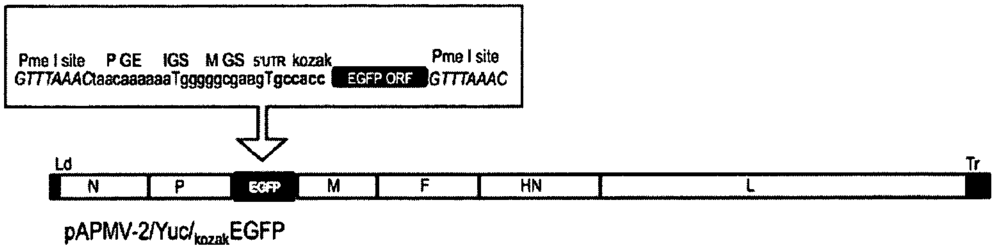
Figure 3. Construction of full length plasmids expressing EGFP, with and without kozak sequence.
Sequence in A, SEQ ID NO: 115, GTTTAAACtaacaaaaaaTgggggcgaagT
Sequence in B, SEQ ID NO: 116, GTTTAAACtaacaaaaaaTgggggcgaagTgcacc Figure 4. Comparison of growth kinetics of wild type APMV-2/Yuc and rAPMV-2/Yuc, rAPMV-2/Yuc/EGFP, and rAPMV-2/Yuc/kozakEGFP.
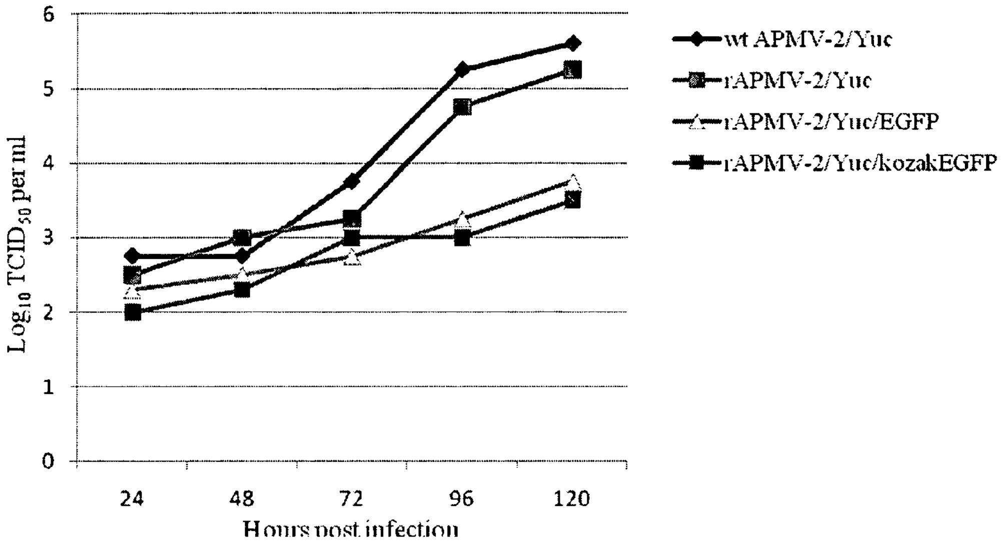

SEQUENCE LISTING

```
<160> NUMBER OF SEQ ID NOS: 118

<210> SEQ ID NO 1
<211> LENGTH: 14904
<212> TYPE: DNA
<213> ORGANISM: Avian Paramixyvirus Type 2
```

-continued

<220> FEATURE:
<223> OTHER INFORMATION: APMV-2/Chicken/California/Yucaipa/56

<400> SEQUENCE: 1

```
accaaacaag gaataggtaa gcaacgtaaa tcttagataa      40
aaccatagaa tccgtggggg cgacatcgcc tgaagccgat      80
ctcgagatcg ataactccgg ttaattggtc tcagcgtgag     120
gagcttatct gtctgtggca atgtcttctg tgttttcaga     160
ataccaggct cttcaggacc aactggtcaa gcctgccact     200
cgaagggctg atgtggcatc gactggattg ttgagagcgg     240
agataccagt ttgtgtaacc ttgtctcagg acccaactga     280
tagatggaac ctcgcatgtc tcaatctgcg atggctgata     320
agtgagtcct ctactactcc catgagacaa ggggcgatcc     360
tgtcactgct gagcttgcac tctgacaaca tgcgagctca     400
cgcaaccctt gcagcgagat ccgctgatgc tgccatcact     440
gtgcttgagg ttgacgccat agacatggcg gatggcacaa     480
tcacttttaa tgccagaagt ggagtatccg agaggcgcag     520
cacacagctc atggcaatcg caaaagatct gccccgctct     560
tgttccaatg actcaccatt caaagatgac actatcgagg     600
atcgcgaccc ccttgacctg tccgagacta tcgatagact     640
gcaggggatt gctgcccaaa tctggatagc ggccatcaag     680
agcatgactg ccccggatac tgctgcggag tcagaaggca     720
agaggcttgc aaagtaccaa caacaaggcc gcttggtgcg     760
acaggtgtta gtgcatgatg cggtgcgtgc ggaattccta     800
cgtgtcatca gaggcagcct ggtcttacgg caattcatgg     840
tatcagaatg taagagggca gcatccatgg gtagcgagac     880
atctaggtac tatgccatgg tgggtgacat cagcctctac     920
atcaagaatg caggacttac cgccttcttc ttgacactca     960
gatttggtat tgggacacac taccccactc ttgccatgag    1000
tgtgttctct ggagaactga agaagatgtc gtccttgatc    1040
aggctgtata agtcaaaagg ggaaaatgct gcatacatgg    1080
cattcctgga ggatgcggac atgggaaact ttgcgcctgc    1120
taactttagt actctctact cctatgcaat gggggtaggt    1160
acagtgctgg aagcatcagt tgcgaaatac cagttcgctc    1200
gagagttcac cagtgagaca tacttcaggc ttggggttga    1240
gaccgcacag aaccaacagt gcgctctaga tgaaaagacc    1280
gccaaggaga tggggcttac tgatgaagcc agaaagcagg    1320
tgcaagcatt ggctagcaac atcgagcagg ggcaacattc    1360
aatgcccatg caacaacagc ccacattcat gagtcagccc    1400
taccaggatg acgatcgtga ccagccaagc accagcagac    1440
cagagccaag accatcgcaa ttgacaagcc aatcagcagc    1480
```

-continued

```
acaggacaat gatgcggcct cattagattg gtgaccgcaa    1520

tcagctcagc caagccattg ttggacgcag gacattcaaa    1560

tcatacattg ccctaagagt attaaagtga tttaagaaaa    1600

aaggaccctg gggcgaagt tgtcccaatc caggcaggcg    1640

ctgaaaccga atccctccaa cctccgagcc ccaggcgacc    1680

atggagttca ccgatgatgc cgaaattgct gagctgttgg    1720

acctcgggac ctcagtgatc caagagctgc agcgagccga    1760

agtcaagggc ccgcaaacaa ccggaaagcc caaagttccc    1800

ccggggaaca ctaagagcct ggctactctc tgggagcatg    1840

agactagcac ccaagggagt gcattgggca cacccgagaa    1880

caacacccag gcacccgatg acaacaacgc aggtgcagat    1920

acgccagcga ctaccgacgt ccatcgcact ctggatacca    1960

tagacaccga cacaccaccg gaagggagca agcccagctc    2000

cactaactcc caacccggtg atgaccttga caaggctctt    2040

tcgaagctag aggcgcgcgc caagctcgga ccagataggg    2080

ccagacaggt taaaaagggg aaggagatcg ggtcgagcac    2120

agggacgagg gaggcagcca gtcaccacat ggaagggagc    2160

cgacagtcgg agccaggagc gggcagccga gcacagccac    2200

aaggccatgg cgaccgggac acaggaggga gtactcattc    2240

atctctcgag atgggagact ggaagtcaca agctggtgca    2280

acccagtctg ctctcccatt agaagcgagc ccaggagaga    2320

aaagtgcaca tgtggaactt gcccagaatc ctgcatttta    2360

tgcaggcaac ccaactgatg caattatggg gttgacaaag    2400

aaagtcaatg atctagagac aaaattggct gaggtattgc    2440

gtctgttagg aatactcccc ggaataaaga atgagattag    2480

tcagctgaaa gcaaccgtgg ctctgatgtc aaatcagatt    2520

gcctccattc agattcttga tcctgggaat gccggagtca    2560

aatcccttaa tgagatgaaa gccctgtcaa aagcagccag    2600

catagttgtg gcaggtccag gagtccttcc tcctgaggtc    2640

acagaaggag gactgatcgc gaaagatgag ctagcaaggc    2680

ccatccccat ccaaccgcaa cgagactcca aacccaaaga    2720

cgacccgcac acatcaccaa atgatgtcct tgctgtacgc    2760

gctatgatcg acacccttgt ggatgatgag aagaagagaa    2800

agagattaaa ccaggccctt gacaaggcaa agaccaagga    2840

tgacgtctta agggtcaagc ggcagatata caatgcctag    2880

gagtccattt gtctaaagaa cctccaatca tatcaccagt    2920

ttcgtgccac atgcttccct gccgagaatc tagccgacac    2960

aaaaactaaa tcatagttta acaaaaaaga agtttggggg    3000

cgaagtctca catcatagag cacccttgca ttctaaaatg    3040

gctcaaacaa ccgtcaggct gtatatcgat gaagctagtc    3080
```

-continued

```
ccgacattga actgttgtct tacccactga taatgaaaga                    3120

cacaggacat gggaccaaag agttgcagca gcaaatcaga                    3160

gttgcagaga tcggtgcatt gcagggaggg aagaatgaat                    3200

cagttttcat caatgcatat ggctttgttc agcaatgcaa                    3240

agttaaaccg gggcaaccc aattcttcca ggtagatgca                     3280

gctacaaagc cagaagtggt cactgcaggg atgattataa                    3320

tcggtgcagt caagggggtg gcaggcatca ctaagctggc                    3360

agaagaggtg ttcgagctgg acatctccat caagaagtcc                    3400

gcatcattcc atgagaaggt tgcggtgtcc tttaatactg                    3440

tgccactatc actcatgaat tcgaccgcat gcagaaatct                    3480

gggttatgtc acaaacgctg aggaggcgat caaatgcccg                    3520

agcaaaatac aagcgggtgt gacgtacaaa tttaagataa                    3560

tgtttgtctc cttgacacga ctgcataacg ggaaattgta                    3600

ccgtgtcccc aaggcagtgt atgctgtaga ggcatcagct                    3640

ctatataaag tgcaactgga agtcgggttc aagcttgacg                    3680

tggccaagga tcacccacac gttaagatgt tgaagaaagt                    3720

ggaacggaat ggtgagactc tgtatcttgg ttatgcatgg                    3760

ttccacctgt gcaacttcaa gaagacaaat gccaagggtg                    3800

agtcccggac aatctccaac ctagaaggga aagtcagagc                    3840

tatggggatc aaggtttcct tgtacgactt atgggggcct                    3880

actttggtgg tgcaaatcac aggtaagacc agcaagtatg                    3920

cacaaggttt cttttcaacc acaggtacct gctgcctccc                    3960

agtgtcgaag gctgcccctg agctggccaa acttatgtgg                    4000

tcctgcaatg caacaatcgt tgaagctgca gtgattatcc                    4040

aagggagtga taggagggca gtcgtgacct cagaggactt                    4080

ggaagtatac ggggcagttg caaaagagaa gcaggctgca                    4120

aaaggatttc acccgttccg caagtgacac gtggggccgc                    4160

acacctcatt accccagaag cccgggcaac tgcaaattca                    4200

cgcttatata atccaattac catgatctag aactgcaatc                    4240

gatactaatc gctcattgat cgtattaaga aaaaacttaa                    4280

ctacataact tcaacattgg gggcgacagc tccagactaa                    4320

gtgggtggct aagctctgac tgataaggaa tcatgaatca                    4360

agcactcgtg attttgttgg tatctttcca gctcggcgtt                    4400

gccttagata actcagtgtt ggctccaata ggagtagcta                    4440

gcgcacagga gtggcaactg gcggcatata caacgaccct                    4480

cacagggacc atcgcagtga gatttatccc ggtcctgcct                    4520

gggaacctat caacatgtgc acaggagacg ctgcaggaat                    4560

ataatagaac tgtgactaat atcttaggcc cgttgagaga                    4600

gaacttggat gctctcctat ctgacttcga taaacctgca                    4640
```

-continued

```
tcgaggttcg tgggcgccat cattgggtcg gtggccttgg        4680
gggtagcaac agctgcacaa atcacagccg ccgtggctct        4720
caatcaagca caagagaatg cccggaatat atggcgtctc        4760
aaggaatcga taaagaaaac caatgcggct gtgttggaat        4800
tgaaggatgg acttgcaacg actgctatag ctttggacaa        4840
agtgcaaaag tttatcaatg atgatattat accacagatt        4880
aaggacattg actgccaggt agttgcaaat aaattaggcg        4920
tctacctctc cttatactta acagagctta caactgtatt        4960
tggttctcag atcactaatc ctgcattatc aacgctctct        5000
taccaggcgc tgtacagctt atgtggaggg gatatgggaa        5040
agctaactga gctgatcggt gtcaatgcaa aggatgtggg        5080
atccctctac gaggctaacc tcataaccgg ccaaatcgtt        5120
ggatatgacc ctgaactaca gataatcctc atacaagtat        5160
cttacccaag tgtgtctgaa gtgacaggag tccgggctac        5200
tgagttagtc actgtcagtg tcactacacc aaaaggagaa        5240
gggcaggcaa ttgttccgag atatgtggca cagagtagag        5280
tgctgacaga ggagttggat gtctcgactt gtaggtttag        5320
caaaacaact ctttattgta ggtcgattct cacacggccc        5360
ctaccaactt tgatcgccag ctgcctgtca gggaagtacg        5400
acgattgtca gtacacaaca gagataggag cgctatcttc        5440
gagattcatc acagtcaatg gtggagtcct tgcaaactgc        5480
agagcaattg tgtgtaagtg tgtctcaccc ccgcatataa        5520
taccacaaaa cgacattggc tccgtaacag ttattgactc        5560
aagtatatgc aaggaagttg tcttagagag tgtgcagctt        5600
aggttagaag gaaagctgtc atcccaatac ttctccaacg        5640
tgacaattga cctttcccaa atcacaacgt cagggtcgct        5680
ggatataagc agtgaaattg gtagcattaa caacacagtt        5720
aatcgggtcg acgagttaat caaggaatcc aacgagtggc        5760
tgaacgctgt gaacccccgc cttgtgaaca atacgagcat        5800
catagtcctc tgtgtccttg ccgccctgat tattgtctgg        5840
ctaatagcgc tgacagtatg cttctgttac tccgcaagat        5880
actcagctaa gtcaaaacag atgaggggcg ctatgacagg        5920
gatcgataat ccatatgtaa tacagagtgc aactaagatg        5960
tagagaggtt gaataagcct aaacatgata tgatttaaga        6000
aaaaattgga aggtgggggc gacagcccat tcaatgaagg        6040
gtgtacactc caacttgatc ttgtgacttg atcatcatac        6080
tcgaggcacc atggatttcc catctaggga gaacctggca        6120
gcaggtgaca tatcggggcg gaagacttgg agattactgt        6160
tccggatcct cacattgagc ataggtgtgg tctgtcttgc        6200
catcaatatt gccacaattg caaaattgga tcacctggat        6240
```

```
aacatggctt cgaacacatg gacaacaact gaggctgacc                 6280
gtgtgatatc tagcatcacg actccgctca aagtccctgt                 6320
caaccagatt aatgacatgt ttcggattgt agcgcttgac                 6360
ctacctctgc agatgacatc attacagaaa gaaataacat                 6400
cccaagtcgg gttcttggct gaaagtatca acaatgtttt                 6440
atccaagaat ggatctgcag gcctggttct tgttaatgac                 6480
cctgaatatg caggggggat cgctgtcagc ttgtaccaag                 6520
gagatgcatc tgcaggccta aatttccagc ccatttcttt                 6560
aatagaacat ccaagttttg tccctggtcc tactactgct                 6600
aagggctgta taaggatccc gaccttccat atgggccctt                 6640
cacattggtg ttactcacat aacatcattg catcaggttg                 6680
ccaggatgcg agccactcca gtatgtatat ctctctgggg                 6720
gtgctgaaag catcgcagac cgggtcgcct atcttcttga                 6760
caacggccag ccatctcgtg gatgacaaca tcaaccggaa                 6800
gtcatgcagc atcgtagcct caaaatacgg ttgtgatatc                 6840
ctatgcagta ttgtgattga aacagagaat gaggattata                 6880
ggtctgatcc ggctactagc atgattatag gtaggctgtt                 6920
cttcaacggg tcatacacag agagcaagat taacacaggg                 6960
tccatcttca gtctattctc tgctaactac cctgcggtgg                 7000
ggtcgggtat tgtagtcggg gatgaagccg cattcccaat                 7040
atatggtggg gtcaagcaga acacatggtt gttcaaccag                 7080
ctcaaggatt ttggttactt cacccataat gatgtgtaca                 7120
agtgcaatcg gactgatata cagcaaacta tcctggatgc                 7160
atacaggcca cctaaaatct caggaaggtt atgggtacaa                 7200
ggcatcctat tgtgcccagt ttcactgaga cctgatcctg                 7240
gctgtcgctt aaaggtgttc aataccagca atgtgatgat                 7280
gggggcagaa gcgaggttga tccaagtagg ctcaaccgtg                 7320
tatctatacc aacgctcatc ctcatggtgg gtggtaggac                 7360
tgacttacaa attagatgtg tcagaaataa cttcacagac                 7400
aggtaacaca ctcaaccatg tagaccccat tgcccataca                 7440
aagttcccaa gaccatcttt caggcgagat gcgtgtgcga                 7480
ggccaaacat atgccctgct gtctgtgtct ccggagttta                 7520
tcaggacatt tggccgatca gtacagccac caataacagc                 7560
aacattgtgt gggttggaca gtacttagaa gcattctatt                 7600
ccaggaaaga cccaagaata gggatagcaa cccagtatga                 7640
gtggaaagtc accaaccagc tgttcaattc gaatactgag                 7680
ggagggtact caaccacaac atgcttccgg aacaccaaac                 7720
gggacaaggc atattgtgta gtgatatcag agtacgctga                 7760
tggggtgttc ggatcataca ggatcgttcc tcagcttata                 7800
```

-continued gagattagaa caaccaccgg taaatctgag tgatgcatca 7840
atcctaaatt ggaatgacca atcaaaagct acgtagtgtc 7880
taacagcatt gcgaagcctg gtttaagaaa aaacttgggg 7920
gcgaatgccc atcaaccatg gatcaaactc aagctgacac 7960
tataatacaa cctgaagtcc atctgaattc accacttgtt 8000
cgcgcaaaat tggttcttct atggaaattg actgggttac 8040
ctttgccgtc tgatttgaga tcatttgtac taactacaca 8080
tgcagctgat gaccaaatcg caaaaaatga gactaggatc 8120
aaggccaaaa ttaattccct aatcgataac ttaatcaaac 8160
actgcaaggc aaggcaagtg gcactttcag ggttgacacc 8200
tgtcgtacat ccaacaactc tacagtggtt gctatccatc 8240
acatgtgaac gagcagacca ccttgcaaaa gtacgcgaga 8280
aatcagttaa gcaagcaatg tcagagaagc aacacgggtt 8320
tagacatctc ttttcggcag taagtcatca gttagttgga 8360
aacgccacac tgttctgtgc acaagactct agcaccgtga 8400
atgtcgactc tccttgctca tcaggttgtg agaggctgat 8440
aatagactct attggagcct tacaaacacg atggacaaga 8480
tgtaggtggg cttggcttca cattaaacag gtaatgagat 8520
accaggtgct tcagagtcgc ctacacgctc atgccaattc 8560
tgttagcaca tggtctgagg cgtgggggtt cattgggatc 8600
acaccagata tagtccttat tgtagactat aagagcaaaa 8640
tgtttactat cctgaccttc gaaatgatgc tgatgtattc 8680
agatgtcata gagggtcgtg ataatgtggt agctgtagga 8720
agtatgtcac caaacctaca gcctgtggtg gagaggattg 8760
aggtgctgtt tgatgtagtg gacaccttgg cgaggaggat 8800
tcatgatcct atttatgatc tggttgctgc cttagaaagc 8840
atggcatacg ctgccgtcca attgcacgat gctagtgaga 8880
cacacgcagg ggaattcttt tcgttcaatt tgacagaaat 8920
agagtccact cttgcccccct tgctggatcc tggccaagtc 8960
ctatcggtga tgaggactat cagttattgt tacagtgggc 9000
tatcgcctga ccaagctgca gagttgctct gtgtgatgcg 9040
cttatttgga caccctctgc tctccgcaca acaagcagcc 9080
aaaaaagtcc gggagtctat gtgtgcccct aaactgttag 9120
agcatgatgc aatactgcaa actctatctt tcttcaaggg 9160
aatcataatc aatggctaca ggaaaagtca ttctggagta 9200
tggcctgcaa ttgacccaga ttctatagtg gacgatgacc 9240
ttagacagct gtattacgag tcggcagaaa tttcacatgc 9280
tttcatgctt aagaaatatc ggtaccttag tatgattgag 9320
ttccgcaaga gcatagagtt tgacttaaat gatgacctga 9360
gcacattcct taaagacaaa gcaatctgca ggccaaaaga 9400

```
tcaatgggca cgcatcttcc ggaaatcatt gttcccttgc              9440

aaaacgaacc ttggcactag tatagatgtt aaaagtaatc              9480

gactgttgat agatttttg gagtcacatg acttcaatcc               9520

tgaggaagaa atgaagtatg tgactacgct agcatacctg              9560

gcagataatc aattctcagc atcatattca ctgaaggaga              9600

aagagatcaa gactactggc cggatcttcg ccaaaatgac              9640

caggaaaatg aggagctgtc aagtaatatt ggaatcacta              9680

ttgtccagtc acgtctgcaa attctttaag gagaacggtg              9720

tgtcaatgga acaactgtct ttgacaaaga gcttgcttgc              9760

aatgtcacag ttagcaccca ggatatcttc agttcgccag              9800

gcgacagcac gtagacagga cccaggactc agccactcta              9840

atggttgtaa tcacattgta ggagacttag gcccacacca              9880

gcaggacaga ccggcccgga agagtgtagt cgcaaccttc              9920

cttacaacag atcttcaaaa atattgcttg aattggcgat              9960

atgggagtat caagcttttc gcccaagcct taaaccagct              10000

attcggaatc gagcatgggt ttgaatggat acacctgaga              10040

ctgatgaata gcaccctgtt tgtcggggac ccattctcgc              10080

ctcctgaaag caaagtgctg agtgatcttg atgatgcgcc              10120

caattcagac atatttatcg tgtccgccag aggggggatt              10160

gaagggttat gccagaagct gtggaccatg atttcaataa              10200

gcataatcca ttgcgtggct gagaagatag gagcaagggt              10240

tgcggcgatg gttcagggag ataatcaggt aattgcaatc              10280

acgagagagc tgtataaggg agagacttac acgcagattc              10320

agccggagtt agatcgatta ggcaatgcat tttttgctga              10360

attcaaaaga cacaactatg caatgggaca taatctgaag              10400

cccaaagaga caatccaaag tcaatcattc tttgtgtatt              10440

cgaaacggat tttctgggaa gggagaattc ttagtcaagc              10480

actgaagaat gctaccaaac tatgcttcat tgcagatcac              10520

ctcggggata atactgtctc atcatgcagc aatctagcct              10560

ctacgataac ccgcttggtt gagaatgggt atgaaaagga              10600

cacagcattc attctgaata tcatctcagc aatgactcag              10640

ttgctgattg atgagcaata ttccctacaa ggagactact              10680

cagctgtgag aaaactgatt gggtcatcaa attaccgtaa              10720

tctcttagtg gcgtcgctca tgcctggtca ggttggcggc              10760

tataatttct tgaatatcag tcgcctattc acacgcaata              10800

ttggtgatcc agtaacatgc gccatagcag atctgaagtg              10840

gttcattagg agcgggttaa tcccagagtt catcctgaag              10880

aatatattac tacgagatcc cggagacgat atgtggagta              10920

ctctatgtgc tgacccttac gcattaaata tcccctacac              10960
```

-continued

```
tcagctaccc acaacatacc tgaagaagca tactcagagg     11000
gcattactat ccgattctaa taatccgctt cttgcagggg     11040
tgcaattgga caatcaatac attgaagagg aggagtttgc     11080
acgattcctt ttggatcggg aatccgtgat gcctcgagtg     11120
gcacacacaa tcatggagtc aagtatacta gggaagagaa     11160
agaacatcca gggtttaatc gacactaccc ctacaatcat     11200
taagactgca ctcatgaggc agcccatatc tcgtagaaag     11240
tgtgataaaa tagttaatta ctcgattaac tacctgactg     11280
agtgccacga ttcattattg tcctgtagga cattcgagcc     11320
aaggaaggaa ataatatggg agtcagctat gatctcagta     11360
gaaacttgca gtgtcacaat tgcggagttc ctgcgcgcca     11400
ccagctggtc caacatcctg aacggtagga ctatttcggg     11440
tgtaacatct ccagacacta tagagctgct caaggggtca     11480
ttaattggag agaatgccca ttgtattctt tgtgagcagg     11520
gagacgagac attcacgtgg atgcacttag ccgggcccat     11560
ctatatacca gacccggggg tgaccgcatc caagatgaga     11600
gtgccgtatc ttgggtcaaa gacagaggaa aggcgtacgg     11640
catccatggc caccattaag ggcatgtctc accacctaaa     11680
ggccgctttg cgaggagcct ctgtgatggt gtgggccttt     11720
ggtgatactg aagaaagttg ggaacatgcc tgccttgtgg     11760
ccaatacaag gtgcaagatt aatcttccgc agctacgcct     11800
gctgaccccg acaccaagca gctctaacat ccaacatcga     11840
ctaaatgatg gtatcagcgt gcaaaaattt acacctgcta     11880
gcttatcccg agtggcgtca tttgttcaca tttgcaacga     11920
tttccaaaag ctagagagag atggatcttc cgtagactct     11960
aacttgatat atcagcaaat catgctgact ggtctaagta     12000
ttatggagac acttcatcct atgcacgtct catgggtata     12040
caacaatcag acaattcact tacataccgg aacatcgtgt     12080
tgtcctaggg aaatagagac aagcattgtt aatcccgcta     12120
ggggagaatt cccaacaata actctcacaa ctaacaatca     12160
gtttctgttt gattgtaatc ccatacatga tgaggcactt     12200
acaaaactgt cagtaagtga gttcaagttc caggagctta     12240
atatagactc aatgcagggt tacagtgctg tgaacctgct     12280
gagcagatgt gtggctaagc tgatagggga atgcattctg     12320
gaagacggta tcggatcgtc aatcaagaat gaagcaatga     12360
tatcatttga taactctatc aactggattt ctgaagcact     12400
caatagtgac ctgcgtttgg tattcctcca gctggggcaa     12440
gaactacttt gtgacctggc gtaccaaatg tactatctga     12480
gggtcatcgg ctatcattcc atcgtggcat atctgcagaa     12520
tactctagaa agaattcctg ttatccaact cgcaaacatg     12560
```

-continued gcactcacca tatcccaccc agaagtatgg aggagagtga 12600
cagtgagcgg attcaaccaa ggttaccgga gtccctatct 12640
ggccactgtc gactttatcg ccgcatgtcg tgatatcatt 12680
gtgcaaggtg cccagcatta tatggctgat ttgttgtcag 12720
gagtagagtg ccaatataca ttctttaatg ttcaagacgg 12760
cgatctgaca ccgaagatgg aacaattttt agcccggcgc 12800
atgtgcttgt ttgtattgtt aactgggacg atccgaccac 12840
tcccaatcat acgatccctt aatgcgattg agaaatgtgc 12880
aattctcact cagttcttgt attacctacc gtcagtcgac 12920
atggcagtag cagacaaggc tcgtgtgtta tatcaactgt 12960
caataaatcc gaaaatagat gctttagtct ccaaccttta 13000
tttcaccaca aggaggttgc tttcaaatat caggggagat 13040
tcttcttcac gagcgcaaat tgcattcctc tacgaggagg 13080
aagtaatcgt tgatgtgcct gcatctaatc aatttgatca 13120
gtaccatcgt gaccccatcc taagaggagg tctatttttc 13160
tctctctcct taaaaatgga aaggatgtct ctgaaccgat 13200
ttgcagtaca gaccctgcca acccaggggt ctaactcgca 13240
gggttcacga cagaccttgt ggcgtgcctc accgttagca 13280
cactgcctta aatcagtagg gcaggtaagt accagctggt 13320
acaagtatgc tgtagtgggg gcgtctgtag agaaagtcca 13360
accaacaaga tcaacaagcc tctacatcgg ggagggcagt 13400
gggagtgtca tgacattatt agagtatctg gaccctgcta 13440
caattatctt ctacaactcg ctattcagca atagcatgaa 13480
ccctccacaa aggaatttcg gactgatgcc cacacagttt 13520
caggactcag tcgtgtataa aaacatatca gcaggagttg 13560
actgcaagta cgggtttaag caagtctttc aaccattatg 13600
gcgtgatgta gatcaagaaa caaatgtggt agagacggcg 13640
ttcctaaact atgtgatgga agtagtgcca gtccactctt 13680
cgaagcgtgt cgtatgtgaa gttgagtttg acagggggat 13720
gcctgacgag atagtaataa cagggtacat acacgtgctg 13760
atggtgaccg catacagtct gcatcgagga gggcgtctaa 13800
taatcaaggt ctatcgtcac tccgaggctg tattccaatt 13840
cgtactctct gcgatagtca tgatgtttgg ggggcttgat 13880
atacaccgga actcgtacat gtcaactaac aaagaggagt 13920
acatcatcat agctgcggcg ccggaggcat taaactattc 13960
ctctgtacca gcaatattgc agagggtgaa gtctgttatt 14000
gaccagcagc ttacattaat ctctcctata gatctagaaa 14040
gattgcgcca tgagactgag tctctccgtg agaaggagaa 14080
taatctagta atatctctga cgagagggaa gtatcaactc 14120

-continued cggccgacac agactgatat gcttctatca tacctaggtg 14160
ggagattcat caccctattc ggacagtctg ctagggattt 14200
gatggccact gatgttgctg accttgatgc taggaagatt 14240
gcattagttg atctactgat ggtggaatcc aacattattt 14280
taagtgagag cacagacttg gaccttgcac tgttgctgag 14320
cccgtttaac ttagacaaag ggcggaagat agttacccta 14360
gcaaaggcta ctacccgcca attgctgccc gtgtatatcg 14400
catcagagat aatgtgcaat cggcaggcat tcacacacct 14440
gacatcaatt atacagcgtg gtgtcataag aatagaaaac 14480
atgcttgcta caacggaatt tgtccgacag tcagttcgcc 14520
cccagttcat aaaggaggtg ataactatag cccaagtcaa 14560
ccaccttttt tcagatctat ccaaactcgt gctttctcga 14600
tctgaagtca agcaagcact taaatttgtc ggttgctgta 14640
tgaagttcag aaatgcaagc aattaaacag gattgttatt 14680
gtcaaatcac cggttactat agtcaaatta atatgtaaag 14720
ttccctcttt caagagtgat taagaaaaaa cgcgtcaaag 14760
gtggcggttt cactgatttg ctcttggaag ttgggcatcc 14800
tccagccaat atatcggtgc cgaaatcgaa agtctgacag 14840
ctgatttgga atataagcac tgcataatca ctgagttacg 14880
ttgctttgct attccatgtc tggt 14904

<210> SEQ ID NO 2
<211> LENGTH: 15024
<212> TYPE: DNA
<213> ORGANISM: Avian Paramixyvirus Type 2
<220> FEATURE:
<223> OTHER INFORMATION: APMV-2/Finch/N.Ireland/Bangor/73

<400> SEQUENCE: 2
accaaacaag gaataggtaa gcaacgtaaa ctgtagataa 40
aaaaactgac ttcgtggggg cgacatcgcc taatctcgac 80
ctcgaaaccg agacacaagg tttgttgccc acttttgtag 120
agtctgtgcg gtgattcgac atgtcatctg tgtttactga 160
gtaccaagcc ctacaggatc aactggtcaa gccttcagct 200
aggcgggctg atgttgcctc aactggattg cttcgggctg 240
aaatacccgt gtgtgtcacg ttgtcacaag acccgaccga 280
ccggtggaat ctggcctgcc ttaacctgcg ctggttaata 320
agtgaatcat ccacgacacc aatgagacaa ggtgcaatcc 360
tctctttact cagcctacat tcggacaaca tgcgtgcgca 400
tgccaccctt gcagcaagat cagcagacgc atccatcacc 440
atccttgagg tcgacagcat tgacatggct gcagacacca 480
tcacatttaa tgcaagaagc ggagtctcag acagaagaag 520
tgcccagctc atggccattg caaaggactt gccaaggtca 560
tgttcgaatg actcaccatt caaggataac aatatcgaag 600

-continued

```
atagagatcc gctggacctc tctgagacaa ttgataggct                        640
acagggcatt gcagctcaaa tttgggtagc tgcaataaag                         680
agcatgactg cccctgacac tgccgctgaa tcagaaggga                         720
agaggttagc aaaataccag cagcaaggac gattggtaag                         760
acaggtactg gttcatgagg ctgtccgagc tgagtttttg                         800
agagtgatta gagggagcct tgtattacgc caatttatgg                         840
tgtctgagtg caagagagcg gcatcaatgg gtagtgacac                         880
ctcacgatac tatgctatgg ttggtgatat tagcctgtat                         920
attaagaatg ctggattgac tgcattcttc ttgactctcc                         960
gattcgggat cggcacccac tacccgactc tagctatgag                        1000
cgtttttttct ggggagctga agaagatgtc gtcgttgata                       1040
aggctgtaca aatctaaggg ggagaatgct gcatacatgg                        1080
cgttccttga agatgcagac atggggaact tcgcacctgc                        1120
aaatttcagc accttatact cttacgccat gggtgtaggg                        1160
accgtcctag aagcttctgt cgcgaagtac cagtttgcaa                        1200
gagagttcac aagtgagacc tattttagac tgggggtaga                        1240
aactgcacag aaccaacagt gtgcattgga tgagaagaca                        1280
gccaaggaaa tggggctgac tgatgaagcc aggcgacaag                        1320
tgcaagcact tgccagcaac atcgagcaag ggcagcactc                        1360
tatccaagct cctcaacaac cctcattcat ggcaacgcag                        1400
agcaccacgc aagagccaga tcagccgtcc acaagcaggc                        1440
aggacacacg gagcacgccc gcaccctctc acaaccaagg                        1480
tcaggaccaa gacgatgcat ctcttgattg gtaatcaaca                        1520
gccgccaccc acctgtacac ccacacaatc accacgacga                        1560
cggacaacca acccagctta gagatcagca attaagaaaa                        1600
aataaggttg ggggcgaatc tcgcccaact tgagacaagg                        1640
ttcgaaatcg tctcttctcg agggagccag ctctccaaag                        1680
atggagttca cagatgatac agagatagcc gagctgcttg                        1720
atctcggaac atctgtaata caagagcttc agagagcaga                        1760
gctaaagggc ccgcaaacaa caggcaaacc aaaggtcccg                        1800
ccaggcaaca cgaggagcct agccacgctt tgggagaaag                        1840
aaagcgaaac tcgaactgaa cctgaagctc tccccactga                        1880
acacgccaat ccggacatga gcccagcgag ccacaatgac                        1920
ccagcgaaag ccgcgcatga gggagcagca gaggaagggg                        1960
aagccgaccc agaaccggac aaggccgcag gatccgacct                        2000
caccaactct cgtccagggg atgacctaga caaggcgctg                        2040
gccaaactcg aatcgagagc caagcaaaac cgcacgcagc                        2080
aactaatagt taaaaagggg aagggggcaa ccaaagcatc                        2120
ccattctacc ccaccaatga gcccccaggt ggcggcatca                        2160
```

-continued

```
accacagtga acaaacccgg cccaatgaca gagccaacac 2200
tcgatcttgg aagccaggac atagaagaga gtactctttt 2240
gcctgtagag atggaagatt ggaagtcatc agctggtgca 2280
accccatatg cactccaatc agagcagaac caagacgaga 2320
agtctgcaag tgtgggaagt gtcctatctc ctgcatccta 2360
tgttgccaat cccaatgatg ctatgtcggc tctaacacgc 2400
aaggtcaacg atatggagtc taagattgga gaggctataa 2440
aactcctagg tatgctccct gtcatcaaga atgagatcag 2480
tcagctgaaa gccacagtgg ctctgatgtc aaatcaattg 2520
gcatcaatcc aaattctcga tcccggtaat gcaggtgtaa 2560
aatccctcaa cgaaatgaag tcactatcaa aagctgccag 2600
cattgtagtt acaggaccag ggtcacttcc tattgaggta 2640
ctaaacaccg acactgtata caaagatgaa cttgctcgcc 2680
cagtgacagc ccaagcccac aaagagacca aacctaaaga 2720
tgagccgggg gcaacatcat ccgatctcac tgccgttcag 2760
gcgctgatcg acacgttagt ggaggacgac cgtagaaaat 2800
caaggctaca tcaggcactt caaagagcca gaaccaaaga 2840
agacatcctc cgcatcaaga gacaaatcta caatgcatag 2880
tgggaattgc agacacagac aggcaatctt tgctctctct 2920
gcccaacaag aacatcctca tctcatcccg ctgatcaatc 2960
cacacaatag cagtagttaa gaaaaaaagt cctgtggggg 3000
cgaatgccca tcagcgaata acacctcccc atctggttcg 3040
aaaatggccc agacaacagt caagctgtat gtcgacgaga 3080
caagcccaga cattgaactg ctatcgtatc ctctagtcat 3120
gaaggataca ggccatggaa ccaaagagtt gcagcagcaa 3160
atcagagtgg cagaaatcgg aacgctccat ggagggaaga 3200
atgagtcagt ctttatcaac gcttatggtt ttgtccaaca 3240
agacaagatt aaacccgggg cggcgcggtt ctatcagatg 3280
gaggaaggcc acaaacccga agtaatcacg gcaggaatga 3320
taataatcgg agcagttaag ggaggaacgg acataacaaa 3360
actggcagaa gatgtcttct ctctagatat aacaatcaag 3400
aaatccgcat catttcatga gaaggtggca gtcaccttca 3440
acactgtgcc actatctctc atgaactcaa cagcctgcaa 3480
gaatctgggt tatttaacca atgcggaaga gtctattaag 3520
tgccccagca aaattcaagc aggagtcaca tataagttta 3560
aggtaatgtt cgtatcctta acaaggctgc ataatggcaa 3600
gctttacaga gtacccaaag ctgtttactc aattgagact 3640
gctgcattat acaaagttca actagaggtt gggttcaaat 3680
tggatgttgc aaaagaccac cctcatgtga agatgttaag 3720
gaaggttaag aaagatgggg aagtaaaata catcggatat 3760
```

-continued

| | |
|---|---|
| gcatggttcc acttgtgcaa tttcaagcga acaactgcta | 3800 |
| aaggggaaac caggactata tcaaatctag aacataaggt | 3840 |
| gaaggcaatg ggtattaaag tcgccctcta tgatctctgg | 3880 |
| gggcctacat tggttgtgca aataaccggc aagaccagta | 3920 |
| agtatgctca aggcttcttc tctaccacag gcacatgttg | 3960 |
| cctccctgtt gcaaaggcag cacccgaact tgccaagctt | 4000 |
| atgtggtcat gcaatgtttc aattattgaa gcctctgtgg | 4040 |
| tcatacaagg aagtgatcgg agagctgctg tgacctcaga | 4080 |
| agatctggag ctttacgggg ctgtggcaaa ggagaagcag | 4120 |
| ccccagaagg ggttccaccc attcagaaag tgacttgatt | 4160 |
| gaaagtatac ctagaggggc taggcctcaa actatcccac | 4200 |
| gatcacaatc cacatgcacg gagattcgac tgcagtaggc | 4240 |
| acaaatatat ccaccactgt catgaccaat cagcagaata | 4280 |
| agattagatt tagaaaaaat tgaaaaggcc cggtggcaac | 4320 |
| gtgggggcga aagcccaaaa aacatcccga gcatggaacc | 4360 |
| tccgaaccaa ccagaaggaa ccatgaaggc aatactaatc | 4400 |
| atgagcatgg tacctatctg tatcgcgctt gacaactcaa | 4440 |
| tccttgcacc ggtagggata gcaagtgcac aggaatggca | 4480 |
| acttgcagcg tacaccaata ccctatcagg gacaatagct | 4520 |
| gtgagatttg tgcctgtctt acctgggaat ctatcaacat | 4560 |
| gtgcgcaagc cacactggcg gaatataaca gaactgtgac | 4600 |
| aaatatccta gggcctctaa aggacaacct gaacgctttg | 4640 |
| ttagctgaat caacactccc ctcagcacga tttgtcggtg | 4680 |
| ccatcatagg aacggtggca ctaggagttg ccacttccgc | 4720 |
| acaaatcaca gcagcagttg ctcttaacca agcccaagag | 4760 |
| aatgcaagga atatctggag gttaaaggag tctataatga | 4800 |
| aaacaaatga ggccgtcttg gagcttaagg atggactagc | 4840 |
| cagtaccgct attgccctag acaaagtcca gcgattcatc | 4880 |
| aatgatgaca tcctcccaca gctgacaggt ctagactgtc | 4920 |
| aagttgtggc aaacaaactc ggcgtctatt tgtccttgta | 4960 |
| tttaactgag ttaaccacca tatttggctc gcagataacc | 5000 |
| aacccggcct taacaccctt atcgtaccag gctttgtaca | 5040 |
| gtctatgtgg aggcgacatg ggaagttga ctgagctaat | 5080 |
| aggtgtaaaa gccaaagaca ttaactctct gtatgaggcc | 5120 |
| aatctgataa ctggacaagt cataggctat gactccgagt | 5160 |
| cacagattat actagtccag gtgtcatacc caagtgtctc | 5200 |
| agaggtgacg ggagtcagag caacagagct cattaccgtt | 5240 |
| agtgtgacaa ccccaaaagg agaaggcaga gcgataacac | 5280 |
| ccaggtacgt ggctcaaagc agagtattga cagaagagct | 5320 |

-continued agatacaagc acatgcagat ttagcaagac tacattgtac 5360
tgtagatcag taataactcg gcctctacct cctttaattg 5400
caagctgtct gagtgggtca taccaggatt gccagtacac 5440
aacagagatt ggcgctttgt cgtcgcgctt tattactgtc 5480
aacgggggta tagtagcgaa ctgtaaggcc accgtatgca 5520
agtgtgtgaa tcccccaaag atcatagcac agaatgacgc 5560
cagctctcta acggttatag atgcaggtgt ctgcaaggaa 5600
gtggtgttag ataatgtaca gttaaagcta gaaggaaagt 5640
ttagcgctca atactttact aatgtgacga tcaacttgtc 5680
acagataact acctctgggt ctttggacat tagcagtgag 5720
atcggcagca tcaacaacac agtgaataga gtggagaatt 5760
taattgcaga gtcaaacgcg tggttacagt ctgtcaaccc 5800
aagactagtg aacaatacta gcatcattgt cttgtgtgtg 5840
ttgggcgcag tcatcgtcgt ctggttagta gcactgactg 5880
tgtgtatggc ttactcgctg cgcagaaaag cagccacgca 5920
gatcgcaagc atgggaacat ccacaatagg gaatccttat 5960
gtgacccaaa gtgcaacaaa gatgtaacag gacgcgatca 6000
cccagcctgg gatcccatgc catgccaatc agaagcaacg 6040
gccccaacac cagtcctttt cctttcatgt gttaagaaaa 6080
aacgatgggg gcgaaagccc aaaacttagt ggttgtctgt 6120
cagattcaac ccgctgtaag cgcccacact gccacaatgg 6160
ccacaatgtc cagagaaaac ctcacaaata ttggccaagg 6200
agaaagaggg acttggcggt tgttatttcg gatctcaacc 6240
ctagccatca ctacagtttg cttggcaatc aacatcgcca 6280
ccatatccaa actagacaac atagacacca gcgggatcca 6320
gacctggacc accatggagt ccgacaggat aatcgggtct 6360
ttgacaagca cgctgaaagt cccaatcaat caggtgaatg 6400
atatgtttcg tattgttgct ttggatctcc cactccagat 6440
gtctacaatg cagaaagaga ttgcttcaca ggttggcttc 6480
ttggcagaaa gcatcaataa tgtgctatct aagaatggat 6520
cagctgggtt ggttctagtc aatgacccag agtatgcagg 6560
cgggatagga gtcagcctgt tccatggtga ctcagcgtct 6600
agtcttgaat ttgagagccc gtcactgatt gaacacccca 6640
gctttatccc gggtcccact acagcaaagg gttgcatcag 6680
gataccgaca tttcacatga ccgcttctca ttggtgctac 6720
tcccacaaca taattgagtc cggctgtcaa gatgcaggac 6760
attccagtat gtacatctct ctgggtgtgc tgaaggccat 6800
gcagacagga tcccccagct ttctcaccac agctagccag 6840
cttatagatg ataaccttaa cagaaagtca tgcagcatca 6880
tatcaacgac gtacggctgc gacatactgt gtagtttggt 6920

-continued

```
agttgagaac gaggattcag attaccggtc cgacccaccg                    6960
actgagatga ttcttgggag gctgttcttc aacggcacct                    7000
accttgagag tcatgtgaat acaaggtcaa tatttgagca                    7040
gttctccgcg aattacccgg cagttggatc tggtttagta                    7080
ttaggagatg agatagcatt cccagtgtac gggggagtca                    7120
aacaggatac acagctgttc aatcagctaa aagatcatgg                    7160
ttactttact cacaatgatg tatacaggtg taacaaaagc                    7200
aatgtgcagc agaccatcct caatgcatac agaccccca                     7240
aaatagcagg acggttgtgg tcacaggtta tcataatctg                    7280
ccctttgggg ttgttcataa acacggattg tagaatcaag                    7320
gtgtttaaca ccagctcagt aatgatgggc gcagaagcta                    7360
gactgataca agtcgggtcc gatatctacc tataccagag                    7400
accatcctcg tggtgggtgg tcgggttgat atataagctt                    7440
gacttccaag agctatcaac aaaagaaggg gtggttctga                    7480
acaaaatagt tcccatcgct catgcaaaat tccctcgacc                    7520
atccttttca aaggacgcct gtgctagacc aaatatctgc                    7560
ccagcagtat gtgtatcagg agtgtaccag gatatttggc                    7600
ctattagtac ggccaccaat ttgagtcaag tagtgtgggt                    7640
gggccaatat cttgaagcat tttatgctag aaaagatccc                    7680
tggataggga tcgcaacgca gtatgattgg aaaaggaatg                    7720
tccgcttatt taattctarc acaraaggag ggtattccac                    7760
taccacatgc ttcaggaaca caaagaggaa taaggcattc                    7800
tgtattatca tatcagagta tgcggacggt gtatttggat                    7840
cttacaggat tgtgcctcaa ctaatcgaaa tcaggacgaa                    7880
taacagggtt aggtttgaca atcattaact gaaaaccact                    7920
gtgtgtacca tacaagcaag cattagattg ccgcttgaga                    7960
aggttagatt taataaaaaa ttgaatgtgg gggcgaatgc                    8000
ccgaacataa tggatcaggt ccaagcggat astattatcc                    8040
agcctgaagt ccacttagat tcaccgatag ttagagcaaa                    8080
gcttgtattg ctatggaaat taacaggttt acccctgcca                    8120
aaagagctaa gatcttttgt cctcacatcc cataccacag                    8160
atgaacagat cttcaaagct gaaacaagag taaaacctaa                    8200
ggtaaattca atagttgatg cactcatcaa acattgcaaa                    8240
tcacggggtt tgtatctatc cgacatacga ccagtggtgc                    8280
acccaaggac actccaatgg ttgctaaata ttaaatgtga                    8320
aagagccaat caactgctaa aggctaggga aaaatccatc                    8360
caacaagtat tttcagagaa acaagtaaac tttaggcatc                    8400
tattctcagc tataagccac caattggtag ggaatcctaa                    8440
cctattttsc tctcaagata atgacccaag atatccagag                    8480
```

-continued

```
tcacccctgc tctacaggct gtcagaagct tcttacacag          8520
cctatatccg caacaacctc tcgatggact gcagctcgat          8560
gggcttggct acatattatg caggttatgc gctaccaaat          8600
tctacagagt acgctgcacg ctacatcagc atcagtgaca          8640
tcatggtcag agacttgggg ctttatagga atttcaccag          8680
atgttgtgct aattgttgtt tatatgtcta tgagctacac          8720
tgtgctgacg tttcagatgg tcctaatgta ctcagatgta          8760
attcaagggc gcgacaatat agcaattgtg ggtcgattat          8800
cccctattct atcccctgtc acagatcgaa tagacatcct          8840
ctttcatcta gtcgacaccc tagcagtttt gatgggtcat          8880
cagatatatc accttgtggc atcattagag agtatggcct          8920
atgcagctgt ccaattgcat catgcaagct actcacacgc          8960
aggtcagttc tttgctttca atctgacaga aattcaatca          9000
gttctcgcag accacctaga tcaaaagcaa gcgcactcta          9040
tcatcagaac tattatcatg tgttacagtt gtctaacacc          9080
cgatcaagcg gctcagatgt tatgcatcat gcggttgttc          9120
ggtcatcccc tgttatccgc ccagcaagca gcaaaaaaag          9160
taagggaatc catgtgcgca cctatgatcc tggagcatgc          9200
gcaattttac agacattgtc cttcttcaag gggatcataa          9240
tcaatggtta taggaagagc cactccggag tatggccaaa          9280
cattgaacct gagtctatca tagatgatga tcttcgtcaa          9320
ttatactatg aatctgcaga gatatcacat gcattcatgc          9360
ttaagaaata tcggtactta agcatggtag aattcaaaaa          9400
gagtattgac ttcgacctca atgatgacct gagcaccttt          9440
ttgaaagaca aagccatatg ccgtccaaag aatcaatggg          9480
ctcggatttt cagaaagtca ctgtttccct tgaaaaatgc          9520
cattgatagc ggagcagaca ctagaagtaa tcgcctgctg          9560
atcgattttt tagaatccca tgactttagc ccagaggagg          9600
agatgaaata tgtcactacg atggcatacc tggatgatga          9640
tcagttctct gctttcatat tccctcaaag agaaggaaat          9680
caagacaaca ggtcgaatat ttgcgaaaat gaccaggaaa          9720
atgcgaagct gccaggttat actagaatca ttgttgtcta          9760
ctcatgtgtg caaattcttc aaagagaacg gagtctccat          9800
ggagcaactc tctttaacaa agagcctcct agcaatgtct          9840
cagttagccc ctcggatctc cgcggtgcga aacgaaacgg          9880
caagagcagg tacccaggga aatcacattt acaaccagta          9920
ggtcccatgt cggctgcgag ggaggtacag cagcatcaaa          9960
gggatcgacc tgctaagaaa agtattgtgg caaccttttt         10000
aacaacagac ctacagaaat attgcctcaa ttggagatac         10040
gggagcatta agttatttgc acaggcacta aaccaactat         10080
```

-continued

```
ttggaataga ccacgggttt gagtggatac atcttagatt      10120
aatgaatagc acattatttg ttggtgaccc cttttctcct      10160
cctgagtgca agggagtgag agatctggat gatgcaccta      10200
actcagacat cttcatagtt tcggcacgag gaggtatcga      10240
aggactgtgt caaaaactgt ggactatgat ttctattagt      10280
attatccatt gtgtgtccga aaaaataggg acaagggtcg      10320
ctgcaatggt ccaaggggac aatcaagtta tagcaattac      10360
cagagaatta ttcaatgggg agacatttga gcaaatccaa      10400
cctgagctgg acaagctagg taatgcattc ttttctgagt      10440
ttaagcaaca caactatgca atgggtcata atcttaagcc      10480
caaggagact atccaaagcc aatcattctt tgtgtattcc      10520
aaacggatat tttgggaagg gaggatcctc agccaggctc      10560
tcaagaatgc aactaagcta tgtttcatcg cagaccattt      10600
gggagacaat acggtgtcat catgcagcaa ccttgcatca      10640
actatcacac gccttgtcga gaatggattt gaaaaagata      10680
ctgcttttgt cttaaacgtg gtctattcaa tgacccagat      10720
cctgatagac gagcaatatt ctctgcaggg tgattatgcg      10760
aatgtcaaga atctaattgg taccaacaac cacagaaatc      10800
tactgactgc tgccctgatt cctgggcaag tcgggggtta      10840
taatttctta aacattagca ggctatttac taggaacata      10880
ggagaccccg tgacctgtgc aatcgctgat cttaagtggt      10920
tcattaagag tgggctagtt gcggaccata tattgaagaa      10960
catcttactc cgggacccag gtgacggtag ttggagcact      11000
ctctgcgcgg acccttatgc acttaatatc ccctatacac      11040
aactaccaac gacctatctg aagaaacata cacaacgggc      11080
actgttagca gagtccaaca acccgctgct ggccggggtc      11120
cagttggatt cacagtacat tgaggaggaa gaactggcac      11160
aatttctctt agaccgtgaa gtagttatgc caagggttgc      11200
gcatactatt atggaagcca gcattctagg gaagaggaag      11240
aatatccaag gcttaataga cactacaccc acaatcatca      11280
aaacagcctt aatgagacag cccatctccc gccgaaagtg      11320
cgaaaagatt atcaattact caattaatta cttggtagag      11360
tgccatgatt ctattattgc tgttaggaaa tttgaaccta      11400
ggaaagaggt catctgggat tcggccatga tctcggtaga      11440
aacttgtagt gtgactgttg ctgagttctt gcgagctact      11480
agctggtcaa atctgttgaa cggaagaaca atctctgggg      11520
ttacatctcc tgacgcagtg gagctgctaa aggggtcact      11560
cattggagaa aaatacacac tgcacgctct gtgcgcaagg      11600
agacgataca ttcactggat gcatatagcg ggccaacgt      11640
```

-continued atatacccga cccaggcctg accggatcta agatgagagt 11680
accatacctg ggatccaaaa ccgaagaaag acggtctgcc 11720
tccatggcaa ctataaaagg aatgtcacat catctcaaag 11760
ctgcactcag aggtgcatct gtattggtct gggcgttcgg 11800
agacacagat gatagttgga accatgcatg tttactagct 11840
aatacaaggt gtaaagtcac catgtcacag ctccgattac 11880
taacaccaac acctagcagc tcaaatatac aacatcgact 11920
aaatgacgga atcagcgtac aaaagttcac accagccagc 11960
ctttcgcgtg ttgcatcctt cgttcacatc tgcaacgatt 12000
tccaaaatct agagaaagat ggcgcatctg ttgactcgaa 12040
cttgatatac cagcaaatca tgctcacagg gttgagcatc 12080
atggagacac ttcaccctat gcagacccaa tggatataca 12120
acaaccagac catacaccta cataccggga cttcttgctg 12160
ccccagagag attgaaacca gcatagtcaa ccccccaaaa 12200
tacgagttcc caaccatcac tctcactaca aataaccagt 12240
tcttgttcga caacaatcca atacacgacg atgccatcac 12280
caagctggca gtaagtgact tcaaattcca agaattaaat 12320
atcgacgcaa tcaggggtta cggtgctgtc aacctgctga 12360
gtcggtgtgt ggccaagcta attggcgagt gtatccttga 12400
agatgggatt gggtcttcta tcaagaacga ggctatggtc 12440
tcattcgata tctctgtcaa ttggatctct gagatcttac 12480
acagtgacct aagactgact tttatgcacc ttggccagga 12520
actcctctgt gatctagcat atcagatgta cttcctaagg 12560
gttacggggt atcatgctat cgtaacatat ctcaagacat 12600
cactagaaag aataccagtc atacaactag caagacatgg 12640
cccttaccat ttctcacccc gaagtgtgga gacgagtcac 12680
attagtcggg ttcaatcaag ggtaccgtac ccctacttgg 12720
ccactgttga cttcatagca gcgtgcaggg atattattgt 12760
gcaaggtgct cagcagtaca tatctgacct cttatcgggc 12800
tcggagtgcc aatatacatt ctttaatgtc caagacggtg 12840
atttgactcc aaagatggaa caattcttgg caaggaggat 12880
gtgcttgctt gtgctcttga cagggacttc ctcttcttta 12920
ccgattataa agtcactcaa tgcaatagag aaatgcgctg 12960
tgttgactca gttcatctat tatctaccaa atgtcgactt 13000
gacagtagct agtaaggcta ggacactata taccctttgcc 13040 gtcaacccta agatcgatgc actcgtatca aacctctact 13080
tcacgaccag gcgagtgtta tccaatataa gaggagacag 13120
gcatgccaaa gctcaggttt cttatctcta tgaagaggaa 13160
gttagctcag agcctctgca agacgagaac tttgatcact 13200
tcatgaaaga ccctataata cgaggaggat tgttcttcac 13240

-continued

```
cgtcattatc aagatggaaa aaatgtcact gaaccaattc        13280
gcatcggggg gtgctacaac ccttgcgtta ccgcctcagg        13320
aggctcattc aataatgtgg cgggcttcgc ctttagccca        13360
ttgcttgaag tctgtggggc aggttagcac tagctggtac        13400
aagtatgcgg tgttgcaagc tgccctcagc aaaacccagc        13440
ctcttaggtc aaatagcatt tacattggtg aagggagtgg        13480
aagtgtcatg acactacttg agtacatgga cccatcaatc        13520
agtcatattc tacaattcgt tgtttataac agcatgaatc        13560
ctccccagcg caattttgga ctaatgccga ctcagttcca        13600
ggaatcaata gtatataaaa atctgtgtgc aggtattgag        13640
agcaaatatg gattctccca gacattctcg cccctgtgga        13680
gagatgttga ccaagaaaca aacatcacgg agacagcatt        13720
cctcaactac ctaatggaag tagtgccaat ccactccgct        13760
aaaaggttgg tgtgtgaagt agagtttgat agaggcatgc        13800
ctgatgaagt aatgatacaa gggtatatga atgtgttgat        13840
tgcagcggca tttagcttac acagagaggg ccgcttgttc        13880
atcaagatat ttcgccatag tgagtccatt ttcaattttg        13920
tcctatcatc tataatgatg atcttcgggt tatgccatat        13960
acatcgcaac tcttacatgt caaccaataa agaggagtat        14000
atcctggtgg gccgaagcac ctcagcccct aagttatgca        14040
tcagtaccgg ccatcctgca tcgagtcaag agcataacag        14080
accagagctt aacggtggtg accctattga tatggcccga        14120
gtgcacaaag agatggattc actgagagaa aaggaatcag        14160
ctcttatttc ctctttaata agagggacag tgagattaag        14200
gccaactcag acagacatgt tgttttccta tttagggggt        14240
aaattcgtca ccttattcgg acactcggca agggatctga        14280
tggaacttga tatagcagtg ctagattctc ggcaaataga        14320
cttaatcgac cttttgatgg tagaagccaa catcatcgta        14360
agcgagagta ctgatttgga tctagccctt cttcttagcc        14400
cattcaattt agataaaggg aggaaaattg taacactcgc        14440
aaaatcaact acgaggcaac taatcccgct ttatattgca        14480
gctgagatct cttgcaacaa gcactcattt tcacacttaa        14520
tatctttggt gcaaaggggc gtaatcagga tcgaaaacat        14560
ggtgtctgtg tcaagcttca tctcaaaatc ctcccggcct        14600
aggtttctaa gggatgttgt gacttttgct caaatcgagc        14640
atatattctc cgatctttca acattaatcc taaccaggtc        14680
ggaaattaag gtagtcctca agttcattgg ttgctgcatg        14720
aagtttaacc atgcctaaat gatgattgat ccgcatcaaa        14760
tcagtaagga ctattatacc tgatacaata cagagaaaac        14800
```

ttagtacttg tcataaaata ggttgtggaa attacaaaga 14840
ttaagaaaaa acgaaaccca aagaaggagc cgataccctc 14880
ctacatacag aaacaaaaaa aggacggcaa cagcaataca 14920
taaaacaacc ctttcgcggt cgggttcgaa cgactgcaag 14960
ccggatacgc acctataatc caattaaatt ttttgtcacg 15000
ttgctttcct aatccttgtt tggt 15024

<210> SEQ ID NO 3
<211> LENGTH: 14904
<212> TYPE: DNA
<213> ORGANISM: Avian Paramixyvirus Type 2
<220> FEATURE:
<223> OTHER INFORMATION: APMV-2/Chicken/England/7702/06

<400> SEQUENCE: 3
accaaacaag gaataggtaa gcaacgtaaa tcttagataa 40
aaccatagaa tccgtggggg cgacatcgcc tgaagccgat 80
ctcgagatcg ataactccgg ttaattggtc tcagcgtgag 120
gagcttatct gtctgtggca atgtcttctg tgttttcaga 160
acaccaggct cttcaggacc aactggtcaa gcctgccact 200
cgaagggctg atgtggcatc gactggattg ttgagagcgg 240
agataccagt ttgtgtaacc ttgtctcagg acccaactga 280
tagatggaac ctcgcatgtc tcaatctgcg atggctgata 320
agtgagtcct ctactactcc catgagacaa ggggcgatcc 360
tgtcactgct gagcttgcac tctgacaaca tgcgagctca 400
cgcaaccctt gcagcgagat ccgctgatgc tgccatcact 440
gtgcttgagg ttgacgccat agacatgacg gatagcacaa 480
tcacttttaa tgccagaagt ggagtatccg agaggcgcag 520
cacacagctc atggcaatcg caaaagatct gccccgctct 560
tgttccaatg actcaccatt caaagatgac actatcgagg 600
atcgcgaccc ccttgacctg tccgagacta tcgatagact 640
gcaggggatt gctgcccaaa tctggatagc ggccatcaag 680
agcatgactg ccccggatac tgctgcggag tcagaaggca 720
agaggcttgc aaagtaccaa caacaaggcc gcttggtgcg 760
acaggtgtta gtgcatgatg cggtgcgtgc ggaattccta 800
cgtgtcatca gaggcagcct ggtcttacgg caattcatgg 840
tatcagaatg taagagggca gcatccatgg gtagcgagac 880
atctaggtac tatgccatgg tgggtgacat cagcctctac 920
atcaagaatg caggacttac cgccttcttc ttgacactca 960
gatttggtat tgggacacac taccccactc ttgccatgag 1000
tgtgttctct ggagaactga agaagatgtc gtccttgatc 1040
aggctgtata agtcaaaagg ggaaaatgct gcatacatgg 1080
cattcctgga ggatgcggac atgggaaact ttgcgcctgc 1120
taactttagt actctctact cctatgcaat gggggtaggt 1160

-continued acagtgctgg aagcatcagt tgcgaaatac cagttcgctc 1200
gagagttcac cagtgagaca tacttcaggc ttggggttga 1240
gaccgcacag aaccaacagt gcgctctaga tgaaaagacc 1280
gccaaggaga tggggcttac tgatgaagcc agaaagcagg 1320
tgcaagcatt ggctagcaac atcgagcagg ggcaacattc 1360
aatgcccatg caacaacagc ccacattcat gagtcagccc 1400
taccaggatg acgatcgtga ccagccaagc accagcagac 1440
cagagccaag accatcgcaa ttgacaagcc aatcagcagc 1480
acaggacaat gatgcggcct cattagattg gtgaccgcaa 1520
tcagctcagc caagccattg ttggacgcag gacattcaaa 1560
tcatacattg ccctaagagt attaaagtga tttaagaaaa 1600
aaggaccctg gggcgaagt tgtcccaatc caggcaggcg 1640
ctgaaaccga atccctccaa cctccgagcc ccaggcgacc 1680
atgggagtca ccgatgatgc cgaaattgct gagctgttgg 1720
acctcgggac ctcagtgatc caagagctgc agcgagccga 1760
agtcaagggc ccgcaaacaa ccggaaagcc caaagttccc 1800
ccggggaaca ctaagagcct ggctactctc tgggagcatg 1840
agactagcac ccaagggagt gcattgggca cacccgagaa 1880
caacacccag gcacccgatg acaacaacgc aggtgcagat 1920
acgccagcga ctaccgacgt ccatcgcact ctggatacca 1960
tagacaccga cacaccaccg gaagggagca agcccagctc 2000
cactaactcc caacccggtg atgaccttga caaggctctt 2040
tcgaagctag aggcgcgcgc caagctcgga ccagataggg 2080
ccagacaggt taaaaagggg aaggagatcg ggtcgagcac 2120
agggacgagg gaggcagcca gtcaccacat ggaagggagc 2160
cgacagtcgg agccaggagc gggcagccga gcacagccac 2200
aaggccatgg cgaccgggac acaggaggga gtactcattc 2240
atctctcgag atgggagact ggaagtcaca agctggtgca 2280
acccagtctg ctctcccatt agaagcgagc ccaggagaga 2320
aaagtgcaca tgtggaactt gcccagaatc ctgcatttta 2360
tgcaggcaac ccaactgatg caattatggg gttgacaaag 2400
aaagtcaatg atctagagac aaaattggct gaggtattgc 2440
gtctgttagg aatactcccc gttattaaga atgagattag 2480
ccaattaaag gctactgtgg ctttgatgtc taatcaattg 2520
gcatccatcc aaatcctcga ccctgggaac gctggagtca 2560
agtcattgaa tgaaatgaaa gcactatcga aatctgctag 2600
catagtggta gcaggcccag gctctatacc ctctgaggtg 2640
ttggagtcca atgttgtata taaggatgaa cttgctcgtc 2680
ctgtgactgc acaagcccac aaagagatca agccccgaga 2720

-continued

```
ggaggcaagt gccacttcct cagagctaac cgccgtccag          2760
gcagtaatcg acatccctgt agaagatgag aggaagaagg          2800
ccaggctcca ccaggcactc gagagagcaa gaaccaagga          2840
ggacatcctc cgcattaaaa ggcagatcta caatgcatga          2880
gagtccattt gtctaaagaa cctccaatca tatcaccagt          2920
ttcgtgccac atgcttccct gccgagaatc tagcggacac          2960
aaaaactaaa tcatagttta acaaaaaaga agtttggggg          3000
cgaagtctca catcatagag caccccttgca ttctaaaatg          3040
gctcaaacaa ccgtcaggct gtatatcgat gaagctagtc          3080
ccgacattga actgttgtct tacccacaga taatgaaaga          3120
cacaggacat gggaccaaag agttgcagca gcaaatcaga          3160
gttgcagaga tcggtgcatt gcagggaggg aagaatgaat          3200
cagttttcat caatgcatat ggctttgttc agcaatgcaa          3240
agttaaaccg gggcaaccc aattcttcca ggtagatgca          3280
gctacaaagc cagaagtggt cactgcaggg atgattataa          3320
tcggtgcagt caagggggtg gcaggcatca ctaagctggc          3360
agaagaggtg ttcgagctgg acatctccat caagaagtcc          3400
gcatcattcc atgagaaggt tgcggtgtcc tttaatactg          3440
tgccactatc actcatgaat tcgaccgcat gcagaaatct          3480
gggttatgtc acaaacgctg aggaggcgat caaatgcccg          3520
agcaaaatac aagcgggtgt gacgtacaaa tttaagataa          3560
tgtttgtctc cttgacacga ctgcataacg ggaaattgta          3600
ccgtgtcccc aaggcagtgt atgctgtaga ggcatcagct          3640
ctatataaag tgcaactgga agtcgggttc aagcttgacg          3680
tggccaagga tcacccacac gttaagatgt tgaagaaagt          3720
ggaacggaat ggtgagactc tgtatcttgg ttatgcatgg          3760
ttccacctgt gcaacttcaa gaagacaaat gccaagggtg          3800
agtcccggac aatctccaac ctagaaggga aagtcagagc          3840
tatggggatc aaggtttcct tgtacgactt atgggggcct          3880
actttggtgg tgcaaatcac aggtaagacc agcaagtatg          3920
cacaaggttt cttttcaacc acaggtacct gctgcctccc          3960
agtgtcgaag gctgcccctg agctggccaa acttatgtgg          4000
tcctgcaatg caacaatcgt tgaagctgca gtgattatcc          4040
aagggagtga taggagggca gtcgtgacct cagaggactt          4080
ggaagtatac ggggcagttg caaaagagaa gcaggctgca          4120
aaaggatttc acccgttccg caagtgacac gtgcggccgc          4160
acacctcatt accccagaag cccgggcaac tgcaaattca          4200
cgcttatata atccaattac catgatctag aactgcaatc          4240
gatactaatc gctcattgat cgtattaaga aaaaacttaa          4280
ctacataact tcaacattgg gggcgacagc tccagactaa          4320
```

-continued

```
gtgggtggct aagctctgac tgataaggaa tcatgaatca      4360
agcactcgtg attttgttgg tatctttcca gctcggcgtt      4400
gccttagata actcagtgtt ggctccaata ggagtagcta      4440
gcgcacagga gtggcaactg gcggcatata caacgaccct      4480
cacagggacc atcgcagtga gatttatccc ggtcctgcct      4520
gggaacctat caacatgtgc acaggagacg ctgcaggaat      4560
ataatagaac tgtgactaat atcttaggcc cgttgagaga      4600
gaacttggat gctctcctat ctgacttcga taaacctgca      4640
tcgaggttcg tgggcgccat cattgggtcg gtggccttgg      4680
gggtagcaac agctgcacaa atcacagccg ccgtggctct      4720
caatcaagca caagagaatg cccggaatat atggcgtctc      4760
aaggaatcga taaagaaaac caatgcggct gtgttggaat      4800
tgaaggatgg acttgcaacg actgctatag ctttggacaa      4840
agtgcaaaag tttatcaatg atgatattat accacagatt      4880
aaggacattg actgccaggt agttgcaaat aaattaggcg      4920
tctacctctc cttatactta acagagctta caactgtatt      4960
tggttctcag atcactaatc ctgcattatc aacgctctct      5000
taccaggcgc tgtacagctt atgtggaggg gatatgggaa      5040
agctaactga gctgatcggt gtcaatgcaa aggatgtggg      5080
atccctctac gaggctaacc tcataaccgg ccaaatcgtt      5120
ggatatgacc ctgaactaca gataatcctc atacaagtat      5160
cttacccaag tgtgtctgaa gtgacaggag tccgggctac      5200
tgagttagtc actgtcagtg tcgctacacc aaaaggagaa      5240
gggcaggcaa ttgttccgag atatgtggca cagagtagag      5280
tgctgacaga ggagttggat gtctcgactt gtaggtttag      5320
caaaacaact ctttattgta ggtcgattct cacacggccc      5360
ctaccaactt tgatcgccag ctgcctgtca gggaagtacg      5400
acgattgtca gtacacaaca gagataggag cgctatcttc      5440
gagattcatc acagtcaatg gtggagtcct tgcaaactgc      5480
agagcaattg tgtgtaagtg tgtctcaccc ccgcatataa      5520
taccacaaaa cgacattggc tccgtaacag ttattgactc      5560
aagtatatgc aaggaagttg tcttagagag tgtgcagctt      5600
aggttagaag gaaagctgtc atcccaatac ttctccaacg      5640
tgacaattga cctttcccaa atcacaacgt cagggtcgct      5680
ggatataagc agtgaaattg gtagcattaa caacacagtt      5720
aatcgggtcg acgagttaat caaggaatcc aacgagtggc      5760
tgaacgctgt gaaccccc gc cttgtgaaca atacgagcat      5800
catagtcctc tgtgtccttg ccgccctgat tattgtctgg      5840
ctaatagcgc tgacagtatg cttctgttac tccgcaagat      5880
```

-continued

```
actcagctaa gtcaaaacag atgaggggcg ctatgacagg          5920
gatcgataat ccatatgtaa tacagagtgc aactaagatg          5960
tagagaggtt aattaagcct aaacatgata tgatttaaga          6000
aaaaattgga aggtgggggc gacagcccat tcaatgaagg          6040
gtgtacactc caacttgatc ttgtgacttg atcatcatac          6080
tcgaggcacc atggatttcc catctaggga gaacctggca          6120
gcaggtgaca tatcggggcg gaagacttgg agattactgt          6160
tccggatcct cacattgagc ataggtgtgg tctgtcttgc          6200
catcaatatt gccacaattg caaaattgga tcacctggat          6240
aacatggctt cgaacacatg gacaacaact gaggctgacc          6280
gtgtgatatc tagcatcacg actccgctca aagtccctgt          6320
caaccagatt aatgacatgt ttcggattgt agcgcttgac          6360
ctacctctgc agatgacatc attacagaaa gaaataacat          6400
cccaagtcgg gttcttggct gaaagtatca acaatgtttt          6440
atccaagaat ggatctgcag gcctggttct tgttaatgac          6480
cctgaatatg caggggggat cgctgtcagc ttgtaccaag          6520
gagatgcatc tgcaggccta aatttccagc ccatttcttt          6560
aatagaacat ccaagttttg tccctggtcc tactactgct          6600
aagggctgta taaggatccc gaccttccat atgggccctt          6640
cacattggtg ttactcacat aacatcattg catcaggttg          6680
ccaggatgcg agccactcca gtatgtatat ctctctgggg          6720
gtgctgaaag catcgcagac cgggtcgcct atcttcttga          6760
caacggccag ccatctcgtg gatgacaaca tcaaccggaa          6800
gtcatgcagc atcgtagcct caaaatacgg ttgtgatatc          6840
ctatgcagta ttgtgattga aacagagaat gaggattata          6880
ggtctgatcc ggctactagc atgattatag gtaggctgtt          6920
cttcaacggg tcatacacag agagcaagat taacacaggg          6960
tccatcttca gtctattctc tgctaactac cctgcggtgg          7000
ggtcgggtat tgtagtcggg gatgaagccg cattcccaat          7040
atatggtggg gtcaagcaga acacatggtt gttcaaccag          7080
ctcaaggatt ttggttactt cacccataat gatgtgtaca          7120
agtgcaatcg gactgatata cagcaaacta tcctggatgc          7160
atacaggcca cctaaaatct caggaaggtt atgggtacaa          7200
ggcatcctat tgtgcccagt ttcactgaga catgatcctg          7240
gctgtcgctt aaaggtgttc aataccagca atgtgatgat          7280
gggggcagaa gcgagggtga tacaagtagg gtcagccgtg          7320
tatctatacc aacgctcatc gacatggtgg gtggtaggac          7360
tgacacacaa attagatgtg tcagaaataa ctagagagag          7400
cgggaacatg gttaacaaag aaagcccaat tggtcgtgca          7440
aaattccctc ggccatcctt ctctcgagat gcttgtgcga          7480
```

-continued

```
gaccaaacat ctgtccggct gtctgtgttt ctggggtata    7520
ccaggacata tggccaatta gtactgcaca taacttgagc    7560
caggtcgttt gggtaggaca gtacctggag gcattttatg    7600
cccgcaagga tccaagaata gggatagcaa cccagtatga    7640
gtggaaagtc accaaccagc tgttcaattc gaatactgag    7680
ggagggtact caaccacaac atgcttccgg aacaccaaac    7720
gggacaaggc atattgtgta gtgatatcag agtacgctga    7760
tggggtgttc ggatcataca ggatcgttcc tcagcttata    7800
gagattagaa caaccaccgg taaatctgag tgatgcatca    7840
atcctaaatt ggaatgacca atcaaaagcc acgtagtgtc    7880
taacagcatt gcgaagcctg gtttaagaaa aaacttgggg    7920
gcgaatgccc atcaaccatg gatcaaactc aagctgacac    7960
tataatacaa cctgaagtcc atctgaattc accacttgtt    8000
cgcgcaaaat tggttcttct atggaaattg actgggttac    8040
ctttgccgtc tgatttgaga tcatttgtac taactacaca    8080
tgcagctgat gaccaaatcg caaaaaatga gactaggatc    8120
aaggccaaaa ttaattccct aatcgataac ttaatcaaac    8160
actgcaaggc aaggcaagtg gcactttcag ggttgacacc    8200
tgtcgtacat ccaacaactc tacagtggtc gctacccatc    8240
acttgtgaac gagcagccca gcctgcaaaa gtacgcgaga    8280
aatcagttaa gcaagcaatg tcagagaagc aacacgggtt    8320
tagacatctc ttttcggcag taagtcatca gttagttgga    8360
aacgccacac tgttctgtgc acaagactct agcaccgtga    8400
atgtcgactc tccttgctca tcaggttgtg agaggctgat    8440
aatagactct attggagcct tacaaacacg atggacaaga    8480
tgtaggtggg cttggcttca cattaaacag gtaatgagat    8520
accaggtgct tcagagtcgc ctacacgctc atgccaattc    8560
tgttagcaca tggtctgagg cgtgggggtt cattgggatc    8600
acaccagata tagtccttat tgtagactat aagagcaaaa    8640
tgtttactat cctgaccttc gaaatgatgc tgatgtattc    8680
agatgtcata gagggtcgtg ataatgtggt agctgtagga    8720
agtatgtcac caaacctaca gcctgtggtg gagaggattg    8760
aggtgctgtt tgatgtagtg gacaccttgg cgaggaggat    8800
tcatgatcct atttatgatc tggttgctgc cttagaaagc    8840
atggcatacg ctgccgtcca attgcacgat gctagtgaga    8880
cacacgcagg ggaattcttt tcgttcaatt tgacagaaat    8920
agagtccact cttgcccccct tgctggatcc tggccaagtc    8960
ctatcggtga tgaggactat cagttattgt tacagtgggc    9000
tatcgcctga ccaagctgca gagttgctct gtgtgatgcg    9040
```

-continued

```
cttatttgga caccctctgc tctccgcaca acaagcagcc          9080
aaaaaagtcc gggagtctat gtgtgcccct aaactgttag          9120
agcatgatgc aatactgcaa actctatctt tcttcaaggg          9160
aatcataatc aatggctaca ggaaaagtca ttctggagta          9200
tggcctgcaa ttgacccaga ttctatagtg gacgatgacc          9240
ttagacagct gtattacgag tcggcagaaa tttcacatgc          9280
tttcatgctt aagaaatatc ggtaccttag tatgattgag          9320
ttccgcaaga gcatagagtt tgacttaaat gatgacctga          9360
gcacattcct taaagacaaa gcaatctgca ggccaaaaga          9400
tcaatgggca cgcatcttcc ggaaatctca gttcccactt          9440
aaattggaca atcgcactag tggagtggac aaaagcaaca          9480
ggttgctcat tgattttctt gaatcacatg attttagccc          9520
agaagaagag atgaagtatg tgagaacaaa agcataccta          9560
gaggatgatc aattctctgc atcctactct ctcaaggaaa          9600
aggagattaa aacaacaggc cggatatttg caaagatgac          9640
aaggaaagtg aggaggtgtc aagtattcat gggatccctc          9680
ttatccggcc atgtgtgtaa gttcttcaaa gagaatggag          9720
tatccatgga acagctttcc ttaacaaaga gcctgcttgc          9760
aatgtcacaa ttatcaccca ggatctctcc cgtgaggaac          9800
gaaccagcta gtacacagga ccgacttgtc aggtactcca          9840
atgggaccca tctctgtgca ggggagttaa aaccacatca          9880
aagggagagg cctgtcaaga aaagcatagt agcaacattc          9920
ctcacaactg acctacagaa atattgcctc aactggagat          9960
acgggagcat taagctgttc gcacaagcat tgaatcaact         10000
ctttggtcta gatcacggct tcgaatggat ccaccttcgg         10040
ttgatgaata gcacactgtt tgtgggtgac cccttttctc         10080
cccctgagtg caaaggggta aaggatcttg atgatgctcc         10120
taattcggac atatttatcg tgtccgctag aggagggata         10160
gaaggactgt gccttaagct ctggactatg atctctatta         10200
gcatcattca ctgtgtctcg gagaaaattg gtacaagggt         10240
agcagcaatg gtacagggag acaaccaagt catagccata         10280
acgagagaat tattcaatgg agagactttc gaacaaatcc         10320
aacccgaatt agacaggcta ggtaatgcat tcttctcaga         10360
gttcaaacaa cacaattacg caatggggca caatctaaag         10400
ccgaaagaga ccatccaaag tcaatcattt tttgtctact         10440
ccaagcgaat tttttgggag ggtagaattt taagccaatc         10480
acttaagaat gctactaaac tctgtttcat tgcagaccat         10520
ctaggagata atactgtgtc atcatgcagc aatctcgcct         10560
ctactgtcac aagcttggta gagaagggat tcgagaagga         10600
cacggccttt gtactaaatc tcatctactc catgactcaa         10640
```

-continued atacttatag atgagcagta ttcgctgcag ggagactaca 10680
cagctgtgaa gggtttgata ggaacagaca accatagaaa 10720
tttctcactg gctgctttaa tacctggaca agtgggcggt 10760
tataatttct tgaacatcag caggctgttt acaaggaata 10800
ttggagatcc agtgacatgt gcaattgcag acatcaaatg 10840
gttcatcaag agcagactga tcgcagagca cgtgttgaag 10880
aacattctac ttagggaccc aggagatggc ggctggagca 10920
ctctctgtgc agacccgtat gctcttaata tcccttatac 10960
ccaattaccc actacttacc tcaagaagca cacccagaga 11000
tcactattag cagactcaaa taatcccatt gttgcagggg 11040
tccagcttga ctctcaatat attgaggagg aagaattcgc 11080
tcaattcctt cttgatagag aagcagtgat gccacattta 11120
gcacacacaa taatggaaac aagcatccta gggaagagaa 11160
agaatataca aggcctaata gacaccacgc ctaccatcat 11200
taaaacagct ctgatgcgcc aacctatctc caggagaaag 11240
tgtgagaaga tcataaacta ttcaattaat tacttagttg 11280
aatgtcatga ctcatcatcg tcgattagga cattcgaacc 11320
acgaaaggaa gtcatctggg attcagcaat gatctcagtc 11360
gagacatgca gtgtcaccat cgcggaattc ctacgtgcca 11400
ccagttggtc gaatattctg aacggtagaa caatatcggg 11440
tgtaacatct cctgatactg tagagctact ccggggctca 11480
ctcatcggag agaatacaca ctgtgttctt tgtgagcagg 11520
gtgatgatac ttttacctgg atgcatatat caggaccaac 11560
atacatacca gatcctggac tcaccggttc aaaaatgcgt 11600
gtgccatatc ttgggtcaaa gactgaagaa aggaggtcag 11640
cctctatggc aactgttaaa gggatgtctc atcatctaaa 11680
agccaccttg cgaggagcct ctgtgatggt gtgggccttt 11720
ggtgatactg aagaaagttg ggaacatgcc tgccttgtgg 11760
ccaatacaag gtgcaagatt aatcttccgc agctacgcct 11800
gctgaccccg acaccaagca gctctaacat ccaacatcga 11840
ctaaatgatg gtatcagcgt gcaaaaattt acacctgcta 11880
gcttatcccg agtggcgtca tttgttcaca tttgcaacga 11920
tttccaaaag ctagagagag atggatcttc cgtagactct 11960
aacttgatat atcagcaaat catgctgact ggtctaagta 12000
ttatggagac acttcatcct atgcacgtct catgggtata 12040
caacaatcag acaattcact tacataccgg aacatcgtgt 12080
tgtcctaggg aaatagagac aagcattgtt aatcccgcta 12120
ggggagaatt cccaacaata actctcacaa ctaacaatca 12160
gtttctgttt gattgtaatc ccatacatga tgaggcactt 12200

-continued

```
acaaaactgt cagtaagtga gttcaagttc caggagctta          12240
atatagactc aatgcagggt tacagtgctg tgaacctgct          12280
gagcagatgt gtggctaagc tgatagggga atgcattctg          12320
gaagacggta tcggatcgtc aatcaagaat gaagcaatga          12360
tatcatttga taactctatc aactggattt ctgaagcact          12400
caatagtgac ctgcgtttgg tattcctcca gctggggcaa          12440
gaactacttt gtgacctggc gtaccaaatg tactatctga          12480
gggtcatcgg ctatcattcc atcgtggcat atctgcagaa          12520
tactctagaa agaattcctg ttatccaact cgcaaacatg          12560
gcactcacca tatcccaccc agaagtatgg aggagagtga          12600
cagtgagcgg attcaaccaa ggttaccgga gtccctatct          12640
ggccactgtc gactttatcg ccgcatgtcg tgatatcatt          12680
gtgcaaggtg cccagcatta tatggctgat ttgttgtcag          12720
gagtagagtg ccaatataca ttctttaatg ttcaagacgg          12760
cgatctgaca ccgaagatgg aacaattttt agcccggcgc          12800
atgtgcttgt ttgtattgtt aactgggacg atccgaccac          12840
tcccaatcat acgatccctt aatgcgattg agaaatgtgc          12880
aattctcact cagttcttgt attacctacc gtcagtcgac          12920
atggcagtag cagacaaggc tcgtgtgtta tatcaactgt          12960
caataaatcc gaaaatagat gctttagtct ccaaccttta          13000
tttcaccaca aggagggtgc tttcttgtat cacgggagat          13040
tcttcttcac gagcgcacat tgcattcctc tacgaggagg          13080
aagtaatcgt tgatgtgcct gcatctaatc aatttgatca          13120
gtaccatcgt gaccccatcc taagaggagg tctatttttc          13160
tctctctcct taaaaatgga aaggatgtct ctgaaccgat          13200
ttgcagtaca gaccctgcca acccaggggt ctaactcgca          13240
gggttcacga cagaccttgt ggcgtgcctc accgttagca          13280
cactgcctta aatcagtagg gcaggtaagt accagctggt          13320
acaagtatgc tgtagtgggg gcgtctgtag agaaagtcca          13360
accaacaaga tcaacaagcc tctacatcgg ggagggcagt          13400
gggagtgtca tgacattatt agagtatctg gaccctgcta          13440
caattatctt ctacaactcg ctattcagca atagcatgaa          13480
ccctccacaa aggaatttcg gactgatgcc cacacagttt          13520
caggactcag tcgtgtataa aaacatatca gcaggagttg          13560
actgcaagta cgggtttaag caagtctttc aaccattatg          13600
gcgtgatgta gatcaagaaa caaatgtggt agagacggcg          13640
ttcctaaact atgtgataga agtagtgcca gtccactctt          13680
cgaagcgtgt cgtatgtgaa gttgagtttg acagggggat          13720
gcctgacgag atagtaataa cagggtacat acacgtgctg          13760
atggtgaccg catacagtct gcatcgagga gggcgtctaa          13800
```

taatcaaggt ctatcgtcac tccgaggctg tattccaatt 13840
cgtactctct gcgatagtca tgatgtttgg ggggcttgat 13880
atacaccgga actcgtacat gtcaactaac aaagaggagt 13920
acatcatcat agctgcggcg ccggaggcat taaactattc 13960
ctctgtacca gcaatattgc agagggtgaa gtctgttatt 14000
gaccagcagc ttacattaat ctctcctata gatctagaaa 14040
gattgcgcca tgagactgag tctctccgtg agaaggagaa 14080
taatctagta atatctctga cgagagggaa gtatcaactc 14120
cggccgacac agactgatat gcttctatca tacctaggtg 14160
ggagattcat caccctattc ggacagtctg ctagggattt 14200
gatggccact gatgttgctg accttgatgc taggaagatt 14240
gcattagttg atctactgat ggtggaatcc aacattattt 14280
taagtgagag cacagacttg gaccttgcac tgttgctgag 14320
cccgtttaac ttagacaaag ggcggaagat agttacccta 14360
gcaaaggcta ctacccgcca attgctgccc gtgtatatcg 14400
catcagagat aatgtgcaat cggcaggcat tcacacacct 14440
gacatcaatt atacagcgtg gtgtcataag aatagaaaac 14480
atgcttgcta caacggaatt tgtccgacag tcagttcgcc 14520
cccagttcat aaaggaggtg ataactatag cccaagtcaa 14560
ccaccttttt tcagatctat ccaaactcgt gctttctcga 14600
tctgaagtca agcaagcact taaatttgtc ggttgctgta 14640
tgaagttcag aaatgcaagc aattaaacag gattgttatt 14680
gtcaaatcac cggttactat agtcaaatta atatgtaaag 14720
ttccctcttt caagagtgat taagaaaaaa cgcgtcaaag 14760
gtggcggttt cactgatttg ctcttggaag ttgggcatcc 14800
tccagccaat atatcggtgc cgaaatcgaa agtctgacag 14840
ctgatttgga atataagcac tgcataatca ctgagttacg 14880
ttgctttgct attccatgtc tggt 14904

<210> SEQ ID NO 4
<211> LENGTH: 14916
<212> TYPE: DNA
<213> ORGANISM: Avian Paramixyvirus Type 2
<220> FEATURE:
<223> OTHER INFORMATION: APMV-2/Gadwell/Kenya/3/80

<400> SEQUENCE: 4
accaaacaag gaataggtaa gcaacgtaaa tcttagataa 40
aaccatagaa tccgtggggg cgacatcgcc tgaagccgac 80
ctcgagatcg ataactccgg ttaattggtc tcagcgtgag 120
gagcttatct gtctgtggca atgtcgtctg tatttactga 160
gtaccaggct ctgcaagatc aactggtcaa gccttcatcc 200
aggagggcag atgtcgcttc aactggattg ctcagagctg 240

-continued

```
agataccagt gtgtgtcaca ctctctcagg accctacaga          280
caggtggaac ctagcgtgtc tcaacttgcg gtggatcata          320
agcgagtcct caacaacacc aatgagagca ggggcaatac          360
tctctttgct cagcttacat tctgacaaca tgagggcaca          400
cgcaaccctt gctgcacggt cagcagatgc atcaatcacg          440
atccttgagg tggacaacat tgacatggca gctgacacaa          480
taacattcaa tgcaagaagc ggtgtgtcgg acagaagaag          520
tgctcaactc atggccattg caaaggacct accacgatca          560
tgttctaatg attcaccgtt taaggacaac aacattgagg          600
accgagaacc ccttgccctg tccgagacga tcgatagaca          640
ggaggaaatt gctgcccaaa tctggatagc ggccatcaag          680
agcatgactg ccccggatac tgctgcggag tcagaaggca          720
agaggcttgc aaagtaccaa caacaaggcc gcttggtgcg          760
acaggtgtta gtgcatgatg cggtgcgtgc ggaattccta          800
cgtgtcatca gaggcagcct ggtcttaccg caattcatgg          840
tatcagaatg taagagggca gcatccatgg gtagcgagac          880
ctctagcccc cacgctatgg tgggtgacat cagcctctac          920
acccataatg caggacttac cgccttcttc ttgacactca          960
gatttggtat tgggacacac taccccactc ttgccatgag         1000
tgtgttctct ggagaactga agaagatgtc gtccttgatc         1040
aggctgtata agtcaaaagg ggaaaatgct gcatacatgg         1080
cattcctgga ggatgcggac atgggaaact ttgcgcctgc         1120
taactttagt actctctact cctatgcaat gggggtaggt         1160
acagtgctgg aagcatcagt tgcgaaatac cagttcgctc         1200
gagagttcac cagtgagaca tacttcaggc ttggggttga         1240
gaccgcacag aaccaacagt gcgctctaga tgaaaagacc         1280
gccaaggaga tggggcttac tgatgaagcc agaaagcagg         1320
tgcaagcatt ggctagcaac atcgagcagg ggcaacattc         1360
aatgcccatg caacaacagc ccacattcat gagtcagccc         1400
taccaggatg acgatcgtga ccagccaagc accagcagac         1440
cagagccaag accatcgcaa ttgacaagcc aatcagcagc         1480
acaggacaat gatgcggcct cattagattg gtgaccgcaa         1520
tcagctcagc caagccattg ttggacgcag gacattcaaa         1560
tcatacattg ccctaagagt attaaagtga tttaagaaaa         1600
aaggaccctg gggcgaagt tgtcccaatc caggcaggcg          1640
ctgaaaccga atccctccaa cctccgagcc ccaggcgacc         1680
atggagttca ccgatgatgc cgaaattgct gagctgttgg         1720
acctcgggac ctcagtgatc caagagctgc agcgagccga         1760
agtcaagggc ccgcaaacaa ccggaaagcc caaagttccc         1800
ccggggaaca ctaagagcct ggctactctc tgggagcatg         1840
```

-continued

| | |
|---|---|
| agactagcac ccaagggagt gcattgggca cacccgagaa | 1880 |
| caacacccag gcacccgatg acaacaacgc aggtgcagat | 1920 |
| acgccagcga ctaccgacgt ccatcgcact ctggatacca | 1960 |
| tagacaccga cacaccaccg gaagggagca agcccagctc | 2000 |
| cactaactcc caacccggtg atgaccttga caaggctctt | 2040 |
| tcgaagctag aggcgcgcgc caagctcgga ccagataggg | 2080 |
| ccagacaggt taaaaagggg aaggagatcg ggtcgagcac | 2120 |
| agggacgagg gaggcagcca gtcaccacat ggaagggagc | 2160 |
| cgacagtcgg agccaggagc gggcagccga gcacagccac | 2200 |
| aaggccatgg cgaccgggac acaggaggga gtactcattc | 2240 |
| atctctcgag atgggagact ggaagtcaca agctggtgca | 2280 |
| acccagtctg ctctcccatt agaagcgagc ccaggagaga | 2320 |
| aaagtgcaca tgtggaactt gcccagaatc ctgcatttta | 2360 |
| tgcaggcaac ccaactgatg caattatggg gttgacaaag | 2400 |
| aaagtcaatg atctaaagac aaaattggct gaggtattgc | 2440 |
| gtctgttagg aatactcccc ggaataaaga atgagattag | 2480 |
| tcagctgaaa gcaaccgtgg ctctgatgtc aaatcagatt | 2520 |
| gcctccattc agattcttgg tcctgggaat gccggagtca | 2560 |
| aatcccttaa tgagatgaaa gccctgtcaa aagcagccag | 2600 |
| catagttgtg gcaggtccag gagtccttcc tcctgaggtc | 2640 |
| acagaaggag gactgatcgc gaaagatgag ctagcaaggc | 2680 |
| ccatccccat ccaaccgcaa cgagactcca aacccaaaga | 2720 |
| cgacccgcac acatcaccaa atgatgtcct tgctgtacgc | 2760 |
| gctatgatcg acacccttgt ggatgatgag aagaagagaa | 2800 |
| agagattaaa ccaggccctt gacaaggcaa agaccaagga | 2840 |
| tgacgtctta agggtcaagc ggcagatata caatgcctag | 2880 |
| gagtccattt gtctaaagaa cctccaatca tatcaccagt | 2920 |
| ttaaacccac atgcttccct gccgagaatc tagccgacac | 2960 |
| aaaaactaaa tcatagttta acaaaaaaga agtttggggg | 3000 |
| cgaagtctca catcatagag cacccttgca ttctaaaatg | 3040 |
| gctcaaacaa ccgtcaggct gtatatcgat gaagctagtc | 3080 |
| ccgacattga actgttgtct tacccactga taatgaaaga | 3120 |
| cacaggacat gggaccaaag agttgcagca gcaaatcaga | 3160 |
| gttgcagaga tcggtgcatt gcagggaggg aagaatgaat | 3200 |
| cagttttcat caatgcatat ggctttgttc agcaatgcaa | 3240 |
| agttaaaccg ggggcaaccc aattcttcca ggtagatgca | 3280 |
| gctacaaagc cagaagtgat cactgcgggg atgataataa | 3320 |
| ttgctgcagc gaagggaggc accggtatca ctaagctggc | 3360 |
| agaagaggtg ttcgagctgg acatctccat caagaagtcc | 3400 |

-continued

```
gcatcattcc atgagaaggt tgcggtgtcc tttaatactg          3440

tgccactatc actcatgaat tcgaccgcat gcagaaatct          3480

gggttatgtc acaaacgctg aggaggcgat caaatgcccg          3520

agcaaaatac aagcgggtgt gacgtacaaa tttaagataa          3560

tgtttgtctc cttgacacga ctgcataacg ggaaattgta          3600

ccgtgtcccc aaggcagtgt atgctgtaga ggcatcagct          3640

ctatataaag tgcaactgga agtcgggttc aagcttgacg          3680

tggccaagga tcacccacac gttaagatgt tgaagaaagt          3720

ggaacggaat ggtgagactc tgtatcttgg ttatgcatgg          3760

ttccacctgt gcaacttcaa gaagacaaat gccaagggtg          3800

agtcccggac aatctccaac ctagaaggca aagtcagagc          3840

tatggggatc aaggtttcct tgtacgactt atgggggcct          3880

actaaggtgg tgcaaatcac aggtaagacc agcaagtatg          3920

cacaaggttt cttttcaacc acaggtacct gctgcctccc          3960

agtgtcgaag gctgcccctg agctggccaa acttatgtgg          4000

tcctgcaatg caacaatcgt tgaagctgca gtgattatcc          4040

aagggagtga taggagggca gtcgtgacct cagaggactt          4080

ggaagtatac ggggcagttg caaaagagaa gcaggctgca          4120

aaaggatttc acccgttccg caagtgacac gtggggccgc          4160

acacctcatt accccagaag cccgggcaac tgcaaattca          4200

cgcttatata atccaattac catgatctag aactgcaatc          4240

gatactaatc gctcattgat cgtattaaga aaaaacttaa          4280

ctacataact tcaacattgg gggcgacagc tccagactaa          4320

gtgggtggct aagctctgac tgataaggaa tcatgaatca          4360

agcactcgtg attttgttgg tatctttcca gctcggcgtt          4400

gccttagata actcagtgtt ggctccaata ggagtagcta          4440

gcgcacagga gtggcaactg gcggcatata cgacgaccct          4480

cacagggacc atcgcagtga gatttatccc ggtcctgcct          4520

gggaacctat caacatgtgc acaggagacg ctgcaggaat          4560

ataatagaac tgtgactaat atcttaggcc cgttgagaga          4600

gaacttggat gctctcctat ctgacttcga taaacctgca          4640

tcgaggttcg tgggcgccat cattgggtcg gtggccttgg          4680

gggtagcaac agctgcacaa atcacagccg ccgtggctct          4720

caatcaagca caagagaatg cccggaatat atggcgtctc          4760

aaggaatcga taaagaaaac caatgcggct gtgttggaat          4800

tgaaggatgg acttgcaacg actgctatag ctttggacaa          4840

agtgcaaaag tttatcaatg atgatattat accacagatt          4880

aaggacattg actgccaggt agttgcaaat aaattaggcg          4920

tctacctctc cttatactta acagagctta caactgtatt          4960

tggttctcag atcactaatc ctgcattatc aacgctctct          5000
```

-continued

```
taccaggcgc tgtacagctt atgtggaggg gatatgggaa                    5040
agctaactga gctgatcggt gtcattgcaa aggatgtggg                    5080
atccctctac gaggttaacc tcataaccgg ccaaatcgtt                    5120
ggatatgacc ctgaactaca gataatcctc atacaagtat                    5160
cttacccaag tgtgtctgaa gtgacaggag tccgggctac                    5200
tgagttagtc actgtcagtg tcactacacc aaaaggagaa                    5240
gggcaggcaa ttgttccgag atatgtggca cagagtagag                    5280
tgctgacaga ggagttggat gtctggattt gtaggtttag                    5320
caaaacaagg gtgtattgta agtcgattct cacacggccc                    5360
ctaccaactt tgatcgccag ctgcctgtca gggaagtacg                    5400
acgattgtca gtgcacaaca gagataggag cgctatcttc                    5440
gagattcatc acagtcaatg gtggagtcct tgcaaactgc                    5480
agagcaaggg tgtgtaattg tgtctcaccc ccgcatataa                    5520
taccacaaaa cgacattggc tccgtaacag ttattgactc                    5560
aagtatatgc aaggaagttg tcttagagag tgtgcagctt                    5600
aggttagaag gaaagctgtc atcccaatac ttctccaacg                    5640
tgacaattga cctttcccaa atcacaacgt cagggtcgct                    5680
ggatataagc agtgaaattg gtagcattaa caacacagtt                    5720
aatcgggtcg acgagttaat caaggaatcc aacgagtggc                    5760
tgaacgctgt gaacccccgc cttgtgaaca atacgagcat                    5800
catagtcctc tgtgtccttg ccgccctgat tattgtctgg                    5840
ctaatagcgc tgacagtatg cttctgttac tccgcaagat                    5880
actcagctaa gtcaaaacag atgaggggcg ctatgacagg                    5920
gatcgataat ccatatgtaa tacagagtgc aactaagatg                    5960
tagagaggtt gaataagcct aaacatgata tgatttaaga                    6000
aaaaattgga aggtgggggc gacagcccat tcaatgaagg                    6040
gtaaatagcg agtttgttat tgtcgctttg atagcaaaac                    6080
aagctcagag tcagcaatgg atgcacggtc aagggagaat                    6120
ctcactgaac ttggccaagg gggacgacga acctggctca                    6160
tgctatttcg ggttctaact ctggccttga cattagcatg                    6200
cttagctatc aacatagcca ctatagccaa gctggatagc                    6240
attgacacag gtagactgca gacatggacc accgctgaat                    6280
cagatagggt aatcggctct ctcactgaca ctctaaaggt                    6320
gcccattaac caagtaaatg acatgtttag aatcgttgcc                    6360
ttggatcttc ctctccagat gaccacacat caaaaagaga                    6400
tcgcttcaca ggtgggcttt cttgctgaaa gtatcaatag                    6440
tgtcttgtca aagaacggat cagcagggtt ggtcctaatt                    6480
aacgacccag agtatgcggg cggtataggg gtgagcttat                    6520
ttcagggcga ctctgcatct agccttgact ttgaagaacc                    6560
```

-continued

```
gcacctaatt gaacacccga gttttatccc ggggcccacg       6600
acggcgaagg gttgtatcag gatcccgacc ttccatatgt       6640
ccgcatcaca ttggtgctat tctcacaaca taattgcatc       6680
aggatgccag gatgccggcc actccagtat gtacatatca       6720
ttgggagttt tgaaagccac acaggccggg tctccgagtt       6760
ttctgacaac agccagccag cttgtggatg ataagctcaa       6800
caggaaatca tgcagtataa tctccacaac atatgggtgt       6840
gacatcctgt gtagtctagt ggttgaaaat gaggatgctg       6880
actaccgatc tgatccccca actgacatga tcctaggccg       6920
actcttcttc aacggaacat attctgagag gaagctgaat       6960
acaggtacaa tcttccagct tttttccgca aattatccag       7000
cagtagggtc cggtttagta ttgggagatg aaattgcgtt       7040
ccctgtgtat gggggtgtga gacaaaatac atggttgttt       7080
aatcagctga aggaccatgg ttacttcgct cacaatgatg       7120
tgtataagtg taataaaagt gatacccatc agactgtcct       7160
taatgcatat cgaccaccta aaatatcagg aaggttgtgg       7200
tcgcaggtcg tgctgatctg tccactggga ttgttcatta       7240
atactgactg caggatcaaa gtgttcaata ctagcactgt       7280
catgatgggt gcagaagcaa gactgattca agtggggtcc       7320
gacatttacc tgtaccagag gtcatcatcg tggtgggtgg       7360
tcggactgac ctataaactt gatttccagg aattgtcatc       7400
aaagacggga aatgttataa ataaagtatc cccgattgct       7440
cacgcaaagt tccctcgtcc ttccttctct cgtgatgcct       7480
gtgcaaggcc aaacatatgt ccagcagtct gtgtgtccgg       7520
tgtatatcag gacatctggc caatcagtac cgcacaaaac       7560
ttgagccagg tggtttgggt agggcagtat ctagaagcat       7600
tctatgcccg taaggatcca tggatcggga ttgcgaccca       7640
atacaactgg aaaaagaatg ttaggctttt caacacaaac       7680
actgaagtcg ggtactcaac aaccacatgt ttcaggaata       7720
caaagagaga caaggcattt tgtgtcataa tatcagaata       7760
tgcagatgga gtctttgggt cataccgggt tgtaccgcag       7800
ctgattgaag tcgaaactac tagtaagaag agactcttca       7840
gttgatggcc agagaaataa tgtgaggcct gcatggggag       7880
aggtgccctg ccgtttatgc tctcgcagtt taataaaaaa       7920
ttagtattgg gggcgaatgc ccaatcacca tggaccaggt       7960
ccaagcagac acaattattc agcccgaagt gcacctagac       8000
tcacctattg tcagagcgaa acttgttcta ttttggaaat       8040
tgactggact cccgctgcca aaggatctaa gatttttgga       8080
gtcgctaccc acgccaccga cgagcaaatt ttcaggaatg       8120
agtccagaat taagtcaaaa atcataccct agtgtgccga       8160
```

-continued

```
atctaatcaa acactgcaag gcaaggcaag tggcactttc 8200
agggttgaca cctgtcgtac atccaacaac tctacagtgg 8240
ttgctatcca tcacatgtga acgagcagac caccttgcaa 8280
aagtacgcga gaaatcagtt aagcaagcaa tgtcagagaa 8320
gcaacacggg tttagacatc tcttttcggc agtaagtcat 8360
cagttagttg gaaacgccac actgttctgt gcacaagact 8400
ctagcaccgt gaatgtcgac tctccttgct catcaggttg 8440
tgagaggctg ataatagact ctattggagc cttacaaaca 8480
cgatggacaa gatgtaggtg ggcttggctt cacattaaac 8520
aggtaatgag ataccaggtg cttcagagtc gcctacacgc 8560
tcatgccaat tctgttagca catggtctga ggcgtggggg 8600
ttcattggga tcacaccaga tatagtcctt attgtagact 8640
ataagagcaa aatgtttact atcctgacct tcgaaatgat 8680
gctgatgtat tcagatgtca tagagggtcg tgataatgtg 8720
gtagctgtag gaagtatgtc accaaaccta cagcctgtgg 8760
tggagaggat tgaggtgctg tttgatgtag tggacacctt 8800
ggcgaggagg attcatgatc ctatttatga tctggttgct 8840
gccttagaaa gcatggcata cgctgccgtc caattgcacg 8880
atgctagtga gacacacgca ggggaattct tttcgttcaa 8920
tttgacagaa atagagtcca ctcttgcccc cttgctggat 8960
cctggccaag tcctatctgt aactaagact atcagtatgt 9000
gctacagttg cctaactcca gaccaggcag cagagatgtt 9040
gtgtatcatg cggttgtttg gccacccctt attgtcagca 9080
caacaggctg caaaaaaagt gagagaatct atgtgtgctc 9120
caaaattgtt agaacatgac gcaatcttac agacactgtc 9160
attctttaaa gggataataa tcaatggtta caggaaaagc 9200
cattccggag tgtggcccaa tattgagcca gaatcgatca 9240
tggatgatga ttttagtcaa ctgtattacg agtctgctga 9280
aatatcacac tcttttatgc tcaaaaaata ccgttatctc 9320
agtatgattg aattcaagaa gagtatagat tttgacctga 9360
acgatgacct cagcacattc ttaaaagata aagctatatg 9400
ccgccccaag agccagtggg ccaagatatt tcggaaatcg 9440
ctattccccc tcaaaatgac aattgatagc ggggcggaca 9480
caagaagcaa taggttactc atcgattttt tagagtcaca 9520
tgattttagt cctgaagaag agatgaagta tgtgaccaca 9560
atggcatact tagaagatga acaattttcc gcatcttact 9600
ccctcaagga aaaggagata aagactacag gccgaatatt 9640
tgcaaaaatg acaaggaaaa tgaggagctg tcaagtgata 9680
ctcgaatccc tattatctag ccatgtatgt aaattcttca 9720
```

-continued

```
aagagaatgg ggtgtctatg gaacagctat ccttgacaaa        9760
gagtctattg gcaatgtcac agctgtcccc cagaatctct        9800
gctgtgagaa acgaaccagc tagaaacagg aaggtgatct        9840
gcaccgacaa ccaagtgtcc gatcacattg taggagaagt        9880
aggcccacac cagcaggaca gaccggcccg gaagagtgta        9920
gtcgcaacct tccttacaac agatcttcaa aaatattgct        9960
tgaactggcg atatgggagt atcaagcttt tcgcccaagc       10000
cttaaaccag ctattcggaa tcgagcatgg gtttgaatgg       10040
atacacctga gactgatgaa tagcaccctg tttgtcgggg       10080
acccattctc gcctcctgaa agcaaagtgc tgagtgatct       10120
tgatgatgcg cccaattcag acatatttat cgtgtccgcc       10160
agagggggga ttgaagggtt atgccagaag ctgtggacca       10200
tgatttcaat aagcataatc cattgcgtgg ctgagaagat       10240
aggagcaagg gttgcggcga tggttcaggg agataatcag       10280
gtaattgcaa tcacgagaga gctgtataag ggagagactt       10320
acacgcagat tcagccggag ttagatcgat taggcaatgc       10360
attttttgct gaattcaaaa gacacaacta tgcaatggga       10400
cataatctga agcccaaaga gacaatccaa agtcaatcat       10440
tctttgtgta ttcgaaacgg attttctggg aagggagaat       10480
tcttagtcaa gcactgaaga atgctaccaa actatgcttc       10520
attgcagatc acctcgggga taatactgtc tcatcatgca       10560
gcaatctagc ctctacgata acccgcttgg ttgagaatgg       10600
gtatgaaaag gacacagcat tcattctgaa tctcatttct       10640
cccatgaccc agatccttat ggacgagcag tactctctgc       10680
agggagatta tagcagcgtg aagggactga taggaacaca       10720
taatcatagg aatttactaa gggcggcttt gatacctgga       10760
caggttggtg gttataactt cttgaacatc agcaggctat       10800
tcacaagaaa cattggagac ccggtgacgt gtgcaatagc       10840
agatattaaa tggttcatta agagtagact gattgcagag       10880
catgttttga aaaacatcct gctcagggac ccaggagatg       10920
gtggttggag taccctctgc gcagatccat atgccctcaa       10960
tatcccttat actcagttgc ctactactta ccttaagaaa       11000
cacacccaga gagcgctatt agcagactca aataacccat       11040
tattggcagg agttcaactt gactcacagt acattgaaga       11080
agaggaattt gctcagtttc tccttgatcg ggaggcggtt       11120
atgccacggg tcgcacatac aataatggag gcaagcatcc       11160
tagggaagag aaagaatata caaggcctaa tagacactac       11200
gcctaccatc atcaaaacag ctctgatgcg ccagcctatt       11240
tctaggagga agtgtgagaa gattgtaaat tactcaatca       11280
attacttagt tgaatgccat gattccatca tctcagctcg       11320
```

-continued gcagtttgaa ccgcgaaaag aggtcatctg ggattcagca 11360
atgatctcag tcgaaacatg cagtgtcaca attgcggagt 11400
tcctgcgcgc caccagctgg tccaacatcc tgaacggtag 11440
gactatttcg ggtgtaacat ctccagacac tatagagctg 11480
ctcaaggggt cattaattgg agagaatgcc cattgtattc 11520
tttgtgagca gggagacgag acattcacgt ggatgcactt 11560
agccgggccc atctatatac cagacccggg ggtgaccgca 11600
tccaagatga gagtgccgta tcttgggtca aagacagagg 11640
aaaggcgtac ggcatccatg gccaccatta agggcatgtc 11680
tcaccaccta aaggccgctt tgcgaggagc ctctgtgatg 11720
gtgtgggcct ttggtgatac tgaagaaagt tgggaacatg 11760
cctgccttgt ggccaataca aggtgcaaga ttaatcttcc 11800
gcagctacgc ctgctgaccc cgacaccaag cagctctaac 11840
atccaacatc gactaaatga tggtatcagc gtgcaaaaat 11880
ttacacctgc tagcttatcc cgagtggcgt catttgttca 11920
catttgcaac gatttccaaa agctagagag agatggatct 11960
tccgtagact ctaacttgat atatcagcaa atcatgctga 12000
ctggtctaag tattatggag acactccatc caatgcacta 12040
cgcaagggat atacaacaac caggccatcc atggcacaca 12080
gggacatctt gttgtcctcg agaaatcgag accagcattg 12120
tcaacccgcc taagtatgaa ttcccaacaa tcaccctcac 12160
cactaacaac cagttcttgt ttgacagcaa tccaatccat 12200
gatgaggcca tcaccagatt aaccgttagt gactttaaat 12240
tccaggaact aaatattgat gcaattaggg gttatgctgc 12280
tatcaacctg ctcagccgat gtgtggctaa gctgatcagt 12320
gagtgcatac tggaggatgg tattgggtcc tcgatcaaaa 12360
acgaagcaat ggtgtcattt gataattctg tcaattggat 12400
atcagaaatc ttacacagtg acatcagact ttcatttatg 12440
cacattggac aagagctttt atgtgatctt gcttaccaaa 12480
tgtacttttt taagaatcac agggtaccat gctattatta 12520
cttatctgaa ggcttcactg aaagaattcc agttatccaa 12560
cttgcaaaca tggccctgac aatctcgcat cctgaagtgt 12600
ggcgcagggt gacattaatc ggattcaatc aaggttatcg 12640
tagcccgtat ctagccaccg tggattttat agcagcttgc 12680
agagatgtca ttgtgcaggg tgcacagcaa tacctctccg 12720
agttactgtc ggaatcagag tgccaataca cgttctttaa 12760
tgtgcaagat ggtgacttaa cacccaaaat ggagcaattc 12800
ttggccagaa ggatgtgcct gttcgtcctc ctaacaggga 12840
cgatcagccc cctccctatt gtacgatctc ttaacgcgat 12880

-continued

```
tgagaaatgt gctgtcttca ctcaattctt atattacttg     12920
cccactgtcg atctggcagt agcaagtagg gcaagaactc     12960
tctacacctt atctatcgct cccaagattg acgcattggt     13000
atcaaatctc tacttcacga cgcggagggt gctctctaac     13040
ataagaggtg acaaacatgc gaaagcccaa atctcttatc     13080
tctacgagga gaagatcagt gccgagccgc accagggtga     13120
gaactttgac cagtttatga aagatccaat cataagagga     13160
gggttattct tcactattat gttgaagatg gagaaaatgt     13200
cacttaatca atttgctgtc cacaggagga caatcctgca     13240
gaatatctcc aagagaacat ggcagtgcct atggcgggca     13280
tcacctctgg ctcattgtct caagtcagtg gggcaggtta     13320
gtaccagctg gtataaatat gctgtattac aggcatcttt     13360
aatcagaggc caacccttac ggtcaacaag cgtctacatg     13400
gtgaagggca gcggtagtgt gatgacacta tttgaataca     13440
tggacccctc agccactatc ttctacaact ctctttttag     13480
caatagtatg aaccctccac aacggaattt cggactgatg     13520
cccacacagt ttcaggactc agtcgtgtat aagaatctaa     13560
gtgcaggggt tgagagcaag tacgggttta agcaaacctt     13600
tacacccctc tggagagatg tagatcaaga gacaaacgtg     13640
acagagactg cattcctcaa ttacgtgatg gaagtgatac     13680
cgattcattc atcaaagcgc ctggtgtgtg aagtggagtt     13720
cgacaggggc atgcccgacg aggtggtaat aacagggtat     13760
atgaatgttc tcatggcatc cgcgtacagc ctgcataaaa     13800
atgggcgtct aataatcaag atctttcgtc actccgaggc     13840
tctattccaa ttgggactct cggtgatagt catgatattg     13880
catgggcttg atatacaccg gaactcgtac atgtcaacta     13920
acaaagagga gtacatcatc atagctgcgg cgccggaggc     13960
attaaactat tcctctgtac cagcaatatt gcagagggtg     14000
aagtctgtta ttgaccagca gcttacatta atctctccta     14040
tagatctaga aagattgcgc catgagactg agtctctccg     14080
tgagaaggag aataatctag taatatctct gacgagaggg     14120
aagtatcaac tccggccgac acagactgat atgcttctat     14160
catacctagg tgggagattc atcaccctat tcggacagtc     14200
tgctagggat ttgatggcca ctgatgttgc tgaccttgat     14240
gctaggaaga ttgcattagt tgatctactg atggtggaat     14280
ccaacattat tttaagtgag agcacagact tggaccttgc     14320
actgttgctg agcccgttta acttagacaa agggcggaag     14360
atagttaccc tagcaaaggc tactacccgc caattgctgc     14400
ccgtgtatat cgcatcagag ataatgtgca atcggcaggc     14440
attcacacac ctgacatcaa ttatacagcg tggtgtcata     14480
```

```
agaatagaaa acatgcttgc tacaacggaa tttgtccgac                         14520

agtcagttcg cccccagttc ataaaggagg tgataactat                         14560

agcccaagtc aaccaccttt tttcagatct atccaaactc                         14600

gtgctttctc gatctgaagt caagcaagca cttaaatttg                         14640

tcggttgctg tatgaagttc agaaatgcaa gcaattaaac                         14680

aggattgtta ttgtcaaatc accggttact atagtcaaat                         14720

taatatgtaa agttccctct ttcaagagtg attaagaaaa                         14760

aacgcgtcaa aggtggcggt ttcactgatt tgctcttgga                         14800

agttgggcat cctccagcca atatatcggt gccgaaatcg                         14840

aaagtctgac agctgatttg gaatataagc actgcataat                         14880

cactgagtta cgttgctttg ctattccatg tctggt                             14916


<210> SEQ ID NO 5
<211> LENGTH: 1374
<212> TYPE: DNA
<213> ORGANISM: Avian Paramixyvirus Type 2
<220> FEATURE:
<223> OTHER INFORMATION: APMV-2/Chicken/California/Yucaipa/56 NP protein

<400> SEQUENCE: 5

atgtcttctg tgttttcaga ataccaggct cttcaggacc                            40

aactggtcaa gcctgccact cgaagggctg atgtggcatc                            80

gactggattg ttgagagcgg agataccagt ttgtgtaacc                           120

ttgtctcagg acccaactga tagatggaac ctcgcatgtc                           160

tcaatctgcg atggctgata agtgagtcct ctactactcc                           200

catgagacaa ggggcgatcc tgtcactgct gagcttgcac                           240

tctgacaaca tgcgagctca cgcaaccctt gcagcgagat                           280

ccgctgatgc tgccatcact gtgcttgagg ttgacgccat                           320

agacatggcg gatggcacaa tcacttttaa tgccagaagt                           360

ggagtatccg agaggcgcag cacacagctc atggcaatcg                           400

caaaagatct gccccgctct tgttccaatg actcaccatt                           440

caaagatgac actatcgagg atcgcgaccc ccttgacctg                           480

tccgagacta tcgatagact gcaggggatt gctgcccaaa                           520

tctggatagc ggccatcaag agcatgactg ccccggatac                           560

tgctgcggag tcagaaggca agaggcttgc aaagtaccaa                           600

caacaaggcc gcttggtgcg acaggtgtta gtgcatgatg                           640

cggtgcgtgc ggaattccta cgtgtcatca gaggcagcct                           680

ggtcttacgg caattcatgg tatcagaatg taagagggca                           720

gcatccatgg gtagcgagac atctaggtac tatgccatgg                           760

tgggtgacat cagcctctac atcaagaatg caggacttac                           800

cgccttcttc ttgacactca gatttggtat tgggacacac                           840

taccccactc ttgccatgag tgtgttctct ggagaactga                           880

agaagatgtc gtccttgatc aggctgtata agtcaaaagg                           920
```

-continued

```
ggaaaatgct gcatacatgg cattcctgga ggatgcggac                   960

atgggaaact ttgcgcctgc taactttagt actctctact                  1000

cctatgcaat gggggtaggt acagtgctgg aagcatcagt                  1040

tgcgaaatac cagttcgctc gagagttcac cagtgagaca                  1080

tacttcaggc ttggggttga gaccgcacag aaccaacagt                  1120

gcgctctaga tgaaaagacc gccaaggaga tggggcttac                  1160

tgatgaagcc agaaagcagg tgcaagcatt ggctagcaac                  1200

atcgagcagg ggcaacattc aatgcccatg caacaacagc                  1240

ccacattcat gagtcagccc taccaggatg acgatcgtga                  1280

ccagccaagc accagcagac cagagccaag accatcgcaa                  1320

ttgacaagcc aatcagcagc acaggacaat gatgcggcct                  1360

cattagattg gtga                                              1374
```

<210> SEQ ID NO 6
<211> LENGTH: 1200
<212> TYPE: DNA
<213> ORGANISM: Avian Paramixyvirus Type 2
<220> FEATURE:
<223> OTHER INFORMATION: APMV-2/Chicken/California/Yucaipa/56 P protein

<400> SEQUENCE: 6

```
atggagttca ccgatgatgc cgaaattgct gagctgttgg                    40

acctcgggac ctcagtgatc caagagctgc agcgagccga                    80

agtcaagggc ccgcaaacaa ccggaaagcc caaagttccc                   120

ccggggaaca ctaagagcct ggctactctc tgggagcatg                   160

agactagcac ccaagggagt gcattgggca cacccgagaa                   200

caacacccag gcacccgatg acaacaacgc aggtgcagat                   240

acgccagcga ctaccgacgt ccatcgcact ctggatacca                   280

tagacaccga cacaccaccg gaagggagca agcccagctc                   320

cactaactcc caacccggtg atgaccttga caaggctctt                   360

tcgaagctag aggcgcgcgc caagctcgga ccagataggg                   400

ccagacaggt taaaaagggg aaggagatcg ggtcgagcac                   440

agggacgagg gaggcagcca gtcaccacat ggaagggagc                   480

cgacagtcgg agccaggagc gggcagccga gcacagccac                   520

aaggccatgg cgaccgggac acaggaggga gtactcattc                   560

atctctcgag atgggagact ggaagtcaca agctggtgca                   600

acccagtctg ctctcccatt agaagcgagc ccaggagaga                   640

aaagtgcaca tgtggaactt gcccagaatc ctgcatttta                   680

tgcaggcaac ccaactgatg caattatggg gttgacaaag                   720

aaagtcaatg atctagagac aaaattggct gaggtattgc                   760

gtctgttagg aatactcccc ggaataaaga atgagattag                   800

tcagctgaaa gcaaccgtgg ctctgatgtc aaatcagatt                   840

gcctccattc agattcttga tcctgggaat gccggagtca                   880

aatcccttaa tgagatgaaa gccctgtcaa aagcagccag                   920
```

```
catagttgtg gcaggtccag gagtccttcc tcctgaggtc                    960

acagaaggag gactgatcgc gaaagatgag ctagcaaggc                   1000

ccatccccat ccaaccgcaa cgagactcca aacccaaaga                   1040

cgacccgcac acatcaccaa atgatgtcct tgctgtacgc                   1080

gctatgatcg acacccttgt ggatgatgag aagaagagaa                   1120

agagattaaa ccaggccctt gacaaggcaa agaccaagga                   1160

tgacgtctta agggtcaagc ggcagatata caatgcctag                   1200


<210> SEQ ID NO 7
<211> LENGTH: 699
<212> TYPE: DNA
<213> ORGANISM: Avian Paramixyvirus Type 2
<220> FEATURE:
<223> OTHER INFORMATION: APMV-2/Chicken/California/Yucaipa/56 V protein

<400> SEQUENCE: 7

atggagttca ccgatgatgc cgaaattgct gagctgttgg                     40

acctcgggac ctcagtgatc caagagctgc agcgagccga                     80

agtcaagggc ccgcaaacaa ccggaaagcc caaagttccc                    120

ccggggaaca ctaagagcct ggctactctc tgggagcatg                    160

agactagcac ccaagggagt gcattgggca cacccgagaa                    200

caacacccag gcacccgatg acaacaacgc aggtgcagat                    240

acgccagcga ctaccgacgt ccatcgcact ctggatacca                    280

tagacaccga cacaccaccg gaagggagca agcccagctc                    320

cactaactcc caacccggtg atgaccttga caaggctctt                    360

tcgaagctag aggcgcgcgc caagctcgga ccagataggg                    400

ccagacaggt taaaaagggg gaaggagatc gggtcgagca                    440

cagggacgag ggaggcagcc agtcaccaca tggaagggag                    480

ccgacagtcg gagccaggag cgggcagccg agcacagcca                    520

caaggccatg gcgaccggga cacaggaggg agtactcatt                    560

catctctcga gatgggagac tggaagtcac aagctggtgc                    600

aacccagtct gctctcccat tagaagcgag cccaggagag                    640

aaaagtgcac atgtggaact tgcccagaat cctgcatttt                    680

atgcaggcaa cccaactga                                           699


<210> SEQ ID NO 8
<211> LENGTH: 624
<212> TYPE: DNA
<213> ORGANISM: Avian Paramixyvirus Type 2
<220> FEATURE:
<223> OTHER INFORMATION: APMV-2/Chicken/California/Yucaipa/56 W protein

<400> SEQUENCE: 8

atggagttca ccgatgatgc cgaaattgct gagctgttgg                     40

acctcgggac ctcagtgatc caagagctgc agcgagccga                     80

agtcaagggc ccgcaaacaa ccggaaagcc caaagttccc                    120

ccggggaaca ctaagagcct ggctactctc tgggagcatg                    160
```

-continued

```
agactagcac ccaagggagt gcattgggca cacccgagaa                    200

caacacccag gcacccgatg acaacaacgc aggtgcagat                    240

acgccagcga ctaccgacgt ccatcgcact ctggatacca                    280

tagacaccga cacaccaccg gaagggagca agcccagctc                    320

cactaactcc caacccggtg atgaccttga caaggctctt                    360

tcgaagctag aggcgcgcgc caagctcgga ccagataggg                    400

ccagacaggt taaaaagggg ggaaggagat cgggtcgagc                    440

acagggacga gggaggcagc cagtcaccac atggaaggga                    480

gccgacagtc ggagccagga gcgggcagcc gagcacagcc                    520

acaaggccat ggcgaccggg acacaggagg gagtactcat                    560

tcatctctcg agatgggaga ctggaagtca caagctggtg                    600

caacccagtc tgctctccca ttag                                     624
```

<210> SEQ ID NO 9
<211> LENGTH: 1110
<212> TYPE: DNA
<213> ORGANISM: Avian Paramixyvirus Type 2
<220> FEATURE:
<223> OTHER INFORMATION: APMV-2/Chicken/California/Yucaipa/56 M protein

<400> SEQUENCE: 9

```
atggctcaaa caaccgtcag gctgtatatc gatgaagcta                     40

gtcccgacat tgaactgttg tcttacccac tgataatgaa                     80

agacacagga catgggacca aagagttgca gcagcaaatc                    120

agagttgcag agatcggtgc attgcaggga gggaagaatg                    160

aatcagtttt catcaatgca tatggctttg ttcagcaatg                    200

caaagttaaa ccgggggcaa cccaattctt ccaggtagat                    240

gcagctacaa agccagaagt ggtcactgca gggatgatta                    280

taatcggtgc agtcaagggg gtggcaggca tcactaagct                    320

ggcagaagag gtgttcgagc tggacatctc catcaagaag                    360

tccgcatcat tccatgagaa ggttgcggtg tcctttaata                    400

ctgtgccact atcactcatg aattcgaccg catgcagaaa                    440

tctgggttat gtcacaaacg ctgaggaggc gatcaaatgc                    480

ccgagcaaaa tacaagcggg tgtgacgtac aaatttaaga                    520

taatgtttgt ctccttgaca cgactgcata acgggaaatt                    560

gtaccgtgtc cccaaggcag tgtatgctgt agaggcatca                    600

gctctatata aagtgcaact ggaagtcggg ttcaagcttg                    640

acgtggccaa ggatcaccca cacgttaaga tgttgaagaa                    680

agtggaacgg aatggtgaga ctctgtatct tggttatgca                    720

tggttccacc tgtgcaactt caagaagaca aatgccaagg                    760

gtgagtcccg gacaatctcc aacctagaag ggaaagtcag                    800

agctatgggg atcaaggttt ccttgtacga cttatggggg                    840

cctactttgg tggtgcaaat cacaggtaag accagcaagt                    880

atgcacaagg tttcttttca accacaggta cctgctgcct                    920
```

```
cccagtgtcg aaggctgccc ctgagctggc caaacttatg 960

tggtcctgca atgcaacaat cgttgaagct gcagtgatta 1000

tccaagggag tgataggagg gcagtcgtga cctcagagga 1040

cttggaagta tacggggcag ttgcaaaaga gaagcaggct 1080

gcaaaaggat ttcacccgtt ccgcaagtga 1110


<210> SEQ ID NO 10
<211> LENGTH: 1611
<212> TYPE: DNA
<213> ORGANISM: Avian Paramixyvirus Type 2
<220> FEATURE:
<223> OTHER INFORMATION: APMV-2/Chicken/California/Yucaipa/56 F protein

<400> SEQUENCE: 10

atgaatcaag cactcgtgat tttgttggta tctttccagc 40

tcggcgttgc cttagataac tcagtgttgg ctccaatagg 80

agtagctagc gcacaggagt ggcaactggc ggcatataca 120

acgaccctca cagggaccat cgcagtgaga tttatcccgg 160

tcctgcctgg gaacctatca acatgtgcac aggagacgct 200

gcaggaatat aatagaactg tgactaatat cttaggcccg 240

ttgagagaga acttggatgc tctcctatct gacttcgata 280

aacctgcatc gaggttcgtg ggcgccatca ttgggtcggt 320

ggccttgggg gtagcaacag ctgcacaaat cacagccgcc 360

gtggctctca atcaagcaca agagaatgcc cggaatatat 400

ggcgtctcaa ggaatcgata aagaaaacca atgcggctgt 440

gttggaattg aaggatggac ttgcaacgac tgctatagct 480

ttggacaaag tgcaaaagtt tatcaatgat gatattatac 520

cacagattaa ggacattgac tgccaggtag ttgcaaataa 560

attaggcgtc tacctctcct tatacttaac agagcttaca 600

actgtatttg gttctcagat cactaatcct gcattatcaa 640

cgctctctta ccaggcgctg tacagcttat gtggaggga 680

tatgggaaag ctaactgagc tgatcggtgt caatgcaaag 720

gatgtgggat ccctctacga ggctaacctc ataaccggcc 760

aaatcgttgg atatgaccct gaactacaga taatcctcat 800

acaagtatct tacccaagtg tgtctgaagt gacaggagtc 840

cgggctactg agttagtcac tgtcagtgtc actacaccaa 880

aaggagaagg gcaggcaatt gttccgagat atgtggcaca 920

gagtagagtg ctgacagagg agttggatgt ctcgacttgt 960

aggtttagca aaacaactct ttattgtagg tcgattctca 1000

cacggcccct accaactttg atcgccagct gcctgtcagg 1040

gaagtacgac gattgtcagt acacaacaga gataggagcg 1080

ctatcttcga gattcatcac agtcaatggt ggagtccttg 1120

caaactgcag agcaattgtg tgtaagtgtg tctcaccccc 1160
```

```
gcatataata ccacaaaacg acattggctc cgtaacagtt        1200

attgactcaa gtatatgcaa ggaagttgtc ttagagagtg        1240

tgcagcttag gttagaagga aagctgtcat cccaatactt        1280

ctccaacgtg acaattgacc tttcccaaat cacaacgtca        1320

gggtcgctgg atataagcag tgaaattggt agcattaaca        1360

acacagttaa tcgggtcgac gagttaatca aggaatccaa        1400

cgagtggctg aacgctgtga acccccgcct tgtgaacaat        1440

acgagcatca tagtcctctg tgtccttgcc gccctgatta        1480

ttgtctggct aatagcgctg acagtatgct tctgttactc        1520

cgcaagatac tcagctaagt caaaacagat gaggggcgct        1560

atgacaggga tcgataatcc atatgtaata cagagtgcaa        1600

ctaagatgta g                                       1611


<210> SEQ ID NO 11
<211> LENGTH: 1743
<212> TYPE: DNA
<213> ORGANISM: Avian Paramixyvirus Type 2
<220> FEATURE:
<223> OTHER INFORMATION: APMV-2/Chicken/California/Yucaipa/56 HN protein

<400> SEQUENCE: 11

atggatttcc catctaggga gaacctggca gcaggtgaca          40

tatcggggcg gaagacttgg agattactgt tccggatcct          80

cacattgagc ataggtgtgg tctgtcttgc catcaatatt         120

gccacaattg caaaattgga tcacctggat aacatggctt         160

cgaacacatg gacaacaact gaggctgacc gtgtgatatc         200

tagcatcacg actccgctca aagtccctgt caaccagatt         240

aatgacatgt ttcggattgt agcgcttgac ctacctctgc         280

agatgacatc attacagaaa gaaataacat cccaagtcgg         320

gttcttggct gaaagtatca acaatgtttt atccaagaat         360

ggatctgcag gcctggttct tgttaatgac cctgaatatg         400

caggggggat cgctgtcagc ttgtaccaag gagatgcatc         440

tgcaggccta aatttccagc ccatttcttt aatagaacat         480

ccaagttttg tccctggtcc tactactgct aagggctgta         520

taaggatccc gaccttccat atgggccctt cacattggtg         560

ttactcacat aacatcattg catcaggttg ccaggatgcg         600

agccactcca gtatgtatat ctctctgggg gtgctgaaag         640

catcgcagac cgggtcgcct atcttcttga caacggccag         680

ccatctcgtg gatgacaaca tcaaccggaa gtcatgcagc         720

atcgtagcct caaaatacgg ttgtgatatc ctatgcagta         760

ttgtgattga aacagagaat gaggattata ggtctgatcc         800

ggctactagc atgattatag gtaggctgtt cttcaacggg         840

tcatacacag agagcaagat taacacaggg tccatcttca         880

gtctattctc tgctaactac cctgcggtgg ggtcgggtat         920
```

tgtagtcggg gatgaagccg cattcccaat atatggtggg 960
gtcaagcaga acacatggtt gttcaaccag ctcaaggatt 1000
ttggttactt cacccataat gatgtgtaca agtgcaatcg 1040
gactgatata cagcaaacta tcctggatgc atacaggcca 1080
cctaaaatct caggaaggtt atgggtacaa ggcatcctat 1120
tgtgcccagt ttcactgaga cctgatcctg gctgtcgctt 1160
aaaggtgttc aataccagca atgtgatgat gggggcagaa 1200
gcgaggttga tccaagtagg ctcaaccgtg tatctatacc 1240
aacgctcatc ctcatggtgg gtggtaggac tgacttacaa 1280
attagatgtg tcagaaataa cttcacagac aggtaacaca 1320
ctcaaccatg tagaccccat tgcccataca aagttcccaa 1360
gaccatcttt caggcgagat gcgtgtgcga ggccaaacat 1400
atgccctgct gtctgtgtct ccggagttta tcaggacatt 1440
tggccgatca gtacagccac caataacagc aacattgtgt 1480
gggttggaca gtacttagaa gcattctatt ccaggaaaga 1520
cccaagaata gggatagcaa cccagtatga gtggaaagtc 1560
accaaccagc tgttcaattc gaatactgag ggagggtact 1600
caaccacaac atgcttccgg aacaccaaac gggacaaggc 1640
atattgtgta gtgatatcag agtacgctga tggggtgttc 1680
ggatcataca ggatcgttcc tcagcttata gagattagaa 1720
caaccaccgg taaatctgag tga 1743

<210> SEQ ID NO 12
<211> LENGTH: 6729
<212> TYPE: DNA
<213> ORGANISM: Avian Paramixyvirus Type 2
<220> FEATURE:
<223> OTHER INFORMATION: APMV-2/Chicken/California/Yucaipa/56 L protein

<400> SEQUENCE: 12
atggatcaaa ctcaagctga cactataata caacctgaag 40
tccatctgaa ttcaccactt gttcgcgcaa aattggttct 80
tctatggaaa ttgactgggt tacctttgcc gtctgatttg 120
agatcatttg tactaactac acatgcagct gatgaccaaa 160
tcgcaaaaaa tgagactagg atcaaggcca aaattaattc 200
cctaatcgat aacttaatca aacactgcaa ggcaaggcaa 240
gtggcacttt cagggttgac acctgtcgta catccaacaa 280
ctctacagtg gttgctatcc atcacatgtg aacgagcaga 320
ccaccttgca aaagtacgcg agaaatcagt taagcaagca 360
atgtcagaga agcaacacgg gtttagacat ctcttttcgg 400
cagtaagtca tcagttagtt ggaaacgcca cactgttctg 440
tgcacaagac tctagcaccg tgaatgtcga ctctccttgc 480
tcatcaggtt gtgagaggct gataatagac tctattggag 520

-continued

```
ccttacaaac acgatggaca agatgtaggt gggcttggct                    560
tcacattaaa caggtaatga gataccaggt gcttcagagt                    600
cgcctacacg ctcatgccaa ttctgttagc acatggtctg                    640
aggcgtgggg gttcattggg atcacaccag atatagtcct                    680
tattgtagac tataagagca aaatgtttac tatcctgacc                    720
ttcgaaatga tgctgatgta ttcagatgtc atagagggtc                    760
gtgataatgt ggtagctgta ggaagtatgt caccaaacct                    800
acagcctgtg gtggagagga ttgaggtgct gtttgatgta                    840
gtggacacct tggcgaggag gattcatgat cctatttatg                    880
atctggttgc tgccttagaa agcatggcat acgctgccgt                    920
ccaattgcac gatgctagtg agacacacgc aggggaattc                    960
ttttcgttca atttgacaga aatagagtcc actcttgccc                   1000
ccttgctgga tcctggccaa gtcctatcgg tgatgaggac                   1040
tatcagttat tgttacagtg ggctatcgcc tgaccaagct                   1080
gcagagttgc tctgtgtgat gcgcttattt ggacaccctc                   1120
tgctctccgc acaacaagca gccaaaaaag tccgggagtc                   1160
tatgtgtgcc cctaaactgt tagagcatga tgcaatactg                   1200
caaactctat ctttcttcaa gggaatcata atcaatggct                   1240
acaggaaaag tcattctgga gtatggcctg caattgaccc                   1280
agattctata gtggacgatg accttagaca gctgtattac                   1320
gagtcggcag aaatttcaca tgctttcatg cttaagaaat                   1360
atcggtacct tagtatgatt gagttccgca agagcataga                   1400
gtttgactta aatgatgacc tgagcacatt ccttaaagac                   1440
aaagcaatct gcaggccaaa agatcaatgg gcacgcatct                   1480
tccggaaatc attgttccct tgcaaaacga accttggcac                   1520
tagtatagat gttaaaagta atcgactgtt gatagatttt                   1560
ttggagtcac atgacttcaa tcctgaggaa gaaatgaagt                   1600
atgtgactac gctagcatac ctggcagata atcaattctc                   1640
agcatcatat tcactgaagg agaaagagat caagactact                   1680
ggccggatct tcgccaaaat gaccaggaaa atgaggagct                   1720
gtcaagtaat attggaatca ctattgtcca gtcacgtctg                   1760
caaattcttt aaggagaacg gtgtgtcaat ggaacaactg                   1800
tctttgacaa agagcttgct tgcaatgtca cagttagcac                   1840
ccaggatatc ttcagttcgc caggcgacag cacgtagaca                   1880
ggacccagga ctcagccact ctaatggttg taatcacatt                   1920
gtaggagact taggcccaca ccagcaggac agaccggccc                   1960
ggaagagtgt agtcgcaacc ttccttacaa cagatcttca                   2000
aaaatattgc ttgaattggc gatatgggag tatcaagctt                   2040
ttcgcccaag ccttaaacca gctattcgga atcgagcatg                   2080
ggtttgaatg gatacacctg agactgatga atagcaccct                   2120
```

-continued

```
gtttgtcggg gacccattct cgcctcctga aagcaaagtg                    2160

ctgagtgatc ttgatgatgc gcccaattca gacatattta                    2200

tcgtgtccgc cagagggggg attgaagggt tatgccagaa                    2240

gctgtggacc atgatttcaa taagcataat ccattgcgtg                    2280

gctgagaaga taggagcaag ggttgcggcg atggttcagg                    2320

gagataatca ggtaattgca atcacgagag agctgtataa                    2360

gggagagact tacacgcaga ttcagccgga gttagatcga                    2400

ttaggcaatg catttttgc tgaattcaaa agacacaact                     2440

atgcaatggg acataatctg aagcccaaag agacaatcca                    2480

aagtcaatca ttctttgtgt attcgaaacg gattttctgg                    2520

gaagggagaa ttcttagtca agcactgaag aatgctacca                    2560

aactatgctt cattgcagat cacctcgggg ataatactgt                    2600

ctcatcatgc agcaatctag cctctacgat aacccgcttg                    2640

gttgagaatg ggtatgaaaa ggacacagca ttcattctga                    2680

atatcatctc agcaatgact cagttgctga ttgatgagca                    2720

atattcccta caaggagact actcagctgt gagaaaactg                    2760

attgggtcat caaattaccg taatctctta gtggcgtcgc                    2800

tcatgcctgg tcaggttggc ggctataatt tcttgaatat                    2840

cagtcgccta ttcacacgca atattggtga tccagtaaca                    2880

tgcgccatag cagatctgaa gtggttcatt aggagcgggt                    2920

taatcccaga gttcatcctg aagaatatat tactacgaga                    2960

tcccggagac gatatgtgga gtactctatg tgctgaccct                    3000

tacgcattaa atatccccta cactcagcta cccacaacat                    3040

acctgaagaa gcatactcag agggcattac tatccgattc                    3080

taataatccg cttcttgcag gggtgcaatt ggacaatcaa                    3120

tacattgaag aggaggagtt tgcacgattc cttttggatc                    3160

gggaatccgt gatgcctcga gtggcacaca caatcatgga                    3200

gtcaagtata ctagggaaga gaaagaacat ccagggttta                    3240

atcgacacta cccctacaat cattaagact gcactcatga                    3280

ggcagcccat atctcgtaga aagtgtgata aaatagttaa                    3320

ttactcgatt aactacctga ctgagtgcca cgattcatta                    3360

ttgtcctgta ggacattcga gccaaggaag gaaataatat                    3400

gggagtcagc tatgatctca gtagaaactt gcagtgtcac                    3440

aattgcggag ttcctgcgcg ccaccagctg gtccaacatc                    3480

ctgaacggta ggactatttc gggtgtaaca tctccagaca                    3520

ctatagagct gctcaagggg tcattaattg gagagaatgc                    3560

ccattgtatt ctttgtgagc agggagacga gacattcacg                    3600

tggatgcact tagccgggcc catctatata ccagacccgg                    3640

gggtgaccgc atccaagatg agagtgccgt atcttgggtc                    3680
```

-continued

```
aaagacagag gaaaggcgta cggcatccat ggccaccatt      3720
aagggcatgt ctcaccacct aaaggccgct ttgcgaggag      3760
cctctgtgat ggtgtgggcc tttggtgata ctgaagaaag      3800
ttgggaacat gcctgccttg tggccaatac aaggtgcaag      3840
attaatcttc cgcagctacg cctgctgacc ccgacaccaa      3880
gcagctctaa catccaacat cgactaaatg atggtatcag      3920
cgtgcaaaaa tttacacctg ctagcttatc ccgagtggcg      3960
tcatttgttc acatttgcaa cgatttccaa aagctagaga      4000
gagatggatc ttccgtagac tctaacttga tatatcagca      4040
aatcatgctg actggtctaa gtattatgga gacacttcat      4080
cctatgcacg tctcatgggt atacaacaat cagacaattc      4120
acttacatac cggaacatcg tgttgtccta gggaaataga      4160
gacaagcatt gttaatcccg ctaggggaga attcccaaca      4200
ataactctca caactaacaa tcagtttctg tttgattgta      4240
atcccataca tgatgaggca cttacaaaac tgtcagtaag      4280
tgagttcaag ttccaggagc ttaatataga ctcaatgcag      4320
ggttacagtg ctgtgaacct gctgagcaga tgtgtggcta      4360
agctgatagg ggaatgcatt ctggaagacg gtatcggatc      4400
gtcaatcaag aatgaagcaa tgatatcatt tgataactct      4440
atcaactgga tttctgaagc actcaatagt gacctgcgtt      4480
tggtattcct ccagctgggg caagaactac tttgtgacct      4520
ggcgtaccaa atgtactatc tgagggtcat cggctatcat      4560
tccatcgtgg catatctgca gaatactcta gaaagaattc      4600
ctgttatcca actcgcaaac atggcactca ccatatccca      4640
cccagaagta tggaggagag tgacagtgag cggattcaac      4680
caaggttacc ggagtcccta tctggccact gtcgacttta      4720
tcgccgcatg tcgtgatatc attgtgcaag gtgcccagca      4760
ttatatggct gatttgttgt caggagtaga gtgccaatat      4800
acattcttta atgttcaaga cggcgatctg acaccgaaga      4840
tggaacaatt tttagcccgg cgcatgtgct tgtttgtatt      4880
gttaactggg acgatccgac cactcccaat catacgatcc      4920
cttaatgcga ttgagaaatg tgcaattctc actcagttct      4960
tgtattacct accgtcagtc gacatggcag tagcagacaa      5000
ggctcgtgtg ttatatcaac tgtcaataaa tccgaaaata      5040
gatgctttag tctccaacct ttatttcacc acaaggaggt      5080
tgctttcaaa tatcagggga gattcttctt cacgagcgca      5120
aattgcattc ctctacgagg aggaagtaat cgttgatgtg      5160
cctgcatcta atcaatttga tcagtaccat cgtgacccca      5200
tcctaagagg aggtctattt ttctctctct ccttaaaaat      5240
ggaaaggatg tctctgaacc gatttgcagt acagaccctg      5280
```

ccaacccagg ggtctaactc gcagggttca cgacagacct 5320
tgtggcgtgc ctcaccgtta gcacactgcc ttaaatcagt 5360
agggcaggta agtaccagct ggtacaagta tgctgtagtg 5400
ggggcgtctg tagagaaagt ccaaccaaca agatcaacaa 5440
gcctctacat cggggagggc agtgggagtg tcatgacatt 5480
attagagtat ctggaccctg ctacaattat cttctacaac 5520
tcgctattca gcaatagcat gaaccctcca caaaggaatt 5560
tcggactgat gcccacacag tttcaggact cagtcgtgta 5600
taaaaacata tcagcaggag ttgactgcaa gtacgggttt 5640
aagcaagtct ttcaaccatt atggcgtgat gtagatcaag 5680
aaacaaatgt ggtagagacg gcgttcctaa actatgtgat 5720
ggaagtagtg ccagtccact cttcgaagcg tgtcgtatgt 5760
gaagttgagt ttgacagggg gatgcctgac gagatagtaa 5800
taacagggta catacacgtg ctgatggtga ccgcatacag 5840
tctgcatcga ggagggcgtc taataatcaa ggtctatcgt 5880
cactccgagg ctgtattcca attcgtactc tctgcgatag 5920
tcatgatgtt tggggggctt gatatacacc ggaactcgta 5960
catgtcaact aacaaagagg agtacatcat catagctgcg 6000
gcgccggagg cattaaacta ttcctctgta ccagcaatat 6040
tgcagagggt gaagtctgtt attgaccagc agcttacatt 6080
aatctctcct atagatctag aaagattgcg ccatgagact 6120
gagtctctcc gtgagaagga gaataatcta gtaatatctc 6160
tgacgagagg gaagtatcaa ctccggccga cacagactga 6200
tatgcttcta tcatacctag gtgggagatt catcacccta 6240
ttcggacagt ctgctaggga tttgatggcc actgatgttg 6280
ctgaccttga tgctaggaag attgcattag ttgatctact 6320
gatggtggaa tccaacatta ttttaagtga gagcacagac 6360
ttggaccttg cactgttgct gagcccgttt aacttagaca 6400
aagggcggaa gatagttacc ctagcaaagg ctactacccg 6440
ccaattgctg cccgtgtata tcgcatcaga gataatgtgc 6480
aatcggcagg cattcacaca cctgacatca attatacagc 6520
gtggtgtcat aagaatagaa aacatgcttg ctacaacgga 6560
atttgtccga cagtcagttc gcccccagtt cataaaggag 6600
gtgataacta tagcccaagt caaccacctt ttttcagatc 6640
tatccaaact cgtgctttct cgatctgaag tcaagcaagc 6680
acttaaattt gtcggttgct gtatgaagtt cagaaatgca 6720
agcaattaa 6729

<210> SEQ ID NO 13
<211> LENGTH: 1374
<212> TYPE: DNA

-continued

```
<213> ORGANISM: Avian Paramixyvirus Type 2
<220> FEATURE:
<223> OTHER INFORMATION: APMV-2/Finch/N.Ireland/Bangor/73 NP protein

<400> SEQUENCE: 13

atgtcatctg tgtttactga gtaccaagcc ctacaggatc                40

aactggtcaa gccttcagct aggcgggctg atgttgcctc                80

aactggattg cttcgggctg aaatacccgt gtgtgtcacg               120

ttgtcacaag acccgaccga ccggtggaat ctggcctgcc               160

ttaacctgcg ctggttaata agtgaatcat ccacgacacc               200

aatgagacaa ggtgcaatcc tctctttact cagcctacat               240

tcggacaaca tgcgtgcgca tgccaccctt gcagcaagat               280

cagcagacgc atccatcacc atccttgagg tcgacagcat               320

tgacatggct gcagacacca tcacatttaa tgcaagaagc               360

ggagtctcag acagaagaag tgcccagctc atggccattg               400

caaaggactt gccaaggtca tgttcgaatg actcaccatt               440

caaggataac aatatcgaag atagagatcc gctggacctc               480

tctgagacaa ttgataggct acagggcatt gcagctcaaa               520

tttgggtagc tgcaataaag agcatgactg cccctgacac               560

tgccgctgaa tcagaaggga agaggttagc aaaataccag               600

cagcaaggac gattggtaag acaggtactg gttcatgagg               640

ctgtccgagc tgagtttttg agagtgatta gagggagcct               680

tgtattacgc caatttatgg tgtctgagtg caagagagcg               720

gcatcaatgg gtagtgacac ctcacgatac tatgctatgg               760

ttggtgatat tagcctgtat attaagaatg ctggattgac               800

tgcattcttc ttgactctcc gattcgggat cggcacccac               840

tacccgactc tagctatgag cgtttttttct ggggagctga               880

agaagatgtc gtcgttgata aggctgtaca aatctaaggg               920

ggagaatgct gcatacatgg cgttccttga agatgcagac               960

atggggaact tcgcacctgc aaatttcagc accttatact              1000

cttacgccat gggtgtaggg accgtcctag aagcttctgt              1040

cgcgaagtac cagtttgcaa gagagttcac aagtgagacc              1080

tattttagac tgggggtaga aactgcacag aaccaacagt              1120

gtgcattgga tgagaagaca gccaaggaaa tggggctgac              1160

tgatgaagcc aggcgacaag tgcaagcact tgccagcaac              1200

atcgagcaag ggcagcactc tatccaagct cctcaacaac              1240

cctcattcat ggcaacgcag agcaccacgc aagagccaga              1280

tcagccgtcc acaagcaggc aggacacacg gagcacgccc              1320

gcaccctctc acaaccaagg tcaggaccaa gacgatgcat              1360

ctcttgattg gtaa                                          1374

<210> SEQ ID NO 14
<211> LENGTH: 1200
```

<212> TYPE: DNA
<213> ORGANISM: Avian Paramixyvirus Type 2
<220> FEATURE:
<223> OTHER INFORMATION: APMV-2/Finch/N.Ireland/Bangor/73 P protein

<400> SEQUENCE: 14
atggagttca cagatgatac agagatagcc gagctgcttg 40
atctcggaac atctgtaata caagagcttc agagagcaga 80
gctaaagggc ccgcaaacaa caggcaaacc aaaggtcccg 120
ccaggcaaca cgaggagcct agccacgctt tgggagaaag 160
aaagcgaaac tcgaactgaa cctgaagctc tccccactga 200
acacgccaat ccggacatga gcccagcgag ccacaatgac 240
ccagcgaaag ccgcgcatga gggagcagca gaggaagggg 280
aagccgaccc agaaccggac aaggccgcag gatccgacct 320
caccaactct cgtccagggg atgacctaga caaggcgctg 360
gccaaactcg aatcgagagc caagcaaaac cgcacgcagc 400
aactaatagt taaaaagggg aagggggcaa ccaaagcatc 440
ccattctacc ccaccaatga gcccccaggt ggcggcatca 480
accacagtga acaaacccgg cccaatgaca gagccaacac 520
tcgatcttgg aagccaggac atagaagaga gtactctttt 560
gcctgtagag atggaagatt ggaagtcatc agctggtgca 600
accccatatg cactccaatc agagcagaac caagacgaga 640
agtctgcaag tgtgggaagt gtcctatctc ctgcatccta 680
tgttgccaat cccaatgatg ctatgtcggc tctaacacgc 720
aaggtcaacg atatggagtc taagattgga gaggctataa 760
aactcctagg tatgctccct gtcatcaaga atgagatcag 800
tcagctgaaa gccacagtgg ctctgatgtc aaatcaattg 840
gcatcaatcc aaattctcga tcccggtaat gcaggtgtaa 880
aatccctcaa cgaaatgaag tcactatcaa aagctgccag 920
cattgtagtt acaggaccag ggtcacttcc tattgaggta 960
ctaaacaccg acactgtata caaagatgaa cttgctcgcc 1000
cagtgacagc ccaagcccac aaagagacca aacctaaaga 1040
tgagccgggg gcaacatcat ccgatctcac tgccgttcag 1080
gcgctgatcg acacgttagt ggaggacgac cgtagaaaat 1120
caaggctaca tcaggcactt caaagagcca gaaccaaaga 1160
agacatcctc cgcatcaaga gacaaatcta caatgcatag 1200

<210> SEQ ID NO 15
<211> LENGTH: 699
<212> TYPE: DNA
<213> ORGANISM: Avian Paramixyvirus Type 2
<220> FEATURE:
<223> OTHER INFORMATION: APMV-2/Finch/N.Ireland/Bangor/73 V protein

<400> SEQUENCE: 15
atggagttca cagatgatac agagatagcc gagctgcttg 40

```
atctcggaac atctgtaata caagagcttc agagagcaga                          80

gctaaagggc ccgcaaacaa caggcaaacc aaaggtcccg                         120

ccaggcaaca cgaggagcct agccacgctt tgggagaaag                         160

aaagcgaaac tcgaactgaa cctgaagctc tccccactga                         200

acacgccaat ccggacatga gcccagcgag ccacaatgac                         240

ccagcgaaag ccgcgcatga gggagcagca gaggaagggg                         280

aagccgaccc agaaccggac aaggccgcag gatccgacct                         320

caccaactct cgtccagggg atgacctaga caaggcgctg                         360

gccaaactcg aatcgagagc caagcaaaac cgcacgcagc                         400

aactaatagt taaaaagggg gaagggggca accaaagcat                         440

cccattctac cccaccaatg agcccccagg tggcggcatc                         480

aaccacagtg aacaaacccg gcccaatgac agagccaaca                         520

ctcgatcttg gaagccagga catagaagag agtactcttt                         560

tgcctgtaga gatggaagat tggaagtcat cagctggtgc                         600

aaccccatat gcactccaat cagagcagaa ccaagacgag                         640

aagtctgcaa gtgtgggaag tgtcctatct cctgcatcct                         680

atgttgccaa tcccaatga                                                699


<210> SEQ ID NO 16
<211> LENGTH: 462
<212> TYPE: DNA
<213> ORGANISM: Avian Paramixyvirus Type 2
<220> FEATURE:
<223> OTHER INFORMATION: APMV-2/Finch/N.Ireland/Bangor/73 W protein

<400> SEQUENCE: 16

atggagttca cagatgatac agagatagcc gagctgcttg                          40

atctcggaac atctgtaata caagagcttc agagagcaga                          80

gctaaagggc ccgcaaacaa caggcaaacc aaaggtcccg                         120

ccaggcaaca cgaggagcct agccacgctt tgggagaaag                         160

aaagcgaaac tcgaactgaa cctgaagctc tccccactga                         200

acacgccaat ccggacatga gcccagcgag ccacaatgac                         240

ccagcgaaag ccgcgcatga gggagcagca gaggaagggg                         280

aagccgaccc agaaccggac aaggccgcag gatccgacct                         320

caccaactct cgtccagggg atgacctaga caaggcgctg                         360

gccaaactcg aatcgagagc caagcaaaac cgcacgcagc                         400

aactaatagt taaaaagggg ggaagggggc aaccaaagca                         440

tcccattcta ccccaccaat ga                                            462


<210> SEQ ID NO 17
<211> LENGTH: 1110
<212> TYPE: DNA
<213> ORGANISM: Avian Paramixyvirus Type 2
<220> FEATURE:
<223> OTHER INFORMATION: APMV-2/Finch/N.Ireland/Bangor/73 M protein

<400> SEQUENCE: 17

atggcccaga caacagtcaa gctgtatgtc gacgagacaa                          40
```

```
gcccagacat tgaactgcta tcgtatcctc tagtcatgaa                          80

ggatacaggc catggaacca aagagttgca gcagcaaatc                         120

agagtggcag aaatcggaac gctccatgga gggaagaatg                         160

agtcagtctt tatcaacgct tatggttttg tccaacaaga                         200

caagattaaa cccggggcgg cgcggttcta tcagatggag                         240

gaaggccaca aacccgaagt aatcacggca ggaatgataa                         280

taatcggagc agttaaggga ggaacggaca taacaaaact                         320

ggcagaagat gtcttctctc tagatataac aatcaagaaa                         360

tccgcatcat ttcatgagaa ggtggcagtc accttcaaca                         400

ctgtgccact atctctcatg aactcaacag cctgcaagaa                         440

tctgggttat ttaaccaatg cggaagagtc tattaagtgc                         480

cccagcaaaa ttcaagcagg agtcacatat aagtttaagg                         520

taatgttcgt atccttaaca aggctgcata atggcaagct                         560

ttacagagta cccaaagctg tttactcaat tgagactgct                         600

gcattataca aagttcaact agaggttggg ttcaaattgg                         640

atgttgcaaa agaccaccct catgtgaaga tgttaaggaa                         680

ggttaagaaa gatggggaag taaaatacat cggatatgca                         720

tggttccact tgtgcaattt caagcgaaca actgctaaag                         760

gggaaaccag gactatatca aatctagaac ataaggtgaa                         800

ggcaatgggt attaaagtcg ccctctatga tctctggggg                         840

cctacattgg ttgtgcaaat aaccggcaag accagtaagt                         880

atgctcaagg cttcttctct accacaggca catgttgcct                         920

ccctgttgca aaggcagcac ccgaacttgc caagcttatg                         960

tggtcatgca atgtttcaat tattgaagcc tctgtggtca                        1000

tacaaggaag tgatcggaga gctgctgtga cctcagaaga                        1040

tctggagctt tacggggctg tggcaaagga gaagcagccc                        1080

cagaaggggt tccacccatt cagaaagtga                                   1110
```

```
<210> SEQ ID NO 18
<211> LENGTH: 1635
<212> TYPE: DNA
<213> ORGANISM: Avian Paramixyvirus Type 2
<220> FEATURE:
<223> OTHER INFORMATION: APMV-2/Finch/N.Ireland/Bangor/73 F protein

<400> SEQUENCE: 18

atggaacctc cgaaccaacc agaaggaacc atgaaggcaa                           40

tactaatcat gagcatggta cctatctgta tcgcgcttga                           80

caactcaatc cttgcaccgg tagggatagc aagtgcacag                         120

gaatggcaac ttgcagcgta caccaatacc ctatcaggga                         160

caatagctgt gagatttgtg cctgtcttac ctgggaatct                         200

atcaacatgt gcgcaagcca cactggcgga atataacaga                         240

actgtgacaa atatcctagg gcctctaaag gacaacctga                         280
```

```
acgctttgtt agctgaatca acactcccct cagcacgatt                          320

tgtcggtgcc atcataggaa cggtggcact aggagttgcc                          360

acttccgcac aaatcacagc agcagttgct cttaaccaag                          400

cccaagagaa tgcaaggaat atctggaggt taaaggagtc                          440

tataatgaaa acaaatgagg ccgtcttgga gcttaaggat                          480

ggactagcca gtaccgctat tgccctagac aaagtccagc                          520

gattcatcaa tgatgacatc ctcccacagc tgacaggtct                          560

agactgtcaa gttgtggcaa acaaactcgg cgtctatttg                          600

tccttgtatt taactgagtt aaccaccata tttggctcgc                          640

agataaccaa cccggcctta acacccttat cgtaccaggc                          680

tttgtacagt ctatgtggag gcgacatggg gaagttgact                          720

gagctaatag gtgtaaaagc caaagacatt aactctctgt                          760

atgaggccaa tctgataact ggacaagtca taggctatga                          800

ctccgagtca cagattatac tagtccaggt gtcataccca                          840

agtgtctcag aggtgacggg agtcagagca acagagctca                          880

ttaccgttag tgtgacaacc ccaaaaggag aaggcagagc                          920

gataacaccc aggtacgtgg ctcaaagcag agtattgaca                          960

gaagagctag atacaagcac atgcagattt agcaagacta                         1000

cattgtactg tagatcagta ataactcggc ctctacctcc                         1040

tttaattgca agctgtctga gtgggtcata ccaggattgc                         1080

cagtacacaa cagagattgg cgctttgtcg tcgcgcttta                         1120

ttactgtcaa cgggggtata gtagcgaact gtaaggccac                         1160

cgtatgcaag tgtgtgaatc ccccaaagat catagcacag                         1200

aatgacgcca gctctctaac ggttatagat gcaggtgtct                         1240

gcaaggaagt ggtgttagat aatgtacagt taaagctaga                         1280

aggaaagttt agcgctcaat actttactaa tgtgacgatc                         1320

aacttgtcac agataactac ctctgggtct ttggacatta                         1360

gcagtgagat cggcagcatc aacaacacag tgaatagagt                         1400

ggagaattta attgcagagt caaacgcgtg gttacagtct                         1440

gtcaacccaa gactagtgaa caatactagc atcattgtct                         1480

tgtgtgtgtt gggcgcagtc atcgtcgtct ggttagtagc                         1520

actgactgtg tgtatggctt actcgctgcg cagaaaagca                         1560

gccacgcaga tcgcaagcat gggaacatcc acaataggga                         1600

atccttatgt gacccaaagt gcaacaaaga tgtaa                              1635
```

<210> SEQ ID NO 19
<211> LENGTH: 1752
<212> TYPE: DNA
<213> ORGANISM: Avian Paramixyvirus Type 2
<220> FEATURE:
<223> OTHER INFORMATION: APMV-2/Finch/N.Ireland/Bangor/73 HN protein

<400> SEQUENCE: 19

```
atggccacaa tgtccagaga aaacctcaca aatattggcc                           40
```

```
aaggagaaag agggacttgg cggttgttat ttcggatctc                80
aaccctagcc atcactacag tttgcttggc aatcaacatc               120
gccaccatat ccaaactaga caacatagac accagcggga               160
tccagacctg gaccaccatg gagtccgaca ggataatcgg               200
gtctttgaca agcacgctga aagtcccaat caatcaggtg               240
aatgatatgt ttcgtattgt tgctttggat ctcccactcc               280
agatgtctac aatgcagaaa gagattgctt cacaggttgg               320
cttcttggca gaaagcatca ataatgtgct atctaagaat               360
ggatcagctg ggttggttct agtcaatgac ccagagtatg               400
caggcgggat aggagtcagc ctgttccatg gtgactcagc               440
gtctagtctt gaatttgaga gcccgtcact gattgaacac               480
cccagcttta tcccgggtcc cactacagca aagggttgca               520
tcaggatacc gacatttcac atgaccgctt ctcattggtg               560
ctactcccac aacataattg agtccggctg tcaagatgca               600
ggacattcca gtatgtacat ctctctgggt gtgctgaagg               640
ccatgcagac aggatccccc agctttctca ccacagctag               680
ccagcttata gatgataacc ttaacagaaa gtcatgcagc               720
atcatatcaa cgacgtacgg ctgcgacata ctgtgtagtt               760
tggtagttga gaacgaggat tcagattacc ggtccgaccc               800
accgactgag atgattcttg ggaggctgtt cttcaacggc               840
acctaccttg agagtcatgt gaatacaagg tcaatatttg               880
agcagttctc cgcgaattac ccggcagttg gatctggttt               920
agtattagga gatgagatag cattcccagt gtacggggga               960
gtcaaacagg atacacagct gttcaatcag ctaaaagatc              1000
atggttactt tactcacaat gatgtataca ggtgtaacaa              1040
aagcaatgtg cagcagacca tcctcaatgc atacagaccc              1080
cccaaaatag caggacggtt gtggtcacag gttatcataa              1120
tctgcccttt ggggttgttc ataaacacgg attgtagaat              1160
caaggtgttt aacaccagct cagtaatgat gggcgcagaa              1200
gctagactga tacaagtcgg gtccgatatc tacctatacc              1240
agagaccatc ctcgtggtgg gtggtcgggt tgatatataa              1280
gcttgacttc caagagctat caacaaaaga aggggtggtt              1320
ctgaacaaaa tagttcccat cgctcatgca aaattccctc              1360
gaccatcctt ttcaaaggac gcctgtgcta gaccaaatat              1400
ctgcccagca gtatgtgtat caggagtgta ccaggatatt              1440
tggcctatta gtacggccac caatttgagt caagtagtgt              1480
gggtgggcca atatcttgaa gcattttatg ctagaaaaga              1520
tccctggata gggatcgcaa cgcagtatga ttggaaaagg              1560
aatgtccgct tatttaattc tarcacaraa ggagggtatt              1600
```

-continued

```
ccactaccac atgcttcagg aacacaaaga ggaataaggc                        1640

attctgtatt atcatatcag agtatgcgga cggtgtattt                        1680

ggatcttaca ggattgtgcc tcaactaatc gaaatcagga                        1720

cgaataacag ggttaggttt gacaatcatt aa                                1752


<210> SEQ ID NO 20
<211> LENGTH: 6729
<212> TYPE: DNA
<213> ORGANISM: Avian Paramixyvirus Type 2
<220> FEATURE:
<223> OTHER INFORMATION: APMV-2/Finch/N.Ireland/Bangor/73 L protein

<400> SEQUENCE: 20

atggatcagg tccaagcgga tastattatc cagcctgaag                          40

tccacttaga ttcaccgata gttagagcaa agcttgtatt                          80

gctatggaaa ttaacaggtt taccccctgcc aaaagagcta                        120

agatcttttg tcctcacatc ccataccaca gatgaacaga                         160

tcttcaaagc tgaaacaaga gtaaaaccta aggtaaattc                         200

aatagttgat gcactcatca aacattgcaa atcacggggt                         240

ttgtatctat ccgacatacg accagtggtg cacccaagga                         280

cactccaatg gttgctaaat attaaatgtg aaagagccaa                         320

tcaactgcta aaggctaggg aaaaatccat ccaacaagta                         360

ttttcagaga aacaagtaaa ctttaggcat ctattctcag                         400

ctataagcca ccaattggta gggaatccta acctatttts                         440

ctctcaagat aatgacccaa gatatccaga gtcacccctg                         480

ctctacaggc tgtcagaagc ttcttacaca gcctatatcc                         520

gcaacaacct ctcgatggac tgcagctcga tgggcttggc                         560

tacatattat gcaggttatg cgctaccaaa ttctacagag                         600

tacgctgcac gctacatcag catcagtgac atcatggtca                         640

gagacttggg gctttatagg aatttcacca gatgttgtgc                         680

taattgttgt ttatatgtct atgagctaca ctgtgctgac                         720

gtttcagatg gtcctaatgt actcagatgt aattcaaggg                         760

cgcgacaata tagcaattgt gggtcgatta tcccctattc                         800

tatcccctgt cacagatcga atagacatcc tctttcatct                         840

agtcgacacc ctagcagttt tgatgggtca tcagatatat                         880

caccttgtgg catcattaga gagtatggcc tatgcagctg                         920

tccaattgca tcatgcaagc tactcacacg caggtcagtt                         960

ctttgctttc aatctgacag aaattcaatc agttctcgca                        1000

gaccacctag atcaaaagca agcgcactct atcatcagaa                        1040

ctattatcat gtgttacagt tgtctaacac ccgatcaagc                        1080

ggctcagatg ttatgcatca tgcggttgtt cggtcatccc                        1120

ctgttatccg cccagcaagc agcaaaaaaa gtaagggaat                        1160

ccatgtgcgc acctatgatc ctggagcatg cgcaatttta                        1200

cagacattgt ccttcttcaa ggggatcata atcaatggtt                        1240
```

-continued

```
ataggaagag ccactccgga gtatggccaa acattgaacc      1280
tgagtctatc atagatgatg atcttcgtca attatactat      1320
gaatctgcag agatatcaca tgcattcatg cttaagaaat      1360
atcggtactt aagcatggta gaattcaaaa agagtattga      1400
cttcgacctc aatgatgacc tgagcacctt tttgaaagac      1440
aaagccatat gccgtccaaa gaatcaatgg gctcggattt      1480
tcagaaagtc actgtttccc ttgaaaaatg ccattgatag      1520
cggagcagac actagaagta atcgcctgct gatcgatttt      1560
ttagaatccc atgactttag cccagaggag gagatgaaat      1600
atgtcactac gatggcatac ctggatgatg atcagttctc      1640
tgctttcata ttccctcaaa gagaaggaaa tcaagacaac      1680
aggtcgaata tttgcgaaaa tgaccaggaa aatgcgaagc      1720
tgccaggtta tactagaatc attgttgtct actcatgtgt      1760
gcaaattctt caaagagaac ggagtctcca tggagcaact      1800
ctctttaaca aagagcctcc tagcaatgtc tcagttagcc      1840
cctcggatct ccgcggtgcg aaacgaaacg gcaagagcag      1880
gtacccaggg aaatcacatt tacaaccagt aggtcccatg      1920
tcggctgcga gggaggtaca gcagcatcaa agggatcgac      1960
ctgctaagaa aagtattgtg gcaacctttt taacaacaga      2000
cctacagaaa tattgcctca attggagata cgggagcatt      2040
aagttatttg cacaggcact aaaccaacta tttggaatag      2080
accacgggtt tgagtggata catcttagat taatgaatag      2120
cacattattt gttggtgacc ccttttctcc tcctgagtgc      2160
aagggagtga gagatctgga tgatgcacct aactcagaca      2200
tcttcatagt ttcggcacga ggaggtatcg aaggactgtg      2240
tcaaaaactg tggactatga tttctattag tattatccat      2280
tgtgtgtccg aaaaaatagg gacaagggtc gctgcaatgg      2320
tccaagggga caatcaagtt atagcaatta ccagagaatt      2360
attcaatggg gagacatttg agcaaatcca acctgagctg      2400
gacaagctag gtaatgcatt cttttctgag tttaagcaac      2440
acaactatgc aatgggtcat aatcttaagc ccaaggagac      2480
tatccaaagc caatcattct ttgtgtattc caaacggata      2520
ttttgggaag ggaggatcct cagccaggct ctcaagaatg      2560
caactaagct atgtttcatc gcagaccatt tgggagacaa      2600
tacggtgtca tcatgcagca accttgcatc aactatcaca      2640
cgccttgtcg agaatggatt tgaaaaagat actgcttttg      2680
tcttaaacgt ggtctattca atgacccaga tcctgataga      2720
cgagcaatat tctctgcagg gtgattatgc gaatgtcaag      2760
aatctaattg gtaccaacaa ccacagaaat ctactgactg      2800
```

-continued ctgccctgat tcctgggcaa gtcgggggtt ataatttctt 2840
aaacattagc aggctattta ctaggaacat aggagacccc 2880
gtgacctgtg caatcgctga tcttaagtgg ttcattaaga 2920
gtgggctagt tgcggaccat atattgaaga acatcttact 2960
ccgggaccca ggtgacggta gttggagcac tctctgcgcg 3000
gacccttatg cacttaatat cccctataca caactaccaa 3040
cgacctatct gaagaaacat acacaacggg cactgttagc 3080
agagtccaac aacccgctgc tggccggggt ccagttggat 3120
tcacagtaca ttgaggagga agaactggca caatttctct 3160
tagaccgtga agtagttatg ccaagggttg cgcatactat 3200
tatggaagcc agcattctag ggaagaggaa gaatatccaa 3240
ggcttaatag acactacacc cacaatcatc aaaacagcct 3280
taatgagaca gcccatctcc cgccgaaagt gcgaaaagat 3320
tatcaattac tcaattaatt acttggtaga gtgccatgat 3360
tctattattg ctgttaggaa atttgaacct aggaaagagg 3400
tcatctggga ttcggccatg atctcggtag aaacttgtag 3440
tgtgactgtt gctgagttct tgcgagctac tagctggtca 3480
aatctgttga acggaagaac aatctctggg gttacatctc 3520
ctgacgcagt ggagctgcta aaggggtcac tcattggaga 3560
aaaatacaca ctgcacgctc tgtgcgcaag gagacgatac 3600
attcactgga tgcatatagc ggggccaacg tatatacccg 3640
acccaggcct gaccggatct aagatgagag taccatacct 3680
gggatccaaa accgaagaaa gacggtctgc ctccatggca 3720
actataaaag gaatgtcaca tcatctcaaa gctgcactca 3760
gaggtgcatc tgtattggtc tgggcgttcg gagacacaga 3800
tgatagttgg aaccatgcat gtttactagc taatacaagg 3840
tgtaaagtca ccatgtcaca gctccgatta ctaacaccaa 3880
cacctagcag ctcaaatata caacatcgac taaatgacgg 3920
aatcagcgta caaaagttca caccagccag cctttcgcgt 3960
gttgcatcct tcgttcacat ctgcaacgat ttccaaaatc 4000
tagagaaaga tggcgcatct gttgactcga acttgatata 4040
ccagcaaatc atgctcacag ggttgagcat catggagaca 4080
cttcacccta tgcagaccca atggatatac aacaaccaga 4120
ccatacacct acataccggg acttcttgct gccccagaga 4160
gattgaaacc agcatagtca accccccaaa atacgagttc 4200
ccaaccatca ctctcactac aaataaccag ttcttgttcg 4240
acaacaatcc aatacacgac gatgccatca ccaagctggc 4280
agtaagtgac ttcaaattcc aagaattaaa tatcgacgca 4320
atcaggggtt acggtgctgt caacctgctg agtcggtgtg 4360
tggccaagct aattggcgag tgtatccttg aagatgggat 4400

-continued

```
tgggtcttct atcaagaacg aggctatggt ctcattcgat           4440
atctctgtca attggatctc tgagatctta cacagtgacc           4480
taagactgac ttttatgcac cttggccagg aactcctctg           4520
tgatctagca tatcagatgt acttcctaag ggttacgggg           4560
tatcatgcta tcgtaacata tctcaagaca tcactagaaa           4600
gaataccagt catacaacta gcaagacatg gcccttacca           4640
tttctcaccc cgaagtgtgg agacgagtca cattagtcgg           4680
gttcaatcaa gggtaccgta cccctacttg gccactgttg           4720
acttcatagc agcgtgcagg gatattattg tgcaaggtgc           4760
tcagcagtac atatctgacc tcttatcggg ctcggagtgc           4800
caatatacat tctttaatgt ccaagacggt gatttgactc           4840
caaagatgga acaattcttg gcaaggagga tgtgcttgct           4880
tgtgctcttg acagggactt cctcttcttt accgattata           4920
aagtcactca atgcaataga gaaatgcgct gtgttgactc           4960
agttcatcta ttatctacca aatgtcgact tgacagtagc           5000
tagtaaggct aggacactat ataccttgc cgtcaaccct           5040
aagatcgatg cactcgtatc aaacctctac ttcacgacca           5080
ggcgagtgtt atccaatata agaggagaca ggcatgccaa           5120
agctcaggtt tcttatctct atgaagagga agttagctca           5160
gagcctctgc aagacgagaa ctttgatcac ttcatgaaag           5200
accctataat acgaggagga ttgttcttca ccgtcattat           5240
caagatggaa aaaatgtcac tgaaccaatt cgcatcgggg           5280
ggtgctacaa cccttgcgtt accgcctcag gaggctcatt           5320
caataatgtg gcgggcttcg cctttagccc attgcttgaa           5360
gtctgtgggg caggttagca ctagctggta caagtatgcg           5400
gtgttgcaag ctgccctcag caaaacccag cctcttaggt           5440
caaatagcat ttacattggt gaagggagtg gaagtgtcat           5480
gacactactt gagtacatgg acccatcaat cagtcatatt           5520
ctacaattcg ttgtttataa cagcatgaat cctccccagc           5560
gcaattttgg actaatgccg actcagttcc aggaatcaat           5600
agtatataaa aatctgtgtg caggtattga gagcaaatat           5640
ggattctccc agacattctc gcccctgtgg agagatgttg           5680
accaagaaac aaacatcacg gagacagcat tcctcaacta           5720
cctaatggaa gtagtgccaa tccactccgc taaaaggttg           5760
gtgtgtgaag tagagtttga tagaggcatg cctgatgaag           5800
taatgataca agggtatatg aatgtgttga ttgcagcggc           5840
atttagctta cacagagagg gccgcttgtt catcaagata           5880
tttcgccata gtgagtccat tttcaatttt gtcctatcat           5920
ctataatgat gatcttcggg ttatgccata tacatcgcaa           5960
```

-continued

```
ctcttacatg tcaaccaata aagaggagta tatcctggtg                    6000

ggccgaagca cctcagcccc taagttatgc atcagtaccg                    6040

gccatcctgc atcgagtcaa gagcataaca gaccagagct                    6080

taacggtggt gaccctattg atatggcccg agtgcacaaa                    6120

gagatggatt cactgagaga aaaggaatca gctcttattt                    6160

cctctttaat aagagggaca gtgagattaa ggccaactca                    6200

gacagacatg ttgttttcct atttaggggg taaattcgtc                    6240

accttattcg gacactcggc aagggatctg atggaacttg                    6280

atatagcagt gctagattct cggcaaatag acttaatcga                    6320

ccttttgatg gtagaagcca acatcatcgt aagcgagagt                    6360

actgatttgg atctagccct tcttcttagc ccattcaatt                    6400

tagataaagg gaggaaaatt gtaacactcg caaaatcaac                    6440

tacgaggcaa ctaatcccgc tttatattgc agctgagatc                    6480

tcttgcaaca agcactcatt ttcacactta atatctttgg                    6520

tgcaaagggg cgtaatcagg atcgaaaaca tggtgtctgt                    6560

gtcaagcttc atctcaaaat cctcccggcc taggtttcta                    6600

agggatgttg tgacttttgc tcaaatcgag catatattct                    6640

ccgatctttc aacattaatc ctaaccaggt cggaaattaa                    6680

ggtagtcctc aagttcattg gttgctgcat gaagtttaac                    6720

catgcctaa                                                      6729
```

<210> SEQ ID NO 21
<211> LENGTH: 1374
<212> TYPE: DNA
<213> ORGANISM: Avian Paramixyvirus Type 2
<220> FEATURE:
<223> OTHER INFORMATION: APMV-2/Chicken/England/7702/06 NP protein

<400> SEQUENCE: 21

```
atgtcttctg tgttttcaga acaccaggct cttcaggacc                      40

aactggtcaa gcctgccact cgaagggctg atgtggcatc                      80

gactggattg ttgagagcgg agataccagt ttgtgtaacc                     120

ttgtctcagg acccaactga tagatggaac ctcgcatgtc                     160

tcaatctgcg atggctgata agtgagtcct ctactactcc                     200

catgagacaa ggggcgatcc tgtcactgct gagcttgcac                     240

tctgacaaca tgcgagctca cgcaaccctt gcagcgagat                     280

ccgctgatgc tgccatcact gtgcttgagg ttgacgccat                     320

agacatgacg gatagcacaa tcacttttaa tgccagaagt                     360

ggagtatccg agaggcgcag cacacagctc atggcaatcg                     400

caaaagatct gccccgctct tgttccaatg actcaccatt                     440

caaagatgac actatcgagg atcgcgaccc ccttgacctg                     480

tccgagacta tcgatagact gcaggggatt gctgcccaaa                     520

tctggatagc ggccatcaag agcatgactg ccccggatac                     560

tgctgcggag tcagaaggca agaggcttgc aaagtaccaa                     600
```

```
caacaaggcc gcttggtgcg acaggtgtta gtgcatgatg                     640

cggtgcgtgc ggaattccta cgtgtcatca gaggcagcct                     680

ggtcttacgg caattcatgg tatcagaatg taagagggca                     720

gcatccatgg gtagcgagac atctaggtac tatgccatgg                     760

tgggtgacat cagcctctac atcaagaatg caggacttac                     800

cgccttcttc ttgacactca gatttggtat tgggacacac                     840

taccccactc ttgccatgag tgtgttctct ggagaactga                     880

agaagatgtc gtccttgatc aggctgtata agtcaaaagg                     920

ggaaaatgct gcatacatgg cattcctgga ggatgcggac                     960

atgggaaact ttgcgcctgc taactttagt actctctact                    1000

cctatgcaat gggggtaggt acagtgctgg aagcatcagt                    1040

tgcgaaatac cagttcgctc gagagttcac cagtgagaca                    1080

tacttcaggc ttggggttga gaccgcacag aaccaacagt                    1120

gcgctctaga tgaaaagacc gccaaggaga tggggcttac                    1160

tgatgaagcc agaaagcagg tgcaagcatt ggctagcaac                    1200

atcgagcagg ggcaacattc aatgcccatg caacaacagc                    1240

ccacattcat gagtcagccc taccaggatg acgatcgtga                    1280

ccagccaagc accagcagac cagagccaag accatcgcaa                    1320

ttgacaagcc aatcagcagc acaggacaat gatgcggcct                    1360

cattagattg gtga                                                1374
```

<210> SEQ ID NO 22
<211> LENGTH: 1200
<212> TYPE: DNA
<213> ORGANISM: Avian Paramixyvirus Type 2
<220> FEATURE:
<223> OTHER INFORMATION: APMV-2/Chicken/England/7702/06 P protein

<400> SEQUENCE: 22

```
atgggagtca ccgatgatgc cgaaattgct gagctgttgg                      40

acctcgggac ctcagtgatc caagagctgc agcgagccga                      80

agtcaagggc ccgcaaacaa ccggaaagcc caaagttccc                     120

ccggggaaca ctaagagcct ggctactctc tgggagcatg                     160

agactagcac ccaagggagt gcattgggca cacccgagaa                     200

caacacccag gcacccgatg acaacaacgc aggtgcagat                     240

acgccagcga ctaccgacgt ccatcgcact ctggatacca                     280

tagacaccga cacaccaccg gaagggagca agcccagctc                     320

cactaactcc caacccggtg atgaccttga caaggctctt                     360

tcgaagctag aggcgcgcgc caagctcgga ccagataggg                     400

ccagacaggt taaaaagggg aaggagatcg ggtcgagcac                     440

agggacgagg gaggcagcca gtcaccacat ggaagggagc                     480

cgacagtcgg agccaggagc gggcagccga gcacagccac                     520

aaggccatgg cgaccgggac acaggaggga gtactcattc                     560
```

-continued atctctcgag atgggagact ggaagtcaca agctggtgca 600
acccagtctg ctctcccatt agaagcgagc ccaggagaga 640
aaagtgcaca tgtggaactt gcccagaatc ctgcatttta 680
tgcaggcaac ccaactgatg caattatggg gttgacaaag 720
aaagtcaatg atctagagac aaaattggct gaggtattgc 760
gtctgttagg aatactcccc gttattaaga atgagattag 800
ccaattaaag gctactgtgg ctttgatgtc taatcaattg 840
gcatccatcc aaatcctcga ccctgggaac gctggagtca 880
agtcattgaa tgaaatgaaa gcactatcga aatctgctag 920
catagtggta gcaggcccag gctctatacc ctctgaggtg 960
ttggagtcca atgttgtata taaggatgaa cttgctcgtc 1000
ctgtgactgc acaagcccac aaagagatca agccccgaga 1040
ggaggcaagt gccacttcct cagagctaac cgccgtccag 1080
gcagtaatcg acatccctgt agaagatgag aggaagaagg 1120
ccaggctcca ccaggcactc gagagagcaa gaaccaagga 1160
ggacatcctc cgcattaaaa ggcagatcta caatgcatga 1200

<210> SEQ ID NO 23
<211> LENGTH: 699
<212> TYPE: DNA
<213> ORGANISM: Avian Paramixyvirus Type 2
<220> FEATURE:
<223> OTHER INFORMATION: APMV-2/Chicken/England/7702/06 V protein

<400> SEQUENCE: 23
atgggagtca ccgatgatgc cgaaattgct gagctgttgg 40
acctcgggac ctcagtgatc caagagctgc agcgagccga 80
agtcaagggc ccgcaaacaa ccggaaagcc caaagttccc 120
ccggggaaca ctaagagcct ggctactctc tgggagcatg 160
agactagcac ccaagggagt gcattgggca cacccgagaa 200
caacacccag gcacccgatg acaacaacgc aggtgcagat 240
acgccagcga ctaccgacgt ccatcgcact ctggatacca 280
tagacaccga cacaccaccg gaagggagca agcccagctc 320
cactaactcc caacccggtg atgaccttga caaggctctt 360
tcgaagctag aggcgcgcgc caagctcgga ccagataggg 400
ccagacaggt taaaaagggg gaaggagatc gggtcgagca 440
cagggacgag ggaggcagcc agtcaccaca tggaagggag 480
ccgacagtcg gagccaggag cgggcagccg agcacagcca 520
caaggccatg gcgaccggga cacaggaggg agtactcatt 560
catctctcga gatgggagac tggaagtcac aagctggtgc 600
aacccagtct gctctcccat tagaagcgag cccaggagag 640
aaaagtgcac atgtggaact tgcccagaat cctgcatttt 680
atgcaggcaa cccaactga 699

<210> SEQ ID NO 24
<211> LENGTH: 624
<212> TYPE: DNA
<213> ORGANISM: Avian Paramixyvirus Type 2
<220> FEATURE:
<223> OTHER INFORMATION: APMV-2/Chicken/England/7702/06 W protein

<400> SEQUENCE: 24
atgggagtca ccgatgatgc cgaaattgct gagctgttgg 40
acctcgggac ctcagtgatc caagagctgc agcgagccga 80
agtcaagggc ccgcaaacaa ccggaaagcc caaagttccc 120
ccggggaaca ctaagagcct ggctactctc tgggagcatg 160
agactagcac ccaagggagt gcattgggca cacccgagaa 200
caacacccag gcacccgatg acaacaacgc aggtgcagat 240
acgccagcga ctaccgacgt ccatcgcact ctggatacca 280
tagacaccga cacaccaccg gaagggagca agcccagctc 320
cactaactcc caacccggtg atgaccttga caaggctctt 360
tcgaagctag aggcgcgcgc caagctcgga ccagataggg 400
ccagacaggt taaaaagggg ggaaggagat cgggtcgagc 440
acagggacga gggaggcagc cagtcaccac atggaaggga 480
gccgacagtc ggagccagga gcgggcagcc gagcacagcc 520
acaaggccat ggcgaccggg acacaggagg gagtactcat 560
tcatctctcg agatgggaga ctggaagtca caagctggtg 600
caacccagtc tgctctccca ttag 624

<210> SEQ ID NO 25
<211> LENGTH: 1110
<212> TYPE: DNA
<213> ORGANISM: Avian Paramixyvirus Type 2
<220> FEATURE:
<223> OTHER INFORMATION: APMV-2/Chicken/England/7702/06 M protein

<400> SEQUENCE: 25
atggctcaaa caaccgtcag gctgtatatc gatgaagcta 40
gtcccgacat tgaactgttg tcttacccac agataatgaa 80
agacacagga catgggacca aagagttgca gcagcaaatc 120
agagttgcag agatcggtgc attgcaggga gggaagaatg 160
aatcagtttt catcaatgca tatggctttg ttcagcaatg 200
caaagttaaa ccgggggcaa cccaattctt ccaggtagat 240
gcagctacaa agccagaagt ggtcactgca gggatgatta 280
taatcggtgc agtcaagggg gtggcaggca tcactaagct 320
ggcagaagag gtgttcgagc tggacatctc catcaagaag 360
tccgcatcat tccatgagaa ggttgcggtg tcctttaata 400
ctgtgccact atcactcatg aattcgaccg catgcagaaa 440
tctgggttat gtcacaaacg ctgaggaggc gatcaaatgc 480
ccgagcaaaa tacaagcggg tgtgacgtac aaatttaaga 520
taatgtttgt ctccttgaca cgactgcata acgggaaatt 560

```
gtaccgtgtc cccaaggcag tgtatgctgt agaggcatca                          600

gctctatata aagtgcaact ggaagtcggg ttcaagcttg                          640

acgtggccaa ggatcaccca cacgttaaga tgttgaagaa                          680

agtggaacgg aatggtgaga ctctgtatct tggttatgca                          720

tggttccacc tgtgcaactt caagaagaca aatgccaagg                          760

gtgagtcccg gacaatctcc aacctagaag ggaaagtcag                          800

agctatgggg atcaaggttt ccttgtacga cttatggggg                          840

cctactttgg tggtgcaaat cacaggtaag accagcaagt                          880

atgcacaagg tttcttttca accacaggta cctgctgcct                          920

cccagtgtcg aaggctgccc ctgagctggc caaacttatg                          960

tggtcctgca atgcaacaat cgttgaagct gcagtgatta                         1000

tccaagggag tgataggagg gcagtcgtga cctcagagga                         1040

cttggaagta tacggggcag ttgcaaaaga gaagcaggct                         1080

gcaaaaggat ttcacccgtt ccgcaagtga                                    1110


<210> SEQ ID NO 26
<211> LENGTH: 1611
<212> TYPE: DNA
<213> ORGANISM: Avian Paramixyvirus Type 2
<220> FEATURE:
<223> OTHER INFORMATION: APMV-2/Chicken/England/7702/06 F protein

<400> SEQUENCE: 26

atgaatcaag cactcgtgat tttgttggta tctttccagc                           40

tcggcgttgc cttagataac tcagtgttgg ctccaatagg                           80

agtagctagc gcacaggagt ggcaactggc ggcatataca                          120

acgaccctca cagggaccat cgcagtgaga tttatcccgg                          160

tcctgcctgg gaacctatca acatgtgcac aggagacgct                          200

gcaggaatat aatagaactg tgactaatat cttaggcccg                          240

ttgagagaga acttggatgc tctcctatct gacttcgata                          280

aacctgcatc gaggttcgtg ggcgccatca ttgggtcggt                          320

ggccttgggg gtagcaacag ctgcacaaat cacagccgcc                          360

gtggctctca atcaagcaca agagaatgcc cggaatatat                          400

ggcgtctcaa ggaatcgata aagaaaacca atgcggctgt                          440

gttggaattg aaggatggac ttgcaacgac tgctatagct                          480

ttggacaaag tgcaaaagtt tatcaatgat gatattatac                          520

cacagattaa ggacattgac tgccaggtag ttgcaaataa                          560

attaggcgtc tacctctcct tatacttaac agagcttaca                          600

actgtatttg gttctcagat cactaatcct gcattatcaa                          640

cgctctctta ccaggcgctg tacagcttat gtggaggggga                          680

tatgggaaag ctaactgagc tgatcggtgt caatgcaaag                          720

gatgtgggat ccctctacga ggctaacctc ataaccggcc                          760

aaatcgttgg atatgaccct gaactacaga taatcctcat                          800

acaagtatct tacccaagtg tgtctgaagt gacaggagtc                          840
```

```
cgggctactg agttagtcac tgtcagtgtc gctacaccaa     880

aaggagaagg gcaggcaatt gttccgagat atgtggcaca     920

gagtagagtg ctgacagagg agttggatgt ctcgacttgt     960

aggtttagca aaacaactct ttattgtagg tcgattctca    1000

cacggcccct accaactttg atcgccagct gcctgtcagg    1040

gaagtacgac gattgtcagt acacaacaga gataggagcg    1080

ctatcttcga gattcatcac agtcaatggt ggagtccttg    1120

caaactgcag agcaattgtg tgtaagtgtg tctcaccccc    1160

gcatataata ccacaaaacg acattggctc cgtaacagtt    1200

attgactcaa gtatatgcaa ggaagttgtc ttagagagtg    1240

tgcagcttag gttagaagga aagctgtcat cccaatactt    1280

ctccaacgtg acaattgacc tttcccaaat cacaacgtca    1320

gggtcgctgg atataagcag tgaaattggt agcattaaca    1360

acacagttaa tcgggtcgac gagttaatca aggaatccaa    1400

cgagtggctg aacgctgtga acccccgcct tgtgaacaat    1440

acgagcatca tagtcctctg tgtccttgcc gccctgatta    1480

ttgtctggct aatagcgctg acagtatgct tctgttactc    1520

cgcaagatac tcagctaagt caaaacagat gaggggcgct    1560

atgacaggga tcgataatcc atatgtaata cagagtgcaa    1600

ctaagatgta g                                   1611
```

<210> SEQ ID NO 27
<211> LENGTH: 1743
<212> TYPE: DNA
<213> ORGANISM: Avian Paramixyvirus Type 2
<220> FEATURE:
<223> OTHER INFORMATION: APMV-2/Chicken/England/7702/06 HN protein

<400> SEQUENCE: 27

```
atggatttcc catctaggga gaacctggca gcaggtgaca      40

tatcggggcg gaagacttgg agattactgt tccggatcct      80

cacattgagc ataggtgtgg tctgtcttgc catcaatatt     120

gccacaattg caaaattgga tcacctggat aacatggctt     160

cgaacacatg gacaacaact gaggctgacc gtgtgatatc     200

tagcatcacg actccgctca aagtccctgt caaccagatt     240

aatgacatgt ttcggattgt agcgcttgac ctacctctgc     280

agatgacatc attacagaaa gaaataacat cccaagtcgg     320

gttcttggct gaaagtatca acaatgtttt atccaagaat     360

ggatctgcag gcctggttct tgttaatgac cctgaatatg     400

caggggggat cgctgtcagc ttgtaccaag gagatgcatc     440

tgcaggccta aatttccagc ccatttcttt aatagaacat     480

ccaagttttg tccctggtcc tactactgct aagggctgta     520

taaggatccc gaccttccat atgggccctt cacattggtg     560
```

ttactcacat aacatcattg catcaggttg ccaggatgcg 600
agccactcca gtatgtatat ctctctgggg gtgctgaaag 640
catcgcagac cgggtcgcct atcttcttga caacggccag 680
ccatctcgtg gatgacaaca tcaaccggaa gtcatgcagc 720
atcgtagcct caaaatacgg ttgtgatatc ctatgcagta 760
ttgtgattga aacagagaat gaggattata ggtctgatcc 800
ggctactagc atgattatag gtaggctgtt cttcaacggg 840
tcatacacag agagcaagat taacacaggg tccatcttca 880
gtctattctc tgctaactac cctgcggtgg ggtcgggtat 920
tgtagtcggg gatgaagccg cattcccaat atatggtggg 960
gtcaagcaga acacatggtt gttcaaccag ctcaaggatt 1000
ttggttactt cacccataat gatgtgtaca agtgcaatcg 1040
gactgatata cagcaaacta tcctggatgc atacaggcca 1080
cctaaaatct caggaaggtt atgggtacaa ggcatcctat 1120
tgtgcccagt ttcactgaga catgatcctg gctgtcgctt 1160
aaaggtgttc aataccagca atgtgatgat gggggcagaa 1200
gcgagggtga tacaagtagg gtcagccgtg tatctatacc 1240
aacgctcatc gacatggtgg gtggtaggac tgacacacaa 1280
attagatgtg tcagaaataa ctagagagag cgggaacatg 1320
gttaacaaag aaagcccaat tggtcgtgca aaattccctc 1360
ggccatcctt ctctcgagat gcttgtgcga gaccaaacat 1400
ctgtccggct gtctgtgttt ctggggtata ccaggacata 1440
tggccaatta gtactgcaca taacttgagc caggtcgttt 1480
gggtaggaca gtacctggag gcattttatg cccgcaagga 1520
tccaagaata gggatagcaa cccagtatga gtggaaagtc 1560
accaaccagc tgttcaattc gaatactgag ggagggtact 1600
caaccacaac atgcttccgg aacaccaaac gggacaaggc 1640
atattgtgta gtgatatcag agtacgctga tggggtgttc 1680
ggatcataca ggatcgttcc tcagcttata gagattagaa 1720
caaccaccgg taaatctgag tga 1743

<210> SEQ ID NO 28
<211> LENGTH: 6729
<212> TYPE: DNA
<213> ORGANISM: Avian Paramixyvirus Type 2
<220> FEATURE:
<223> OTHER INFORMATION: APMV-2/Chicken/England/7702/06 L protein

<400> SEQUENCE: 28
atggatcaaa ctcaagctga cactataata caacctgaag 40
tccatctgaa ttcaccactt gttcgcgcaa aattggttct 80
tctatggaaa ttgactgggt tacctttgcc gtctgatttg 120
agatcatttg tactaactac acatgcagct gatgaccaaa 160
tcgcaaaaaa tgagactagg atcaaggcca aaattaattc 200

```
cctaatcgat aacttaatca aacactgcaa ggcaaggcaa        240
gtggcacttt cagggttgac acctgtcgta catccaacaa        280
ctctacagtg gtcgctaccc atcacttgtg aacgagcagc        320
ccagcctgca aaagtacgcg agaaatcagt taagcaagca        360
atgtcagaga agcaacacgg gtttagacat ctcttttcgg        400
cagtaagtca tcagttagtt ggaaacgcca cactgttctg        440
tgcacaagac tctagcaccg tgaatgtcga ctctccttgc        480
tcatcaggtt gtgagaggct gataatagac tctattggag        520
ccttacaaac acgatggaca agatgtaggt gggcttggct        560
tcacattaaa caggtaatga gataccaggt gcttcagagt        600
cgcctacacg ctcatgccaa ttctgttagc acatggtctg        640
aggcgtgggg gttcattggg atcacaccag atatagtcct        680
tattgtagac tataagagca aaatgtttac tatcctgacc        720
ttcgaaatga tgctgatgta ttcagatgtc atagagggtc        760
gtgataatgt ggtagctgta ggaagtatgt caccaaacct        800
acagcctgtg gtggagagga ttgaggtgct gtttgatgta        840
gtggacacct tggcgaggag gattcatgat cctatttatg        880
atctggttgc tgccttagaa agcatggcat acgctgccgt        920
ccaattgcac gatgctagtg agacacacgc aggggaattc        960
ttttcgttca atttgacaga aatagagtcc actcttgccc       1000
ccttgctgga tcctggccaa gtcctatcgg tgatgaggac       1040
tatcagttat tgttacagtg ggctatcgcc tgaccaagct       1080
gcagagttgc tctgtgtgat gcgcttattt ggacaccctc       1120
tgctctccgc acaacaagca gccaaaaaag tccgggagtc       1160
tatgtgtgcc cctaaactgt tagagcatga tgcaatactg       1200
caaactctat ctttcttcaa gggaatcata atcaatggct       1240
acaggaaaag tcattctgga gtatggcctg caattgaccc       1280
agattctata gtggacgatg accttagaca gctgtattac       1320
gagtcggcag aaatttcaca tgctttcatg cttaagaaat       1360
atcggtacct tagtatgatt gagttccgca agagcataga       1400
gtttgactta aatgatgacc tgagcacatt ccttaaagac       1440
aaagcaatct gcaggccaaa agatcaatgg gcacgcatct       1480
tccggaaatc tcagttccca cttaaattgg acaatcgcac       1520
tagtggagtg gacaaaagca acaggttgct cattgatttt       1560
cttgaatcac atgattttag cccagaagaa gagatgaagt       1600
atgtgagaac aaaagcatac ctagaggatg atcaattctc       1640
tgcatcctac tctctcaagg aaaaggagat taaaacaaca       1680
ggccggatat ttgcaaagat gacaaggaaa gtgaggaggt       1720
gtcaagtatt catgggatcc ctcttatccg gccatgtgtg       1760
```

-continued

```
taagttcttc aaagagaatg gagtatccat ggaacagctt          1800

tccttaacaa agagcctgct tgcaatgtca caattatcac          1840

ccaggatctc tcccgtgagg aacgaaccag ctagtacaca          1880

ggaccgactt gtcaggtact ccaatgggac ccatctctgt          1920

gcaggggagt taaaaccaca tcaaagggag aggcctgtca          1960

agaaaagcat agtagcaaca ttcctcacaa ctgacctaca          2000

gaaatattgc ctcaactgga gatacgggag cattaagctg          2040

ttcgcacaag cattgaatca actctttggt ctagatcacg          2080

gcttcgaatg gatccacctt cggttgatga atagcacact          2120

gtttgtgggt gaccccttt ctccccctga gtgcaaaggg          2160

gtaaaggatc ttgatgatgc tcctaattcg gacatattta          2200

tcgtgtccgc tagaggaggg atagaaggac tgtgccttaa          2240

gctctggact atgatctcta ttagcatcat tcactgtgtc          2280

tcggagaaaa ttggtacaag ggtagcagca atggtacagg          2320

gagacaacca agtcatagcc ataacgagag aattattcaa          2360

tggagagact ttcgaacaaa tccaacccga attagacagg          2400

ctaggtaatg cattcttctc agagttcaaa caacacaatt          2440

acgcaatggg gcacaatcta aagccgaaag agaccatcca          2480

aagtcaatca tttttgtct actccaagcg aatttttgg          2520

gagggtagaa ttttaagcca atcacttaag aatgctacta          2560

aactctgttt cattgcagac catctaggag ataatactgt          2600

gtcatcatgc agcaatctcg cctctactgt cacaagcttg          2640

gtagagaagg gattcgagaa ggacacggcc tttgtactaa          2680

atctcatcta ctccatgact caaatactta tagatgagca          2720

gtattcgctg cagggagact acacagctgt gaagggtttg          2760

ataggaacag acaaccatag aaatttctca ctggctgctt          2800

taatacctgg acaagtgggc ggttataatt tcttgaacat          2840

cagcaggctg tttacaagga atattggaga tccagtgaca          2880

tgtgcaattg cagacatcaa atggttcatc aagagcagac          2920

tgatcgcaga gcacgtgttg aagaacattc tacttaggga          2960

cccaggagat ggcggctgga gcactctctg tgcagacccg          3000

tatgctctta atatccctta tacccaatta cccactactt          3040

acctcaagaa gcacacccag agatcactat tagcagactc          3080

aaataatccc attgttgcag ggtccagct tgactctcaa          3120

tatattgagg aggaagaatt cgctcaattc cttcttgata          3160

gagaagcagt gatgccacat ttagcacaca caataatgga          3200

aacaagcatc ctagggaaga gaaagaatat acaaggccta          3240

atagacacca cgcctaccat cattaaaaca gctctgatgc          3280

gccaacctat ctccaggaga aagtgtgaga agatcataaa          3320

ctattcaatt aattacttag ttgaatgtca tgactcatca          3360
```

-continued

```
tcgtcgatta ggacattcga accacgaaag gaagtcatct                 3400
gggattcagc aatgatctca gtcgagacat gcagtgtcac                 3440
catcgcggaa ttcctacgtg ccaccagttg gtcgaatatt                 3480
ctgaacggta gaacaatatc gggtgtaaca tctcctgata                 3520
ctgtagagct actccggggc tcactcatcg gagagaatac                 3560
acactgtgtt ctttgtgagc agggtgatga tacttttacc                 3600
tggatgcata tatcaggacc aacatacata ccagatcctg                 3640
gactcaccgg ttcaaaaatg cgtgtgccat atcttgggtc                 3680
aaagactgaa gaaaggaggt cagcctctat ggcaactgtt                 3720
aaagggatgt ctcatcatct aaaagccacc ttgcgaggag                 3760
cctctgtgat ggtgtgggcc tttggtgata ctgaagaaag                 3800
ttgggaacat gcctgccttg tggccaatac aaggtgcaag                 3840
attaatcttc cgcagctacg cctgctgacc ccgacaccaa                 3880
gcagctctaa catccaacat cgactaaatg atggtatcag                 3920
cgtgcaaaaa tttacacctg ctagcttatc ccgagtggcg                 3960
tcatttgttc acatttgcaa cgatttccaa aagctagaga                 4000
gagatggatc ttccgtagac tctaacttga tatatcagca                 4040
aatcatgctg actggtctaa gtattatgga gacacttcat                 4080
cctatgcacg tctcatgggt atacaacaat cagacaattc                 4120
acttacatac cggaacatcg tgttgtccta gggaaataga                 4160
gacaagcatt gttaatcccg ctaggggaga attcccaaca                 4200
ataactctca caactaacaa tcagtttctg tttgattgta                 4240
atcccataca tgatgaggca cttacaaaac tgtcagtaag                 4280
tgagttcaag ttccaggagc ttaatataga ctcaatgcag                 4320
ggttacagtg ctgtgaacct gctgagcaga tgtgtggcta                 4360
agctgatagg ggaatgcatt ctggaagacg gtatcggatc                 4400
gtcaatcaag aatgaagcaa tgatatcatt tgataactct                 4440
atcaactgga tttctgaagc actcaatagt gacctgcgtt                 4480
tggtattcct ccagctgggg caagaactac tttgtgacct                 4520
ggcgtaccaa atgtactatc tgagggtcat cggctatcat                 4560
tccatcgtgg catatctgca gaatactcta gaaagaattc                 4600
ctgttatcca actcgcaaac atggcactca ccatatccca                 4640
cccagaagta tggaggagag tgacagtgag cggattcaac                 4680
caaggttacc ggagtcccta tctggccact gtcgacttta                 4720
tcgccgcatg tcgtgatatc attgtgcaag gtgcccagca                 4760
ttatatggct gatttgttgt caggagtaga gtgccaatat                 4800
acattcttta atgttcaaga cggcgatctg acaccgaaga                 4840
tggaacaatt tttagcccgg cgcatgtgct tgtttgtatt                 4880
gttaactggg acgatccgac cactcccaat catacgatcc                 4920
```

-continued

```
cttaatgcga ttgagaaatg tgcaattctc actcagttct     4960
tgtattacct accgtcagtc gacatggcag tagcagacaa     5000
ggctcgtgtg ttatatcaac tgtcaataaa tccgaaaata     5040
gatgctttag tctccaacct ttatttcacc acaaggaggg     5080
tgctttcttg tatcacggga gattcttctt cacgagcgca     5120
cattgcattc ctctacgagg aggaagtaat cgttgatgtg     5160
cctgcatcta atcaatttga tcagtaccat cgtgacccca     5200
tcctaagagg aggtctattt ttctctctct ccttaaaaat     5240
ggaaaggatg tctctgaacc gatttgcagt acagaccctg     5280
ccaacccagg ggtctaactc gcagggttca cgacagacct     5320
tgtggcgtgc ctcaccgtta gcacactgcc ttaaatcagt     5360
agggcaggta agtaccagct ggtacaagta tgctgtagtg     5400
ggggcgtctg tagagaaagt ccaaccaaca agatcaacaa     5440
gcctctacat cggggagggc agtgggagtg tcatgacatt     5480
attagagtat ctggaccctg ctacaattat cttctacaac     5520
tcgctattca gcaatagcat gaaccctcca caaaggaatt     5560
tcggactgat gcccacacag tttcaggact cagtcgtgta     5600
taaaaacata tcagcaggag ttgactgcaa gtacgggttt     5640
aagcaagtct ttcaaccatt atggcgtgat gtagatcaag     5680
aaacaaatgt ggtagagacg gcgttcctaa actatgtgat     5720
agaagtagtg ccagtccact cttcgaagcg tgtcgtatgt     5760
gaagttgagt ttgacagggg gatgcctgac gagatagtaa     5800
taacagggta catacacgtg ctgatggtga ccgcatacag     5840
tctgcatcga ggagggcgtc taataatcaa ggtctatcgt     5880
cactccgagg ctgtattcca attcgtactc tctgcgatag     5920
tcatgatgtt tggggggctt gatatacacc ggaactcgta     5960
catgtcaact aacaaagagg agtacatcat catagctgcg     6000
gcgccggagg cattaaacta ttcctctgta ccagcaatat     6040
tgcagagggt gaagtctgtt attgaccagc agcttacatt     6080
aatctctcct atagatctag aaagattgcg ccatgagact     6120
gagtctctcc gtgagaagga gaataatcta gtaatatctc     6160
tgacgagagg gaagtatcaa ctccggccga cacagactga     6200
tatgcttcta tcatacctag gtgggagatt catcacccta     6240
ttcggacagt ctgctaggga tttgatggcc actgatgttg     6280
ctgaccttga tgctaggaag attgcattag ttgatctact     6320
gatggtggaa tccaacatta ttttaagtga gagcacagac     6360
ttggaccttg cactgttgct gagcccgttt aacttagaca     6400
aagggcggaa gatagttacc ctagcaaagg ctactacccg     6440
ccaattgctg cccgtgtata tcgcatcaga gataatgtgc     6480
aatcggcagg cattcacaca cctgacatca attatacagc     6520
```

gtggtgtcat aagaatagaa aacatgcttg ctacaacgga 6560
atttgtccga cagtcagttc gcccccagtt cataaaggag 6600
gtgataacta tagcccaagt caaccacctt ttttcagatc 6640
tatccaaact cgtgctttct cgatctgaag tcaagcaagc 6680
acttaaattt gtcggttgct gtatgaagtt cagaaatgca 6720
agcaattaa 6729

<210> SEQ ID NO 29
<211> LENGTH: 1374
<212> TYPE: DNA
<213> ORGANISM: Avian Paramixyvirus Type 2
<220> FEATURE:
<223> OTHER INFORMATION: APMV-2/Gadwell/Kenya/3/80 NP protein

<400> SEQUENCE: 29
atgtcgtctg tatttactga gtaccaggct ctgcaagatc 40
aactggtcaa gccttcatcc aggagggcag atgtcgcttc 80
aactggattg ctcagagctg agataccagt gtgtgtcaca 120
ctctctcagg accctacaga caggtggaac ctagcgtgtc 160
tcaacttgcg gtggatcata agcgagtcct caacaacacc 200
aatgagagca ggggcaatac tctctttgct cagcttacat 240
tctgacaaca tgagggcaca cgcaaccctt gctgcacggt 280
cagcagatgc atcaatcacg atccttgagg tggacaacat 320
tgacatggca gctgacacaa taacattcaa tgcaagaagc 360
ggtgtgtcgg acagaagaag tgctcaactc atggccattg 400
caaaggacct accacgatca tgttctaatg attcaccgtt 440
taaggacaac aacattgagg accgagaacc ccttgccctg 480
tccgagacga tcgatagaca ggaggaaatt gctgcccaaa 520
tctggatagc ggccatcaag agcatgactg ccccggatac 560
tgctgcggag tcagaaggca agaggcttgc aaagtaccaa 600
caacaaggcc gcttggtgcg acaggtgtta gtgcatgatg 640
cggtgcgtgc ggaattccta cgtgtcatca gaggcagcct 680
ggtcttaccg caattcatgg tatcagaatg taagagggca 720
gcatccatgg gtagcgagac ctctagcccc cacgctatgg 760
tgggtgacat cagcctctac acccataatg caggacttac 800
cgccttcttc ttgacactca gatttggtat tgggacacac 840
taccccactc ttgccatgag tgtgttctct ggagaactga 880
agaagatgtc gtccttgatc aggctgtata agtcaaaagg 920
ggaaaatgct gcatacatgg cattcctgga ggatgcggac 960
atgggaaact ttgcgcctgc taactttagt actctctact 1000
cctatgcaat gggggtaggt acagtgctgg aagcatcagt 1040
tgcgaaatac cagttcgctc gagagttcac cagtgagaca 1080
tacttcaggc ttggggttga gaccgcacag aaccaacagt 1120

-continued gcgctctaga tgaaaagacc gccaaggaga tggggcttac 1160
tgatgaagcc agaaagcagg tgcaagcatt ggctagcaac 1200
atcgagcagg ggcaacattc aatgcccatg caacaacagc 1240
ccacattcat gagtcagccc taccaggatg acgatcgtga 1280
ccagccaagc accagcagac cagagccaag accatcgcaa 1320
ttgacaagcc aatcagcagc acaggacaat gatgcggcct 1360
cattagattg gtga 1374

<210> SEQ ID NO 30
<211> LENGTH: 1200
<212> TYPE: DNA
<213> ORGANISM: Avian Paramixyvirus Type 2
<220> FEATURE:
<223> OTHER INFORMATION: APMV-2/Gadwell/Kenya/3/80 P protein

<400> SEQUENCE: 30
atggagttca ccgatgatgc cgaaattgct gagctgttgg 40
acctcgggac ctcagtgatc caagagctgc agcgagccga 80
agtcaagggc ccgcaaacaa ccggaaagcc caaagttccc 120
ccggggaaca ctaagagcct ggctactctc tgggagcatg 160
agactagcac ccaagggagt gcattgggca cacccgagaa 200
caacacccag gcacccgatg acaacaacgc aggtgcagat 240
acgccagcga ctaccgacgt ccatcgcact ctggatacca 280
tagacaccga cacaccaccg gaagggagca agcccagctc 320
cactaactcc caacccggtg atgaccttga caaggctctt 360
tcgaagctag aggcgcgcgc caagctcgga ccagataggg 400
ccagacaggt taaaaagggg aaggagatcg ggtcgagcac 440
agggacgagg gaggcagcca gtcaccacat ggaagggagc 480
cgacagtcgg agccaggagc gggcagccga gcacagccac 520
aaggccatgg cgaccgggac acaggaggga gtactcattc 560
atctctcgag atgggagact ggaagtcaca agctggtgca 600
acccagtctg ctctcccatt agaagcgagc ccaggagaga 640
aaagtgcaca tgtggaactt gcccagaatc ctgcatttta 680
tgcaggcaac ccaactgatg caattatggg gttgacaaag 720
aaagtcaatg atctaaagac aaaattggct gaggtattgc 760
gtctgttagg aatactcccc ggaataaaga atgagattag 800
tcagctgaaa gcaaccgtgg ctctgatgtc aaatcagatt 840
gcctccattc agattcttgg tcctgggaat gccggagtca 880
aatcccttaa tgagatgaaa gccctgtcaa aagcagccag 920
catagttgtg gcaggtccag gagtccttcc tcctgaggtc 960
acagaaggag gactgatcgc gaaagatgag ctagcaaggc 1000
ccatccccat ccaaccgcaa cgagactcca aacccaaaga 1040
cgacccgcac acatcaccaa atgatgtcct tgctgtacgc 1080
gctatgatcg acacccttgt ggatgatgag aagaagagaa 1120
agagattaaa ccaggccctt gacaaggcaa agaccaagga 1160
tgacgtctta agggtcaagc ggcagatata caatgcctag 1200

<210> SEQ ID NO 31
<211> LENGTH: 699
<212> TYPE: DNA
<213> ORGANISM: Avian Paramixyvirus Type 2
<220> FEATURE:
<223> OTHER INFORMATION: APMV-2/Gadwell/Kenya/3/80 V protein

<400> SEQUENCE: 31
atggagttca ccgatgatgc cgaaattgct gagctgttgg 40
acctcgggac ctcagtgatc caagagctgc agcgagccga 80
agtcaagggc ccgcaaacaa ccggaaagcc caaagttccc 120
ccggggaaca ctaagagcct ggctactctc tgggagcatg 160
agactagcac ccaagggagt gcattgggca cacccgagaa 200
caacacccag gcacccgatg acaacaacgc aggtgcagat 240
acgccagcga ctaccgacgt ccatcgcact ctggatacca 280
tagacaccga cacaccaccg gaagggagca agcccagctc 320
cactaactcc caacccggtg atgaccttga caaggctctt 360
tcgaagctag aggcgcgcgc caagctcgga ccagataggg 400
ccagacaggt taaaaagggg gaaggagatc gggtcgagca 440
cagggacgag ggaggcagcc agtcaccaca tggaagggag 480
ccgacagtcg gagccaggag cgggcagccg agcacagcca 520
caaggccatg gcgaccggga cacaggaggg agtactcatt 560
catctctcga gatgggagac tggaagtcac aagctggtgc 600
aacccagtct gctctcccat tagaagcgag cccaggagag 640
aaaagtgcac atgtggaact tgcccagaat cctgcatttt 680
atgcaggcaa cccaactga 699

<210> SEQ ID NO 32
<211> LENGTH: 624
<212> TYPE: DNA
<213> ORGANISM: Avian Paramixyvirus Type 2
<220> FEATURE:
<223> OTHER INFORMATION: APMV-2/Gadwell/Kenya/3/80 W protein

<400> SEQUENCE: 32
atggagttca ccgatgatgc cgaaattgct gagctgttgg 40
acctcgggac ctcagtgatc caagagctgc agcgagccga 80
agtcaagggc ccgcaaacaa ccggaaagcc caaagttccc 120
ccggggaaca ctaagagcct ggctactctc tgggagcatg 160
agactagcac ccaagggagt gcattgggca cacccgagaa 200
caacacccag gcacccgatg acaacaacgc aggtgcagat 240
acgccagcga ctaccgacgt ccatcgcact ctggatacca 280
tagacaccga cacaccaccg gaagggagca agcccagctc 320
cactaactcc caacccggtg atgaccttga caaggctctt 360

| | |
|---|---|
| tcgaagctag aggcgcgcgc caagctcgga ccagataggg | 400 |
| ccagacaggt taaaaagggg ggaaggagat cgggtcgagc | 440 |
| acagggacga gggaggcagc cagtcaccac atggaaggga | 480 |
| gccgacagtc ggagccagga gcgggcagcc gagcacagcc | 520 |
| acaaggccat ggcgaccggg acacaggagg gagtactcat | 560 |
| tcatctctcg agatgggaga ctggaagtca caagctggtg | 600 |
| caacccagtc tgctctccca ttag | 624 |

<210> SEQ ID NO 33
<211> LENGTH: 1110
<212> TYPE: DNA
<213> ORGANISM: Avian Paramixyvirus Type 2
<220> FEATURE:
<223> OTHER INFORMATION: APMV-2/Gadwell/Kenya/3/80 M protein

<400> SEQUENCE: 33

```
atggctcaaa caaccgtcag gctgtatatc gatgaagcta                     40
gtcccgacat tgaactgttg tcttacccac tgataatgaa                     80
agacacagga catgggacca aagagttgca gcagcaaatc                    120
agagttgcag agatcggtgc attgcaggga gggaagaatg                    160
aatcagtttt catcaatgca tatggctttg ttcagcaatg                    200
caaagttaaa ccgggggcaa cccaattctt ccaggtagat                    240
gcagctacaa agccagaagt gatcactgcg gggatgataa                    280
taattgctgc agcgaaggga ggcaccggta tcactaagct                    320
ggcagaagag gtgttcgagc tggacatctc catcaagaag                    360
tccgcatcat tccatgagaa ggttgcggtg tcctttaata                    400
ctgtgccact atcactcatg aattcgaccg catgcagaaa                    440
tctgggttat gtcacaaacg ctgaggaggc gatcaaatgc                    480
ccgagcaaaa tacaagcggg tgtgacgtac aaatttaaga                    520
taatgtttgt ctccttgaca cgactgcata acgggaaatt                    560
gtaccgtgtc cccaaggcag tgtatgctgt agaggcatca                    600
gctctatata aagtgcaact ggaagtcggg ttcaagcttg                    640
acgtggccaa ggatcaccca cacgttaaga tgttgaagaa                    680
agtggaacgg aatggtgaga ctctgtatct tggttatgca                    720
tggttccacc tgtgcaactt caagaagaca aatgccaagg                    760
gtgagtcccg gacaatctcc aacctagaag gcaaagtcag                    800
agctatgggg atcaaggttt ccttgtacga cttatggggg                    840
cctactaagg tggtgcaaat cacaggtaag accagcaagt                    880
atgcacaagg tttcttttca accacaggta cctgctgcct                    920
cccagtgtcg aaggctgccc ctgagctggc caaacttatg                    960
tggtcctgca atgcaacaat cgttgaagct gcagtgatta                   1000
tccaagggag tgataggagg gcagtcgtga cctcagagga                   1040
cttggaagta tacggggcag ttgcaaaaga gaagcaggct                   1080
gcaaaaggat ttcacccgtt ccgcaagtga                              1110
```

<210> SEQ ID NO 34
<211> LENGTH: 1611
<212> TYPE: DNA
<213> ORGANISM: Avian Paramixyvirus Type 2
<220> FEATURE:
<223> OTHER INFORMATION: APMV-2/Gadwell/Kenya/3/80 F protein

<400> SEQUENCE: 34

```
atgaatcaag cactcgtgat tttgttggta tctttccagc      40
tcggcgttgc cttagataac tcagtgttgg ctccaatagg      80
agtagctagc gcacaggagt ggcaactggc ggcatatacg     120
acgaccctca cagggaccat cgcagtgaga tttatcccgg     160
tcctgcctgg gaacctatca acatgtgcac aggagacgct     200
gcaggaatat aatagaactg tgactaatat cttaggcccg     240
ttgagagaga acttggatgc tctcctatct gacttcgata     280
aacctgcatc gaggttcgtg ggcgccatca ttgggtcggt     320
ggccttgggg gtagcaacag ctgcacaaat cacagccgcc     360
gtggctctca atcaagcaca agagaatgcc cggaatatat     400
ggcgtctcaa ggaatcgata aagaaaacca atgcggctgt     440
gttggaattg aaggatggac ttgcaacgac tgctatagct     480
ttggacaaag tgcaaaagtt tatcaatgat gatattatac     520
cacagattaa ggacattgac tgccaggtag ttgcaaataa     560
attaggcgtc tacctctcct tatacttaac agagcttaca     600
actgtatttg gttctcagat cactaatcct gcattatcaa     640
cgctctctta ccaggcgctg tacagcttat gtggaggga      680
tatgggaaag ctaactgagc tgatcggtgt cattgcaaag     720
gatgtgggat ccctctacga ggttaacctc ataaccggcc     760
aaatcgttgg atatgaccct gaactacaga taatcctcat     800
acaagtatct tacccaagtg tgtctgaagt gacaggagtc     840
cgggctactg agttagtcac tgtcagtgtc actacaccaa     880
aaggagaagg gcaggcaatt gttccgagat atgtggcaca     920
gagtagagtg ctgacagagg agttggatgt ctggatttgt     960
aggtttagca aaacaagggt gtattgtaag tcgattctca    1000
cacggcccct accaactttg atcgccagct gcctgtcagg    1040
gaagtacgac gattgtcagt gcacaacaga gataggagcg    1080
ctatcttcga gattcatcac agtcaatggt ggagtccttg    1120
caaactgcag agcaagggtg tgtaattgtg tctcaccccc    1160
gcatataata ccacaaaacg acattggctc cgtaacagtt    1200
attgactcaa gtatatgcaa ggaagttgtc ttagagagtg    1240
tgcagcttag gttagaagga aagctgtcat cccaatactt    1280
ctccaacgtg acaattgacc tttcccaaat cacaacgtca    1320
gggtcgctgg atataagcag tgaaattggt agcattaaca    1360
```

-continued

```
acacagttaa tcgggtcgac gagttaatca aggaatccaa                       1400

cgagtggctg aacgctgtga acccccgcct tgtgaacaat                       1440

acgagcatca tagtcctctg tgtccttgcc gccctgatta                       1480

ttgtctggct aatagcgctg acagtatgct tctgttactc                       1520

cgcaagatac tcagctaagt caaaacagat gaggggcgct                       1560

atgacaggga tcgataatcc atatgtaata cagagtgcaa                       1600

ctaagatgta g                                                      1611


<210> SEQ ID NO 35
<211> LENGTH: 1749
<212> TYPE: DNA
<213> ORGANISM: Avian Paramixyvirus Type 2
<220> FEATURE:
<223> OTHER INFORMATION: APMV-2/Gadwell/Kenya/3/80 HN protein

<400> SEQUENCE: 35

atggatgcac ggtcaaggga gaatctcact gaacttggcc                         40

aagggggacg acgaacctgg ctcatgctat ttcgggttct                         80

aactctggcc ttgacattag catgcttagc tatcaacata                        120

gccactatag ccaagctgga tagcattgac acaggtagac                        160

tgcagacatg gaccaccgct gaatcagata gggtaatcgg                        200

ctctctcact gacactctaa aggtgcccat taaccaagta                        240

aatgacatgt ttagaatcgt tgccttggat cttcctctcc                        280

agatgaccac acatcaaaaa gagatcgctt cacaggtggg                        320

ctttcttgct gaaagtatca atagtgtctt gtcaaagaac                        360

ggatcagcag ggttggtcct aattaacgac ccagagtatg                        400

cgggcggtat aggggtgagc ttatttcagg gcgactctgc                        440

atctagcctt gactttgaag aaccgcacct aattgaacac                        480

ccgagtttta tcccggggcc cacgacggcg aagggttgta                        520

tcaggatccc gaccttccat atgtccgcat cacattggtg                        560

ctattctcac aacataattg catcaggatg ccaggatgcc                        600

ggccactcca gtatgtacat atcattggga gttttgaaag                        640

ccacacaggc cgggtctccg agttttctga caacagccag                        680

ccagcttgtg gatgataagc tcaacaggaa atcatgcagt                        720

ataatctcca caacatatgg gtgtgacatc ctgtgtagtc                        760

tagtggttga aaatgaggat gctgactacc gatctgatcc                        800

cccaactgac atgatcctag gccgactctt cttcaacgga                        840

acatattctg agaggaagct gaatacaggt acaatcttcc                        880

agctttttc cgcaaattat ccagcagtag ggtccggttt                         920

agtattggga gatgaaattg cgttccctgt gtatgggggt                        960

gtgagacaaa atacatggtt gtttaatcag ctgaaggacc                       1000

atggttactt cgctcacaat gatgtgtata agtgtaataa                       1040

aagtgatacc catcagactg tccttaatgc atatcgacca                       1080

cctaaaatat caggaaggtt gtggtcgcag gtcgtgctga                       1120
```

```
tctgtccact gggattgttc attaatactg actgcaggat                    1160

caaagtgttc aatactagca ctgtcatgat gggtgcagaa                    1200

gcaagactga ttcaagtggg gtccgacatt tacctgtacc                    1240

agaggtcatc atcgtggtgg gtggtcggac tgacctataa                    1280

acttgatttc caggaattgt catcaaagac gggaaatgtt                    1320

ataaataaag tatccccgat tgctcacgca aagttccctc                    1360

gtccttcctt ctctcgtgat gcctgtgcaa ggccaaacat                    1400

atgtccagca gtctgtgtgt ccggtgtata tcaggacatc                    1440

tggccaatca gtaccgcaca aaacttgagc caggtggttt                    1480

gggtagggca gtatctagaa gcattctatg cccgtaagga                    1520

tccatggatc gggattgcga cccaatacaa ctggaaaaag                    1560

aatgttaggc ttttcaacac aaacactgaa gtcgggtact                    1600

caacaaccac atgtttcagg aatacaaaga gagacaaggc                    1640

attttgtgtc ataatatcag aatatgcaga tggagtcttt                    1680

gggtcatacc gggttgtacc gcagctgatt gaagtcgaaa                    1720

ctactagtaa gaagagactc ttcagttga                                1749
```

<210> SEQ ID NO 36
<211> LENGTH: 6729
<212> TYPE: DNA
<213> ORGANISM: Avian Paramixyvirus Type 2
<220> FEATURE:
<223> OTHER INFORMATION: APMV-2/Gadwell/Kenya/3/80 L protein

<400> SEQUENCE: 36

```
atggaccagg tccaagcaga cacaattatt cagcccgaag                      40

tgcacctaga ctcacctatt gtcagagcga aacttgttct                      80

attttggaaa ttgactggac tcccgctgcc aaaggatcta                     120

agattttttg agtcgctacc cacgccaccg acgagcaaat                     160

tttcaggaat gagtccagaa ttaagtcaaa aatcataccc                     200

tagtgtgccg aatctaatca aacactgcaa ggcaaggcaa                     240

gtggcacttt cagggttgac acctgtcgta catccaacaa                     280

ctctacagtg gttgctatcc atcacatgtg aacgagcaga                     320

ccaccttgca aaagtacgcg agaaatcagt taagcaagca                     360

atgtcagaga agcaacacgg gtttagacat ctcttttcgg                     400

cagtaagtca tcagttagtt ggaaacgcca cactgttctg                     440

tgcacaagac tctagcaccg tgaatgtcga ctctccttgc                     480

tcatcaggtt gtgagaggct gataatagac tctattggag                     520

ccttacaaac acgatggaca agatgtaggt gggcttggct                     560

tcacattaaa caggtaatga gataccaggt gcttcagagt                     600

cgcctacacg ctcatgccaa ttctgttagc acatggtctg                     640

aggcgtgggg gttcattggg atcacaccag atatagtcct                     680

tattgtagac tataagagca aaatgtttac tatcctgacc                     720
```

-continued

```
ttcgaaatga tgctgatgta ttcagatgtc atagagggtc     760
gtgataatgt ggtagctgta ggaagtatgt caccaaacct     800
acagcctgtg gtggagagga ttgaggtgct gtttgatgta     840
gtggacacct tggcgaggag gattcatgat cctatttatg     880
atctggttgc tgccttagaa agcatggcat acgctgccgt     920
ccaattgcac gatgctagtg agacacacgc aggggaattc     960
ttttcgttca atttgacaga aatagagtcc actcttgccc    1000
ccttgctgga tcctggccaa gtcctatctg taactaagac    1040
tatcagtatg tgctacagtt gcctaactcc agaccaggca    1080
gcagagatgt tgtgtatcat gcggttgttt ggccacccct    1120
tattgtcagc acaacaggct gcaaaaaaag tgagagaatc    1160
tatgtgtgct ccaaaattgt tagaacatga cgcaatctta    1200
cagacactgt cattctttaa agggataata atcaatggtt    1240
acaggaaaag ccattccgga gtgtggccca atattgagcc    1280
agaatcgatc atggatgatg attttagtca actgtattac    1320
gagtctgctg aaatatcaca ctcttttatg ctcaaaaaat    1360
accgttatct cagtatgatt gaattcaaga agagtataga    1400
ttttgacctg aacgatgacc tcagcacatt cttaaaagat    1440
aaagctatat gccgccccaa gagccagtgg gccaagatat    1480
ttcggaaatc gctattcccc ctcaaaatga caattgatag    1520
cggggcggac acaagaagca ataggttact catcgatttt    1560
ttagagtcac atgattttag tcctgaagaa gagatgaagt    1600
atgtgaccac aatggcatac ttagaagatg aacaattttc    1640
cgcatcttac tccctcaagg aaaaggagat aaagactaca    1680
ggccgaatat ttgcaaaaat gacaaggaaa atgaggagct    1720
gtcaagtgat actcgaatcc ctattatcta gccatgtatg    1760
taaattcttc aaagagaatg ggtgtctat ggaacagcta    1800
tccttgacaa agagtctatt ggcaatgtca cagctgtccc    1840
ccagaatctc tgctgtgaga aacgaaccag ctagaaacag    1880
gaaggtgatc tgcaccgaca accaagtgtc cgatcacatt    1920
gtaggagaag taggcccaca ccagcaggac agaccggccc    1960
ggaagagtgt agtcgcaacc ttccttacaa cagatcttca    2000
aaaatattgc ttgaactggc gatatgggag tatcaagctt    2040
ttcgcccaag ccttaaacca gctattcgga atcgagcatg    2080
ggtttgaatg gatacacctg agactgatga atagcaccct    2120
gtttgtcggg gacccattct cgcctcctga aagcaaagtg    2160
ctgagtgatc ttgatgatgc gcccaattca gacatattta    2200
tcgtgtccgc cagagggggg attgaagggt tatgccagaa    2240
gctgtggacc atgatttcaa taagcataat ccattgcgtg    2280
gctgagaaga taggagcaag ggttgcggcg atggttcagg    2320
```

```
gagataatca ggtaattgca atcacgagag agctgtataa 2360
gggagagact tacacgcaga ttcagccgga gttagatcga 2400
ttaggcaatg catttttttgc tgaattcaaa agacacaact 2440
atgcaatggg acataatctg aagcccaaag agacaatcca 2480
aagtcaatca ttctttgtgt attcgaaacg gattttctgg 2520
gaagggagaa ttcttagtca agcactgaag aatgctacca 2560
aactatgctt cattgcagat cacctcgggg ataatactgt 2600
ctcatcatgc agcaatctag cctctacgat aacccgcttg 2640
gttgagaatg ggtatgaaaa ggacacagca ttcattctga 2680
atctcatttc tcccatgacc cagatcctta tggacgagca 2720
gtactctctg cagggagatt atagcagcgt gaagggactg 2760
ataggaacac ataatcatag gaatttacta agggcggctt 2800
tgatacctgg acaggttggt ggttataact tcttgaacat 2840
cagcaggcta ttcacaagaa acattggaga cccggtgacg 2880
tgtgcaatag cagatattaa atggttcatt aagagtagac 2920
tgattgcaga gcatgttttg aaaaacatcc tgctcaggga 2960
cccaggagat ggtggttgga gtaccctctg cgcagatcca 3000
tatgccctca atatccctta tactcagttg cctactactt 3040
accttaagaa acacacccag agagcgctat tagcagactc 3080
aaataaccca ttattggcag gagttcaact tgactcacag 3120
tacattgaag aagaggaatt tgctcagttt ctccttgatc 3160
gggaggcggt tatgccacgg gtcgcacata caataatgga 3200
ggcaagcatc ctagggaaga gaaagaatat acaaggccta 3240
atagacacta cgcctaccat catcaaaaca gctctgatgc 3280
gccagcctat ttctaggagg aagtgtgaga agattgtaaa 3320
ttactcaatc aattacttag ttgaatgcca tgattccatc 3360
atctcagctc ggcagtttga accgcgaaaa gaggtcatct 3400
gggattcagc aatgatctca gtcgaaacat gcagtgtcac 3440
aattgcggag ttcctgcgcg ccaccagctg gtccaacatc 3480
ctgaacggta ggactatttc gggtgtaaca tctccagaca 3520
ctatagagct gctcaagggg tcattaattg gagagaatgc 3560
ccattgtatt ctttgtgagc agggagacga gacattcacg 3600
tggatgcact tagccgggcc catctatata ccagacccgg 3640
gggtgaccgc atccaagatg agagtgccgt atcttgggtc 3680
aaagacagag gaaaggcgta cggcatccat ggccaccatt 3720
aagggcatgt ctcaccacct aaaggccgct ttgcgaggag 3760
cctctgtgat ggtgtgggcc tttggtgata ctgaagaaag 3800
ttgggaacat gcctgccttg tggccaatac aaggtgcaag 3840
attaatcttc cgcagctacg cctgctgacc ccgacaccaa 3880
```

-continued gcagctctaa catccaacat cgactaaatg atggtatcag 3920
cgtgcaaaaa tttacacctg ctagcttatc ccgagtggcg 3960
tcatttgttc acatttgcaa cgatttccaa aagctagaga 4000
gagatggatc ttccgtagac tctaacttga tatatcagca 4040
aatcatgctg actggtctaa gtattatgga gacactccat 4080
ccaatgcact acgcaaggga tatacaacaa ccaggccatc 4120
catggcacac agggacatct tgttgtcctc gagaaatcga 4160
gaccagcatt gtcaacccgc ctaagtatga attcccaaca 4200
atcaccctca ccactaacaa ccagttcttg tttgacagca 4240
atccaatcca tgatgaggcc atcaccagat taaccgttag 4280
tgactttaaa ttccaggaac taaatattga tgcaattagg 4320
ggttatgctg ctatcaacct gctcagccga tgtgtggcta 4360
agctgatcag tgagtgcata ctggaggatg gtattgggtc 4400
ctcgatcaaa aacgaagcaa tggtgtcatt tgataattct 4440
gtcaattgga tatcagaaat cttacacagt gacatcagac 4480
tttcatttat gcacattgga caagagcttt tatgtgatct 4520
tgcttaccaa atgtactttt ttaagaatca cagggtacca 4560
tgctattatt acttatctga aggcttcact gaaagaattc 4600
cagttatcca acttgcaaac atggccctga caatctcgca 4640
tcctgaagtg tggcgcaggg tgacattaat cggattcaat 4680
caaggttatc gtagcccgta tctagccacc gtggatttta 4720
tagcagcttg cagagatgtc attgtgcagg gtgcacagca 4760
atacctctcc gagttactgt cggaatcaga gtgccaatac 4800
acgttcttta atgtgcaaga tggtgactta acacccaaaa 4840
tggagcaatt cttggccaga aggatgtgcc tgttcgtcct 4880
cctaacaggg acgatcagcc ccctccctat tgtacgatct 4920
cttaacgcga ttgagaaatg tgctgtcttc actcaattct 4960
tatattactt gcccactgtc gatctggcag tagcaagtag 5000
ggcaagaact ctctacacct tatctatcgc tcccaagatt 5040
gacgcattgg tatcaaatct ctacttcacg acgcggaggg 5080
tgctctctaa cataagaggt gacaaacatg cgaaagccca 5120
aatctcttat ctctacgagg agaagatcag tgccgagccg 5160
caccagggtg agaactttga ccagtttatg aaagatccaa 5200
tcataagagg agggttattc ttcactatta tgttgaagat 5240
ggagaaaatg tcacttaatc aatttgctgt ccacaggagg 5280
acaatcctgc agaatatctc caagagaaca tggcagtgcc 5320
tatggcgggc atcacctctg gctcattgtc tcaagtcagt 5360
ggggcaggtt agtaccagct ggtataaata tgctgtatta 5400
caggcatctt taatcagagg ccaaccctta cggtcaacaa 5440
gcgtctacat ggtgaagggc agcggtagtg tgatgacact 5480
atttgaatac atggacccct cagccactat cttctacaac 5520
tctcttttta gcaatagtat gaaccctcca caacggaatt 5560
tcggactgat gcccacacag tttcaggact cagtcgtgta 5600
taagaatcta agtgcagggg ttgagagcaa gtacgggttt 5640
aagcaaacct ttacacccct ctggagagat gtagatcaag 5680
agacaaacgt gacagagact gcattcctca attacgtgat 5720
ggaagtgata ccgattcatt catcaaagcg cctggtgtgt 5760
gaagtggagt tcgacagggg catgcccgac gaggtggtaa 5800
taacagggta tatgaatgtt ctcatggcat ccgcgtacag 5840
cctgcataaa aatgggcgtc taataatcaa gatctttcgt 5880
cactccgagg ctctattcca attgggactc tcggtgatag 5920
tcatgatatt gcatgggctt gatatacacc ggaactcgta 5960
catgtcaact aacaaagagg agtacatcat catagctgcg 6000
gcgccggagg cattaaacta ttcctctgta ccagcaatat 6040
tgcagagggt gaagtctgtt attgaccagc agcttacatt 6080
aatctctcct atagatctag aaagattgcg ccatgagact 6120
gagtctctcc gtgagaagga gaataatcta gtaatatctc 6160
tgacgagagg gaagtatcaa ctccggccga cacagactga 6200
tatgcttcta tcatacctag gtgggagatt catcacccta 6240
ttcggacagt ctgctaggga tttgatggcc actgatgttg 6280
ctgaccttga tgctaggaag attgcattag ttgatctact 6320
gatggtggaa tccaacatta ttttaagtga gagcacagac 6360
ttggaccttg cactgttgct gagcccgttt aacttagaca 6400
aagggcggaa gatagttacc ctagcaaagg ctactacccg 6440
ccaattgctg cccgtgtata tcgcatcaga gataatgtgc 6480
aatcggcagg cattcacaca cctgacatca attatacagc 6520
gtggtgtcat aagaatagaa aacatgcttg ctacaacgga 6560
atttgtccga cagtcagttc gcccccagtt cataaaggag 6600
gtgataacta tagcccaagt caaccacctt ttttcagatc 6640
tatccaaact cgtgctttct cgatctgaag tcaagcaagc 6680
acttaaattt gtcggttgct gtatgaagtt cagaaatgca 6720
agcaattaa 6729

<210> SEQ ID NO 37
<211> LENGTH: 457
<212> TYPE: PRT
<213> ORGANISM: Avian Paramixyvirus Type 2
<220> FEATURE:
<223> OTHER INFORMATION: APMV-2/Chicken/California/Yucaipa/56 NP protein

<400> SEQUENCE: 37

Met Ser Ser Val Phe Ser Glu Tyr Gln Ala Leu Gln Asp Gln Leu
1 5 10 15

Val Lys Pro Ala Thr Arg Arg Ala Asp Val Ala Ser Thr Gly Leu

```
                20                  25                  30

Val Lys Pro Ala Thr Arg Arg Ala Asp Val Ala Ser Thr Gly Leu
                35                  40                  45

Thr Asp Arg Trp Asn Leu Ala Cys Leu Asn Leu Arg Trp Leu Ile
                50                  55                  60

Ser Glu Ser Ser Thr Thr Pro Met Arg Gln Gly Ala Ile Leu Ser
                65                  70                  75

Leu Leu Ser Leu His Ser Asp Asn Met Arg Ala His Ala Thr Leu
                80                  85                  90

Ala Ala Arg Ser Ala Asp Ala Ala Ile Thr Val Leu Glu Val Asp
                95                  100                 105

Ala Ile Asp Met Ala Asp Gly Thr Ile Thr Phe Asn Ala Arg Ser
                110                 115                 120

Gly Val Ser Glu Arg Arg Ser Thr Gln Leu Met Ala Ile Ala Lys
                125                 130                 135

Asp Leu Pro Arg Ser Cys Ser Asn Asp Ser Pro Phe Lys Asp Asp
                140                 145                 150

Thr Ile Glu Asp Arg Asp Pro Leu Asp Leu Ser Glu Thr Ile Asp
                155                 160                 165

Arg Leu Gln Gly Ile Ala Ala Gln Ile Trp Ile Ala Ala Ile Lys
                170                 175                 180

Ser Met Thr Ala Pro Asp Thr Ala Ala Glu Ser Glu Gly Lys Arg
                185                 190                 195

Leu Ala Lys Tyr Gln Gln Gln Gly Arg Leu Val Arg Gln Val Leu
                200                 205                 210

Val His Asp Ala Val Arg Ala Glu Phe Leu Arg Val Ile Arg Gly
                215                 220                 225

Ser Leu Val Leu Arg Gln Phe Met Val Ser Glu Cys Lys Arg Ala
                230                 235                 240

Ala Ser Met Gly Ser Glu Thr Ser Arg Tyr Tyr Ala Met Val Gly
                245                 250                 255

Asp Ile Ser Leu Tyr Ile Lys Asn Ala Gly Leu Thr Ala Phe Phe
                260                 265                 270

Leu Thr Leu Arg Phe Gly Ile Gly Thr His Tyr Pro Thr Leu Ala
                275                 280                 285

Met Ser Val Phe Ser Gly Glu Leu Lys Lys Met Ser Ser Leu Ile
                290                 295                 300

Arg Leu Tyr Lys Ser Lys Gly Glu Asn Ala Ala Tyr Met Ala Phe
                305                 310                 315

Leu Glu Asp Ala Asp Met Gly Asn Phe Ala Pro Ala Asn Phe Ser
                320                 325                 330

Thr Leu Tyr Ser Tyr Ala Met Gly Val Gly Thr Val Leu Glu Ala
                335                 340                 345

Ser Val Ala Lys Tyr Gln Phe Ala Arg Glu Phe Thr Ser Glu Thr
                350                 355                 360

Tyr Phe Arg Leu Gly Val Glu Thr Ala Gln Asn Gln Gln Cys Ala
                365                 370                 375

Leu Asp Glu Lys Thr Ala Lys Glu Met Gly Leu Thr Asp Glu Ala
                380                 385                 390

Arg Lys Gln Val Gln Ala Leu Ala Ser Asn Ile Glu Gln Gly Gln
                395                 400                 405

His Ser Met Pro Met Gln Gln Gln Pro Thr Phe Met Ser Gln Pro
                410                 415                 420
```

```
Tyr Gln Asp Asp Asp Arg Asp Gln Pro Ser Thr Ser Arg Pro Glu
                425                 430                 435

Pro Arg Pro Ser Gln Leu Thr Ser Gln Ser Ala Ala Gln Asp Asn
                440                 445                 450

Asp Ala Ala Ser Leu Asp Trp
                455


<210> SEQ ID NO 38
<211> LENGTH: 399
<212> TYPE: PRT
<213> ORGANISM: Avian Paramixyvirus Type 2
<220> FEATURE:
<223> OTHER INFORMATION: APMV-2/Chicken/California/Yucaipa/56 P protein

<400> SEQUENCE: 38

Met Glu Phe Thr Asp Asp Ala Glu Ile Ala Glu Leu Leu Asp Leu
1               5                   10                  15

Gly Thr Ser Val Ile Gln Glu Leu Gln Arg Ala Glu Val Lys Gly
                20                  25                  30

Pro Gln Thr Thr Gly Lys Pro Lys Val Pro Pro Gly Asn Thr Lys
                35                  40                  45

Ser Leu Ala Thr Leu Trp Glu His Glu Thr Ser Thr Gln Gly Ser
                50                  55                  60

Ala Leu Gly Thr Pro Glu Asn Asn Thr Gln Ala Pro Asp Asp Asn
                65                  70                  75

Asn Ala Gly Ala Asp Thr Pro Ala Thr Thr Asp Val His Arg Thr
                80                  85                  90

Leu Asp Thr Ile Asp Thr Asp Thr Pro Pro Glu Gly Ser Lys Pro
                95                  100                 105

Ser Ser Thr Asn Ser Gln Pro Gly Asp Asp Leu Asp Lys Ala Leu
                110                 115                 120

Ser Lys Leu Glu Ala Arg Ala Lys Leu Gly Pro Asp Arg Ala Arg
                125                 130                 135

Gln Val Lys Lys Gly Lys Glu Ile Gly Ser Ser Thr Gly Thr Arg
                140                 145                 150

Glu Ala Ala Ser His His Met Glu Gly Ser Arg Gln Ser Glu Pro
                155                 160                 165

Gly Ala Gly Ser Arg Ala Gln Pro Gln Gly His Gly Asp Arg Asp
                170                 175                 180

Thr Gly Gly Ser Thr His Ser Ser Leu Glu Met Gly Asp Trp Lys
                185                 190                 195

Ser Gln Ala Gly Ala Thr Gln Ser Ala Leu Pro Leu Glu Ala Ser
                200                 205                 210

Pro Gly Glu Lys Ser Ala His Val Glu Leu Ala Gln Asn Pro Ala
                215                 220                 225

Phe Tyr Ala Gly Asn Pro Thr Asp Ala Ile Met Gly Leu Thr Lys
                230                 235                 240

Lys Val Asn Asp Leu Glu Thr Lys Leu Ala Glu Val Leu Arg Leu
                245                 250                 255

Leu Gly Ile Leu Pro Gly Ile Lys Asn Glu Ile Ser Gln Leu Lys
                260                 265                 270

Ala Thr Val Ala Leu Met Ser Asn Gln Ile Ala Ser Ile Gln Ile
                275                 280                 285

Leu Asp Pro Gly Asn Ala Gly Val Lys Ser Leu Asn Glu Met Lys
                290                 295                 300
```

```
Ala Leu Ser Lys Ala Ala Ser Ile Val Val Ala Gly Pro Gly Val
                305                 310                 315

Leu Pro Pro Glu Val Thr Glu Gly Gly Leu Ile Ala Lys Asp Glu
                320                 325                 330

Leu Ala Arg Pro Ile Pro Ile Gln Pro Gln Arg Asp Ser Lys Pro
                335                 340                 345

Lys Asp Asp Pro His Thr Ser Pro Asn Asp Val Leu Ala Val Arg
                350                 355                 360

Ala Met Ile Asp Thr Leu Val Asp Asp Glu Lys Lys Arg Lys Arg
                365                 370                 375

Leu Asn Gln Ala Leu Asp Lys Ala Lys Thr Lys Asp Asp Val Leu
                380                 385                 390

Arg Val Lys Arg Gln Ile Tyr Asn Ala
                395


<210> SEQ ID NO 39
<211> LENGTH: 227
<212> TYPE: PRT
<213> ORGANISM: Avian Paramixyvirus Type 2
<220> FEATURE:
<223> OTHER INFORMATION: APMV-2/Chicken/California/Yucaipa/56 V protein

<400> SEQUENCE: 39

Met Glu Phe Thr Asp Asp Ala Glu Ile Ala Glu Leu Leu Asp Leu
1               5                   10                  15

Gly Thr Ser Val Ile Gln Glu Leu Gln Arg Ala Glu Val Lys Gly
                20                  25                  30

Pro Gln Thr Thr Gly Lys Pro Lys Val Pro Pro Gly Asn Thr Lys
                35                  40                  45

Ser Leu Ala Thr Leu Trp Glu His Glu Thr Ser Thr Gln Gly Ser
                50                  55                  60

Ala Leu Gly Thr Pro Glu Asn Asn Thr Gln Ala Pro Asp Asp Asn
                65                  70                  75

Asn Ala Gly Ala Asp Thr Pro Ala Thr Thr Asp Val His Arg Thr
                80                  85                  90

Leu Asp Thr Ile Asp Thr Asp Thr Pro Pro Glu Gly Ser Lys Pro
                95                  100                 105

Ser Ser Thr Asn Ser Gln Pro Gly Asp Asp Leu Asp Lys Ala Leu
                110                 115                 120

Ser Lys Leu Glu Ala Arg Ala Lys Leu Gly Pro Asp Arg Ala Arg
                125                 130                 135

Glu Gly Asp Arg Val Glu His Arg Asp Glu Gly Gly Ser Gln Ser
                140                 145                 150

Pro His Gly Arg Glu Pro Thr Val Gly Ala Arg Ser Gly Gln Pro
                155                 160                 165

Ser Thr Ala Thr Arg Pro Trp Arg Pro Gly His Arg Arg Glu Tyr
                170                 175                 180

Ser Phe Ile Ser Arg Asp Gly Arg Leu Glu Val Thr Ser Trp Cys
                185                 190                 195

Asn Pro Val Cys Ser Pro Ile Arg Ser Glu Pro Arg Arg Glu Lys
                200                 205                 210

Cys Thr Cys Gly Thr Cys Pro Glu Ser Cys Ile Leu Cys Arg Gln
                215                 220                 225

Pro Asn
```

<210> SEQ ID NO 40
<211> LENGTH: 207
<212> TYPE: PRT
<213> ORGANISM: Avian Paramixyvirus Type 2
<220> FEATURE:
<223> OTHER INFORMATION: APMV-2/Chicken/California/Yucaipa/56 W protein

<400> SEQUENCE: 40

```
Met Glu Phe Thr Asp Asp Ala Glu Ile Ala Glu Leu Leu Asp Leu
1               5                   10                  15

Gly Thr Ser Val Ile Gln Glu Leu Gln Arg Ala Glu Val Lys Gly
                20                  25                  30

Pro Gln Thr Thr Gly Lys Pro Lys Val Pro Pro Gly Asn Thr Lys
                35                  40                  45

Ser Leu Ala Thr Leu Trp Glu His Glu Thr Ser Thr Gln Gly Ser
                50                  55                  60

Ala Leu Gly Thr Pro Glu Asn Asn Thr Gln Ala Pro Asp Asp Asn
                65                  70                  75

Asn Ala Gly Ala Asp Thr Pro Ala Thr Thr Asp Val His Arg Thr
                80                  85                  90

Leu Asp Thr Ile Asp Thr Asp Thr Pro Pro Glu Gly Ser Lys Pro
                95                  100                 105

Ser Ser Thr Asn Ser Gln Pro Gly Asp Asp Leu Asp Lys Ala Leu
                110                 115                 120

Ser Lys Leu Glu Ala Arg Ala Lys Leu Gly Pro Asp Arg Ala Arg
                125                 130                 135

Gln Val Lys Lys Gly Gly Arg Arg Ser Gly Arg Ala Gln Gly Arg
                140                 145                 150

Gly Arg Gln Pro Val Thr Thr Trp Lys Gly Ala Asp Ser Arg Ser
                155                 160                 165

Gln Glu Arg Ala Ala Glu His Ser His Lys Ala Met Ala Thr Gly
                170                 175                 180

Thr Gln Glu Gly Val Leu Ile His Leu Ser Arg Trp Glu Thr Gly
                185                 190                 195

Ser His Lys Leu Val Gln Pro Ser Leu Leu Ser His
                200                 205
```

<210> SEQ ID NO 41
<211> LENGTH: 369
<212> TYPE: PRT
<213> ORGANISM: Avian Paramixyvirus Type 2
<220> FEATURE:
<223> OTHER INFORMATION: APMV-2/Chicken/California/Yucaipa/56 M protein

<400> SEQUENCE: 41

```
Met Ala Gln Thr Thr Val Arg Leu Tyr Ile Asp Glu Ala Ser Pro
1               5                   10                  15

Asp Ile Glu Leu Leu Ser Tyr Pro Leu Ile Met Lys Asp Thr Gly
                20                  25                  30

His Gly Thr Lys Glu Leu Gln Gln Gln Ile Arg Val Ala Glu Ile
                35                  40                  45

Gly Ala Leu Gln Gly Gly Lys Asn Glu Ser Val Phe Ile Asn Ala
                50                  55                  60

Tyr Gly Phe Val Gln Gln Cys Lys Val Lys Pro Gly Ala Thr Gln
                65                  70                  75

Phe Phe Gln Val Asp Ala Ala Thr Lys Pro Glu Val Val Thr Ala
                80                  85                  90
```

```
Gly Met Ile Ile Ile Gly Ala Val Lys Gly Val Ala Gly Ile Thr
                95                  100                 105

Lys Leu Ala Glu Glu Val Phe Glu Leu Asp Ile Ser Ile Lys Lys
                110                 115                 120

Ser Ala Ser Phe His Glu Lys Val Ala Val Ser Phe Asn Thr Val
                125                 130                 135

Pro Leu Ser Leu Met Asn Ser Thr Ala Cys Arg Asn Leu Gly Tyr
                140                 145                 150

Val Thr Asn Ala Glu Glu Ala Ile Lys Cys Pro Ser Lys Ile Gln
                155                 160                 165

Ala Gly Val Thr Tyr Lys Phe Lys Ile Met Phe Val Ser Leu Thr
                170                 175                 180

Arg Leu His Asn Gly Lys Leu Tyr Arg Val Pro Lys Ala Val Tyr
                185                 190                 195

Ala Val Glu Ala Ser Ala Leu Tyr Lys Val Gln Leu Glu Val Gly
                200                 205                 210

Phe Lys Leu Asp Val Ala Lys Asp His Pro His Val Lys Met Leu
                215                 220                 225

Lys Lys Val Glu Arg Asn Gly Glu Thr Leu Tyr Leu Gly Tyr Ala
                230                 235                 240

Trp Phe His Leu Cys Asn Phe Lys Lys Thr Asn Ala Lys Gly Glu
                245                 250                 255

Ser Arg Thr Ile Ser Asn Leu Glu Gly Lys Val Arg Ala Met Gly
                260                 265                 270

Ile Lys Val Ser Leu Tyr Asp Leu Trp Gly Pro Thr Leu Val Val
                275                 280                 285

Gln Ile Thr Gly Lys Thr Ser Lys Tyr Ala Gln Gly Phe Phe Ser
                290                 295                 300

Thr Thr Gly Thr Cys Cys Leu Pro Val Ser Lys Ala Ala Pro Glu
                305                 310                 315

Leu Ala Lys Leu Met Trp Ser Cys Asn Ala Thr Ile Val Glu Ala
                320                 325                 330

Ala Val Ile Ile Gln Gly Ser Asp Arg Arg Ala Val Val Thr Ser
                335                 340                 345

Glu Asp Leu Glu Val Tyr Gly Ala Val Ala Lys Glu Lys Gln Ala
                350                 355                 360

Ala Lys Gly Phe His Pro Phe Arg Lys
                365
```

<210> SEQ ID NO 42
<211> LENGTH: 536
<212> TYPE: PRT
<213> ORGANISM: Avian Paramixyvirus Type 2
<220> FEATURE:
<223> OTHER INFORMATION: APMV-2/Chicken/California/Yucaipa/56 F protein

<400> SEQUENCE: 42

```
Met Asn Gln Ala Leu Val Ile Leu Leu Val Ser Phe Gln Leu Gly
1               5                   10                  15

Val Ala Leu Asp Asn Ser Val Leu Ala Pro Ile Gly Val Ala Ser
                20                  25                  30

Ala Gln Glu Trp Gln Leu Ala Ala Tyr Thr Thr Thr Leu Thr Gly
                35                  40                  45

Thr Ile Ala Val Arg Phe Ile Pro Val Leu Pro Gly Asn Leu Ser
                50                  55                  60
```

-continued

```
Thr Cys Ala Gln Glu Thr Leu Gln Glu Tyr Asn Arg Thr Val Thr
                65                  70                  75

Asn Ile Leu Gly Pro Leu Arg Glu Asn Leu Asp Ala Leu Leu Ser
                80                  85                  90

Asp Phe Asp Lys Pro Ala Ser Arg Phe Val Gly Ala Ile Ile Gly
                95                  100                 105

Ser Val Ala Leu Gly Val Ala Thr Ala Ala Gln Ile Thr Ala Ala
                110                 115                 120

Val Ala Leu Asn Gln Ala Gln Glu Asn Ala Arg Asn Ile Trp Arg
                125                 130                 135

Leu Lys Glu Ser Ile Lys Lys Thr Asn Ala Ala Val Leu Glu Leu
                140                 145                 150

Lys Asp Gly Leu Ala Thr Thr Ala Ile Ala Leu Asp Lys Val Gln
                155                 160                 165

Lys Phe Ile Asn Asp Asp Ile Ile Pro Gln Ile Lys Asp Ile Asp
                170                 175                 180

Cys Gln Val Val Ala Asn Lys Leu Gly Val Tyr Leu Ser Leu Tyr
                185                 190                 195

Leu Thr Glu Leu Thr Thr Val Phe Gly Ser Gln Ile Thr Asn Pro
                200                 205                 210

Ala Leu Ser Thr Leu Ser Tyr Gln Ala Leu Tyr Ser Leu Cys Gly
                215                 220                 225

Gly Asp Met Gly Lys Leu Thr Glu Leu Ile Gly Val Asn Ala Lys
                230                 235                 240

Asp Val Gly Ser Leu Tyr Glu Ala Asn Leu Ile Thr Gly Gln Ile
                245                 250                 255

Val Gly Tyr Asp Pro Glu Leu Gln Ile Ile Leu Ile Gln Val Ser
                260                 265                 270

Tyr Pro Ser Val Ser Glu Val Thr Gly Val Arg Ala Thr Glu Leu
                275                 280                 285

Val Thr Val Ser Val Thr Thr Pro Lys Gly Glu Gly Gln Ala Ile
                290                 295                 300

Val Pro Arg Tyr Val Ala Gln Ser Arg Val Leu Thr Glu Glu Leu
                305                 310                 315

Asp Val Ser Thr Cys Arg Phe Ser Lys Thr Thr Leu Tyr Cys Arg
                320                 325                 330

Ser Ile Leu Thr Arg Pro Leu Pro Thr Leu Ile Ala Ser Cys Leu
                335                 340                 345

Ser Gly Lys Tyr Asp Asp Cys Gln Tyr Thr Thr Glu Ile Gly Ala
                350                 355                 360

Leu Ser Ser Arg Phe Ile Thr Val Asn Gly Gly Val Leu Ala Asn
                365                 370                 375

Cys Arg Ala Ile Val Cys Lys Cys Val Ser Pro Pro His Ile Ile
                380                 385                 390

Pro Gln Asn Asp Ile Gly Ser Val Thr Val Ile Asp Ser Ser Ile
                395                 400                 405

Cys Lys Glu Val Val Leu Glu Ser Val Gln Leu Arg Leu Glu Gly
                410                 415                 420

Lys Leu Ser Ser Gln Tyr Phe Ser Asn Val Thr Ile Asp Leu Ser
                425                 430                 435

Gln Ile Thr Thr Ser Gly Ser Leu Asp Ile Ser Ser Glu Ile Gly
                440                 445                 450
```

```
Ser Ile Asn Asn Thr Val Asn Arg Val Asp Glu Leu Ile Lys Glu
                455                 460                 465

Ser Asn Glu Trp Leu Asn Ala Val Asn Pro Arg Leu Val Asn Asn
                470                 475                 480

Thr Ser Ile Ile Val Leu Cys Val Leu Ala Ala Leu Ile Ile Val
                485                 490                 495

Trp Leu Ile Ala Leu Thr Val Cys Phe Cys Tyr Ser Ala Arg Tyr
                500                 505                 510

Ser Ala Lys Ser Lys Gln Met Arg Gly Ala Met Thr Gly Ile Asp
                515                 520                 525

Asn Pro Tyr Val Ile Gln Ser Ala Thr Lys Met
                530                 535


<210> SEQ ID NO 43
<211> LENGTH: 580
<212> TYPE: PRT
<213> ORGANISM: Avian Paramixyvirus Type 2
<220> FEATURE:
<223> OTHER INFORMATION: APMV-2/Chicken/California/Yucaipa/56 HN protein

<400> SEQUENCE: 43

Met Asp Phe Pro Ser Arg Glu Asn Leu Ala Ala Gly Asp Ile Ser
1                5                  10                  15

Gly Arg Lys Thr Trp Arg Leu Leu Phe Arg Ile Leu Thr Leu Ser
                20                  25                  30

Ile Gly Val Val Cys Leu Ala Ile Asn Ile Ala Thr Ile Ala Lys
                35                  40                  45

Leu Asp His Leu Asp Asn Met Ala Ser Asn Thr Trp Thr Thr Thr
                50                  55                  60

Glu Ala Asp Arg Val Ile Ser Ser Ile Thr Thr Pro Leu Lys Val
                65                  70                  75

Pro Val Asn Gln Ile Asn Asp Met Phe Arg Ile Val Ala Leu Asp
                80                  85                  90

Leu Pro Leu Gln Met Thr Ser Leu Gln Lys Glu Ile Thr Ser Gln
                95                  100                 105

Val Gly Phe Leu Ala Glu Ser Ile Asn Asn Val Leu Ser Lys Asn
                110                 115                 120

Gly Ser Ala Gly Leu Val Leu Val Asn Asp Pro Glu Tyr Ala Gly
                125                 130                 135

Gly Ile Ala Val Ser Leu Tyr Gln Gly Asp Ala Ser Ala Gly Leu
                140                 145                 150

Asn Phe Gln Pro Ile Ser Leu Ile Glu His Pro Ser Phe Val Pro
                155                 160                 165

Gly Pro Thr Thr Ala Lys Gly Cys Ile Arg Ile Pro Thr Phe His
                170                 175                 180

Met Gly Pro Ser His Trp Cys Tyr Ser His Asn Ile Ile Ala Ser
                185                 190                 195

Gly Cys Gln Asp Ala Ser His Ser Ser Met Tyr Ile Ser Leu Gly
                200                 205                 210

Val Leu Lys Ala Ser Gln Thr Gly Ser Pro Ile Phe Leu Thr Thr
                215                 220                 225

Ala Ser His Leu Val Asp Asp Asn Ile Asn Arg Lys Ser Cys Ser
                230                 235                 240

Ile Val Ala Ser Lys Tyr Gly Cys Asp Ile Leu Cys Ser Ile Val
                245                 250                 255
```

```
Ile Glu Thr Glu Asn Glu Asp Tyr Arg Ser Asp Pro Ala Thr Ser
                260                 265                 270

Met Ile Ile Gly Arg Leu Phe Phe Asn Gly Ser Tyr Thr Glu Ser
                275                 280                 285

Lys Ile Asn Thr Gly Ser Ile Phe Ser Leu Phe Ser Ala Asn Tyr
                290                 295                 300

Pro Ala Val Gly Ser Gly Ile Val Val Gly Asp Glu Ala Ala Phe
                305                 310                 315

Pro Ile Tyr Gly Gly Val Lys Gln Asn Thr Trp Leu Phe Asn Gln
                320                 325                 330

Leu Lys Asp Phe Gly Tyr Phe Thr His Asn Asp Val Tyr Lys Cys
                335                 340                 345

Asn Arg Thr Asp Ile Gln Gln Thr Ile Leu Asp Ala Tyr Arg Pro
                350                 355                 360

Pro Lys Ile Ser Gly Arg Leu Trp Val Gln Gly Ile Leu Leu Cys
                365                 370                 375

Pro Val Ser Leu Arg Pro Asp Pro Gly Cys Arg Leu Lys Val Phe
                380                 385                 390

Asn Thr Ser Asn Val Met Met Gly Ala Glu Ala Arg Leu Ile Gln
                395                 400                 405

Val Gly Ser Thr Val Tyr Leu Tyr Gln Arg Ser Ser Ser Trp Trp
                410                 415                 420

Val Val Gly Leu Thr Tyr Lys Leu Asp Val Ser Glu Ile Thr Ser
                425                 430                 435

Gln Thr Gly Asn Thr Leu Asn His Val Asp Pro Ile Ala His Thr
                440                 445                 450

Lys Phe Pro Arg Pro Ser Phe Arg Arg Asp Ala Cys Ala Arg Pro
                455                 460                 465

Asn Ile Cys Pro Ala Val Cys Val Ser Gly Val Tyr Gln Asp Ile
                470                 475                 480

Trp Pro Ile Ser Thr Ala Thr Asn Asn Ser Asn Ile Val Trp Val
                485                 490                 495

Gly Gln Tyr Leu Glu Ala Phe Tyr Ser Arg Lys Asp Pro Arg Ile
                500                 505                 510

Gly Ile Ala Thr Gln Tyr Glu Trp Lys Val Thr Asn Gln Leu Phe
                515                 520                 525

Asn Ser Asn Thr Glu Gly Gly Tyr Ser Thr Thr Thr Cys Phe Arg
                530                 535                 540

Asn Thr Lys Arg Asp Lys Ala Tyr Cys Val Val Ile Ser Glu Tyr
                545                 550                 555

Ala Asp Gly Val Val Gly Ser Tyr Arg Ile Val Pro Gln Leu Ile
                560                 565                 570

Glu Ile Arg Thr Thr Thr Gly Lys Ser Glu
                575                 580
```

<210> SEQ ID NO 44
<211> LENGTH: 2242
<212> TYPE: PRT
<213> ORGANISM: Avian Paramixyvirus Type 2
<220> FEATURE:
<223> OTHER INFORMATION: APMV-2/Chicken/California/Yucaipa/56 L protein

<400> SEQUENCE: 44

```
Met Asp Gln Thr Gln Ala Asp Thr Ile Ile Gln Pro Glu Val His
1               5                   10                  15
```

-continued

```
Leu Asn Ser Pro Leu Val Arg Ala Lys Leu Val Leu Leu Trp Lys
                20                  25                  30

Leu Thr Gly Leu Pro Leu Pro Ser Asp Leu Arg Ser Phe Val Leu
                35                  40                  45

Thr Thr His Ala Ala Asp Asp Gln Ile Ala Lys Asn Glu Thr Arg
                50                  55                  60

Ile Lys Ala Lys Ile Asn Ser Leu Ile Asp Asn Leu Ile Lys His
                65                  70                  75

Cys Lys Ala Arg Gln Val Ala Leu Ser Gly Leu Thr Pro Val Val
                80                  85                  90

His Pro Thr Thr Leu Gln Trp Leu Leu Ser Ile Thr Cys Glu Arg
                95                  100                 105

Ala Asp His Leu Ala Lys Val Arg Glu Lys Ser Val Lys Gln Ala
                110                 115                 120

Met Ser Glu Lys Gln His Gly Phe Arg His Leu Phe Ser Ala Val
                125                 130                 135

Ser His Gln Leu Val Gly Asn Ala Thr Leu Phe Cys Ala Gln Asp
                140                 145                 150

Ser Ser Thr Val Asn Val Asp Ser Pro Cys Ser Ser Gly Cys Glu
                155                 160                 165

Arg Leu Ile Ile Asp Ser Ile Gly Ala Leu Gln Thr Arg Trp Thr
                170                 175                 180

Arg Cys Arg Trp Ala Trp Leu His Ile Lys Gln Val Met Arg Tyr
                185                 190                 195

Gln Val Leu Gln Ser Arg Leu His Ala His Ala Asn Ser Val Ser
                200                 205                 210

Thr Trp Ser Glu Ala Trp Gly Phe Ile Gly Ile Thr Pro Asp Ile
                215                 220                 225

Val Leu Ile Val Asp Tyr Lys Ser Lys Met Phe Thr Ile Leu Thr
                230                 235                 240

Phe Glu Met Met Leu Met Tyr Ser Asp Val Ile Glu Gly Arg Asp
                245                 250                 255

Asn Val Val Ala Val Gly Ser Met Ser Pro Asn Leu Gln Pro Val
                260                 265                 270

Val Glu Arg Ile Glu Val Leu Phe Asp Val Val Asp Thr Leu Ala
                275                 280                 285

Arg Arg Ile His Asp Pro Ile Tyr Asp Leu Val Ala Ala Leu Glu
                290                 295                 300

Ser Met Ala Tyr Ala Ala Val Gln Leu His Asp Ala Ser Glu Thr
                305                 310                 315

His Ala Gly Glu Phe Phe Ser Phe Asn Leu Thr Glu Ile Glu Ser
                320                 325                 330

Thr Leu Ala Pro Leu Leu Asp Pro Gly Gln Val Leu Ser Val Met
                335                 340                 345

Arg Thr Ile Ser Tyr Cys Tyr Ser Gly Leu Ser Pro Asp Gln Ala
                350                 355                 360

Ala Glu Leu Leu Cys Val Met Arg Leu Phe Gly His Pro Leu Leu
                365                 370                 375

Ser Ala Gln Gln Ala Ala Lys Lys Val Arg Glu Ser Met Cys Ala
                380                 385                 390

Pro Lys Leu Leu Glu His Asp Ala Ile Leu Gln Thr Leu Ser Phe
                395                 400                 405

Phe Lys Gly Ile Ile Ile Asn Gly Tyr Arg Lys Ser His Ser Gly
```

-continued

```
                410                 415                 420

Val Trp Pro Ala Ile Asp Pro Asp Ser Ile Val Asp Asp Asp Leu
                425                 430                 435

Arg Gln Leu Tyr Tyr Glu Ser Ala Glu Ile Ser His Ala Phe Met
                440                 445                 450

Leu Lys Lys Tyr Arg Tyr Leu Ser Met Ile Glu Phe Arg Lys Ser
                455                 460                 465

Ile Glu Phe Asp Leu Asn Asp Asp Leu Ser Thr Phe Leu Lys Asp
                470                 475                 480

Lys Ala Ile Cys Arg Pro Lys Asp Gln Trp Ala Arg Ile Phe Arg
                485                 490                 495

Lys Ser Leu Phe Pro Cys Lys Thr Asn Leu Gly Thr Ser Ile Asp
                500                 505                 510

Val Lys Ser Asn Arg Leu Leu Ile Asp Phe Leu Glu Ser His Asp
                515                 520                 525

Phe Asn Pro Glu Glu Glu Met Lys Tyr Val Thr Thr Leu Ala Tyr
                530                 535                 540

Leu Ala Asp Asn Gln Phe Ser Ala Ser Tyr Ser Leu Lys Glu Lys
                545                 550                 555

Glu Ile Lys Thr Thr Gly Arg Ile Phe Ala Lys Met Thr Arg Lys
                560                 565                 570

Met Arg Ser Cys Gln Val Ile Leu Glu Ser Leu Leu Ser Ser His
                575                 580                 585

Val Cys Lys Phe Phe Lys Glu Asn Gly Val Ser Met Glu Gln Leu
                590                 595                 600

Ser Leu Thr Lys Ser Leu Leu Ala Met Ser Gln Leu Ala Pro Arg
                605                 610                 615

Ile Ser Ser Val Arg Gln Ala Thr Ala Arg Arg Gln Asp Pro Gly
                620                 625                 630

Leu Ser His Ser Asn Gly Cys Asn His Ile Val Gly Asp Leu Gly
                635                 640                 645

Pro His Gln Gln Asp Arg Pro Ala Arg Lys Ser Val Val Ala Thr
                650                 655                 660

Phe Leu Thr Thr Asp Leu Gln Lys Tyr Cys Leu Asn Trp Arg Tyr
                665                 670                 675

Gly Ser Ile Lys Leu Phe Ala Gln Ala Leu Asn Gln Leu Phe Gly
                680                 685                 690

Ile Glu His Gly Phe Glu Trp Ile His Leu Arg Leu Met Asn Ser
                695                 700                 705

Thr Leu Phe Val Gly Asp Pro Phe Ser Pro Pro Glu Ser Lys Val
                710                 715                 720

Leu Ser Asp Leu Asp Asp Ala Pro Asn Ser Asp Ile Phe Ile Val
                725                 730                 735

Ser Ala Arg Gly Gly Ile Glu Gly Leu Cys Gln Lys Leu Trp Thr
                740                 745                 750

Met Ile Ser Ile Ser Ile Ile His Cys Val Ala Glu Lys Ile Gly
                755                 760                 765

Ala Arg Val Ala Ala Met Val Gln Gly Asp Asn Gln Val Ile Ala
                770                 775                 780

Ile Thr Arg Glu Leu Tyr Lys Gly Glu Thr Tyr Thr Gln Ile Gln
                785                 790                 795

Pro Glu Leu Asp Arg Leu Gly Asn Ala Phe Phe Ala Glu Phe Lys
                800                 805                 810
```

-continued

```
Arg His Asn Tyr Ala Met Gly His Asn Leu Lys Pro Lys Glu Thr
                815                 820                 825

Ile Gln Ser Gln Ser Phe Phe Val Tyr Ser Lys Arg Ile Phe Trp
                830                 835                 840

Glu Gly Arg Ile Leu Ser Gln Ala Leu Lys Asn Ala Thr Lys Leu
                845                 850                 855

Cys Phe Ile Ala Asp His Leu Gly Asp Asn Thr Val Ser Ser Cys
                860                 865                 870

Ser Asn Leu Ala Ser Thr Ile Thr Arg Leu Val Glu Asn Gly Tyr
                875                 880                 885

Glu Lys Asp Thr Ala Phe Ile Leu Asn Ile Ile Ser Ala Met Thr
                890                 895                 900

Gln Leu Leu Ile Asp Glu Gln Tyr Ser Leu Gln Gly Asp Tyr Ser
                905                 910                 915

Ala Val Arg Lys Leu Ile Gly Ser Ser Asn Tyr Arg Asn Leu Leu
                920                 925                 930

Val Ala Ser Leu Met Pro Gly Gln Val Gly Gly Tyr Asn Phe Leu
                935                 940                 945

Asn Ile Ser Arg Leu Phe Thr Arg Asn Ile Gly Asp Pro Val Thr
                950                 955                 960

Cys Ala Ile Ala Asp Leu Lys Trp Phe Ile Arg Ser Gly Leu Ile
                965                 970                 975

Pro Glu Phe Ile Leu Lys Asn Ile Leu Leu Arg Asp Pro Gly Asp
                980                 985                 990

Asp Met Trp Ser Thr Leu Cys Ala Asp Pro Tyr Ala Leu Asn Ile
                995                 1000                1005

Pro Tyr Thr Gln Leu Pro Thr Thr Tyr Leu Lys Lys His Thr Gln
                1010                1015                1020

Arg Ala Leu Leu Ser Asp Ser Asn Asn Pro Leu Leu Ala Gly Val
                1025                1030                1035

Gln Leu Asp Asn Gln Tyr Ile Glu Glu Glu Glu Phe Ala Arg Phe
                1040                1045                1050

Leu Leu Asp Arg Glu Ser Val Met Pro Arg Val Ala His Thr Ile
                1055                1060                1065

Met Glu Ser Ser Ile Leu Gly Lys Arg Lys Asn Ile Gln Gly Leu
                1070                1075                1080

Ile Asp Thr Thr Pro Thr Ile Ile Lys Thr Ala Leu Met Arg Gln
                1085                1090                1095

Pro Ile Ser Arg Arg Lys Cys Asp Lys Ile Val Asn Tyr Ser Ile
                1100                1105                1110

Asn Tyr Leu Thr Glu Cys His Asp Ser Leu Leu Ser Cys Arg Thr
                1115                1120                1125

Phe Glu Pro Arg Lys Glu Ile Ile Trp Glu Ser Ala Met Ile Ser
                1130                1135                1140

Val Glu Thr Cys Ser Val Thr Ile Ala Glu Phe Leu Arg Ala Thr
                1145                1150                1155

Ser Trp Ser Asn Ile Leu Asn Gly Arg Thr Ile Ser Gly Val Thr
                1160                1165                1170

Ser Pro Asp Thr Ile Glu Leu Leu Lys Gly Ser Leu Ile Gly Glu
                1175                1180                1185

Asn Ala His Cys Ile Leu Cys Glu Gln Gly Asp Glu Thr Phe Thr
                1190                1195                1200
```

-continued

```
Trp Met His Leu Ala Gly Pro Ile Tyr Ile Pro Asp Pro Gly Val
                1205                1210                1215

Thr Ala Ser Lys Met Arg Val Pro Tyr Leu Gly Ser Lys Thr Glu
                1220                1225                1230

Glu Arg Arg Thr Ala Ser Met Ala Thr Ile Lys Gly Met Ser His
                1235                1240                1245

His Leu Lys Ala Ala Leu Arg Gly Ala Ser Val Met Val Trp Ala
                1250                1255                1260

Phe Gly Asp Thr Glu Glu Ser Trp Glu His Ala Cys Leu Val Ala
                1265                1270                1275

Asn Thr Arg Cys Lys Ile Asn Leu Pro Gln Leu Arg Leu Leu Thr
                1280                1285                1290

Pro Thr Pro Ser Ser Ser Asn Ile Gln His Arg Leu Asn Asp Gly
                1295                1300                1305

Ile Ser Val Gln Lys Phe Thr Pro Ala Ser Leu Ser Arg Val Ala
                1310                1315                1320

Ser Phe Val His Ile Cys Asn Asp Phe Gln Lys Leu Glu Arg Asp
                1325                1330                1335

Gly Ser Ser Val Asp Ser Asn Leu Ile Tyr Gln Gln Ile Met Leu
                1340                1345                1350

Thr Gly Leu Ser Ile Met Glu Thr Leu His Pro Met His Val Ser
                1355                1360                1365

Trp Val Tyr Asn Asn Gln Thr Ile His Leu His Thr Gly Thr Ser
                1370                1375                1380

Cys Cys Pro Arg Glu Ile Glu Thr Ser Ile Val Asn Pro Ala Arg
                1385                1390                1395

Gly Glu Phe Pro Thr Ile Thr Leu Thr Thr Asn Asn Gln Phe Leu
                1400                1405                1410

Phe Asp Cys Asn Pro Ile His Asp Glu Ala Leu Thr Lys Leu Ser
                1415                1420                1425

Val Ser Glu Phe Lys Phe Gln Glu Leu Asn Ile Asp Ser Met Gln
                1430                1435                1440

Gly Tyr Ser Ala Val Asn Leu Leu Ser Arg Cys Val Ala Lys Leu
                1445                1450                1455

Ile Gly Glu Cys Ile Leu Glu Asp Gly Ile Gly Ser Ser Ile Lys
                1460                1465                1470

Asn Glu Ala Met Ile Ser Phe Asp Asn Ser Ile Asn Trp Ile Ser
                1475                1480                1485

Glu Ala Leu Asn Ser Asp Leu Arg Leu Val Phe Leu Gln Leu Gly
                1490                1495                1500

Gln Glu Leu Leu Cys Asp Leu Ala Tyr Gln Met Tyr Tyr Leu Arg
                1505                1510                1515

Val Ile Gly Tyr His Ser Ile Val Ala Tyr Leu Gln Asn Thr Leu
                1520                1525                1530

Glu Arg Ile Pro Val Ile Gln Leu Ala Asn Met Ala Leu Thr Ile
                1535                1540                1545

Ser His Pro Glu Val Trp Arg Arg Val Thr Val Ser Gly Phe Asn
                1550                1555                1560

Gln Gly Tyr Arg Ser Pro Tyr Leu Ala Thr Val Asp Phe Ile Ala
                1565                1570                1575

Ala Cys Arg Asp Ile Ile Val Gln Gly Ala Gln His Tyr Met Ala
                1580                1585                1590

Asp Leu Leu Ser Gly Val Glu Cys Gln Tyr Thr Phe Phe Asn Val
```

-continued

```
                1595                1600                1605

Gln Asp Gly Asp Leu Thr Pro Lys Met Glu Gln Phe Leu Ala Arg
                1610                1615                1620

Arg Met Cys Leu Phe Val Leu Leu Thr Gly Thr Ile Arg Pro Leu
                1625                1630                1635

Pro Ile Ile Arg Ser Leu Asn Ala Ile Glu Lys Cys Ala Ile Leu
                1640                1645                1650

Thr Gln Phe Leu Tyr Tyr Leu Pro Ser Val Asp Met Ala Val Ala
                1655                1660                1665

Asp Lys Ala Arg Val Leu Tyr Gln Leu Ser Ile Asn Pro Lys Ile
                1670                1675                1680

Asp Ala Leu Val Ser Asn Leu Tyr Phe Thr Thr Arg Arg Leu Leu
                1685                1690                1695

Ser Asn Ile Arg Gly Asp Ser Ser Ser Arg Ala Gln Ile Ala Phe
                1700                1705                1710

Leu Tyr Glu Glu Glu Val Ile Val Asp Val Pro Ala Ser Asn Gln
                1715                1720                1725

Phe Asp Gln Tyr His Arg Asp Pro Ile Leu Arg Gly Gly Leu Phe
                1730                1735                1740

Phe Ser Leu Ser Leu Lys Met Glu Arg Met Ser Leu Asn Arg Phe
                1745                1750                1755

Ala Val Gln Thr Leu Pro Thr Gln Gly Ser Asn Ser Gln Gly Ser
                1760                1765                1770

Arg Gln Thr Leu Trp Arg Ala Ser Pro Leu Ala His Cys Leu Lys
                1775                1780                1785

Ser Val Gly Gln Val Ser Thr Ser Trp Tyr Lys Tyr Ala Val Val
                1790                1795                1800

Gly Ala Ser Val Glu Lys Val Gln Pro Thr Arg Ser Thr Ser Leu
                1805                1810                1815

Tyr Ile Gly Glu Gly Ser Gly Ser Val Met Thr Leu Leu Glu Tyr
                1820                1825                1830

Leu Asp Pro Ala Thr Ile Ile Phe Tyr Asn Ser Leu Phe Ser Asn
                1835                1840                1845

Ser Met Asn Pro Pro Gln Arg Asn Phe Gly Leu Met Pro Thr Gln
                1850                1855                1860

Phe Gln Asp Ser Val Val Tyr Lys Asn Ile Ser Ala Gly Val Asp
                1865                1870                1875

Cys Lys Tyr Gly Phe Lys Gln Val Phe Gln Pro Leu Trp Arg Asp
                1880                1885                1890

Val Asp Gln Glu Thr Asn Val Val Glu Thr Ala Phe Leu Asn Tyr
                1895                1900                1905

Val Met Glu Val Val Pro Val His Ser Ser Lys Arg Val Val Cys
                1910                1915                1920

Glu Val Glu Phe Asp Arg Gly Met Pro Asp Glu Ile Val Ile Thr
                1925                1930                1935

Gly Tyr Ile His Val Leu Met Val Thr Ala Tyr Ser Leu His Arg
                1940                1945                1950

Gly Gly Arg Leu Ile Ile Lys Val Tyr Arg His Ser Glu Ala Val
                1955                1960                1965

Phe Gln Phe Val Leu Ser Ala Ile Val Met Met Phe Gly Gly Leu
                1970                1975                1980

Asp Ile His Arg Asn Ser Tyr Met Ser Thr Asn Lys Glu Glu Tyr
                1985                1990                1995
```

Ile Ile Ile Ala Ala Ala Pro Glu Ala Leu Asn Tyr Ser Ser Val
2000 2005 2010

Pro Ala Ile Leu Gln Arg Val Lys Ser Val Ile Asp Gln Gln Leu
2015 2020 2025

Thr Leu Ile Ser Pro Ile Asp Leu Glu Arg Leu Arg His Glu Thr
2030 2035 2040

Glu Ser Leu Arg Glu Lys Glu Asn Asn Leu Val Ile Ser Leu Thr
2045 2050 2055

Arg Gly Lys Tyr Gln Leu Arg Pro Thr Gln Thr Asp Met Leu Leu
2060 2065 2070

Ser Tyr Leu Gly Gly Arg Phe Ile Thr Leu Phe Gly Gln Ser Ala
2075 2080 2085

Arg Asp Leu Met Ala Thr Asp Val Ala Asp Leu Asp Ala Arg Lys
2090 2095 2100

Ile Ala Leu Val Asp Leu Leu Met Val Glu Ser Asn Ile Ile Leu
2105 2110 2115

Ser Glu Ser Thr Asp Leu Asp Leu Ala Leu Leu Leu Ser Pro Phe
2120 2125 2130

Asn Leu Asp Lys Gly Arg Lys Ile Val Thr Leu Ala Lys Ala Thr
2135 2140 2145

Thr Arg Gln Leu Leu Pro Val Tyr Ile Ala Ser Glu Ile Met Cys
2150 2155 2160

Asn Arg Gln Ala Phe Thr His Leu Thr Ser Ile Ile Gln Arg Gly
2165 2170 2175

Val Ile Arg Ile Glu Asn Met Leu Ala Thr Thr Glu Phe Val Arg
2180 2185 2190

Gln Ser Val Arg Pro Gln Phe Ile Lys Glu Val Ile Thr Ile Ala
2195 2200 2205

Gln Val Asn His Leu Phe Ser Asp Leu Ser Lys Leu Val Leu Ser
2210 2215 2220

Arg Ser Glu Val Lys Gln Ala Leu Lys Phe Val Gly Cys Cys Met
2225 2230 2235

Lys Phe Arg Asn Ala Ser Asn
2240

<210> SEQ ID NO 45
<211> LENGTH: 457
<212> TYPE: PRT
<213> ORGANISM: Avian Paramixyvirus Type 2
<220> FEATURE:
<223> OTHER INFORMATION: APMV-2/Finch/N.Ireland/Bangor/73 NP protein

<400> SEQUENCE: 45

Met Ser Ser Val Phe Thr Glu Tyr Gln Ala Leu Gln Asp Gln Leu
1 5 10 15

Val Lys Pro Ser Ala Arg Arg Ala Asp Val Ala Ser Thr Gly Leu
20 25 30

Leu Arg Ala Glu Ile Pro Val Cys Val Thr Leu Ser Gln Asp Pro
35 40 45

Thr Asp Arg Trp Asn Leu Ala Cys Leu Asn Leu Arg Trp Leu Ile
50 55 60

Ser Glu Ser Ser Thr Thr Pro Met Arg Gln Gly Ala Ile Leu Ser
65 70 75

Leu Leu Ser Leu His Ser Asp Asn Met Arg Ala His Ala Thr Leu
80 85 90

-continued

```
Ala Ala Arg Ser Ala Asp Ala Ser Ile Thr Ile Leu Glu Val Asp
                95                  100                 105

Ser Ile Asp Met Ala Ala Asp Thr Ile Thr Phe Asn Ala Arg Ser
                110                 115                 120

Gly Val Ser Asp Arg Arg Ser Ala Gln Leu Met Ala Ile Ala Lys
                125                 130                 135

Asp Leu Pro Arg Ser Cys Ser Asn Asp Ser Pro Phe Lys Asp Asn
                140                 145                 150

Asn Ile Glu Asp Arg Asp Pro Leu Asp Leu Ser Glu Thr Ile Asp
                155                 160                 165

Arg Leu Gln Gly Ile Ala Ala Gln Ile Trp Val Ala Ala Ile Lys
                170                 175                 180

Ser Met Thr Ala Pro Asp Thr Ala Ala Glu Ser Glu Gly Lys Arg
                185                 190                 195

Leu Ala Lys Tyr Gln Gln Gln Gly Arg Leu Val Arg Gln Val Leu
                200                 205                 210

Val His Glu Ala Val Arg Ala Glu Phe Leu Arg Val Ile Arg Gly
                215                 220                 225

Ser Leu Val Leu Arg Gln Phe Met Val Ser Glu Cys Lys Arg Ala
                230                 235                 240

Ala Ser Met Gly Ser Asp Thr Ser Arg Tyr Tyr Ala Met Val Gly
                245                 250                 255

Asp Ile Ser Leu Tyr Ile Lys Asn Ala Gly Leu Thr Ala Phe Phe
                260                 265                 270

Leu Thr Leu Arg Phe Gly Ile Gly Thr His Tyr Pro Thr Leu Ala
                275                 280                 285

Met Ser Val Phe Ser Gly Glu Leu Lys Lys Met Ser Ser Leu Ile
                290                 295                 300

Arg Leu Tyr Lys Ser Lys Gly Glu Asn Ala Ala Tyr Met Ala Phe
                305                 310                 315

Leu Glu Asp Ala Asp Met Gly Asn Phe Ala Pro Ala Asn Phe Ser
                320                 325                 330

Thr Leu Tyr Ser Tyr Ala Met Gly Val Gly Thr Val Leu Glu Ala
                335                 340                 345

Ser Val Ala Lys Tyr Gln Phe Ala Arg Glu Phe Thr Ser Glu Thr
                350                 355                 360

Tyr Phe Arg Leu Gly Val Glu Thr Ala Gln Asn Gln Gln Cys Ala
                365                 370                 375

Leu Asp Glu Lys Thr Ala Lys Glu Met Gly Leu Thr Asp Glu Ala
                380                 385                 390

Arg Arg Gln Val Gln Ala Leu Ala Ser Asn Ile Glu Gln Gly Gln
                395                 400                 405

His Ser Ile Gln Ala Pro Gln Gln Pro Ser Phe Met Ala Thr Gln
                410                 415                 420

Ser Thr Thr Gln Glu Pro Asp Gln Pro Ser Thr Ser Arg Gln Asp
                425                 430                 435

Thr Arg Ser Thr Pro Ala Pro Ser His Asn Gln Gly Gln Asp Gln
                440                 445                 450

Asp Asp Ala Ser Leu Asp Trp
                455
```

<210> SEQ ID NO 46
<211> LENGTH: 399

<212> TYPE: PRT
<213> ORGANISM: Avian Paramixyvirus Type 2
<220> FEATURE:
<223> OTHER INFORMATION: APMV-2/Finch/N.Ireland/Bangor/73 P protein

<400> SEQUENCE: 46

```
Met Glu Phe Thr Asp Asp Thr Glu Ile Ala Glu Leu Leu Asp Leu
1               5                   10                  15

Gly Thr Ser Val Ile Gln Glu Leu Gln Arg Ala Glu Leu Lys Gly
                20                  25                  30

Pro Gln Thr Thr Gly Lys Pro Lys Val Pro Pro Gly Asn Thr Arg
                35                  40                  45

Ser Leu Ala Thr Leu Trp Glu Lys Glu Ser Glu Thr Arg Thr Glu
                50                  55                  60

Pro Glu Ala Leu Pro Thr Glu His Ala Asn Pro Asp Met Ser Pro
                65                  70                  75

Ala Ser His Asn Asp Pro Ala Lys Ala Ala His Glu Gly Ala Ala
                80                  85                  90

Glu Glu Gly Glu Ala Asp Pro Glu Pro Asp Lys Ala Ala Gly Ser
                95                  100                 105

Asp Leu Thr Asn Ser Arg Pro Gly Asp Asp Leu Asp Lys Ala Leu
                110                 115                 120

Ala Lys Leu Glu Ser Arg Ala Lys Gln Asn Arg Thr Gln Gln Leu
                125                 130                 135

Ile Val Lys Lys Gly Lys Gly Ala Thr Lys Ala Ser His Ser Thr
                140                 145                 150

Pro Pro Met Ser Pro Gln Val Ala Ala Ser Thr Thr Val Asn Lys
                155                 160                 165

Pro Gly Pro Met Thr Glu Pro Thr Leu Asp Leu Gly Ser Gln Asp
                170                 175                 180

Ile Glu Glu Ser Thr Leu Leu Pro Val Glu Met Glu Asp Trp Lys
                185                 190                 195

Ser Ser Ala Gly Ala Thr Pro Tyr Ala Leu Gln Ser Glu Gln Asn
                200                 205                 210

Gln Asp Glu Lys Ser Ala Ser Val Gly Ser Val Leu Ser Pro Ala
                215                 220                 225

Ser Tyr Val Ala Asn Pro Asn Asp Ala Met Ser Ala Leu Thr Arg
                230                 235                 240

Lys Val Asn Asp Met Glu Ser Lys Ile Gly Glu Ala Ile Lys Leu
                245                 250                 255

Leu Gly Met Leu Pro Val Ile Lys Asn Glu Ile Ser Gln Leu Lys
                260                 265                 270

Ala Thr Val Ala Leu Met Ser Asn Gln Leu Ala Ser Ile Gln Ile
                275                 280                 285

Leu Asp Pro Gly Asn Ala Gly Val Lys Ser Leu Asn Glu Met Lys
                290                 295                 300

Ser Leu Ser Lys Ala Ala Ser Ile Val Val Thr Gly Pro Gly Ser
                305                 310                 315

Leu Pro Ile Glu Val Leu Asn Thr Asp Thr Val Tyr Lys Asp Glu
                320                 325                 330

Leu Ala Arg Pro Val Thr Ala Gln Ala His Lys Glu Thr Lys Pro
                335                 340                 345

Lys Asp Glu Pro Gly Ala Thr Ser Ser Asp Leu Thr Ala Val Gln
                350                 355                 360
```

```
Ala Leu Ile Asp Thr Leu Val Glu Asp Asp Arg Arg Lys Ser Arg
                365                 370                 375

Leu His Gln Ala Leu Gln Arg Ala Arg Thr Lys Glu Asp Ile Leu
                380                 385                 390

Arg Ile Lys Arg Gln Ile Tyr Asn Ala
                395


<210> SEQ ID NO 47
<211> LENGTH: 232
<212> TYPE: PRT
<213> ORGANISM: Avian Paramixyvirus Type 2
<220> FEATURE:
<223> OTHER INFORMATION: APMV-2/Finch/N.Ireland/Bangor/73 V protein

<400> SEQUENCE: 47

Met Glu Phe Thr Asp Asp Thr Glu Ile Ala Glu Leu Leu Asp Leu
1                5                  10                  15

Gly Thr Ser Val Ile Gln Glu Leu Gln Arg Ala Glu Leu Lys Gly
                20                  25                  30

Pro Gln Thr Thr Gly Lys Pro Lys Val Pro Pro Gly Asn Thr Arg
                35                  40                  45

Ser Leu Ala Thr Leu Trp Glu Lys Glu Ser Glu Thr Arg Thr Glu
                50                  55                  60

Pro Glu Ala Leu Pro Thr Glu His Ala Asn Pro Asp Met Ser Pro
                65                  70                  75

Ala Ser His Asn Asp Pro Ala Lys Ala Ala His Glu Gly Ala Ala
                80                  85                  90

Glu Glu Gly Glu Ala Asp Pro Glu Pro Asp Lys Ala Ala Gly Ser
                95                  100                 105

Asp Leu Thr Asn Ser Arg Pro Gly Asp Asp Leu Asp Lys Ala Leu
                110                 115                 120

Ala Lys Leu Glu Ser Arg Ala Lys Gln Asn Arg Thr Gln Gln Leu
                125                 130                 135

Ile Val Lys Lys Gly Glu Gly Gly Asn Gln Ser Ile Pro Phe Tyr
                140                 145                 150

Pro Thr Asn Glu Pro Pro Gly Gly Gly Ile Asn His Ser Glu Gln
                155                 160                 165

Thr Arg Pro Asn Asp Arg Ala Asn Thr Arg Ser Trp Lys Pro Gly
                170                 175                 180

His Arg Arg Glu Tyr Ser Phe Ala Cys Arg Asp Gly Arg Leu Glu
                185                 190                 195

Val Ile Ser Trp Cys Asn Pro Ile Cys Thr Pro Ile Arg Ala Glu
                200                 205                 210

Pro Arg Arg Glu Val Cys Lys Cys Gly Lys Cys Pro Ile Ser Cys
                215                 220                 225

Ile Leu Cys Cys Gln Ser Gln
                230


<210> SEQ ID NO 48
<211> LENGTH: 153
<212> TYPE: PRT
<213> ORGANISM: Avian Paramixyvirus Type 2
<220> FEATURE:
<223> OTHER INFORMATION: APMV-2/Finch/N.Ireland/Bangor/73 W protein

<400> SEQUENCE: 48

Met Glu Phe Thr Asp Asp Thr Glu Ile Ala Glu Leu Leu Asp Leu
1                5                  10                  15
```

```
Gly Thr Ser Val Ile Gln Glu Leu Gln Arg Ala Glu Leu Lys Gly
                20                  25                  30

Pro Gln Thr Thr Gly Lys Pro Lys Val Pro Pro Gly Asn Thr Arg
                35                  40                  45

Ser Leu Ala Thr Leu Trp Glu Lys Glu Ser Glu Thr Arg Thr Glu
                50                  55                  60

Pro Glu Ala Leu Pro Thr Glu His Ala Asn Pro Asp Met Ser Pro
                65                  70                  75

Ala Ser His Asn Asp Pro Ala Lys Ala Ala His Glu Gly Ala Ala
                80                  85                  90

Glu Glu Gly Glu Ala Asp Pro Glu Pro Asp Lys Ala Ala Gly Ser
                95                  100                 105

Asp Leu Thr Asn Ser Arg Pro Gly Asp Asp Leu Asp Lys Ala Leu
                110                 115                 120

Ala Lys Leu Glu Ser Arg Ala Lys Gln Asn Arg Thr Gln Gln Leu
                125                 130                 135

Ile Val Lys Lys Gly Gly Arg Gly Gln Pro Lys His Pro Ile Leu
                140                 145                 150

Pro His Gln


<210> SEQ ID NO 49
<211> LENGTH: 369
<212> TYPE: PRT
<213> ORGANISM: Avian Paramixyvirus Type 2
<220> FEATURE:
<223> OTHER INFORMATION: APMV-2/Finch/N.Ireland/Bangor/73 M protein

<400> SEQUENCE: 49

Met Ala Gln Thr Thr Val Lys Leu Tyr Val Asp Glu Thr Ser Pro
1                5                  10                  15

Asp Ile Glu Leu Leu Ser Tyr Pro Leu Val Met Lys Asp Thr Gly
                20                  25                  30

His Gly Thr Lys Glu Leu Gln Gln Gln Ile Arg Val Ala Glu Ile
                35                  40                  45

Gly Thr Leu His Gly Gly Lys Asn Glu Ser Val Phe Ile Asn Ala
                50                  55                  60

Tyr Gly Phe Val Gln Gln Asp Lys Ile Lys Pro Gly Ala Ala Arg
                65                  70                  75

Phe Tyr Gln Met Glu Glu Gly His Lys Pro Glu Val Ile Thr Ala
                80                  85                  90

Gly Met Ile Ile Ile Gly Ala Val Lys Gly Gly Thr Asp Ile Thr
                95                  100                 105

Lys Leu Ala Glu Asp Val Phe Ser Leu Asp Ile Thr Ile Lys Lys
                110                 115                 120

Ser Ala Ser Phe His Glu Lys Val Ala Val Thr Phe Asn Thr Val
                125                 130                 135

Pro Leu Ser Leu Met Asn Ser Thr Ala Cys Lys Asn Leu Gly Tyr
                140                 145                 150

Leu Thr Asn Ala Glu Glu Ser Ile Lys Cys Pro Ser Lys Ile Gln
                155                 160                 165

Ala Gly Val Thr Tyr Lys Phe Lys Val Met Phe Val Ser Leu Thr
                170                 175                 180

Arg Leu His Asn Gly Lys Leu Tyr Arg Val Pro Lys Ala Val Tyr
                185                 190                 195
```

```
Ser Ile Glu Thr Ala Ala Leu Tyr Lys Val Gln Leu Glu Val Gly
                200                 205                 210

Phe Lys Leu Asp Val Ala Lys Asp His Pro His Val Lys Met Leu
                215                 220                 225

Arg Lys Val Lys Lys Asp Gly Glu Val Lys Tyr Ile Gly Tyr Ala
                230                 235                 240

Trp Phe His Leu Cys Asn Phe Lys Arg Thr Thr Ala Lys Gly Glu
                245                 250                 255

Thr Arg Thr Ile Ser Asn Leu Glu His Lys Val Lys Ala Met Gly
                260                 265                 270

Ile Lys Val Ala Leu Tyr Asp Leu Trp Gly Pro Thr Leu Val Val
                275                 280                 285

Gln Ile Thr Gly Lys Thr Ser Lys Tyr Ala Gln Gly Phe Phe Ser
                290                 295                 300

Thr Thr Gly Thr Cys Cys Leu Pro Val Ala Lys Ala Ala Pro Glu
                305                 310                 315

Leu Ala Lys Leu Met Trp Ser Cys Asn Val Ser Ile Ile Glu Ala
                320                 325                 330

Ser Val Val Ile Gln Gly Ser Asp Arg Arg Ala Ala Val Thr Ser
                335                 340                 345

Glu Asp Leu Glu Leu Tyr Gly Ala Val Ala Lys Glu Lys Gln Pro
                350                 355                 360

Gln Lys Gly Phe His Pro Phe Arg Lys
                365


<210> SEQ ID NO 50
<211> LENGTH: 544
<212> TYPE: PRT
<213> ORGANISM: Avian Paramixyvirus Type 2
<220> FEATURE:
<223> OTHER INFORMATION: APMV-2/Finch/N.Ireland/Bangor/73 F protein

<400> SEQUENCE: 50

Met Glu Pro Pro Asn Gln Pro Glu Gly Thr Met Lys Ala Ile Leu
1               5                   10                  15

Ile Met Ser Met Val Pro Ile Cys Ile Ala Leu Asp Asn Ser Ile
                20                  25                  30

Leu Ala Pro Val Gly Ile Ala Ser Ala Gln Glu Trp Gln Leu Ala
                35                  40                  45

Ala Tyr Thr Asn Thr Leu Ser Gly Thr Ile Ala Val Arg Phe Val
                50                  55                  60

Pro Val Leu Pro Gly Asn Leu Ser Thr Cys Ala Gln Ala Thr Leu
                65                  70                  75

Ala Glu Tyr Asn Arg Thr Val Thr Asn Ile Leu Gly Pro Leu Lys
                80                  85                  90

Asp Asn Leu Asn Ala Leu Leu Ala Glu Ser Thr Leu Pro Ser Ala
                95                  100                 105

Arg Phe Val Gly Ala Ile Ile Gly Thr Val Ala Leu Gly Val Ala
                110                 115                 120

Thr Ser Ala Gln Ile Thr Ala Ala Val Ala Leu Asn Gln Ala Gln
                125                 130                 135

Glu Asn Ala Arg Asn Ile Trp Arg Leu Lys Glu Ser Ile Met Lys
                140                 145                 150

Thr Asn Glu Ala Val Leu Glu Leu Lys Asp Gly Leu Ala Ser Thr
                155                 160                 165
```

-continued

```
Ala Ile Ala Leu Asp Lys Val Gln Arg Phe Ile Asn Asp Asp Ile
                170                 175                 180

Leu Pro Gln Leu Thr Gly Leu Asp Cys Gln Val Val Ala Asn Lys
                185                 190                 195

Leu Gly Val Tyr Leu Ser Leu Tyr Leu Thr Glu Leu Thr Thr Ile
                200                 205                 210

Phe Gly Ser Gln Ile Thr Asn Pro Ala Leu Thr Pro Leu Ser Tyr
                215                 220                 225

Gln Ala Leu Tyr Ser Leu Cys Gly Gly Asp Met Gly Lys Leu Thr
                230                 235                 240

Glu Leu Ile Gly Val Lys Ala Lys Asp Ile Asn Ser Leu Tyr Glu
                245                 250                 255

Ala Asn Leu Ile Thr Gly Gln Val Ile Gly Tyr Asp Ser Glu Ser
                260                 265                 270

Gln Ile Ile Leu Val Gln Val Ser Tyr Pro Ser Val Ser Glu Val
                275                 280                 285

Thr Gly Val Arg Ala Thr Glu Leu Ile Thr Val Ser Val Thr Thr
                290                 295                 300

Pro Lys Gly Glu Gly Arg Ala Ile Thr Pro Arg Tyr Val Ala Gln
                305                 310                 315

Ser Arg Val Leu Thr Glu Glu Leu Asp Thr Ser Thr Cys Arg Phe
                320                 325                 330

Ser Lys Thr Thr Leu Tyr Cys Arg Ser Val Ile Thr Arg Pro Leu
                335                 340                 345

Pro Pro Leu Ile Ala Ser Cys Leu Ser Gly Ser Tyr Gln Asp Cys
                350                 355                 360

Gln Tyr Thr Thr Glu Ile Gly Ala Leu Ser Ser Arg Phe Ile Thr
                365                 370                 375

Val Asn Gly Gly Ile Val Ala Asn Cys Lys Ala Thr Val Cys Lys
                380                 385                 390

Cys Val Asn Pro Pro Lys Ile Ile Ala Gln Asn Asp Ala Ser Ser
                395                 400                 405

Leu Thr Val Ile Asp Ala Gly Val Cys Lys Glu Val Val Leu Asp
                410                 415                 420

Asn Val Gln Leu Lys Leu Glu Gly Lys Phe Ser Ala Gln Tyr Phe
                425                 430                 435

Thr Asn Val Thr Ile Asn Leu Ser Gln Ile Thr Thr Ser Gly Ser
                440                 445                 450

Leu Asp Ile Ser Ser Glu Ile Gly Ser Ile Asn Asn Thr Val Asn
                455                 460                 465

Arg Val Glu Asn Leu Ile Ala Glu Ser Asn Ala Trp Leu Gln Ser
                470                 475                 480

Val Asn Pro Arg Leu Val Asn Asn Thr Ser Ile Ile Val Leu Cys
                485                 490                 495

Val Leu Gly Ala Val Ile Val Val Trp Leu Val Ala Leu Thr Val
                500                 505                 510

Cys Met Ala Tyr Ser Leu Arg Arg Lys Ala Ala Thr Gln Ile Ala
                515                 520                 525

Ser Met Gly Thr Ser Thr Ile Gly Asn Pro Tyr Val Thr Gln Ser
                530                 535                 540

Ala Thr Lys Met
```

<210> SEQ ID NO 51

```
<211> LENGTH: 583
<212> TYPE: PRT
<213> ORGANISM: Avian Paramixyvirus Type 2
<220> FEATURE:
<223> OTHER INFORMATION: APMV-2/Finch/N.Ireland/Bangor/73 HN protein

<400> SEQUENCE: 51

Met Ala Thr Met Ser Arg Glu Asn Leu Thr Asn Ile Gly Gln Gly
1               5                   10                  15

Glu Arg Gly Thr Trp Arg Leu Leu Phe Arg Ile Ser Thr Leu Ala
                20                  25                  30

Ile Thr Thr Val Cys Leu Ala Ile Asn Ile Ala Thr Ile Ser Lys
                35                  40                  45

Leu Asp Asn Ile Asp Thr Ser Gly Ile Gln Thr Trp Thr Thr Met
                50                  55                  60

Glu Ser Asp Arg Ile Ile Gly Ser Leu Thr Ser Thr Leu Lys Val
                65                  70                  75

Pro Ile Asn Gln Val Asn Asp Met Phe Arg Ile Val Ala Leu Asp
                80                  85                  90

Leu Pro Leu Gln Met Ser Thr Met Gln Lys Glu Ile Ala Ser Gln
                95                  100                 105

Val Gly Phe Leu Ala Glu Ser Ile Asn Asn Val Leu Ser Lys Asn
                110                 115                 120

Gly Ser Ala Gly Leu Val Leu Val Asn Asp Pro Glu Tyr Ala Gly
                125                 130                 135

Gly Ile Gly Val Ser Leu Phe His Gly Asp Ser Ala Ser Ser Leu
                140                 145                 150

Glu Phe Glu Ser Pro Ser Leu Ile Glu His Pro Ser Phe Ile Pro
                155                 160                 165

Gly Pro Thr Thr Ala Lys Gly Cys Ile Arg Ile Pro Thr Phe His
                170                 175                 180

Met Thr Ala Ser His Trp Cys Tyr Ser His Asn Ile Ile Glu Ser
                185                 190                 195

Gly Cys Gln Asp Ala Gly His Ser Ser Met Tyr Ile Ser Leu Gly
                200                 205                 210

Val Leu Lys Ala Met Gln Thr Gly Ser Pro Ser Phe Leu Thr Thr
                215                 220                 225

Ala Ser Gln Leu Ile Asp Asp Asn Leu Asn Arg Lys Ser Cys Ser
                230                 235                 240

Ile Ile Ser Thr Thr Tyr Gly Cys Asp Ile Leu Cys Ser Leu Val
                245                 250                 255

Val Glu Asn Glu Asp Ser Asp Tyr Arg Ser Asp Pro Pro Thr Glu
                260                 265                 270

Met Ile Leu Gly Arg Leu Phe Phe Asn Gly Thr Tyr Leu Glu Ser
                275                 280                 285

His Val Asn Thr Arg Ser Ile Phe Glu Gln Phe Ser Ala Asn Tyr
                290                 295                 300

Pro Ala Val Gly Ser Gly Leu Val Leu Gly Asp Glu Ile Ala Phe
                305                 310                 315

Pro Val Tyr Gly Gly Val Lys Gln Asp Thr Gln Leu Phe Asn Gln
                320                 325                 330

Leu Lys Asp His Gly Tyr Phe Thr His Asn Asp Val Tyr Arg Cys
                335                 340                 345

Asn Lys Ser Asn Val Gln Gln Thr Ile Leu Asn Ala Tyr Arg Pro
                350                 355                 360
```

```
Pro Lys Ile Ala Gly Arg Leu Trp Ser Gln Val Ile Ile Ile Cys
                365                 370                 375

Pro Leu Gly Leu Phe Ile Asn Thr Asp Cys Arg Ile Lys Val Phe
                380                 385                 390

Asn Thr Ser Ser Val Met Met Gly Ala Glu Ala Arg Leu Ile Gln
                395                 400                 405

Val Gly Ser Asp Ile Tyr Leu Tyr Gln Arg Pro Ser Ser Trp Trp
                410                 415                 420

Val Val Gly Leu Ile Tyr Lys Leu Asp Phe Gln Glu Leu Ser Thr
                425                 430                 435

Lys Glu Gly Val Val Leu Asn Lys Ile Val Pro Ile Ala His Ala
                440                 445                 450

Lys Phe Pro Arg Pro Ser Phe Ser Lys Asp Ala Cys Ala Arg Pro
                455                 460                 465

Asn Ile Cys Pro Ala Val Cys Val Ser Gly Val Tyr Gln Asp Ile
                470                 475                 480

Trp Pro Ile Ser Thr Ala Thr Asn Leu Ser Gln Val Val Trp Val
                485                 490                 495

Gly Gln Tyr Leu Glu Ala Phe Tyr Ala Arg Lys Asp Pro Trp Ile
                500                 505                 510

Gly Ile Ala Thr Gln Tyr Asp Trp Lys Arg Asn Val Arg Leu Phe
                515                 520                 525

Asn Ser Asn Thr Glu Gly Gly Tyr Ser Thr Thr Thr Cys Phe Arg
                530                 535                 540

Asn Thr Lys Arg Asn Lys Ala Phe Cys Ile Ile Ile Ser Glu Tyr
                545                 550                 555

Ala Asp Gly Val Phe Gly Ser Tyr Arg Ile Val Pro Gln Leu Ile
                560                 565                 570

Glu Ile Arg Thr Asn Asn Arg Val Arg Phe Asp Asn His
                575                 580
```

<210> SEQ ID NO 52
<211> LENGTH: 2242
<212> TYPE: PRT
<213> ORGANISM: Avian Paramixyvirus Type 2
<220> FEATURE:
<223> OTHER INFORMATION: APMV-2/Finch/N.Ireland/Bangor/73 L protein

<400> SEQUENCE: 52

```
Met Asp Gln Val Gln Ala Asp Thr Ile Ile Gln Pro Glu Val His
1                5                  10                  15

Leu Asp Ser Pro Ile Val Arg Ala Lys Leu Val Leu Leu Trp Lys
                20                  25                  30

Leu Thr Gly Leu Pro Leu Pro Lys Glu Leu Arg Ser Phe Val Leu
                35                  40                  45

Thr Ser His Thr Thr Asp Glu Gln Ile Phe Lys Ala Glu Thr Arg
                50                  55                  60

Val Lys Pro Lys Val Asn Ser Ile Val Asp Ala Leu Ile Lys His
                65                  70                  75

Cys Lys Ser Arg Gly Leu Tyr Leu Ser Asp Ile Arg Pro Val Val
                80                  85                  90

His Pro Arg Thr Leu Gln Trp Leu Leu Asn Ile Lys Cys Glu Arg
                95                  100                 105

Ala Asn Gln Leu Leu Lys Ala Arg Glu Lys Ser Ile Gln Gln Val
                110                 115                 120
```

```
Phe Ser Glu Lys Gln Val Asn Phe Arg His Leu Phe Ser Ala Ile
                125                 130                 135

Ser His Gln Leu Val Gly Asn Pro Asn Leu Phe Cys Ser Gln Asp
                140                 145                 150

Asn Asp Pro Arg Tyr Pro Glu Ser Pro Leu Leu Tyr Arg Leu Ser
                155                 160                 165

Glu Ala Ser Tyr Thr Ala Tyr Ile Arg Asn Asn Leu Ser Met Asp
                170                 175                 180

Cys Ser Ser Met Gly Leu Ala Thr Tyr Tyr Ala Gly Tyr Ala Leu
                185                 190                 195

Pro Asn Ser Thr Glu Tyr Ala Ala Arg Tyr Ile Ser Ile Ser Asp
                200                 205                 210

Ile Met Val Arg Asp Leu Gly Leu Tyr Arg Asn Phe Thr Arg Cys
                215                 220                 225

Cys Ala Asn Cys Cys Leu Tyr Val Tyr Glu Leu His Cys Ala Asp
                230                 235                 240

Val Ser Asp Gly Pro Asn Val Leu Arg Cys Asn Ser Arg Ala Arg
                245                 250                 255

Gln Tyr Ser Asn Cys Gly Ser Ile Ile Pro Tyr Ser Ile Pro Cys
                260                 265                 270

His Arg Ser Asn Arg His Pro Leu Ser Ser Ser Arg His Pro Ser
                275                 280                 285

Ser Phe Asp Gly Ser Ser Asp Ile Ser Pro Cys Gly Ile Ile Arg
                290                 295                 300

Glu Tyr Gly Leu Cys Ser Cys Pro Ile Ala Ser Cys Lys Leu Leu
                305                 310                 315

Thr Arg Arg Ser Val Leu Cys Phe Gln Ser Asp Arg Asn Ser Ile
                320                 325                 330

Ser Ser Arg Arg Pro Pro Arg Ser Lys Ala Ser Ala Leu Tyr His
                335                 340                 345

Gln Asn Tyr Tyr His Val Leu Gln Leu Ser Asn Thr Arg Ser Ser
                350                 355                 360

Gly Ser Asp Val Met His His Ala Val Val Arg Ser Ser Pro Val
                365                 370                 375

Ile Arg Pro Ala Ser Ser Lys Lys Ser Lys Gly Ile His Val Arg
                380                 385                 390

Thr Tyr Asp Pro Gly Ala Cys Ala Ile Leu Gln Thr Leu Ser Phe
                395                 400                 405

Phe Lys Gly Ile Ile Ile Asn Gly Tyr Arg Lys Ser His Ser Gly
                410                 415                 420

Val Trp Pro Asn Ile Glu Pro Glu Ser Ile Ile Asp Asp Asp Leu
                425                 430                 435

Arg Gln Leu Tyr Tyr Glu Ser Ala Glu Ile Ser His Ala Phe Met
                440                 445                 450

Leu Lys Lys Tyr Arg Tyr Leu Ser Met Val Glu Phe Lys Lys Ser
                455                 460                 465

Ile Asp Phe Asp Leu Asn Asp Asp Leu Ser Thr Phe Leu Lys Asp
                470                 475                 480

Lys Ala Ile Cys Arg Pro Lys Asn Gln Trp Ala Arg Ile Phe Arg
                485                 490                 495

Lys Ser Leu Phe Pro Leu Lys Asn Ala Ile Asp Ser Gly Ala Asp
                500                 505                 510
```

-continued

```
Thr Arg Ser Asn Arg Leu Leu Ile Asp Phe Leu Glu Ser His Asp
                515                 520                 525

Phe Ser Pro Glu Glu Glu Met Lys Tyr Val Thr Thr Met Ala Tyr
                530                 535                 540

Leu Asp Asp Asp Gln Phe Ser Ala Phe Ile Phe Pro Gln Arg Glu
                545                 550                 555

Gly Asn Gln Asp Asn Arg Ser Asn Ile Cys Glu Asn Asp Gln Glu
                560                 565                 570

Asn Ala Lys Leu Pro Gly Tyr Thr Arg Ile Ile Val Val Tyr Ser
                575                 580                 585

Cys Val Gln Ile Leu Gln Arg Glu Arg Ser Leu His Gly Ala Thr
                590                 595                 600

Leu Phe Asn Lys Glu Pro Pro Ser Asn Val Ser Val Ser Pro Ser
                605                 610                 615

Asp Leu Arg Gly Ala Lys Arg Asn Gly Lys Ser Arg Tyr Pro Gly
                620                 625                 630

Lys Ser His Leu Gln Pro Val Gly Pro Met Ser Ala Ala Arg Glu
                635                 640                 645

Val Gln Gln His Gln Arg Asp Arg Pro Ala Lys Lys Ser Ile Val
                650                 655                 660

Ala Thr Phe Leu Thr Thr Asp Leu Gln Lys Tyr Cys Leu Asn Trp
                665                 670                 675

Arg Tyr Gly Ser Ile Lys Leu Phe Ala Gln Ala Leu Asn Gln Leu
                680                 685                 690

Phe Gly Ile Asp His Gly Phe Glu Trp Ile His Leu Arg Leu Met
                695                 700                 705

Asn Ser Thr Leu Phe Val Gly Asp Pro Phe Ser Pro Pro Glu Cys
                710                 715                 720

Lys Gly Val Arg Asp Leu Asp Asp Ala Pro Asn Ser Asp Ile Phe
                725                 730                 735

Ile Val Ser Ala Arg Gly Gly Ile Glu Gly Leu Cys Gln Lys Leu
                740                 745                 750

Trp Thr Met Ile Ser Ile Ser Ile Ile His Cys Val Ser Glu Lys
                755                 760                 765

Ile Gly Thr Arg Val Ala Ala Met Val Gln Gly Asp Asn Gln Val
                770                 775                 780

Ile Ala Ile Thr Arg Glu Leu Phe Asn Gly Glu Thr Phe Glu Gln
                785                 790                 795

Ile Gln Pro Glu Leu Asp Lys Leu Gly Asn Ala Phe Phe Ser Glu
                800                 805                 810

Phe Lys Gln His Asn Tyr Ala Met Gly His Asn Leu Lys Pro Lys
                815                 820                 825

Glu Thr Ile Gln Ser Gln Ser Phe Phe Val Tyr Ser Lys Arg Ile
                830                 835                 840

Phe Trp Glu Gly Arg Ile Leu Ser Gln Ala Leu Lys Asn Ala Thr
                845                 850                 855

Lys Leu Cys Phe Ile Ala Asp His Leu Gly Asp Asn Thr Val Ser
                860                 865                 870

Ser Cys Ser Asn Leu Ala Ser Thr Ile Thr Arg Leu Val Glu Asn
                875                 880                 885

Gly Phe Glu Lys Asp Thr Ala Phe Val Leu Asn Val Val Tyr Ser
                890                 895                 900

Met Thr Gln Ile Leu Ile Asp Glu Gln Tyr Ser Leu Gln Gly Asp
```

-continued

```
                905                 910                 915

Tyr Ala Asn Val Lys Asn Leu Ile Gly Thr Asn Asn His Arg Asn
                920                 925                 930

Leu Leu Thr Ala Ala Leu Ile Pro Gly Gln Val Gly Gly Tyr Asn
                935                 940                 945

Phe Leu Asn Ile Ser Arg Leu Phe Thr Arg Asn Ile Gly Asp Pro
                950                 955                 960

Val Thr Cys Ala Ile Ala Asp Leu Lys Trp Phe Ile Lys Ser Gly
                965                 970                 975

Leu Val Ala Asp His Ile Leu Lys Asn Ile Leu Leu Arg Asp Pro
                980                 985                 990

Gly Asp Gly Ser Trp Ser Thr Leu Cys Ala Asp Pro Tyr Ala Leu
                995                 1000                1005

Asn Ile Pro Tyr Thr Gln Leu Pro Thr Thr Tyr Leu Lys Lys His
                1010                1015                1020

Thr Gln Arg Ala Leu Leu Ala Glu Ser Asn Asn Pro Leu Leu Ala
                1025                1030                1035

Gly Val Gln Leu Asp Ser Gln Tyr Ile Glu Glu Glu Leu Ala
                1040                1045                1050

Gln Phe Leu Leu Asp Arg Glu Val Val Met Pro Arg Val Ala His
                1055                1060                1065

Thr Ile Met Glu Ala Ser Ile Leu Gly Lys Arg Lys Asn Ile Gln
                1070                1075                1080

Gly Leu Ile Asp Thr Thr Pro Thr Ile Ile Lys Thr Ala Leu Met
                1085                1090                1095

Arg Gln Pro Ile Ser Arg Arg Lys Cys Glu Lys Ile Ile Asn Tyr
                1100                1105                1110

Ser Ile Asn Tyr Leu Val Glu Cys His Asp Ser Ile Ile Ala Val
                1115                1120                1125

Arg Lys Phe Glu Pro Arg Lys Glu Val Ile Trp Asp Ser Ala Met
                1130                1135                1140

Ile Ser Val Glu Thr Cys Ser Val Thr Val Ala Glu Phe Leu Arg
                1145                1150                1155

Ala Thr Ser Trp Ser Asn Leu Leu Asn Gly Arg Thr Ile Ser Gly
                1160                1165                1170

Val Thr Ser Pro Asp Ala Val Glu Leu Leu Lys Gly Ser Leu Ile
                1175                1180                1185

Gly Glu Lys Tyr Thr Leu His Ala Leu Cys Ala Arg Arg Arg Tyr
                1190                1195                1200

Ile His Trp Met His Ile Ala Gly Pro Thr Tyr Ile Pro Asp Pro
                1205                1210                1215

Gly Leu Thr Gly Ser Lys Met Arg Val Pro Tyr Leu Gly Ser Lys
                1220                1225                1230

Thr Glu Glu Arg Arg Ser Ala Ser Met Ala Thr Ile Lys Gly Met
                1235                1240                1245

Ser His His Leu Lys Ala Ala Leu Arg Gly Ala Ser Val Leu Val
                1250                1255                1260

Trp Ala Phe Gly Asp Thr Asp Asp Ser Trp Asn His Ala Cys Leu
                1265                1270                1275

Leu Ala Asn Thr Arg Cys Lys Val Thr Met Ser Gln Leu Arg Leu
                1280                1285                1290

Leu Thr Pro Thr Pro Ser Ser Ser Asn Ile Gln His Arg Leu Asn
                1295                1300                1305
```

```
Asp Gly Ile Ser Val Gln Lys Phe Thr Pro Ala Ser Leu Ser Arg
                1310                1315                1320

Val Ala Ser Phe Val His Ile Cys Asn Asp Phe Gln Asn Leu Glu
                1325                1330                1335

Lys Asp Gly Ala Ser Val Asp Ser Asn Leu Ile Tyr Gln Gln Ile
                1340                1345                1350

Met Leu Thr Gly Leu Ser Ile Met Glu Thr Leu His Pro Met Gln
                1355                1360                1365

Thr Gln Trp Ile Tyr Asn Asn Gln Thr Ile His Leu His Thr Gly
                1370                1375                1380

Thr Ser Cys Cys Pro Arg Glu Ile Glu Thr Ser Ile Val Asn Pro
                1385                1390                1395

Pro Lys Tyr Glu Phe Pro Thr Ile Thr Leu Thr Thr Asn Asn Gln
                1400                1405                1410

Phe Leu Phe Asp Asn Asn Pro Ile His Asp Asp Ala Ile Thr Lys
                1415                1420                1425

Leu Ala Val Ser Asp Phe Lys Phe Gln Glu Leu Asn Ile Asp Ala
                1430                1435                1440

Ile Arg Gly Tyr Gly Ala Val Asn Leu Leu Ser Arg Cys Val Ala
                1445                1450                1455

Lys Leu Ile Gly Glu Cys Ile Leu Glu Asp Gly Ile Gly Ser Ser
                1460                1465                1470

Ile Lys Asn Glu Ala Met Val Ser Phe Asp Ile Ser Val Asn Trp
                1475                1480                1485

Ile Ser Glu Ile Leu His Ser Asp Leu Arg Leu Thr Phe Met His
                1490                1495                1500

Leu Gly Gln Glu Leu Leu Cys Asp Leu Ala Tyr Gln Met Tyr Phe
                1505                1510                1515

Leu Arg Val Thr Gly Tyr His Ala Ile Val Thr Tyr Leu Lys Thr
                1520                1525                1530

Ser Leu Glu Arg Ile Pro Val Ile Gln Leu Ala Arg His Gly Pro
                1535                1540                1545

Tyr His Phe Ser Pro Arg Ser Val Glu Thr Ser His Ile Ser Arg
                1550                1555                1560

Val Gln Ser Arg Val Pro Tyr Pro Tyr Leu Ala Thr Val Asp Phe
                1565                1570                1575

Ile Ala Ala Cys Arg Asp Ile Ile Val Gln Gly Ala Gln Gln Tyr
                1580                1585                1590

Ile Ser Asp Leu Leu Ser Gly Ser Glu Cys Gln Tyr Thr Phe Phe
                1595                1600                1605

Asn Val Gln Asp Gly Asp Leu Thr Pro Lys Met Glu Gln Phe Leu
                1610                1615                1620

Ala Arg Arg Met Cys Leu Leu Val Leu Leu Thr Gly Thr Ser Ser
                1625                1630                1635

Ser Leu Pro Ile Ile Lys Ser Leu Asn Ala Ile Glu Lys Cys Ala
                1640                1645                1650

Val Leu Thr Gln Phe Ile Tyr Tyr Leu Pro Asn Val Asp Leu Thr
                1655                1660                1665

Val Ala Ser Lys Ala Arg Thr Leu Tyr Thr Leu Ala Val Asn Pro
                1670                1675                1680

Lys Ile Asp Ala Leu Val Ser Asn Leu Tyr Phe Thr Thr Arg Arg
                1685                1690                1695
```

```
Val Leu Ser Asn Ile Arg Gly Asp Arg His Ala Lys Ala Gln Val
                1700                1705                1710

Ser Tyr Leu Tyr Glu Glu Glu Val Ser Ser Glu Pro Leu Gln Asp
                1715                1720                1725

Glu Asn Phe Asp His Phe Met Lys Asp Pro Ile Ile Arg Gly Gly
                1730                1735                1740

Leu Phe Phe Thr Val Ile Ile Lys Met Glu Lys Met Ser Leu Asn
                1745                1750                1755

Gln Phe Ala Ser Gly Gly Ala Thr Thr Leu Ala Leu Pro Pro Gln
                1760                1765                1770

Glu Ala His Ser Ile Met Trp Arg Ala Ser Pro Leu Ala His Cys
                1775                1780                1785

Leu Lys Ser Val Gly Gln Val Ser Thr Ser Trp Tyr Lys Tyr Ala
                1790                1795                1800

Val Leu Gln Ala Ala Leu Ser Lys Thr Gln Pro Leu Arg Ser Asn
                1805                1810                1815

Ser Ile Tyr Ile Gly Glu Gly Ser Gly Ser Val Met Thr Leu Leu
                1820                1825                1830

Glu Tyr Met Asp Pro Ser Ile Ser His Ile Leu Gln Phe Val Val
                1835                1840                1845

Tyr Asn Ser Met Asn Pro Pro Gln Arg Asn Phe Gly Leu Met Pro
                1850                1855                1860

Thr Gln Phe Gln Glu Ser Ile Val Tyr Lys Asn Leu Cys Ala Gly
                1865                1870                1875

Ile Glu Ser Lys Tyr Gly Phe Ser Gln Thr Phe Ser Pro Leu Trp
                1880                1885                1890

Arg Asp Val Asp Gln Glu Thr Asn Ile Thr Glu Thr Ala Phe Leu
                1895                1900                1905

Asn Tyr Leu Met Glu Val Val Pro Ile His Ser Ala Lys Arg Leu
                1910                1915                1920

Val Cys Glu Val Glu Phe Asp Arg Gly Met Pro Asp Glu Val Met
                1925                1930                1935

Ile Gln Gly Tyr Met Asn Val Leu Ile Ala Ala Ala Phe Ser Leu
                1940                1945                1950

His Arg Glu Gly Arg Leu Phe Ile Lys Ile Phe Arg His Ser Glu
                1955                1960                1965

Ser Ile Phe Asn Phe Val Leu Ser Ser Ile Met Met Ile Phe Gly
                1970                1975                1980

Leu Cys His Ile His Arg Asn Ser Tyr Met Ser Thr Asn Lys Glu
                1985                1990                1995

Glu Tyr Ile Leu Val Gly Arg Ser Thr Ser Ala Pro Lys Leu Cys
                2000                2005                2010

Ile Ser Thr Gly His Pro Ala Ser Ser Gln Glu His Asn Arg Pro
                2015                2020                2025

Glu Leu Asn Gly Gly Asp Pro Ile Asp Met Ala Arg Val His Lys
                2030                2035                2040

Glu Met Asp Ser Leu Arg Glu Lys Glu Ser Ala Leu Ile Ser Ser
                2045                2050                2055

Leu Ile Arg Gly Thr Val Arg Leu Arg Pro Thr Gln Thr Asp Met
                2060                2065                2070

Leu Phe Ser Tyr Leu Gly Gly Lys Phe Val Thr Leu Phe Gly His
                2075                2080                2085

Ser Ala Arg Asp Leu Met Glu Leu Asp Ile Ala Val Leu Asp Ser
```

```
                2090                2095                2100

Arg Gln Ile Asp Leu Ile Asp Leu Leu Met Val Glu Ala Asn Ile
                2105                2110                2115

Ile Val Ser Glu Ser Thr Asp Leu Asp Leu Ala Leu Leu Leu Ser
                2120                2125                2130

Pro Phe Asn Leu Asp Lys Gly Arg Lys Ile Val Thr Leu Ala Lys
                2135                2140                2145

Ser Thr Thr Arg Gln Leu Ile Pro Leu Tyr Ile Ala Ala Glu Ile
                2150                2155                2160

Ser Cys Asn Lys His Ser Phe Ser His Leu Ile Ser Leu Val Gln
                2165                2170                2175

Arg Gly Val Ile Arg Ile Glu Asn Met Val Ser Val Ser Ser Phe
                2180                2185                2190

Ile Ser Lys Ser Ser Arg Pro Arg Phe Leu Arg Asp Val Val Thr
                2195                2200                2205

Phe Ala Gln Ile Glu His Ile Phe Ser Asp Leu Ser Thr Leu Ile
                2210                2215                2220

Leu Thr Arg Ser Glu Ile Lys Val Val Leu Lys Phe Ile Gly Cys
                2225                2230                2235

Cys Met Lys Phe Asn His Ala
                2240


<210> SEQ ID NO 53
<211> LENGTH: 457
<212> TYPE: PRT
<213> ORGANISM: Avian Paramixyvirus Type 2
<220> FEATURE:
<223> OTHER INFORMATION: APMV-2/Chicken/England/7702/06 NP protein

<400> SEQUENCE: 53

Met Ser Ser Val Phe Ser Glu His Gln Ala Leu Gln Asp Gln Leu
1               5                   10                  15

Val Lys Pro Ala Thr Arg Arg Ala Asp Val Ala Ser Thr Gly Leu
                20                  25                  30

Leu Arg Ala Glu Ile Pro Val Cys Val Thr Leu Ser Gln Asp Pro
                35                  40                  45

Thr Asp Arg Trp Asn Leu Ala Cys Leu Asn Leu Arg Trp Leu Ile
                50                  55                  60

Ser Glu Ser Ser Thr Thr Pro Met Arg Gln Gly Ala Ile Leu Ser
                65                  70                  75

Leu Leu Ser Leu His Ser Asp Asn Met Arg Ala His Ala Thr Leu
                80                  85                  90

Ala Ala Arg Ser Ala Asp Ala Ala Ile Thr Val Leu Glu Val Asp
                95                  100                 105

Ala Ile Asp Met Thr Asp Ser Thr Ile Thr Phe Asn Ala Arg Ser
                110                 115                 120

Gly Val Ser Glu Arg Arg Ser Thr Gln Leu Met Ala Ile Ala Lys
                125                 130                 135

Asp Leu Pro Arg Ser Cys Ser Asn Asp Ser Pro Phe Lys Asp Asp
                140                 145                 150

Thr Ile Glu Asp Arg Asp Pro Leu Asp Leu Ser Glu Thr Ile Asp
                155                 160                 165

Arg Leu Gln Gly Ile Ala Ala Gln Ile Trp Ile Ala Ala Ile Lys
                170                 175                 180

Ser Met Thr Ala Pro Asp Thr Ala Ala Glu Ser Glu Gly Lys Arg
```

```
                185                 190                 195

Leu Ala Lys Tyr Gln Gln Gln Gly Arg Leu Val Arg Gln Val Leu
                200                 205                 210

Val His Asp Ala Val Arg Ala Glu Phe Leu Arg Val Ile Arg Gly
                215                 220                 225

Ser Leu Val Leu Arg Gln Phe Met Val Ser Glu Cys Lys Arg Ala
                230                 235                 240

Ala Ser Met Gly Ser Glu Thr Ser Arg Tyr Tyr Ala Met Val Gly
                245                 250                 255

Asp Ile Ser Leu Tyr Ile Lys Asn Ala Gly Leu Thr Ala Phe Phe
                260                 265                 270

Leu Thr Leu Arg Phe Gly Ile Gly Thr His Tyr Pro Thr Leu Ala
                275                 280                 285

Met Ser Val Phe Ser Gly Glu Leu Lys Lys Met Ser Ser Leu Ile
                290                 295                 300

Arg Leu Tyr Lys Ser Lys Gly Glu Asn Ala Ala Tyr Met Ala Phe
                305                 310                 315

Leu Glu Asp Ala Asp Met Gly Asn Phe Ala Pro Ala Asn Phe Ser
                320                 325                 330

Thr Leu Tyr Ser Tyr Ala Met Gly Val Gly Thr Val Leu Glu Ala
                335                 340                 345

Ser Val Ala Lys Tyr Gln Phe Ala Arg Glu Phe Thr Ser Glu Thr
                350                 355                 360

Tyr Phe Arg Leu Gly Val Glu Thr Ala Gln Asn Gln Gln Cys Ala
                365                 370                 375

Leu Asp Glu Lys Thr Ala Lys Glu Met Gly Leu Thr Asp Glu Ala
                380                 385                 390

Arg Lys Gln Val Gln Ala Leu Ala Ser Asn Ile Glu Gln Gly Gln
                395                 400                 405

His Ser Met Pro Met Gln Gln Gln Pro Thr Phe Met Ser Gln Pro
                410                 415                 420

Tyr Gln Asp Asp Asp Arg Asp Gln Pro Ser Thr Ser Arg Pro Glu
                425                 430                 435

Pro Arg Pro Ser Gln Leu Thr Ser Gln Ser Ala Ala Gln Asp Asn
                440                 445                 450

Asp Ala Ala Ser Leu Asp Trp
                455


<210> SEQ ID NO 54
<211> LENGTH: 399
<212> TYPE: PRT
<213> ORGANISM: Avian Paramixyvirus Type 2
<220> FEATURE:
<223> OTHER INFORMATION: APMV-2/Chicken/England/7702/06 P protein

<400> SEQUENCE: 54

Met Gly Val Thr Asp Asp Ala Glu Ile Ala Glu Leu Leu Asp Leu
1                5                  10                  15

Gly Thr Ser Val Ile Gln Glu Leu Gln Arg Ala Glu Val Lys Gly
                20                  25                  30

Pro Gln Thr Thr Gly Lys Pro Lys Val Pro Pro Gly Asn Thr Lys
                35                  40                  45

Ser Leu Ala Thr Leu Trp Glu His Glu Thr Ser Thr Gln Gly Ser
                50                  55                  60

Ala Leu Gly Thr Pro Glu Asn Asn Thr Gln Ala Pro Asp Asp Asn
```

```
                65                  70                  75

Asn Ala Gly Ala Asp Thr Pro Ala Thr Thr Asp Val His Arg Thr
                80                  85                  90

Leu Asp Thr Ile Asp Thr Asp Thr Pro Pro Glu Gly Ser Lys Pro
                95                  100                 105

Ser Ser Thr Asn Ser Gln Pro Gly Asp Asp Leu Asp Lys Ala Leu
                110                 115                 120

Ser Lys Leu Glu Ala Arg Ala Lys Leu Gly Pro Asp Arg Ala Arg
                125                 130                 135

Gln Val Lys Lys Gly Lys Glu Ile Gly Ser Ser Thr Gly Thr Arg
                140                 145                 150

Glu Ala Ala Ser His His Met Glu Gly Ser Arg Gln Ser Glu Pro
                155                 160                 165

Gly Ala Gly Ser Arg Ala Gln Pro Gln Gly His Gly Asp Arg Asp
                170                 175                 180

Thr Gly Gly Ser Thr His Ser Ser Leu Glu Met Gly Asp Trp Lys
                185                 190                 195

Ser Gln Ala Gly Ala Thr Gln Ser Ala Leu Pro Leu Glu Ala Ser
                200                 205                 210

Pro Gly Glu Lys Ser Ala His Val Glu Leu Ala Gln Asn Pro Ala
                215                 220                 225

Phe Tyr Ala Gly Asn Pro Thr Asp Ala Ile Met Gly Leu Thr Lys
                230                 235                 240

Lys Val Asn Asp Leu Glu Thr Lys Leu Ala Glu Val Leu Arg Leu
                245                 250                 255

Leu Gly Ile Leu Pro Val Ile Lys Asn Glu Ile Ser Gln Leu Lys
                260                 265                 270

Ala Thr Val Ala Leu Met Ser Asn Gln Leu Ala Ser Ile Gln Ile
                275                 280                 285

Leu Asp Pro Gly Asn Ala Gly Val Lys Ser Leu Asn Glu Met Lys
                290                 295                 300

Ala Leu Ser Lys Ser Ala Ser Ile Val Val Ala Gly Pro Gly Ser
                305                 310                 315

Ile Pro Ser Glu Val Leu Glu Ser Asn Val Val Tyr Lys Asp Glu
                320                 325                 330

Leu Ala Arg Pro Val Thr Ala Gln Ala His Lys Glu Ile Lys Pro
                335                 340                 345

Arg Glu Glu Ala Ser Ala Thr Ser Ser Glu Leu Thr Ala Val Gln
                350                 355                 360

Ala Val Ile Asp Ile Pro Val Glu Asp Glu Arg Lys Lys Ala Arg
                365                 370                 375

Leu His Gln Ala Leu Glu Arg Ala Arg Thr Lys Glu Asp Ile Leu
                380                 385                 390

Arg Ile Lys Arg Gln Ile Tyr Asn Ala
                395


<210> SEQ ID NO 55
<211> LENGTH: 232
<212> TYPE: PRT
<213> ORGANISM: Avian Paramixyvirus Type 2
<220> FEATURE:
<223> OTHER INFORMATION: APMV-2/Chicken/England/7702/06 V protein

<400> SEQUENCE: 55

Met Gly Val Thr Asp Asp Ala Glu Ile Ala Glu Leu Leu Asp Leu
```

```
1               5                   10                  15

Gly Thr Ser Val Ile Gln Glu Leu Gln Arg Ala Glu Val Lys Gly
                20                  25                  30

Pro Gln Thr Thr Gly Lys Pro Lys Val Pro Pro Gly Asn Thr Lys
                35                  40                  45

Ser Leu Ala Thr Leu Trp Glu His Glu Thr Ser Thr Gln Gly Ser
                50                  55                  60

Ala Leu Gly Thr Pro Glu Asn Asn Thr Gln Ala Pro Asp Asp Asn
                65                  70                  75

Asn Ala Gly Ala Asp Thr Pro Ala Thr Thr Asp Val His Arg Thr
                80                  85                  90

Leu Asp Thr Ile Asp Thr Asp Thr Pro Pro Glu Gly Ser Lys Pro
                95                  100                 105

Ser Ser Thr Asn Ser Gln Pro Gly Asp Asp Leu Asp Lys Ala Leu
                110                 115                 120

Ser Lys Leu Glu Ala Arg Ala Lys Leu Gly Pro Asp Arg Ala Arg
                125                 130                 135

Gln Val Lys Lys Gly Glu Gly Asp Arg Val Glu His Arg Asp Glu
                140                 145                 150

Gly Gly Ser Gln Ser Pro His Gly Arg Glu Pro Thr Val Gly Ala
                155                 160                 165

Arg Ser Gly Gln Pro Ser Thr Ala Thr Arg Pro Trp Arg Pro Gly
                170                 175                 180

His Arg Arg Glu Tyr Ser Phe Ile Ser Arg Asp Gly Arg Leu Glu
                185                 190                 195

Val Thr Ser Trp Cys Asn Pro Val Cys Ser Pro Ile Arg Ser Glu
                200                 205                 210

Pro Arg Arg Glu Lys Cys Thr Cys Gly Thr Cys Pro Glu Ser Cys
                215                 220                 225

Ile Leu Cys Arg Gln Pro Asn
                230


<210> SEQ ID NO 56
<211> LENGTH: 207
<212> TYPE: PRT
<213> ORGANISM: Avian Paramixyvirus Type 2
<220> FEATURE:
<223> OTHER INFORMATION: APMV-2/Chicken/England/7702/06 W protein

<400> SEQUENCE: 56

Met Gly Val Thr Asp Asp Ala Glu Ile Ala Glu Leu Leu Asp Leu
1               5                   10                  15

Gly Thr Ser Val Ile Gln Glu Leu Gln Arg Ala Glu Val Lys Gly
                20                  25                  30

Pro Gln Thr Thr Gly Lys Pro Lys Val Pro Pro Gly Asn Thr Lys
                35                  40                  45

Ser Leu Ala Thr Leu Trp Glu His Glu Thr Ser Thr Gln Gly Ser
                50                  55                  60

Ala Leu Gly Thr Pro Glu Asn Asn Thr Gln Ala Pro Asp Asp Asn
                65                  70                  75

Asn Ala Gly Ala Asp Thr Pro Ala Thr Thr Asp Val His Arg Thr
                80                  85                  90

Leu Asp Thr Ile Asp Thr Asp Thr Pro Pro Glu Gly Ser Lys Pro
                95                  100                 105

Ser Ser Thr Asn Ser Gln Pro Gly Asp Asp Leu Asp Lys Ala Leu
```

```
                110                 115                 120

Ser Lys Leu Glu Ala Arg Ala Lys Leu Gly Pro Asp Arg Ala Arg
                125                 130                 135

Gln Val Lys Lys Gly Gly Arg Arg Ser Gly Arg Ala Gln Gly Arg
                140                 145                 150

Gly Arg Gln Pro Val Thr Thr Trp Lys Gly Ala Asp Ser Arg Ser
                155                 160                 165

Gln Glu Arg Ala Ala Glu His Ser His Lys Ala Met Ala Thr Gly
                170                 175                 180

Thr Gln Glu Gly Val Leu Ile His Leu Ser Arg Trp Glu Thr Gly
                185                 190                 195

Ser His Lys Leu Val Gln Pro Ser Leu Leu Ser His
                200                 205


<210> SEQ ID NO 57
<211> LENGTH: 369
<212> TYPE: PRT
<213> ORGANISM: Avian Paramixyvirus Type 2
<220> FEATURE:
<223> OTHER INFORMATION: APMV-2/Chicken/England/7702/06 M protein

<400> SEQUENCE: 57

Met Ala Gln Thr Thr Val Arg Leu Tyr Ile Asp Glu Ala Ser Pro
1                5                  10                  15

Asp Ile Glu Leu Leu Ser Tyr Pro Gln Ile Met Lys Asp Thr Gly
                20                  25                  30

His Gly Thr Lys Glu Leu Gln Gln Gln Ile Arg Val Ala Glu Ile
                35                  40                  45

Gly Ala Leu Gln Gly Gly Lys Asn Glu Ser Val Phe Ile Asn Ala
                50                  55                  60

Tyr Gly Phe Val Gln Gln Cys Lys Val Lys Pro Gly Ala Thr Gln
                65                  70                  75

Phe Phe Gln Val Asp Ala Ala Thr Lys Pro Glu Val Val Thr Ala
                80                  85                  90

Gly Met Ile Ile Ile Gly Ala Val Lys Gly Val Ala Gly Ile Thr
                95                  100                 105

Lys Leu Ala Glu Glu Val Phe Glu Leu Asp Ile Ser Ile Lys Lys
                110                 115                 120

Ser Ala Ser Phe His Glu Lys Val Ala Val Ser Phe Asn Thr Val
                125                 130                 135

Pro Leu Ser Leu Met Asn Ser Thr Ala Cys Arg Asn Leu Gly Tyr
                140                 145                 150

Val Thr Asn Ala Glu Glu Ala Ile Lys Cys Pro Ser Lys Ile Gln
                155                 160                 165

Ala Gly Val Thr Tyr Lys Phe Lys Ile Met Phe Val Ser Leu Thr
                170                 175                 180

Arg Leu His Asn Gly Lys Leu Tyr Arg Val Pro Lys Ala Val Tyr
                185                 190                 195

Ala Val Glu Ala Ser Ala Leu Tyr Lys Val Gln Leu Glu Val Gly
                200                 205                 210

Phe Lys Leu Asp Val Ala Lys Asp His Pro His Val Lys Met Leu
                215                 220                 225

Lys Lys Val Glu Arg Asn Gly Glu Thr Leu Tyr Leu Gly Tyr Ala
                230                 235                 240

Trp Phe His Leu Cys Asn Phe Lys Lys Thr Asn Ala Lys Gly Glu
```

```
                245                 250                 255

Ser Arg Thr Ile Ser Asn Leu Glu Gly Lys Val Arg Ala Met Gly
                260                 265                 270

Ile Lys Val Ser Leu Tyr Asp Leu Trp Gly Pro Thr Leu Val Val
                275                 280                 285

Gln Ile Thr Gly Lys Thr Ser Lys Tyr Ala Gln Gly Phe Phe Ser
                290                 295                 300

Thr Thr Gly Thr Cys Cys Leu Pro Val Ser Lys Ala Ala Pro Glu
                305                 310                 315

Leu Ala Lys Leu Met Trp Ser Cys Asn Ala Thr Ile Val Glu Ala
                320                 325                 330

Ala Val Ile Ile Gln Gly Ser Asp Arg Arg Ala Val Val Thr Ser
                335                 340                 345

Glu Asp Leu Glu Val Tyr Gly Ala Val Ala Lys Glu Lys Gln Ala
                350                 355                 360

Ala Lys Gly Phe His Pro Phe Arg Lys
                365


<210> SEQ ID NO 58
<211> LENGTH: 536
<212> TYPE: PRT
<213> ORGANISM: Avian Paramixyvirus Type 2
<220> FEATURE:
<223> OTHER INFORMATION: APMV-2/Chicken/England/7702/06 F protein

<400> SEQUENCE: 58

Met Asn Gln Ala Leu Val Ile Leu Leu Val Ser Phe Gln Leu Gly
1               5                   10                  15

Val Ala Leu Asp Asn Ser Val Leu Ala Pro Ile Gly Val Ala Ser
                20                  25                  30

Ala Gln Glu Trp Gln Leu Ala Ala Tyr Thr Thr Thr Leu Thr Gly
                35                  40                  45

Thr Ile Ala Val Arg Phe Ile Pro Val Leu Pro Gly Asn Leu Ser
                50                  55                  60

Thr Cys Ala Gln Glu Thr Leu Gln Glu Tyr Asn Arg Thr Val Thr
                65                  70                  75

Asn Ile Leu Gly Pro Leu Arg Glu Asn Leu Asp Ala Leu Leu Ser
                80                  85                  90

Asp Phe Asp Lys Pro Ala Ser Arg Phe Val Gly Ala Ile Ile Gly
                95                  100                 105

Ser Val Ala Leu Gly Val Ala Thr Ala Ala Gln Ile Thr Ala Ala
                110                 115                 120

Val Ala Leu Asn Gln Ala Gln Glu Asn Ala Arg Asn Ile Trp Arg
                125                 130                 135

Leu Lys Glu Ser Ile Lys Lys Thr Asn Ala Ala Val Leu Glu Leu
                140                 145                 150

Lys Asp Gly Leu Ala Thr Thr Ala Ile Ala Leu Asp Lys Val Gln
                155                 160                 165

Lys Phe Ile Asn Asp Asp Ile Ile Pro Gln Ile Lys Asp Ile Asp
                170                 175                 180

Cys Gln Val Val Ala Asn Lys Leu Gly Val Tyr Leu Ser Leu Tyr
                185                 190                 195

Leu Thr Glu Leu Thr Thr Val Phe Gly Ser Gln Ile Thr Asn Pro
                200                 205                 210

Ala Leu Ser Thr Leu Ser Tyr Gln Ala Leu Tyr Ser Leu Cys Gly
```

```
                215                 220                 225

Gly Asp Met Gly Lys Leu Thr Glu Leu Ile Gly Val Asn Ala Lys
                230                 235                 240

Asp Val Gly Ser Leu Tyr Glu Ala Asn Leu Ile Thr Gly Gln Ile
                245                 250                 255

Val Gly Tyr Asp Pro Glu Leu Gln Ile Ile Leu Ile Gln Val Ser
                260                 265                 270

Tyr Pro Ser Val Ser Glu Val Thr Gly Val Arg Ala Thr Glu Leu
                275                 280                 285

Val Thr Val Ser Val Ala Thr Pro Lys Gly Glu Gly Gln Ala Ile
                290                 295                 300

Val Pro Arg Tyr Val Ala Gln Ser Arg Val Leu Thr Glu Glu Leu
                305                 310                 315

Asp Val Ser Thr Cys Arg Phe Ser Lys Thr Thr Leu Tyr Cys Arg
                320                 325                 330

Ser Ile Leu Thr Arg Pro Leu Pro Thr Leu Ile Ala Ser Cys Leu
                335                 340                 345

Ser Gly Lys Tyr Asp Asp Cys Gln Tyr Thr Thr Glu Ile Gly Ala
                350                 355                 360

Leu Ser Ser Arg Phe Ile Thr Val Asn Gly Gly Val Leu Ala Asn
                365                 370                 375

Cys Arg Ala Ile Val Cys Lys Cys Val Ser Pro Pro His Ile Ile
                380                 385                 390

Pro Gln Asn Asp Ile Gly Ser Val Thr Val Ile Asp Ser Ser Ile
                395                 400                 405

Cys Lys Glu Val Val Leu Glu Ser Val Gln Leu Arg Leu Glu Gly
                410                 415                 420

Lys Leu Ser Ser Gln Tyr Phe Ser Asn Val Thr Ile Asp Leu Ser
                425                 430                 435

Gln Ile Thr Thr Ser Gly Ser Leu Asp Ile Ser Ser Glu Ile Gly
                440                 445                 450

Ser Ile Asn Asn Thr Val Asn Arg Val Asp Glu Leu Ile Lys Glu
                455                 460                 465

Ser Asn Glu Trp Leu Asn Ala Val Asn Pro Arg Leu Val Asn Asn
                470                 475                 480

Thr Ser Ile Ile Val Leu Cys Val Leu Ala Ala Leu Ile Ile Val
                485                 490                 495

Trp Leu Ile Ala Leu Thr Val Cys Phe Cys Tyr Ser Ala Arg Tyr
                500                 505                 510

Ser Ala Lys Ser Lys Gln Met Arg Gly Ala Met Thr Gly Ile Asp
                515                 520                 525

Asn Pro Tyr Val Ile Gln Ser Ala Thr Lys Met
                530                 535


<210> SEQ ID NO 59
<211> LENGTH: 580
<212> TYPE: PRT
<213> ORGANISM: Avian Paramixyvirus Type 2
<220> FEATURE:
<223> OTHER INFORMATION: APMV-2/Chicken/England/7702/06 HN protein

<400> SEQUENCE: 59

Met Asp Phe Pro Ser Arg Glu Asn Leu Ala Ala Gly Asp Ile Ser
1               5                   10                  15

Gly Arg Lys Thr Trp Arg Leu Leu Phe Arg Ile Leu Thr Leu Ser
```

-continued

```
                20                  25                  30

Ile Gly Val Val Cys Leu Ala Ile Asn Ile Ala Thr Ile Ala Lys
                35                  40                  45

Leu Asp His Leu Asp Asn Met Ala Ser Asn Thr Trp Thr Thr Thr
                50                  55                  60

Glu Ala Asp Arg Val Ile Ser Ser Ile Thr Thr Pro Leu Lys Val
                65                  70                  75

Pro Val Asn Gln Ile Asn Asp Met Phe Arg Ile Val Ala Leu Asp
                80                  85                  90

Leu Pro Leu Gln Met Thr Ser Leu Gln Lys Glu Ile Thr Ser Gln
                95                  100                 105

Val Gly Phe Leu Ala Glu Ser Ile Asn Asn Val Leu Ser Lys Asn
                110                 115                 120

Gly Ser Ala Gly Leu Val Leu Val Asn Asp Pro Glu Tyr Ala Gly
                125                 130                 135

Gly Ile Ala Val Ser Leu Tyr Gln Gly Asp Ala Ser Ala Gly Leu
                140                 145                 150

Asn Phe Gln Pro Ile Ser Leu Ile Glu His Pro Ser Phe Val Pro
                155                 160                 165

Gly Pro Thr Thr Ala Lys Gly Cys Ile Arg Ile Pro Thr Phe His
                170                 175                 180

Met Gly Pro Ser His Trp Cys Tyr Ser His Asn Ile Ile Ala Ser
                185                 190                 195

Gly Cys Gln Asp Ala Ser His Ser Ser Met Tyr Ile Ser Leu Gly
                200                 205                 210

Val Leu Lys Ala Ser Gln Thr Gly Ser Pro Ile Phe Leu Thr Thr
                215                 220                 225

Ala Ser His Leu Val Asp Asp Asn Ile Asn Arg Lys Ser Cys Ser
                230                 235                 240

Ile Val Ala Ser Lys Tyr Gly Cys Asp Ile Leu Cys Ser Ile Val
                245                 250                 255

Ile Glu Thr Glu Asn Glu Asp Tyr Arg Ser Asp Pro Ala Thr Ser
                260                 265                 270

Met Ile Ile Gly Arg Leu Phe Phe Asn Gly Ser Tyr Thr Glu Ser
                275                 280                 285

Lys Ile Asn Thr Gly Ser Ile Phe Ser Leu Phe Ser Ala Asn Tyr
                290                 295                 300

Pro Ala Val Gly Ser Gly Ile Val Val Gly Asp Glu Ala Ala Phe
                305                 310                 315

Pro Ile Tyr Gly Gly Val Lys Gln Asn Thr Trp Leu Phe Asn Gln
                320                 325                 330

Leu Lys Asp Phe Gly Tyr Phe Thr His Asn Asp Val Tyr Lys Cys
                335                 340                 345

Asn Arg Thr Asp Ile Gln Gln Thr Ile Leu Asp Ala Tyr Arg Pro
                350                 355                 360

Pro Lys Ile Ser Gly Arg Leu Trp Val Gln Gly Ile Leu Leu Cys
                365                 370                 375

Pro Val Ser Leu Arg His Asp Pro Gly Cys Arg Leu Lys Val Phe
                380                 385                 390

Asn Thr Ser Asn Val Met Met Gly Ala Glu Ala Arg Val Ile Gln
                395                 400                 405

Val Gly Ser Ala Val Tyr Leu Tyr Gln Arg Ser Ser Thr Trp Trp
                410                 415                 420
```

-continued

```
Val Val Gly Leu Thr His Lys Leu Asp Val Ser Glu Ile Thr Arg
                425                 430                 435

Glu Ser Gly Asn Met Val Asn Lys Glu Ser Pro Ile Gly Arg Ala
                440                 445                 450

Lys Phe Pro Arg Pro Ser Phe Ser Arg Asp Ala Cys Ala Arg Pro
                455                 460                 465

Asn Ile Cys Pro Ala Val Cys Val Ser Gly Val Tyr Gln Asp Ile
                470                 475                 480

Trp Pro Ile Ser Thr Ala His Asn Leu Ser Gln Val Val Trp Val
                485                 490                 495

Gly Gln Tyr Leu Glu Ala Phe Tyr Ala Arg Lys Asp Pro Arg Ile
                500                 505                 510

Gly Ile Ala Thr Gln Tyr Glu Trp Lys Val Thr Asn Gln Leu Phe
                515                 520                 525

Asn Ser Asn Thr Glu Gly Gly Tyr Ser Thr Thr Thr Cys Phe Arg
                530                 535                 540

Asn Thr Lys Arg Asp Lys Ala Tyr Cys Val Val Ile Ser Glu Tyr
                545                 550                 555

Ala Asp Gly Val Phe Gly Ser Tyr Arg Ile Val Pro Gln Leu Ile
                560                 565                 570

Glu Ile Arg Thr Thr Thr Gly Lys Ser Glu
                575                 580


<210> SEQ ID NO 60
<211> LENGTH: 2242
<212> TYPE: PRT
<213> ORGANISM: Avian Paramixyvirus Type 2
<220> FEATURE:
<223> OTHER INFORMATION: APMV-2/Chicken/England/7702/06 L protein

<400> SEQUENCE: 60

Met Asp Gln Thr Gln Ala Asp Thr Ile Ile Gln Pro Glu Val His
1                5                  10                  15

Leu Asn Ser Pro Leu Val Arg Ala Lys Leu Val Leu Leu Trp Lys
                20                  25                  30

Leu Thr Gly Leu Pro Leu Pro Ser Asp Leu Arg Ser Phe Val Leu
                35                  40                  45

Thr Thr His Ala Ala Asp Asp Gln Ile Ala Lys Asn Glu Thr Arg
                50                  55                  60

Ile Lys Ala Lys Ile Asn Ser Leu Ile Asp Asn Leu Ile Lys His
                65                  70                  75

Cys Lys Ala Arg Gln Val Ala Leu Ser Gly Leu Thr Pro Val Val
                80                  85                  90

His Pro Thr Thr Leu Gln Trp Ser Leu Pro Ile Thr Cys Glu Arg
                95                  100                 105

Ala Ala Gln Pro Ala Lys Val Arg Glu Lys Ser Val Lys Gln Ala
                110                 115                 120

Met Ser Glu Lys Gln His Gly Phe Arg His Leu Phe Ser Ala Val
                125                 130                 135

Ser His Gln Leu Val Gly Asn Ala Thr Leu Phe Cys Ala Gln Asp
                140                 145                 150

Ser Ser Thr Val Asn Val Asp Ser Pro Cys Ser Ser Gly Cys Glu
                155                 160                 165

Arg Leu Ile Ile Asp Ser Ile Gly Ala Leu Gln Thr Arg Trp Thr
                170                 175                 180
```

-continued

```
Arg Cys Arg Trp Ala Trp Leu His Ile Lys Gln Val Met Arg Tyr
                185                 190                 195

Gln Val Leu Gln Ser Arg Leu His Ala His Ala Asn Ser Val Ser
                200                 205                 210

Thr Trp Ser Glu Ala Trp Gly Phe Ile Gly Ile Thr Pro Asp Ile
                215                 220                 225

Val Leu Ile Val Asp Tyr Lys Ser Lys Met Phe Thr Ile Leu Thr
                230                 235                 240

Phe Glu Met Met Leu Met Tyr Ser Asp Val Ile Glu Gly Arg Asp
                245                 250                 255

Asn Val Val Ala Val Gly Ser Met Ser Pro Asn Leu Gln Pro Val
                260                 265                 270

Val Glu Arg Ile Glu Val Leu Phe Asp Val Val Asp Thr Leu Ala
                275                 280                 285

Arg Arg Ile His Asp Pro Ile Tyr Asp Leu Val Ala Ala Leu Glu
                290                 295                 300

Ser Met Ala Tyr Ala Ala Val Gln Leu His Asp Ala Ser Glu Thr
                305                 310                 315

His Ala Gly Glu Phe Phe Ser Phe Asn Leu Thr Glu Ile Glu Ser
                320                 325                 330

Thr Leu Ala Pro Leu Leu Asp Pro Gly Gln Val Leu Ser Val Met
                335                 340                 345

Arg Thr Ile Ser Tyr Cys Tyr Ser Gly Leu Ser Pro Asp Gln Ala
                350                 355                 360

Ala Glu Leu Leu Cys Val Met Arg Leu Phe Gly His Pro Leu Leu
                365                 370                 375

Ser Ala Gln Gln Ala Ala Lys Lys Val Arg Glu Ser Met Cys Ala
                380                 385                 390

Pro Lys Leu Leu Glu His Asp Ala Ile Leu Gln Thr Leu Ser Phe
                395                 400                 405

Phe Lys Gly Ile Ile Ile Asn Gly Tyr Arg Lys Ser His Ser Gly
                410                 415                 420

Val Trp Pro Ala Ile Asp Pro Asp Ser Ile Val Asp Asp Asp Leu
                425                 430                 435

Arg Gln Leu Tyr Tyr Glu Ser Ala Glu Ile Ser His Ala Phe Met
                440                 445                 450

Leu Lys Lys Tyr Arg Tyr Leu Ser Met Ile Glu Phe Arg Lys Ser
                455                 460                 465

Ile Glu Phe Asp Leu Asn Asp Asp Leu Ser Thr Phe Leu Lys Asp
                470                 475                 480

Lys Ala Ile Cys Arg Pro Lys Asp Gln Trp Ala Arg Ile Phe Arg
                485                 490                 495

Lys Ser Gln Phe Pro Leu Lys Leu Asp Asn Arg Thr Ser Gly Val
                500                 505                 510

Asp Lys Ser Asn Arg Leu Leu Ile Asp Phe Leu Glu Ser His Asp
                515                 520                 525

Phe Ser Pro Glu Glu Glu Met Lys Tyr Val Arg Thr Lys Ala Tyr
                530                 535                 540

Leu Glu Asp Asp Gln Phe Ser Ala Ser Tyr Ser Leu Lys Glu Lys
                545                 550                 555

Glu Ile Lys Thr Thr Gly Arg Ile Phe Ala Lys Met Thr Arg Lys
                560                 565                 570
```

-continued

```
Val Arg Arg Cys Gln Val Phe Met Gly Ser Leu Leu Ser Gly His
                575                 580                 585

Val Cys Lys Phe Phe Lys Glu Asn Gly Val Ser Met Glu Gln Leu
                590                 595                 600

Ser Leu Thr Lys Ser Leu Leu Ala Met Ser Gln Leu Ser Pro Arg
                605                 610                 615

Ile Ser Pro Val Arg Asn Glu Pro Ala Ser Thr Gln Asp Arg Leu
                620                 625                 630

Val Arg Tyr Ser Asn Gly Thr His Leu Cys Ala Gly Glu Leu Lys
                635                 640                 645

Pro His Gln Arg Glu Arg Pro Val Lys Lys Ser Ile Val Ala Thr
                650                 655                 660

Phe Leu Thr Thr Asp Leu Gln Lys Tyr Cys Leu Asn Trp Arg Tyr
                665                 670                 675

Gly Ser Ile Lys Leu Phe Ala Gln Ala Leu Asn Gln Leu Phe Gly
                680                 685                 690

Leu Asp His Gly Phe Glu Trp Ile His Leu Arg Leu Met Asn Ser
                695                 700                 705

Thr Leu Phe Val Gly Asp Pro Phe Ser Pro Pro Glu Cys Lys Gly
                710                 715                 720

Val Lys Asp Leu Asp Asp Ala Pro Asn Ser Asp Ile Phe Ile Val
                725                 730                 735

Ser Ala Arg Gly Gly Ile Glu Gly Leu Cys Leu Lys Leu Trp Thr
                740                 745                 750

Met Ile Ser Ile Ser Ile Ile His Cys Val Ser Glu Lys Ile Gly
                755                 760                 765

Thr Arg Val Ala Ala Met Val Gln Gly Asp Asn Gln Val Ile Ala
                770                 775                 780

Ile Thr Arg Glu Leu Phe Asn Gly Glu Thr Phe Glu Gln Ile Gln
                785                 790                 795

Pro Glu Leu Asp Arg Leu Gly Asn Ala Phe Phe Ser Glu Phe Lys
                800                 805                 810

Gln His Asn Tyr Ala Met Gly His Asn Leu Lys Pro Lys Glu Thr
                815                 820                 825

Ile Gln Ser Gln Ser Phe Phe Val Tyr Ser Lys Arg Ile Phe Trp
                830                 835                 840

Glu Gly Arg Ile Leu Ser Gln Ser Leu Lys Asn Ala Thr Lys Leu
                845                 850                 855

Cys Phe Ile Ala Asp His Leu Gly Asp Asn Thr Val Ser Ser Cys
                860                 865                 870

Ser Asn Leu Ala Ser Thr Val Thr Ser Leu Val Glu Lys Gly Phe
                875                 880                 885

Glu Lys Asp Thr Ala Phe Val Leu Asn Leu Ile Tyr Ser Met Thr
                890                 895                 900

Gln Ile Leu Ile Asp Glu Gln Tyr Ser Leu Gln Gly Asp Tyr Thr
                905                 910                 915

Ala Val Lys Gly Leu Ile Gly Thr Asp Asn His Arg Asn Phe Ser
                920                 925                 930

Leu Ala Ala Leu Ile Pro Gly Gln Val Gly Gly Tyr Asn Phe Leu
                935                 940                 945

Asn Ile Ser Arg Leu Phe Thr Arg Asn Ile Gly Asp Pro Val Thr
                950                 955                 960

Cys Ala Ile Ala Asp Ile Lys Trp Phe Ile Lys Ser Arg Leu Ile
```

```
                965                 970                 975

Ala Glu His Val Leu Lys Asn Ile Leu Leu Arg Asp Pro Gly Asp
                980                 985                 990

Gly Gly Trp Ser Thr Leu Cys Ala Asp Pro Tyr Ala Leu Asn Ile
                995                 1000                1005

Pro Tyr Thr Gln Leu Pro Thr Thr Tyr Leu Lys Lys His Thr Gln
                1010                1015                1020

Arg Ser Leu Leu Ala Asp Ser Asn Asn Pro Ile Val Ala Gly Val
                1025                1030                1035

Gln Leu Asp Ser Gln Tyr Ile Glu Glu Glu Glu Phe Ala Gln Phe
                1040                1045                1050

Leu Leu Asp Arg Glu Ala Val Met Pro His Leu Ala His Thr Ile
                1055                1060                1065

Met Glu Thr Ser Ile Leu Gly Lys Arg Lys Asn Ile Gln Gly Leu
                1070                1075                1080

Ile Asp Thr Thr Pro Thr Ile Ile Lys Thr Ala Leu Met Arg Gln
                1085                1090                1095

Pro Ile Ser Arg Arg Lys Cys Glu Lys Ile Ile Asn Tyr Ser Ile
                1100                1105                1110

Asn Tyr Leu Val Glu Cys His Asp Ser Ser Ser Ser Ile Arg Thr
                1115                1120                1125

Phe Glu Pro Arg Lys Glu Val Ile Trp Asp Ser Ala Met Ile Ser
                1130                1135                1140

Val Glu Thr Cys Ser Val Thr Ile Ala Glu Phe Leu Arg Ala Thr
                1145                1150                1155

Ser Trp Ser Asn Ile Leu Asn Gly Arg Thr Ile Ser Gly Val Thr
                1160                1165                1170

Ser Pro Asp Thr Val Glu Leu Leu Arg Gly Ser Leu Ile Gly Glu
                1175                1180                1185

Asn Thr His Cys Val Leu Cys Glu Gln Gly Asp Asp Thr Phe Thr
                1190                1195                1200

Trp Met His Ile Ser Gly Pro Thr Tyr Ile Pro Asp Pro Gly Leu
                1205                1210                1215

Thr Gly Ser Lys Met Arg Val Pro Tyr Leu Gly Ser Lys Thr Glu
                1220                1225                1230

Glu Arg Arg Ser Ala Ser Met Ala Thr Val Lys Gly Met Ser His
                1235                1240                1245

His Leu Lys Ala Thr Leu Arg Gly Ala Ser Val Met Val Trp Ala
                1250                1255                1260

Phe Gly Asp Thr Glu Glu Ser Trp Glu His Ala Cys Leu Val Ala
                1265                1270                1275

Asn Thr Arg Cys Lys Ile Asn Leu Pro Gln Leu Arg Leu Leu Thr
                1280                1285                1290

Pro Thr Pro Ser Ser Ser Asn Ile Gln His Arg Leu Asn Asp Gly
                1295                1300                1305

Ile Ser Val Gln Lys Phe Thr Pro Ala Ser Leu Ser Arg Val Ala
                1310                1315                1320

Ser Phe Val His Ile Cys Asn Asp Phe Gln Lys Leu Glu Arg Asp
                1325                1330                1335

Gly Ser Ser Val Asp Ser Asn Leu Ile Tyr Gln Gln Ile Met Leu
                1340                1345                1350

Thr Gly Leu Ser Ile Met Glu Thr Leu His Pro Met His Val Ser
                1355                1360                1365
```

-continued

```
Trp Val Tyr Asn Asn Gln Thr Ile His Leu His Thr Gly Thr Ser
                1370                1375                1380

Cys Cys Pro Arg Glu Ile Glu Thr Ser Ile Val Asn Pro Ala Arg
                1385                1390                1395

Gly Glu Phe Pro Thr Ile Thr Leu Thr Thr Asn Asn Gln Phe Leu
                1400                1405                1410

Phe Asp Cys Asn Pro Ile His Asp Glu Ala Leu Thr Lys Leu Ser
                1415                1420                1425

Val Ser Glu Phe Lys Phe Gln Glu Leu Asn Ile Asp Ser Met Gln
                1430                1435                1440

Gly Tyr Ser Ala Val Asn Leu Leu Ser Arg Cys Val Ala Lys Leu
                1445                1450                1455

Ile Gly Glu Cys Ile Leu Glu Asp Gly Ile Gly Ser Ser Ile Lys
                1460                1465                1470

Asn Glu Ala Met Ile Ser Phe Asp Asn Ser Ile Asn Trp Ile Ser
                1475                1480                1485

Glu Ala Leu Asn Ser Asp Leu Arg Leu Val Phe Leu Gln Leu Gly
                1490                1495                1500

Gln Glu Leu Leu Cys Asp Leu Ala Tyr Gln Met Tyr Tyr Leu Arg
                1505                1510                1515

Val Ile Gly Tyr His Ser Ile Val Ala Tyr Leu Gln Asn Thr Leu
                1520                1525                1530

Glu Arg Ile Pro Val Ile Gln Leu Ala Asn Met Ala Leu Thr Ile
                1535                1540                1545

Ser His Pro Glu Val Trp Arg Arg Val Thr Val Ser Gly Phe Asn
                1550                1555                1560

Gln Gly Tyr Arg Ser Pro Tyr Leu Ala Thr Val Asp Phe Ile Ala
                1565                1570                1575

Ala Cys Arg Asp Ile Ile Val Gln Gly Ala Gln His Tyr Met Ala
                1580                1585                1590

Asp Leu Leu Ser Gly Val Glu Cys Gln Tyr Thr Phe Phe Asn Val
                1595                1600                1605

Gln Asp Gly Asp Leu Thr Pro Lys Met Glu Gln Phe Leu Ala Arg
                1610                1615                1620

Arg Met Cys Leu Phe Val Leu Leu Thr Gly Thr Ile Arg Pro Leu
                1625                1630                1635

Pro Ile Ile Arg Ser Leu Asn Ala Ile Glu Lys Cys Ala Ile Leu
                1640                1645                1650

Thr Gln Phe Leu Tyr Tyr Leu Pro Ser Val Asp Met Ala Val Ala
                1655                1660                1665

Asp Lys Ala Arg Val Leu Tyr Gln Leu Ser Ile Asn Pro Lys Ile
                1670                1675                1680

Asp Ala Leu Val Ser Asn Leu Tyr Phe Thr Thr Arg Arg Val Leu
                1685                1690                1695

Ser Cys Ile Thr Gly Asp Ser Ser Ser Arg Ala His Ile Ala Phe
                1700                1705                1710

Leu Tyr Glu Glu Glu Val Ile Val Asp Val Pro Ala Ser Asn Gln
                1715                1720                1725

Phe Asp Gln Tyr His Arg Asp Pro Ile Leu Arg Gly Gly Leu Phe
                1730                1735                1740

Phe Ser Leu Ser Leu Lys Met Glu Arg Met Ser Leu Asn Arg Phe
                1745                1750                1755
```

```
Ala Val Gln Thr Leu Pro Thr Gln Gly Ser Asn Ser Gln Gly Ser
                1760                1765                1770

Arg Gln Thr Leu Trp Arg Ala Ser Pro Leu Ala His Cys Leu Lys
                1775                1780                1785

Ser Val Gly Gln Val Ser Thr Ser Trp Tyr Lys Tyr Ala Val Val
                1790                1795                1800

Gly Ala Ser Val Glu Lys Val Gln Pro Thr Arg Ser Thr Ser Leu
                1805                1810                1815

Tyr Ile Gly Glu Gly Ser Gly Ser Val Met Thr Leu Leu Glu Tyr
                1820                1825                1830

Leu Asp Pro Ala Thr Ile Ile Phe Tyr Asn Ser Leu Phe Ser Asn
                1835                1840                1845

Ser Met Asn Pro Pro Gln Arg Asn Phe Gly Leu Met Pro Thr Gln
                1850                1855                1860

Phe Gln Asp Ser Val Val Tyr Lys Asn Ile Ser Ala Gly Val Asp
                1865                1870                1875

Cys Lys Tyr Gly Phe Lys Gln Val Phe Gln Pro Leu Trp Arg Asp
                1880                1885                1890

Val Asp Gln Glu Thr Asn Val Val Glu Thr Ala Phe Leu Asn Tyr
                1895                1900                1905

Val Ile Glu Val Val Pro Val His Ser Ser Lys Arg Val Val Cys
                1910                1915                1920

Glu Val Glu Phe Asp Arg Gly Met Pro Asp Glu Ile Val Ile Thr
                1925                1930                1935

Gly Tyr Ile His Val Leu Met Val Thr Ala Tyr Ser Leu His Arg
                1940                1945                1950

Gly Gly Arg Leu Ile Ile Lys Val Tyr Arg His Ser Glu Ala Val
                1955                1960                1965

Phe Gln Phe Val Leu Ser Ala Ile Val Met Met Phe Gly Gly Leu
                1970                1975                1980

Asp Ile His Arg Asn Ser Tyr Met Ser Thr Asn Lys Glu Glu Tyr
                1985                1990                1995

Ile Ile Ile Ala Ala Ala Pro Glu Ala Leu Asn Tyr Ser Ser Val
                2000                2005                2010

Pro Ala Ile Leu Gln Arg Val Lys Ser Val Ile Asp Gln Gln Leu
                2015                2020                2025

Thr Leu Ile Ser Pro Ile Asp Leu Glu Arg Leu Arg His Glu Thr
                2030                2035                2040

Glu Ser Leu Arg Glu Lys Glu Asn Asn Leu Val Ile Ser Leu Thr
                2045                2050                2055

Arg Gly Lys Tyr Gln Leu Arg Pro Thr Gln Thr Asp Met Leu Leu
                2060                2065                2070

Ser Tyr Leu Gly Gly Arg Phe Ile Thr Leu Phe Gly Gln Ser Ala
                2075                2080                2085

Arg Asp Leu Met Ala Thr Asp Val Ala Asp Leu Asp Ala Arg Lys
                2090                2095                2100

Ile Ala Leu Val Asp Leu Leu Met Val Glu Ser Asn Ile Ile Leu
                2105                2110                2115

Ser Glu Ser Thr Asp Leu Asp Leu Ala Leu Leu Leu Ser Pro Phe
                2120                2125                2130

Asn Leu Asp Lys Gly Arg Lys Ile Val Thr Leu Ala Lys Ala Thr
                2135                2140                2145

Thr Arg Gln Leu Leu Pro Val Tyr Ile Ala Ser Glu Ile Met Cys
```

2150 2155 2160

Asn Arg Gln Ala Phe Thr His Leu Thr Ser Ile Ile Gln Arg Gly
2165 2170 2175

Val Ile Arg Ile Glu Asn Met Leu Ala Thr Thr Glu Phe Val Arg
2180 2185 2190

Gln Ser Val Arg Pro Gln Phe Ile Lys Glu Val Ile Thr Ile Ala
2195 2200 2205

Gln Val Asn His Leu Phe Ser Asp Leu Ser Lys Leu Val Leu Ser
2210 2215 2220

Arg Ser Glu Val Lys Gln Ala Leu Lys Phe Val Gly Cys Cys Met
2225 2230 2235

Lys Phe Arg Asn Ala Ser Asn
2240

<210> SEQ ID NO 61
<211> LENGTH: 457
<212> TYPE: PRT
<213> ORGANISM: Avian Paramixyvirus Type 2
<220> FEATURE:
<223> OTHER INFORMATION: APMV-2/Gadwell/Kenya/3/80 NP protein

<400> SEQUENCE: 61

Met Ser Ser Val Phe Thr Glu Tyr Gln Ala Leu Gln Asp Gln Leu
1 5 10 15

Val Lys Pro Ser Ser Arg Arg Ala Asp Val Ala Ser Thr Gly Leu
20 25 30

Leu Arg Ala Glu Ile Pro Val Cys Val Thr Leu Ser Gln Asp Pro
35 40 45

Thr Asp Arg Trp Asn Leu Ala Cys Leu Asn Leu Arg Trp Ile Ile
50 55 60

Ser Glu Ser Ser Thr Thr Pro Met Arg Ala Gly Ala Ile Leu Ser
65 70 75

Leu Leu Ser Leu His Ser Asp Asn Met Arg Ala His Ala Thr Leu
80 85 90

Ala Ala Arg Ser Ala Asp Ala Ser Ile Thr Ile Leu Glu Val Asp
95 100 105

Asn Ile Asp Met Ala Ala Asp Thr Ile Thr Phe Asn Ala Arg Ser
110 115 120

Gly Val Ser Asp Arg Arg Ser Ala Gln Leu Met Ala Ile Ala Lys
125 130 135

Asp Leu Pro Arg Ser Cys Ser Asn Asp Ser Pro Phe Lys Asp Asn
140 145 150

Asn Ile Glu Asp Arg Glu Pro Leu Ala Leu Ser Glu Thr Ile Asp
155 160 165

Arg Gln Glu Glu Ile Ala Ala Gln Ile Trp Ile Ala Ala Ile Lys
170 175 180

Ser Met Thr Ala Pro Asp Thr Ala Ala Glu Ser Glu Gly Lys Arg
185 190 195

Leu Ala Lys Tyr Gln Gln Gln Gly Arg Leu Val Arg Gln Val Leu
200 205 210

Val His Asp Ala Val Arg Ala Glu Phe Leu Arg Val Ile Arg Gly
215 220 225

Ser Leu Val Leu Pro Gln Phe Met Val Ser Glu Cys Lys Arg Ala
230 235 240

Ala Ser Met Gly Ser Glu Thr Ser Ser Pro His Ala Met Val Gly

```
                245                 250                 255

Asp Ile Ser Leu Tyr Thr His Asn Ala Gly Leu Thr Ala Phe Phe
                260                 265                 270

Leu Thr Leu Arg Phe Gly Ile Gly Thr His Tyr Pro Thr Leu Ala
                275                 280                 285

Met Ser Val Phe Ser Gly Glu Leu Lys Lys Met Ser Ser Leu Ile
                290                 295                 300

Arg Leu Tyr Lys Ser Lys Gly Glu Asn Ala Ala Tyr Met Ala Phe
                305                 310                 315

Leu Glu Asp Ala Asp Met Gly Asn Phe Ala Pro Ala Asn Phe Ser
                320                 325                 330

Thr Leu Tyr Ser Tyr Ala Met Gly Val Gly Thr Val Leu Glu Ala
                335                 340                 345

Ser Val Ala Lys Tyr Gln Phe Ala Arg Glu Phe Thr Ser Glu Thr
                350                 355                 360

Tyr Phe Arg Leu Gly Val Glu Thr Ala Gln Asn Gln Gln Cys Ala
                365                 370                 375

Leu Asp Glu Lys Thr Ala Lys Glu Met Gly Leu Thr Asp Glu Ala
                380                 385                 390

Arg Lys Gln Val Gln Ala Leu Ala Ser Asn Ile Glu Gln Gly Gln
                395                 400                 405

His Ser Met Pro Met Gln Gln Gln Pro Thr Phe Met Ser Gln Pro
                410                 415                 420

Tyr Gln Asp Asp Asp Arg Asp Gln Pro Ser Thr Ser Arg Pro Glu
                425                 430                 435

Pro Arg Pro Ser Gln Leu Thr Ser Gln Ser Ala Ala Gln Asp Asn
                440                 445                 450

Asp Ala Ala Ser Leu Asp Trp
                455


<210> SEQ ID NO 62
<211> LENGTH: 399
<212> TYPE: PRT
<213> ORGANISM: Avian Paramixyvirus Type 2
<220> FEATURE:
<223> OTHER INFORMATION: APMV-2/Gadwell/Kenya/3/80 P protein

<400> SEQUENCE: 62

Met Glu Phe Thr Asp Asp Ala Glu Ile Ala Glu Leu Leu Asp Leu
1               5                   10                  15

Gly Thr Ser Val Ile Gln Glu Leu Gln Arg Ala Glu Val Lys Gly
                20                  25                  30

Pro Gln Thr Thr Gly Lys Pro Lys Val Pro Pro Gly Asn Thr Lys
                35                  40                  45

Ser Leu Ala Thr Leu Trp Glu His Glu Thr Ser Thr Gln Gly Ser
                50                  55                  60

Ala Leu Gly Thr Pro Glu Asn Asn Thr Gln Ala Pro Asp Asp Asn
                65                  70                  75

Asn Ala Gly Ala Asp Thr Pro Ala Thr Thr Asp Val His Arg Thr
                80                  85                  90

Leu Asp Thr Ile Asp Thr Asp Thr Pro Pro Glu Gly Ser Lys Pro
                95                  100                 105

Ser Ser Thr Asn Ser Gln Pro Gly Asp Asp Leu Asp Lys Ala Leu
                110                 115                 120

Ser Lys Leu Glu Ala Arg Ala Lys Leu Gly Pro Asp Arg Ala Arg
```

```
                125                 130                 135

Gln Val Lys Lys Gly Lys Glu Ile Gly Ser Ser Thr Gly Thr Arg
                140                 145                 150

Glu Ala Ala Ser His His Met Glu Gly Ser Arg Gln Ser Glu Pro
                155                 160                 165

Gly Ala Gly Ser Arg Ala Gln Pro Gln Gly His Gly Asp Arg Asp
                170                 175                 180

Thr Gly Gly Ser Thr His Ser Ser Leu Glu Met Gly Asp Trp Lys
                185                 190                 195

Ser Gln Ala Gly Ala Thr Gln Ser Ala Leu Pro Leu Glu Ala Ser
                200                 205                 210

Pro Gly Glu Lys Ser Ala His Val Glu Leu Ala Gln Asn Pro Ala
                215                 220                 225

Phe Tyr Ala Gly Asn Pro Thr Asp Ala Ile Met Gly Leu Thr Lys
                230                 235                 240

Lys Val Asn Asp Leu Lys Thr Lys Leu Ala Glu Val Leu Arg Leu
                245                 250                 255

Leu Gly Ile Leu Pro Gly Ile Lys Asn Glu Ile Ser Gln Leu Lys
                260                 265                 270

Ala Thr Val Ala Leu Met Ser Asn Gln Ile Ala Ser Ile Gln Ile
                275                 280                 285

Leu Gly Pro Gly Asn Ala Gly Val Lys Ser Leu Asn Glu Met Lys
                290                 295                 300

Ala Leu Ser Lys Ala Ala Ser Ile Val Val Ala Gly Pro Gly Val
                305                 310                 315

Leu Pro Pro Glu Val Thr Glu Gly Gly Leu Ile Ala Lys Asp Glu
                320                 325                 330

Leu Ala Arg Pro Ile Pro Ile Gln Pro Gln Arg Asp Ser Lys Pro
                335                 340                 345

Lys Asp Asp Pro His Thr Ser Pro Asn Asp Val Leu Ala Val Arg
                350                 355                 360

Ala Met Ile Asp Thr Leu Val Asp Asp Glu Lys Lys Arg Lys Arg
                365                 370                 375

Leu Asn Gln Ala Leu Asp Lys Ala Lys Thr Lys Asp Asp Val Leu
                380                 385                 390

Arg Val Lys Arg Gln Ile Tyr Asn Ala
                395


<210> SEQ ID NO 63
<211> LENGTH: 232
<212> TYPE: PRT
<213> ORGANISM: Avian Paramixyvirus Type 2
<220> FEATURE:
<223> OTHER INFORMATION: APMV-2/Gadwell/Kenya/3/80 V protein

<400> SEQUENCE: 63

Met Glu Phe Thr Asp Asp Ala Glu Ile Ala Glu Leu Leu Asp Leu
1                5                  10                  15

Gly Thr Ser Val Ile Gln Glu Leu Gln Arg Ala Glu Val Lys Gly
                20                  25                  30

Pro Gln Thr Thr Gly Lys Pro Lys Val Pro Pro Gly Asn Thr Lys
                35                  40                  45

Ser Leu Ala Thr Leu Trp Glu His Glu Thr Ser Thr Gln Gly Ser
                50                  55                  60

Ala Leu Gly Thr Pro Glu Asn Asn Thr Gln Ala Pro Asp Asp Asn
```

```
                65                  70                  75

Asn Ala Gly Ala Asp Thr Pro Ala Thr Thr Asp Val His Arg Thr
                80                  85                  90

Leu Asp Thr Ile Asp Thr Asp Thr Pro Pro Glu Gly Ser Lys Pro
                95                  100                 105

Ser Ser Thr Asn Ser Gln Pro Gly Asp Asp Leu Asp Lys Ala Leu
                110                 115                 120

Ser Lys Leu Glu Ala Arg Ala Lys Leu Gly Pro Asp Arg Ala Arg
                125                 130                 135

Gln Val Lys Lys Gly Glu Gly Asp Arg Val Glu His Arg Asp Glu
                140                 145                 150

Gly Gly Ser Gln Ser Pro His Gly Arg Glu Pro Thr Val Gly Ala
                155                 160                 165

Arg Ser Gly Gln Pro Ser Thr Ala Thr Arg Pro Trp Arg Pro Gly
                170                 175                 180

His Arg Arg Glu Tyr Ser Phe Ile Ser Arg Asp Gly Arg Leu Glu
                185                 190                 195

Val Thr Ser Trp Cys Asn Pro Val Cys Ser Pro Ile Arg Ser Glu
                200                 205                 210

Pro Arg Arg Glu Lys Cys Thr Cys Gly Thr Cys Pro Glu Ser Cys
                215                 220                 225

Ile Leu Cys Arg Gln Pro Asn
                230


<210> SEQ ID NO 64
<211> LENGTH: 207
<212> TYPE: PRT
<213> ORGANISM: Avian Paramixyvirus Type 2
<220> FEATURE:
<223> OTHER INFORMATION: APMV-2/Gadwell/Kenya/3/80 W protein

<400> SEQUENCE: 64

Met Glu Phe Thr Asp Asp Ala Glu Ile Ala Glu Leu Leu Asp Leu
1                5                  10                  15

Gly Thr Ser Val Ile Gln Glu Leu Gln Arg Ala Glu Val Lys Gly
                20                  25                  30

Pro Gln Thr Thr Gly Lys Pro Lys Val Pro Pro Gly Asn Thr Lys
                35                  40                  45

Ser Leu Ala Thr Leu Trp Glu His Glu Thr Ser Thr Gln Gly Ser
                50                  55                  60

Ala Leu Gly Thr Pro Glu Asn Asn Thr Gln Ala Pro Asp Asp Asn
                65                  70                  75

Asn Ala Gly Ala Asp Thr Pro Ala Thr Thr Asp Val His Arg Thr
                80                  85                  90

Leu Asp Thr Ile Asp Thr Asp Thr Pro Pro Glu Gly Ser Lys Pro
                95                  100                 105

Ser Ser Thr Asn Ser Gln Pro Gly Asp Asp Leu Asp Lys Ala Leu
                110                 115                 120

Ser Lys Leu Glu Ala Arg Ala Lys Leu Gly Pro Asp Arg Ala Arg
                125                 130                 135

Gln Val Lys Lys Gly Gly Arg Arg Ser Gly Arg Ala Gln Gly Arg
                140                 145                 150

Gly Arg Gln Pro Val Thr Thr Trp Lys Gly Ala Asp Ser Arg Ser
                155                 160                 165

Gln Glu Arg Ala Ala Glu His Ser His Lys Ala Met Ala Thr Gly
```

```
                170                 175                 180

Thr Gln Glu Gly Val Leu Ile His Leu Ser Arg Trp Glu Thr Gly
                185                 190                 195

Ser His Lys Leu Val Gln Pro Ser Leu Leu Ser His
                200                 205


<210> SEQ ID NO 65
<211> LENGTH: 369
<212> TYPE: PRT
<213> ORGANISM: Avian Paramixyvirus Type 2
<220> FEATURE:
<223> OTHER INFORMATION: APMV-2/Gadwell/Kenya/3/80 M protein

<400> SEQUENCE: 65

Met Ala Gln Thr Thr Val Arg Leu Tyr Ile Asp Glu Ala Ser Pro
1               5                   10                  15

Asp Ile Glu Leu Leu Ser Tyr Pro Leu Ile Met Lys Asp Thr Gly
                20                  25                  30

His Gly Thr Lys Glu Leu Gln Gln Gln Ile Arg Val Ala Glu Ile
                35                  40                  45

Gly Ala Leu Gln Gly Gly Lys Asn Glu Ser Val Phe Ile Asn Ala
                50                  55                  60

Tyr Gly Phe Val Gln Gln Cys Lys Val Lys Pro Gly Ala Thr Gln
                65                  70                  75

Phe Phe Gln Val Asp Ala Ala Thr Lys Pro Glu Val Ile Thr Ala
                80                  85                  90

Gly Met Ile Ile Ile Ala Ala Ala Lys Gly Gly Thr Gly Ile Thr
                95                  100                 105

Lys Leu Ala Glu Glu Val Phe Glu Leu Asp Ile Ser Ile Lys Lys
                110                 115                 120

Ser Ala Ser Phe His Glu Lys Val Ala Val Ser Phe Asn Thr Val
                125                 130                 135

Pro Leu Ser Leu Met Asn Ser Thr Ala Cys Arg Asn Leu Gly Tyr
                140                 145                 150

Val Thr Asn Ala Glu Glu Ala Ile Lys Cys Pro Ser Lys Ile Gln
                155                 160                 165

Ala Gly Val Thr Tyr Lys Phe Lys Ile Met Phe Val Ser Leu Thr
                170                 175                 180

Arg Leu His Asn Gly Lys Leu Tyr Arg Val Pro Lys Ala Val Tyr
                185                 190                 195

Ala Val Glu Ala Ser Ala Leu Tyr Lys Val Gln Leu Glu Val Gly
                200                 205                 210

Phe Lys Leu Asp Val Ala Lys Asp His Pro His Val Lys Met Leu
                215                 220                 225

Lys Lys Val Glu Arg Asn Gly Glu Thr Leu Tyr Leu Gly Tyr Ala
                230                 235                 240

Trp Phe His Leu Cys Asn Phe Lys Lys Thr Asn Ala Lys Gly Glu
                245                 250                 255

Ser Arg Thr Ile Ser Asn Leu Glu Gly Lys Val Arg Ala Met Gly
                260                 265                 270

Ile Lys Val Ser Leu Tyr Asp Leu Trp Gly Pro Thr Lys Val Val
                275                 280                 285

Gln Ile Thr Gly Lys Thr Ser Lys Tyr Ala Gln Gly Phe Phe Ser
                290                 295                 300

Thr Thr Gly Thr Cys Cys Leu Pro Val Ser Lys Ala Ala Pro Glu
```

```
                305                 310                 315

Leu Ala Lys Leu Met Trp Ser Cys Asn Ala Thr Ile Val Glu Ala
                320                 325                 330

Ala Val Ile Ile Gln Gly Ser Asp Arg Arg Ala Val Val Thr Ser
                335                 340                 345

Glu Asp Leu Glu Val Tyr Gly Ala Val Ala Lys Glu Lys Gln Ala
                350                 355                 360

Ala Lys Gly Phe His Pro Phe Arg Lys
                365


<210> SEQ ID NO 66
<211> LENGTH: 536
<212> TYPE: PRT
<213> ORGANISM: Avian Paramixyvirus Type 2
<220> FEATURE:
<223> OTHER INFORMATION: APMV-2/Gadwell/Kenya/3/80 F protein

<400> SEQUENCE: 66

Met Asn Gln Ala Leu Val Ile Leu Leu Val Ser Phe Gln Leu Gly
1                5                  10                  15

Val Ala Leu Asp Asn Ser Val Leu Ala Pro Ile Gly Val Ala Ser
                20                  25                  30

Ala Gln Glu Trp Gln Leu Ala Ala Tyr Thr Thr Thr Leu Thr Gly
                35                  40                  45

Thr Ile Ala Val Arg Phe Ile Pro Val Leu Pro Gly Asn Leu Ser
                50                  55                  60

Thr Cys Ala Gln Glu Thr Leu Gln Glu Tyr Asn Arg Thr Val Thr
                65                  70                  75

Asn Ile Leu Gly Pro Leu Arg Glu Asn Leu Asp Ala Leu Leu Ser
                80                  85                  90

Asp Phe Asp Lys Pro Ala Ser Arg Phe Val Gly Ala Ile Ile Gly
                95                  100                 105

Ser Val Ala Leu Gly Val Ala Thr Ala Ala Gln Ile Thr Ala Ala
                110                 115                 120

Val Ala Leu Asn Gln Ala Gln Glu Asn Ala Arg Asn Ile Trp Arg
                125                 130                 135

Leu Lys Glu Ser Ile Lys Lys Thr Asn Ala Ala Val Leu Glu Leu
                140                 145                 150

Lys Asp Gly Leu Ala Thr Thr Ala Ile Ala Leu Asp Lys Val Gln
                155                 160                 165

Lys Phe Ile Asn Asp Asp Ile Ile Pro Gln Ile Lys Asp Ile Asp
                170                 175                 180

Cys Gln Val Val Ala Asn Lys Leu Gly Val Tyr Leu Ser Leu Tyr
                185                 190                 195

Leu Thr Glu Leu Thr Thr Val Phe Gly Ser Gln Ile Thr Asn Pro
                200                 205                 210

Ala Leu Ser Thr Leu Ser Tyr Gln Ala Leu Tyr Ser Leu Cys Gly
                215                 220                 225

Gly Asp Met Gly Lys Leu Thr Glu Leu Ile Gly Val Ile Ala Lys
                230                 235                 240

Asp Val Gly Ser Leu Tyr Glu Val Asn Leu Ile Thr Gly Gln Ile
                245                 250                 255

Val Gly Tyr Asp Pro Glu Leu Gln Ile Ile Leu Ile Gln Val Ser
                260                 265                 270

Tyr Pro Ser Val Ser Glu Val Thr Gly Val Arg Ala Thr Glu Leu
```

```
                275                 280                 285

Val Thr Val Ser Val Thr Thr Pro Lys Gly Glu Gly Gln Ala Ile
                290                 295                 300

Val Pro Arg Tyr Val Ala Gln Ser Arg Val Leu Thr Glu Glu Leu
                305                 310                 315

Asp Val Trp Ile Cys Arg Phe Ser Lys Thr Arg Val Tyr Cys Lys
                320                 325                 330

Ser Ile Leu Thr Arg Pro Leu Pro Thr Leu Ile Ala Ser Cys Leu
                335                 340                 345

Ser Gly Lys Tyr Asp Asp Cys Gln Cys Thr Thr Glu Ile Gly Ala
                350                 355                 360

Leu Ser Ser Arg Phe Ile Thr Val Asn Gly Gly Val Leu Ala Asn
                365                 370                 375

Cys Arg Ala Arg Val Cys Asn Cys Val Ser Pro Pro His Ile Ile
                380                 385                 390

Pro Gln Asn Asp Ile Gly Ser Val Thr Val Ile Asp Ser Ser Ile
                395                 400                 405

Cys Lys Glu Val Val Leu Glu Ser Val Gln Leu Arg Leu Glu Gly
                410                 415                 420

Lys Leu Ser Ser Gln Tyr Phe Ser Asn Val Thr Ile Asp Leu Ser
                425                 430                 435

Gln Ile Thr Thr Ser Gly Ser Leu Asp Ile Ser Ser Glu Ile Gly
                440                 445                 450

Ser Ile Asn Asn Thr Val Asn Arg Val Asp Glu Leu Ile Lys Glu
                455                 460                 465

Ser Asn Glu Trp Leu Asn Ala Val Asn Pro Arg Leu Val Asn Asn
                470                 475                 480

Thr Ser Ile Ile Val Leu Cys Val Leu Ala Ala Leu Ile Ile Val
                485                 490                 495

Trp Leu Ile Ala Leu Thr Val Cys Phe Cys Tyr Ser Ala Arg Tyr
                500                 505                 510

Ser Ala Lys Ser Lys Gln Met Arg Gly Ala Met Thr Gly Ile Asp
                515                 520                 525

Asn Pro Tyr Val Ile Gln Ser Ala Thr Lys Met
                530                 535


<210> SEQ ID NO 67
<211> LENGTH: 582
<212> TYPE: PRT
<213> ORGANISM: Avian Paramixyvirus Type 2
<220> FEATURE:
<223> OTHER INFORMATION: APMV-2/Gadwell/Kenya/3/80 HN protein

<400> SEQUENCE: 67

Met Asp Ala Arg Ser Arg Glu Asn Leu Thr Glu Leu Gly Gln Gly
1                5                  10                  15

Gly Arg Arg Thr Trp Leu Met Leu Phe Arg Val Leu Thr Leu Ala
                20                  25                  30

Leu Thr Leu Ala Cys Leu Ala Ile Asn Ile Ala Thr Ile Ala Lys
                35                  40                  45

Leu Asp Ser Ile Asp Thr Gly Arg Leu Gln Thr Trp Thr Thr Ala
                50                  55                  60

Glu Ser Asp Arg Val Ile Gly Ser Leu Thr Asp Thr Leu Lys Val
                65                  70                  75

Pro Ile Asn Gln Val Asn Asp Met Phe Arg Ile Val Ala Leu Asp
```

-continued

```
                80                  85                  90

Pro Ile Asn Gln Val Asn Asp Met Phe Arg Ile Val Ala Leu Asp
                95                  100                 105

Val Gly Phe Leu Ala Glu Ser Ile Asn Ser Val Leu Ser Lys Asn
                110                 115                 120

Gly Ser Ala Gly Leu Val Leu Ile Asn Asp Pro Glu Tyr Ala Gly
                125                 130                 135

Gly Ile Gly Val Ser Leu Phe Gln Gly Asp Ser Ala Ser Ser Leu
                140                 145                 150

Asp Phe Glu Glu Pro His Leu Ile Glu His Pro Ser Phe Ile Pro
                155                 160                 165

Gly Pro Thr Thr Ala Lys Gly Cys Ile Arg Ile Pro Thr Phe His
                170                 175                 180

Met Ser Ala Ser His Trp Cys Tyr Ser His Asn Ile Ile Ala Ser
                185                 190                 195

Gly Cys Gln Asp Ala Gly His Ser Ser Met Tyr Ile Ser Leu Gly
                200                 205                 210

Val Leu Lys Ala Thr Gln Ala Gly Ser Pro Ser Phe Leu Thr Thr
                215                 220                 225

Ala Ser Gln Leu Val Asp Asp Lys Leu Asn Arg Lys Ser Cys Ser
                230                 235                 240

Ile Ile Ser Thr Thr Tyr Gly Cys Asp Ile Leu Cys Ser Leu Val
                245                 250                 255

Val Glu Asn Glu Asp Ala Asp Tyr Arg Ser Asp Pro Pro Thr Asp
                260                 265                 270

Met Ile Leu Gly Arg Leu Phe Phe Asn Gly Thr Tyr Ser Glu Arg
                275                 280                 285

Lys Leu Asn Thr Gly Thr Ile Phe Gln Leu Phe Ser Ala Asn Tyr
                290                 295                 300

Pro Ala Val Gly Ser Gly Leu Val Leu Gly Asp Glu Ile Ala Phe
                305                 310                 315

Pro Val Tyr Gly Gly Val Arg Gln Asn Thr Trp Leu Phe Asn Gln
                320                 325                 330

Leu Lys Asp His Gly Tyr Phe Ala His Asn Asp Val Tyr Lys Cys
                335                 340                 345

Asn Lys Ser Asp Thr His Gln Thr Val Leu Asn Ala Tyr Arg Pro
                350                 355                 360

Pro Lys Ile Ser Gly Arg Leu Trp Ser Gln Val Val Leu Ile Cys
                365                 370                 375

Pro Leu Gly Leu Phe Ile Asn Thr Asp Cys Arg Ile Lys Val Phe
                380                 385                 390

Asn Thr Ser Thr Val Met Met Gly Ala Glu Ala Arg Leu Ile Gln
                395                 400                 405

Val Gly Ser Asp Ile Tyr Leu Tyr Gln Arg Ser Ser Ser Trp Trp
                410                 415                 420

Val Val Gly Leu Thr Tyr Lys Leu Asp Phe Gln Glu Leu Ser Ser
                425                 430                 435

Lys Thr Gly Asn Val Ile Asn Lys Val Ser Pro Ile Ala His Ala
                440                 445                 450

Lys Phe Pro Arg Pro Ser Phe Ser Arg Asp Ala Cys Ala Arg Pro
                455                 460                 465

Asn Ile Cys Pro Ala Val Cys Val Ser Gly Val Tyr Gln Asp Ile
                470                 475                 480
```

```
Trp Pro Ile Ser Thr Ala Gln Asn Leu Ser Gln Val Val Trp Val
                485                 490                 495

Gly Gln Tyr Leu Glu Ala Phe Tyr Ala Arg Lys Asp Pro Trp Ile
                500                 505                 510

Gly Ile Ala Thr Gln Tyr Asn Trp Lys Lys Asn Val Arg Leu Phe
                515                 520                 525

Asn Thr Asn Thr Glu Val Gly Tyr Ser Thr Thr Thr Cys Phe Arg
                530                 535                 540

Asn Thr Lys Arg Asp Lys Ala Phe Cys Val Ile Ile Ser Glu Tyr
                545                 550                 555

Ala Asp Gly Val Phe Gly Ser Tyr Arg Val Val Pro Gln Leu Ile
                560                 565                 570

Glu Val Glu Thr Thr Ser Lys Lys Arg Leu Phe Ser
                575                 580


<210> SEQ ID NO 68
<211> LENGTH: 2242
<212> TYPE: PRT
<213> ORGANISM: Avian Paramixyvirus Type 2
<220> FEATURE:
<223> OTHER INFORMATION: APMV-2/Gadwell/Kenya/3/80 L protein

<400> SEQUENCE: 68

Met Asp Gln Val Gln Ala Asp Thr Ile Ile Gln Pro Glu Val His
1               5                   10                  15

Leu Asp Ser Pro Ile Val Arg Ala Lys Leu Val Leu Phe Trp Lys
                20                  25                  30

Leu Thr Gly Leu Pro Leu Pro Lys Asp Leu Arg Phe Phe Glu Ser
                35                  40                  45

Leu Pro Thr Pro Pro Thr Ser Lys Phe Ser Gly Met Ser Pro Glu
                50                  55                  60

Leu Ser Gln Lys Ser Tyr Pro Ser Val Pro Asn Leu Ile Lys His
                65                  70                  75

Cys Lys Ala Arg Gln Val Ala Leu Ser Gly Leu Thr Pro Val Val
                80                  85                  90

His Pro Thr Thr Leu Gln Trp Leu Leu Ser Ile Thr Cys Glu Arg
                95                  100                 105

Ala Asp His Leu Ala Lys Val Arg Glu Lys Ser Val Lys Gln Ala
                110                 115                 120

Met Ser Glu Lys Gln His Gly Phe Arg His Leu Phe Ser Ala Val
                125                 130                 135

Ser His Gln Leu Val Gly Asn Ala Thr Leu Phe Cys Ala Gln Asp
                140                 145                 150

Ser Ser Thr Val Asn Val Asp Ser Pro Cys Ser Ser Gly Cys Glu
                155                 160                 165

Arg Leu Ile Ile Asp Ser Ile Gly Ala Leu Gln Thr Arg Trp Thr
                170                 175                 180

Arg Cys Arg Trp Ala Trp Leu His Ile Lys Gln Val Met Arg Tyr
                185                 190                 195

Gln Val Leu Gln Ser Arg Leu His Ala His Ala Asn Ser Val Ser
                200                 205                 210

Thr Trp Ser Glu Ala Trp Gly Phe Ile Gly Ile Thr Pro Asp Ile
                215                 220                 225

Val Leu Ile Val Asp Tyr Lys Ser Lys Met Phe Thr Ile Leu Thr
                230                 235                 240
```

```
Phe Glu Met Met Leu Met Tyr Ser Asp Val Ile Glu Gly Arg Asp
                245                 250                 255

Asn Val Val Ala Val Gly Ser Met Ser Pro Asn Leu Gln Pro Val
                260                 265                 270

Val Glu Arg Ile Glu Val Leu Phe Asp Val Val Asp Thr Leu Ala
                275                 280                 285

Arg Arg Ile His Asp Pro Ile Tyr Asp Leu Val Ala Ala Leu Glu
                290                 295                 300

Ser Met Ala Tyr Ala Ala Val Gln Leu His Asp Ala Ser Glu Thr
                305                 310                 315

His Ala Gly Glu Phe Phe Ser Phe Asn Leu Thr Glu Ile Glu Ser
                320                 325                 330

Thr Leu Ala Pro Leu Leu Asp Pro Gly Gln Val Leu Ser Val Thr
                335                 340                 345

Lys Thr Ile Ser Met Cys Tyr Ser Cys Leu Thr Pro Asp Gln Ala
                350                 355                 360

Ala Glu Met Leu Cys Ile Met Arg Leu Phe Gly His Pro Leu Leu
                365                 370                 375

Ser Ala Gln Gln Ala Ala Lys Lys Val Arg Glu Ser Met Cys Ala
                380                 385                 390

Pro Lys Leu Leu Glu His Asp Ala Ile Leu Gln Thr Leu Ser Phe
                395                 400                 405

Phe Lys Gly Ile Ile Ile Asn Gly Tyr Arg Lys Ser His Ser Gly
                410                 415                 420

Val Trp Pro Asn Ile Glu Pro Glu Ser Ile Met Asp Asp Asp Phe
                425                 430                 435

Ser Gln Leu Tyr Tyr Glu Ser Ala Glu Ile Ser His Ser Phe Met
                440                 445                 450

Leu Lys Lys Tyr Arg Tyr Leu Ser Met Ile Glu Phe Lys Lys Ser
                455                 460                 465

Ile Asp Phe Asp Leu Asn Asp Asp Leu Ser Thr Phe Leu Lys Asp
                470                 475                 480

Lys Ala Ile Cys Arg Pro Lys Ser Gln Trp Ala Lys Ile Phe Arg
                485                 490                 495

Lys Ser Leu Phe Pro Leu Lys Met Thr Ile Asp Ser Gly Ala Asp
                500                 505                 510

Thr Arg Ser Asn Arg Leu Leu Ile Asp Phe Leu Glu Ser His Asp
                515                 520                 525

Phe Ser Pro Glu Glu Glu Met Lys Tyr Val Thr Thr Met Ala Tyr
                530                 535                 540

Leu Glu Asp Glu Gln Phe Ser Ala Ser Tyr Ser Leu Lys Glu Lys
                545                 550                 555

Glu Ile Lys Thr Thr Gly Arg Ile Phe Ala Lys Met Thr Arg Lys
                560                 565                 570

Met Arg Ser Cys Gln Val Ile Leu Glu Ser Leu Leu Ser Ser His
                575                 580                 585

Val Cys Lys Phe Phe Lys Glu Asn Gly Val Ser Met Glu Gln Leu
                590                 595                 600

Ser Leu Thr Lys Ser Leu Leu Ala Met Ser Gln Leu Ser Pro Arg
                605                 610                 615

Ile Ser Ala Val Arg Asn Glu Pro Ala Arg Asn Arg Lys Val Ile
                620                 625                 630
```

-continued

```
Cys Thr Asp Asn Gln Val Ser Asp His Ile Val Gly Glu Val Gly
                635                 640                 645

Pro His Gln Gln Asp Arg Pro Ala Arg Lys Ser Val Val Ala Thr
                650                 655                 660

Phe Leu Thr Thr Asp Leu Gln Lys Tyr Cys Leu Asn Trp Arg Tyr
                665                 670                 675

Gly Ser Ile Lys Leu Phe Ala Gln Ala Leu Asn Gln Leu Phe Gly
                680                 685                 690

Ile Glu His Gly Phe Glu Trp Ile His Leu Arg Leu Met Asn Ser
                695                 700                 705

Thr Leu Phe Val Gly Asp Pro Phe Ser Pro Pro Glu Ser Lys Val
                710                 715                 720

Leu Ser Asp Leu Asp Asp Ala Pro Asn Ser Asp Ile Phe Ile Val
                725                 730                 735

Ser Ala Arg Gly Gly Ile Glu Gly Leu Cys Gln Lys Leu Trp Thr
                740                 745                 750

Met Ile Ser Ile Ser Ile Ile His Cys Val Ala Glu Lys Ile Gly
                755                 760                 765

Ala Arg Val Ala Ala Met Val Gln Gly Asp Asn Gln Val Ile Ala
                770                 775                 780

Ile Thr Arg Glu Leu Tyr Lys Gly Glu Thr Tyr Thr Gln Ile Gln
                785                 790                 795

Pro Glu Leu Asp Arg Leu Gly Asn Ala Phe Phe Ala Glu Phe Lys
                800                 805                 810

Arg His Asn Tyr Ala Met Gly His Asn Leu Lys Pro Lys Glu Thr
                815                 820                 825

Ile Gln Ser Gln Ser Phe Phe Val Tyr Ser Lys Arg Ile Phe Trp
                830                 835                 840

Glu Gly Arg Ile Leu Ser Gln Ala Leu Lys Asn Ala Thr Lys Leu
                845                 850                 855

Cys Phe Ile Ala Asp His Leu Gly Asp Asn Thr Val Ser Ser Cys
                860                 865                 870

Ser Asn Leu Ala Ser Thr Ile Thr Arg Leu Val Glu Asn Gly Tyr
                875                 880                 885

Glu Lys Asp Thr Ala Phe Ile Leu Asn Leu Ile Ser Pro Met Thr
                890                 895                 900

Gln Ile Leu Met Asp Glu Gln Tyr Ser Leu Gln Gly Asp Tyr Ser
                905                 910                 915

Ser Val Lys Gly Leu Ile Gly Thr His Asn His Arg Asn Leu Leu
                920                 925                 930

Arg Ala Ala Leu Ile Pro Gly Gln Val Gly Gly Tyr Asn Phe Leu
                935                 940                 945

Asn Ile Ser Arg Leu Phe Thr Arg Asn Ile Gly Asp Pro Val Thr
                950                 955                 960

Cys Ala Ile Ala Asp Ile Lys Trp Phe Ile Lys Ser Arg Leu Ile
                965                 970                 975

Ala Glu His Val Leu Lys Asn Ile Leu Leu Arg Asp Pro Gly Asp
                980                 985                 990

Gly Gly Trp Ser Thr Leu Cys Ala Asp Pro Tyr Ala Leu Asn Ile
                995                1000                1005

Pro Tyr Thr Gln Leu Pro Thr Thr Tyr Leu Lys Lys His Thr Gln
               1010                1015                1020

Arg Ala Leu Leu Ala Asp Ser Asn Asn Pro Leu Leu Ala Gly Val
```

```
                1025                1030                1035

Gln Leu Asp Ser Gln Tyr Ile Glu Glu Glu Phe Ala Gln Phe
                1040                1045                1050

Leu Leu Asp Arg Glu Ala Val Met Pro Arg Val Ala His Thr Ile
                1055                1060                1065

Met Glu Ala Ser Ile Leu Gly Lys Arg Lys Asn Ile Gln Gly Leu
                1070                1075                1080

Ile Asp Thr Thr Pro Thr Ile Ile Lys Thr Ala Leu Met Arg Gln
                1085                1090                1095

Pro Ile Ser Arg Arg Lys Cys Glu Lys Ile Val Asn Tyr Ser Ile
                1100                1105                1110

Asn Tyr Leu Val Glu Cys His Asp Ser Ile Ile Ser Ala Arg Gln
                1115                1120                1125

Phe Glu Pro Arg Lys Glu Val Ile Trp Asp Ser Ala Met Ile Ser
                1130                1135                1140

Val Glu Thr Cys Ser Val Thr Ile Ala Glu Phe Leu Arg Ala Thr
                1145                1150                1155

Ser Trp Ser Asn Ile Leu Asn Gly Arg Thr Ile Ser Gly Val Thr
                1160                1165                1170

Ser Pro Asp Thr Ile Glu Leu Leu Lys Gly Ser Leu Ile Gly Glu
                1175                1180                1185

Asn Ala His Cys Ile Leu Cys Glu Gln Gly Asp Glu Thr Phe Thr
                1190                1195                1200

Trp Met His Leu Ala Gly Pro Ile Tyr Ile Pro Asp Pro Gly Val
                1205                1210                1215

Thr Ala Ser Lys Met Arg Val Pro Tyr Leu Gly Ser Lys Thr Glu
                1220                1225                1230

Glu Arg Arg Thr Ala Ser Met Ala Thr Ile Lys Gly Met Ser His
                1235                1240                1245

His Leu Lys Ala Ala Leu Arg Gly Ala Ser Val Met Val Trp Ala
                1250                1255                1260

Phe Gly Asp Thr Glu Glu Ser Trp Glu His Ala Cys Leu Val Ala
                1265                1270                1275

Asn Thr Arg Cys Lys Ile Asn Leu Pro Gln Leu Arg Leu Leu Thr
                1280                1285                1290

Pro Thr Pro Ser Ser Ser Asn Ile Gln His Arg Leu Asn Asp Gly
                1295                1300                1305

Ile Ser Val Gln Lys Phe Thr Pro Ala Ser Leu Ser Arg Val Ala
                1310                1315                1320

Ser Phe Val His Ile Cys Asn Asp Phe Gln Lys Leu Glu Arg Asp
                1325                1330                1335

Gly Ser Ser Val Asp Ser Asn Leu Ile Tyr Gln Gln Ile Met Leu
                1340                1345                1350

Thr Gly Leu Ser Ile Met Glu Thr Leu His Pro Met His Tyr Ala
                1355                1360                1365

Arg Asp Ile Gln Gln Pro Gly His Pro Trp His Thr Gly Thr Ser
                1370                1375                1380

Cys Cys Pro Arg Glu Ile Glu Thr Ser Ile Val Asn Pro Pro Lys
                1385                1390                1395

Tyr Glu Phe Pro Thr Ile Thr Leu Thr Thr Asn Asn Gln Phe Leu
                1400                1405                1410

Phe Asp Ser Asn Pro Ile His Asp Glu Ala Ile Thr Arg Leu Thr
                1415                1420                1425
```

-continued

Val Ser Asp Phe Lys Phe Gln Glu Leu Asn Ile Asp Ala Ile Arg
1430 1435 1440

Gly Tyr Ala Ala Ile Asn Leu Leu Ser Arg Cys Val Ala Lys Leu
1445 1450 1455

Ile Ser Glu Cys Ile Leu Glu Asp Gly Ile Gly Ser Ser Ile Lys
1460 1465 1470

Asn Glu Ala Met Val Ser Phe Asp Asn Ser Val Asn Trp Ile Ser
1475 1480 1485

Glu Ile Leu His Ser Asp Ile Arg Leu Ser Phe Met His Ile Gly
1490 1495 1500

Gln Glu Leu Leu Cys Asp Leu Ala Tyr Gln Met Tyr Phe Phe Lys
1505 1510 1515

Asn His Arg Val Pro Cys Tyr Tyr Tyr Leu Ser Glu Gly Phe Thr
1520 1525 1530

Glu Arg Ile Pro Val Ile Gln Leu Ala Asn Met Ala Leu Thr Ile
1535 1540 1545

Ser His Pro Glu Val Trp Arg Arg Val Thr Leu Ile Gly Phe Asn
1550 1555 1560

Gln Gly Tyr Arg Ser Pro Tyr Leu Ala Thr Val Asp Phe Ile Ala
1565 1570 1575

Ala Cys Arg Asp Val Ile Val Gln Gly Ala Gln Gln Tyr Leu Ser
1580 1585 1590

Glu Leu Leu Ser Glu Ser Glu Cys Gln Tyr Thr Phe Phe Asn Val
1595 1600 1605

Gln Asp Gly Asp Leu Thr Pro Lys Met Glu Gln Phe Leu Ala Arg
1610 1615 1620

Arg Met Cys Leu Phe Val Leu Leu Thr Gly Thr Ile Ser Pro Leu
1625 1630 1635

Pro Ile Val Arg Ser Leu Asn Ala Ile Glu Lys Cys Ala Val Phe
1640 1645 1650

Thr Gln Phe Leu Tyr Tyr Leu Pro Thr Val Asp Leu Ala Val Ala
1655 1660 1665

Ser Arg Ala Arg Thr Leu Tyr Thr Leu Ser Ile Ala Pro Lys Ile
1670 1675 1680

Asp Ala Leu Val Ser Asn Leu Tyr Phe Thr Thr Arg Arg Val Leu
1685 1690 1695

Ser Asn Ile Arg Gly Asp Lys His Ala Lys Ala Gln Ile Ser Tyr
1700 1705 1710

Leu Tyr Glu Glu Lys Ile Ser Ala Glu Pro His Gln Gly Glu Asn
1715 1720 1725

Phe Asp Gln Phe Met Lys Asp Pro Ile Ile Arg Gly Gly Leu Phe
1730 1735 1740

Phe Thr Ile Met Leu Lys Met Glu Lys Met Ser Leu Asn Gln Phe
1745 1750 1755

Ala Val His Arg Arg Thr Ile Leu Gln Asn Ile Ser Lys Arg Thr
1760 1765 1770

Trp Gln Cys Leu Trp Arg Ala Ser Pro Leu Ala His Cys Leu Lys
1775 1780 1785

Ser Val Gly Gln Val Ser Thr Ser Trp Tyr Lys Tyr Ala Val Leu
1790 1795 1800

Gln Ala Ser Leu Ile Arg Gly Gln Pro Leu Arg Ser Thr Ser Val
1805 1810 1815

```
Tyr Met Val Lys Gly Ser Gly Ser Val Met Thr Leu Phe Glu Tyr
                1820                1825                1830

Met Asp Pro Ser Ala Thr Ile Phe Tyr Asn Ser Leu Phe Ser Asn
                1835                1840                1845

Ser Met Asn Pro Pro Gln Arg Asn Phe Gly Leu Met Pro Thr Gln
                1850                1855                1860

Phe Gln Asp Ser Val Val Tyr Lys Asn Leu Ser Ala Gly Val Glu
                1865                1870                1875

Ser Lys Tyr Gly Phe Lys Gln Thr Phe Thr Pro Leu Trp Arg Asp
                1880                1885                1890

Val Asp Gln Glu Thr Asn Val Thr Glu Thr Ala Phe Leu Asn Tyr
                1895                1900                1905

Val Met Glu Val Ile Pro Ile His Ser Ser Lys Arg Leu Val Cys
                1910                1915                1920

Glu Val Glu Phe Asp Arg Gly Met Pro Asp Glu Val Val Ile Thr
                1925                1930                1935

Gly Tyr Met Asn Val Leu Met Ala Ser Ala Tyr Ser Leu His Lys
                1940                1945                1950

Asn Gly Arg Leu Ile Ile Lys Ile Phe Arg His Ser Glu Ala Leu
                1955                1960                1965

Phe Gln Leu Gly Leu Ser Val Ile Val Met Ile Leu His Gly Leu
                1970                1975                1980

Asp Ile His Arg Asn Ser Tyr Met Ser Thr Asn Lys Glu Glu Tyr
                1985                1990                1995

Ile Ile Ile Ala Ala Ala Pro Glu Ala Leu Asn Tyr Ser Ser Val
                2000                2005                2010

Pro Ala Ile Leu Gln Arg Val Lys Ser Val Ile Asp Gln Gln Leu
                2015                2020                2025

Thr Leu Ile Ser Pro Ile Asp Leu Glu Arg Leu Arg His Glu Thr
                2030                2035                2040

Glu Ser Leu Arg Glu Lys Glu Asn Asn Leu Val Ile Ser Leu Thr
                2045                2050                2055

Arg Gly Lys Tyr Gln Leu Arg Pro Thr Gln Thr Asp Met Leu Leu
                2060                2065                2070

Ser Tyr Leu Gly Gly Arg Phe Ile Thr Leu Phe Gly Gln Ser Ala
                2075                2080                2085

Arg Asp Leu Met Ala Thr Asp Val Ala Asp Leu Asp Ala Arg Lys
                2090                2095                2100

Ile Ala Leu Val Asp Leu Leu Met Val Glu Ser Asn Ile Ile Leu
                2105                2110                2115

Ser Glu Ser Thr Asp Leu Asp Leu Ala Leu Leu Leu Ser Pro Phe
                2120                2125                2130

Asn Leu Asp Lys Gly Arg Lys Ile Val Thr Leu Ala Lys Ala Thr
                2135                2140                2145

Thr Arg Gln Leu Leu Pro Val Tyr Ile Ala Ser Glu Ile Met Cys
                2150                2155                2160

Asn Arg Gln Ala Phe Thr His Leu Thr Ser Ile Ile Gln Arg Gly
                2165                2170                2175

Val Ile Arg Ile Glu Asn Met Leu Ala Thr Thr Glu Phe Val Arg
                2180                2185                2190

Gln Ser Val Arg Pro Gln Phe Ile Lys Glu Val Ile Thr Ile Ala
                2195                2200                2205

Gln Val Asn His Leu Phe Ser Asp Leu Ser Lys Leu Val Leu Ser
```

```
            2210                2215                2220

Arg Ser Glu Val Lys Gln Ala Leu Lys Phe Val Gly Cys Cys Met
            2225                2230                2235

Lys Phe Arg Asn Ala Ser Asn
            2240


<210> SEQ ID NO 69
<211> LENGTH: 20
<212> TYPE: DNA
<213> ORGANISM: Artificial sequence
<220> FEATURE:
<223> OTHER INFORMATION: forward primer

<400> SEQUENCE: 69

gaagatgatg caccagaaga                                              20


<210> SEQ ID NO 70
<211> LENGTH: 20
<212> TYPE: DNA
<213> ORGANISM: Artificial sequence
<220> FEATURE:
<223> OTHER INFORMATION: reverse primer

<400> SEQUENCE: 70

actgcgatgg tccctgtgag                                              20


<210> SEQ ID NO 71
<211> LENGTH: 27
<212> TYPE: DNA
<213> ORGANISM: Artificial sequence
<220> FEATURE:
<223> OTHER INFORMATION: reverse primer
<220> FEATURE:
<221> NAME/KEY: misc_feature
<222> LOCATION: (1)?(27)
<223> OTHER INFORMATION: N = A/C/G/T, R = A/G, K= G/T, Y = C/T
<220> FEATURE:
<221> NAME/KEY: misc_feature
<222> LOCATION: (26)
<223> OTHER INFORMATION: N=inosine

<400> SEQUENCE: 71

nggnccraar tgnckytgng gnggrnt                                      27


<210> SEQ ID NO 72
<211> LENGTH: 33
<212> TYPE: DNA
<213> ORGANISM: Artificial sequence
<220> FEATURE:
<223> OTHER INFORMATION: reverse primer
<220> FEATURE:
<221> NAME/KEY: misc_feature
<222> LOCATION: (1)?(33)
<223> OTHER INFORMATION: N= A/C/G/T, S = G/C, W= A/T, R = A/G, Y = C/T,
      D=G/A/T

<400> SEQUENCE: 72

nswrtartan ccyttngcng crttnccdat ngt                               33


<210> SEQ ID NO 73
<211> LENGTH: 19
<212> TYPE: DNA
<213> ORGANISM: Artificial sequence
<220> FEATURE:
<223> OTHER INFORMATION: forward primer

<400> SEQUENCE: 73
```

ggaaaacttg ggggcgaca 19

<210> SEQ ID NO 74
<211> LENGTH: 21
<212> TYPE: DNA
<213> ORGANISM: Artificial sequence
<220> FEATURE:
<223> OTHER INFORMATION: reverse primer

<400> SEQUENCE: 74
ttttttctta aaccaggctt c 21

<210> SEQ ID NO 75
<211> LENGTH: 27
<212> TYPE: DNA
<213> ORGANISM: Artificial sequence
<220> FEATURE:
<223> OTHER INFORMATION: RNA oligonucleotide

<400> SEQUENCE: 75
ccaaaacgcc atttccaccu tctcttc 27

<210> SEQ ID NO 76
<211> LENGTH: 26
<212> TYPE: DNA
<213> ORGANISM: Artificial sequence
<220> FEATURE:
<223> OTHER INFORMATION: adaptor primer

<400> SEQUENCE: 76
gaagagaagg tgaaatggcg ttttgg 26

<210> SEQ ID NO 77
<211> LENGTH: 19
<212> TYPE: DNA
<213> ORGANISM: Artificial sequence
<220> FEATURE:
<223> OTHER INFORMATION: reverse primer

<400> SEQUENCE: 77
ggatcgcccc ttgtctcat 19

<210> SEQ ID NO 78
<211> LENGTH: 21
<212> TYPE: DNA
<213> ORGANISM: Artificial sequence
<220> FEATURE:
<223> OTHER INFORMATION: L-gene specific primer

<400> SEQUENCE: 78
aagagtttga cagggggatg c 21

<210> SEQ ID NO 79
<211> LENGTH: 24
<212> TYPE: DNA
<213> ORGANISM: Artificial sequence
<220> FEATURE:
<223> OTHER INFORMATION: forward primer

<400> SEQUENCE: 79
ggcttgatat acaccggaac tcgt 24

<210> SEQ ID NO 80
<211> LENGTH: 23
<212> TYPE: DNA
<213> ORGANISM: Artificial sequence
<220> FEATURE:
<223> OTHER INFORMATION: intergenic RNA sequence

<400> SEQUENCE: 80
gaattgatgt attgaagttg taa 23

<210> SEQ ID NO 81
<211> LENGTH: 5
<212> TYPE: PRT
<213> ORGANISM: Artificial sequence
<220> FEATURE:
<223> OTHER INFORMATION: cleavage site
<220> FEATURE:
<221> NAME/KEY: misc_feature
<222> LOCATION: 2
<223> OTHER INFORMATION: Xaa is any amino acid

<400> SEQUENCE: 81

Arg Xaa Lys Arg Arg
1 5

<210> SEQ ID NO 82
<211> LENGTH: 6
<212> TYPE: PRT
<213> ORGANISM: Artificial sequence
<220> FEATURE:
<223> OTHER INFORMATION: cleavage site

<400> SEQUENCE: 82

Gly Ala Pro Gln Ser Arg
1 5

<210> SEQ ID NO 83
<211> LENGTH: 6
<212> TYPE: PRT
<213> ORGANISM: Artificial sequence
<220> FEATURE:
<223> OTHER INFORMATION: cleavage site

<400> SEQUENCE: 83

Asp Pro Arg Thr Lys Arg
1 5

<210> SEQ ID NO 84
<211> LENGTH: 6
<212> TYPE: PRT
<213> ORGANISM: Artificial sequence
<220> FEATURE:
<223> OTHER INFORMATION: cleavage site,

<400> SEQUENCE: 84

Gly Gly Arg Gln Gly Arg
1 5

<210> SEQ ID NO 85
<211> LENGTH: 6
<212> TYPE: PRT
<213> ORGANISM: Artificial sequence
<220> FEATURE:
<223> OTHER INFORMATION: cleavage site

<400> SEQUENCE: 85

Gly Arg Arg Gln Lys Arg
1 5

<210> SEQ ID NO 86
<211> LENGTH: 6

```
<212> TYPE: PRT
<213> ORGANISM: Artificial sequence
<220> FEATURE:
<223> OTHER INFORMATION: cleavage site

<400> SEQUENCE: 86

Ala Arg Pro Arg Gly Arg
1               5


<210> SEQ ID NO 87
<211> LENGTH: 6
<212> TYPE: PRT
<213> ORGANISM: Artificial sequence
<220> FEATURE:
<223> OTHER INFORMATION: cleavage site

<400> SEQUENCE: 87

Pro Arg Pro Ser Gly Arg
1               5


<210> SEQ ID NO 88
<211> LENGTH: 6
<212> TYPE: PRT
<213> ORGANISM: Artificial sequence
<220> FEATURE:
<223> OTHER INFORMATION: cleavage site

<400> SEQUENCE: 88

Ala Asp Ile Gln Pro Arg
1               5


<210> SEQ ID NO 89
<211> LENGTH: 6
<212> TYPE: PRT
<213> ORGANISM: Artificial sequence
<220> FEATURE:
<223> OTHER INFORMATION: cleavage site

<400> SEQUENCE: 89

Gly Lys Arg Lys Lys Arg
1              5


<210> SEQ ID NO 90
<211> LENGTH: 6
<212> TYPE: PRT
<213> ORGANISM: Artificial sequence
<220> FEATURE:
<223> OTHER INFORMATION: cleavage site

<400> SEQUENCE: 90

Pro Ala Pro Glu Pro Arg
1               5


<210> SEQ ID NO 91
<211> LENGTH: 6
<212> TYPE: PRT
<213> ORGANISM: Artificial sequence
<220> FEATURE:
<223> OTHER INFORMATION: cleavage site

<400> SEQUENCE: 91

Ser Ile Arg Glu Pro Arg
1               5


<210> SEQ ID NO 92
<211> LENGTH: 6
<212> TYPE: PRT
```

<213> ORGANISM: Artificial sequence
<220> FEATURE:
<223> OTHER INFORMATION: cleavage site

<400> SEQUENCE: 92

Thr Leu Pro Ser Ser Arg
1 5

<210> SEQ ID NO 93
<211> LENGTH: 6
<212> TYPE: PRT
<213> ORGANISM: Artificial sequence
<220> FEATURE:
<223> OTHER INFORMATION: cleavage site

<400> SEQUENCE: 93

Thr Tyr Pro Gln Thr Arg
1 5

<210> SEQ ID NO 94
<211> LENGTH: 6
<212> TYPE: PRT
<213> ORGANISM: Artificial sequence
<220> FEATURE:
<223> OTHER INFORMATION: cleavage site

<400> SEQUENCE: 94

Ile Arg Glu Gly Arg Ile
1 5

<210> SEQ ID NO 95
<211> LENGTH: 38
<212> TYPE: DNA
<213> ORGANISM: Artificial sequence
<220> FEATURE:
<223> OTHER INFORMATION: primer

<400> SEQUENCE: 95
acatgcatgc atgtcttctg tgttttcaga ataccagg 38

<210> SEQ ID NO 96
<211> LENGTH: 37
<212> TYPE: DNA
<213> ORGANISM: Artificial sequence
<220> FEATURE:
<223> OTHER INFORMATION: primer

<400> SEQUENCE: 96
cccaagcttt caccaatcta atgaggccgc atcattg 37

<210> SEQ ID NO 97
<211> LENGTH: 45
<212> TYPE: DNA
<213> ORGANISM: Artificial sequence
<220> FEATURE:
<223> OTHER INFORMATION: primer

<400> SEQUENCE: 97
ccggaattca tggagttcac cgatgatgcc gaaattgctg 40
agctg 45

<210> SEQ ID NO 98
<211> LENGTH: 28
<212> TYPE: DNA
<213> ORGANISM: Artificial sequence
<220> FEATURE:

<223> OTHER INFORMATION: primer

<400> SEQUENCE: 98
tgacgagctc ctaggcattg tatatctg 28

<210> SEQ ID NO 99
<211> LENGTH: 28
<212> TYPE: DNA
<213> ORGANISM: Artificial sequence
<220> FEATURE:
<223> OTHER INFORMATION: primer

<400> SEQUENCE: 99
catgccatgg atcaaactca agctgaca 28

<210> SEQ ID NO 100
<211> LENGTH: 30
<212> TYPE: DNA
<213> ORGANISM: Artificial sequence
<220> FEATURE:
<223> OTHER INFORMATION: primer

<400> SEQUENCE: 100
ccccttgagg agctctatag tgtctggaga 30

<210> SEQ ID NO 101
<211> LENGTH: 30
<212> TYPE: DNA
<213> ORGANISM: Artificial sequence
<220> FEATURE:
<223> OTHER INFORMATION: primer

<400> SEQUENCE: 101
tctccagaca ctatagagct cctcaagggg 30

<210> SEQ ID NO 102
<211> LENGTH: 41
<212> TYPE: DNA
<213> ORGANISM: Artificial sequence
<220> FEATURE:
<223> OTHER INFORMATION: primer

<400> SEQUENCE: 102
aaaaggcctt taattgcttg catttctgaa cttcatacag 40
c 41

<210> SEQ ID NO 103
<211> LENGTH: 44
<212> TYPE: DNA
<213> ORGANISM: Artificial sequence
<220> FEATURE:
<223> OTHER INFORMATION: primer

<400> SEQUENCE: 103
tcattggcgc gcctaatacg actcactata gggaccaaac 40
aagg 44

<210> SEQ ID NO 104
<211> LENGTH: 25
<212> TYPE: DNA
<213> ORGANISM: Artificial sequence
<220> FEATURE:
<223> OTHER INFORMATION: primer

<400> SEQUENCE: 104
catgtgggtt taaactggtg atatg 25

<210> SEQ ID NO 105
<211> LENGTH: 30
<212> TYPE: DNA
<213> ORGANISM: Artificial sequence
<220> FEATURE:
<223> OTHER INFORMATION: primer

<400> SEQUENCE: 105
tcaccagttt aaacccacat gcttccctgc 30

<210> SEQ ID NO 106
<211> LENGTH: 22
<212> TYPE: DNA
<213> ORGANISM: Artificial sequence
<220> FEATURE:
<223> OTHER INFORMATION: primer

<400> SEQUENCE: 106
gaggtgtgcg gccgcacgtg tc 22

<210> SEQ ID NO 107
<211> LENGTH: 22
<212> TYPE: DNA
<213> ORGANISM: Artificial sequence
<220> FEATURE:
<223> OTHER INFORMATION: primer

<400> SEQUENCE: 107
gacacgtgcg gccgcacacc tc 22

<210> SEQ ID NO 108
<211> LENGTH: 26
<212> TYPE: DNA
<213> ORGANISM: Artificial sequence
<220> FEATURE:
<223> OTHER INFORMATION: primer

<400> SEQUENCE: 108
gtttaggctt aattaacctc tctaca 26

<210> SEQ ID NO 109
<211> LENGTH: 27
<212> TYPE: DNA
<213> ORGANISM: Artificial sequence
<220> FEATURE:
<223> OTHER INFORMATION: primer

<400> SEQUENCE: 109
gagaggttaa ttaagcctaa acatgat 27

<210> SEQ ID NO 110
<211> LENGTH: 25
<212> TYPE: DNA
<213> ORGANISM: Artificial sequence
<220> FEATURE:
<223> OTHER INFORMATION: primer

<400> SEQUENCE: 110
gctgttagac actacgtggc ttttg 25

<210> SEQ ID NO 111
<211> LENGTH: 25
<212> TYPE: DNA

```
<213> ORGANISM: Artificial sequence
<220> FEATURE:
<223> OTHER INFORMATION: primer

<400> SEQUENCE: 111

caaaagccac gtagtgtcta acagc                                           25

<210> SEQ ID NO 112
<211> LENGTH: 23
<212> TYPE: DNA
<213> ORGANISM: Artificial sequence
<220> FEATURE:
<223> OTHER INFORMATION: primer

<400> SEQUENCE: 112

tatttccttc cgcggctcga atg                                             23

<210> SEQ ID NO 113
<211> LENGTH: 23
<212> TYPE: DNA
<213> ORGANISM: Artificial sequence
<220> FEATURE:
<223> OTHER INFORMATION: primer

<400> SEQUENCE: 113

cattcgagcc gcggaaggaa ata                                             23

<210> SEQ ID NO 114
<211> LENGTH: 55
<212> TYPE: DNA
<213> ORGANISM: Artificial sequence
<220> FEATURE:
<223> OTHER INFORMATION: primer

<400> SEQUENCE: 114

atgcccaggt ccggaccgcg aggaggtgga gatgccatgc                           40

cgaccaccag acatg                                                      55

<210> SEQ ID NO 115
<211> LENGTH: 30
<212> TYPE: DNA
<213> ORGANISM: Artificial sequence
<220> FEATURE:
<223> OTHER INFORMATION: cloning fragment

<400> SEQUENCE: 115

gtttaaacta acaaaaaatg ggggcgaagt                                      30

<210> SEQ ID NO 116
<211> LENGTH: 35
<212> TYPE: DNA
<213> ORGANISM: Artificial sequence
<220> FEATURE:
<223> OTHER INFORMATION: cloning fragment

<400> SEQUENCE: 116

gtttaaacta acaaaaaatg ggggcgaagt gcacc                                35

<210> SEQ ID NO 117
<211> LENGTH: 14904
<212> TYPE: DNA
<213> ORGANISM: Artificial sequence
<220> FEATURE:
<223> OTHER INFORMATION: pAMPV-2/Yucaipa with mutations

<400> SEQUENCE: 117
```

-continued

```
accaaacaag gaataggtaa gcaacgtaaa tcttagataa      40
aaccatagaa tccgtggggg cgacatcgcc tgaagccgat      80
ctcgagatcg ataactccgg ttaattggtc tcagcgtgag     120
gagcttatct gtctgtggca atgtcttctg tgttttcaga     160
ataccaggct cttcaggacc aactggtcaa gcctgccact     200
cgaagggctg atgtggcatc gactggattg ttgagagcgg     240
agataccagt ttgtgtaacc ttgtctcagg acccaactga     280
tagatggaac ctcgcatgtc tcaatctgcg atggctgata     320
agtgagtcct ctactactcc catgagacaa ggggcgatcc     360
tgtcactgct gagcttgcac tctgacaaca tgcgagctca     400
cgcaaccctt gcagcgagat ccgctgatgc tgccatcact     440
gtgcttgagg ttgacgccat agacatggcg gatggcacaa     480
tcacttttaa tgccagaagt ggagtatccg agaggcgcag     520
cacacagctc atggcaatcg caaaagatct gccccgctct     560
tgttccaatg actcaccatt caaagatgac actatcgagg     600
atcgcgaccc ccttgacctg tccgagacta tcgatagact     640
gcaggggatt gctgcccaaa tctggatagc ggccatcaag     680
agcatgactg ccccggatac tgctgcggag tcagaaggca     720
agaggcttgc aaagtaccaa caacaaggcc gcttggtgcg     760
acaggtgtta gtgcatgatg cggtgcgtgc ggaattccta     800
cgtgtcatca gaggcagcct ggtcttacgg caattcatgg     840
tatcagaatg taagagggca gcatccatgg gtagcgagac     880
atctaggtac tatgccatgg tgggtgacat cagcctctac     920
atcaagaatg caggacttac cgccttcttc ttgacactca     960
gatttggtat tgggacacac taccccactc ttgccatgag    1000
tgtgttctct ggagaactga agaagatgtc gtccttgatc    1040
aggctgtata agtcaaaagg ggaaaatgct gcatacatgg    1080
cattcctgga ggatgcggac atgggaaact ttgcgcctgc    1120
taactttagt actctctact cctatgcaat gggggtaggt    1160
acagtgctgg aagcatcagt tgcgaaatac cagttcgctc    1200
gagagttcac cagtgagaca tacttcaggc ttggggttga    1240
gaccgcacag aaccaacagt gcgctctaga tgaaaagacc    1280
gccaaggaga tggggcttac tgatgaagcc agaaagcagg    1320
tgcaagcatt ggctagcaac atcgagcagg ggcaacattc    1360
aatgcccatg caacaacagc ccacattcat gagtcagccc    1400
taccaggatg acgatcgtga ccagccaagc accagcagac    1440
cagagccaag accatcgcaa ttgacaagcc aatcagcagc    1480
acaggacaat gatgcggcct cattagattg gtgaccgcaa    1520
tcagctcagc caagccattg ttggacgcag gacattcaaa    1560
```

-continued

```
tcatacattg ccctaagagt attaaagtga tttaagaaaa          1600
aaggaccctg ggggcgaagt tgtcccaatc caggcaggcg          1640
ctgaaaccga atccctccaa cctccgagcc ccaggcgacc          1680
atggagttca ccgatgatgc cgaaattgct gagctgttgg          1720
acctcgggac ctcagtgatc caagagctgc agcgagccga          1760
agtcaagggc ccgcaaacaa ccggaaagcc caaagttccc          1800
ccggggaaca ctaagagcct ggctactctc tgggagcatg          1840
agactagcac ccaagggagt gcattgggca cacccgagaa          1880
caacacccag gcacccgatg acaacaacgc aggtgcagat          1920
acgccagcga ctaccgacgt ccatcgcact ctggatacca          1960
tagacaccga cacaccaccg gaagggagca agcccagctc          2000
cactaactcc caacccggtg atgaccttga caaggctctt          2040
tcgaagctag aggcgcgcgc caagctcgga ccagataggg          2080
ccagacaggt taaaaagggg aaggagatcg ggtcgagcac          2120
agggacgagg gaggcagcca gtcaccacat ggaagggagc          2160
cgacagtcgg agccaggagc gggcagccga gcacagccac          2200
aaggccatgg cgaccgggac acaggaggga gtactcattc          2240
atctctcgag atgggagact ggaagtcaca agctggtgca          2280
acccagtctg ctctcccatt agaagcgagc ccaggagaga          2320
aaagtgcaca tgtggaactt gcccagaatc ctgcatttta          2360
tgcaggcaac ccaactgatg caattatggg gttgacaaag          2400
aaagtcaatg atctagagac aaaattggct gaggtattgc          2440
gtctgttagg aatactcccc ggaataaaga atgagattag          2480
tcagctgaaa gcaaccgtgg ctctgatgtc aaatcagatt          2520
gcctccattc agattcttga tcctgggaat gccggagtca          2560
aatcccttaa tgagatgaaa gccctgtcaa aagcagccag          2600
catagttgtg gcaggtccag gagtccttcc tcctgaggtc          2640
acagaaggag gactgatcgc gaaagatgag ctagcaaggc          2680
ccatccccat ccaaccgcaa cgagactcca aacccaaaga          2720
cgacccgcac acatcaccaa atgatgtcct tgctgtacgc          2760
gctatgatcg acacccttgt ggatgatgag aagaagagaa          2800
agagattaaa ccaggccctt gacaaggcaa agaccaagga          2840
tgacgtctta agggtcaagc ggcagatata caatgcctag          2880
gagtccattt gtctaaagaa cctccaatca tatcaccagt          2920
ttaaacccac atgcttccct gccgagaatc tagccgacac          2960
aaaaactaaa tcatagttta acaaaaaaga agtttggggg          3000
cgaagtctca catcatagag cacccttgca ttctaaaatg          3040
gctcaaacaa ccgtcaggct gtatatcgat gaagctagtc          3080
ccgacattga actgttgtct tacccactga taatgaaaga          3120
cacaggacat gggaccaaag agttgcagca gcaaatcaga          3160
```

-continued

```
gttgcagaga tcggtgcatt gcagggaggg aagaatgaat                     3200
cagttttcat caatgcatat ggctttgttc agcaatgcaa                     3240
agttaaaccg gggcaaccc aattcttcca ggtagatgca                      3280
gctacaaagc cagaagtggt cactgcaggg atgattataa                     3320
tcggtgcagt caagggggtg gcaggcatca ctaagctggc                     3360
agaagaggtg ttcgagctgg acatctccat caagaagtcc                     3400
gcatcattcc atgagaaggt tgcggtgtcc tttaatactg                     3440
tgccactatc actcatgaat tcgaccgcat gcagaaatct                     3480
gggttatgtc acaaacgctg aggaggcgat caaatgcccg                     3520
agcaaaatac aagcgggtgt gacgtacaaa tttaagataa                     3560
tgtttgtctc cttgacacga ctgcataacg ggaaattgta                     3600
ccgtgtcccc aaggcagtgt atgctgtaga ggcatcagct                     3640
ctatataaag tgcaactgga agtcgggttc aagcttgacg                     3680
tggccaagga tcacccacac gttaagatgt tgaagaaagt                     3720
ggaacggaat ggtgagactc tgtatcttgg ttatgcatgg                     3760
ttccacctgt gcaacttcaa gaagacaaat gccaagggtg                     3800
agtcccggac aatctccaac ctagaaggga aagtcagagc                     3840
tatggggatc aaggtttcct tgtacgactt atgggggcct                     3880
actttggtgg tgcaaatcac aggtaagacc agcaagtatg                     3920
cacaaggttt cttttcaacc acaggtacct gctgcctccc                     3960
agtgtcgaag gctgcccctg agctggccaa acttatgtgg                     4000
tcctgcaatg caacaatcgt tgaagctgca gtgattatcc                     4040
aagggagtga taggagggca gtcgtgacct cagaggactt                     4080
ggaagtatac ggggcagttg caaaagagaa gcaggctgca                     4120
aaaggatttc acccgttccg caactgacac gtggggccgc                     4160
acacctcatt accccagaag cccgggcaac tgcaaattca                     4200
cgcttatata atccaattac catgatctag aactgcaatc                     4240
gatactaatc gctcattgat cgtattaaga aaaaacttaa                     4280
ctacataact tcaacattgg gggcgacagc tccagactaa                     4320
gtgggtggct aagctctgac tgataaggaa tcatgaatca                     4360
agcactcgtg attttgttgg tatctttcca gctcggcgtt                     4400
gccttagata actcagtgtt ggctccaata ggagtagcta                     4440
gcgcacagga gtggcaactg gcggcatata caacgaccct                     4480
cacagggacc atcgcagtga gatttatccc ggtcctgcct                     4520
gggaacctat caacatgtgc acaggagacg ctgcaggaat                     4560
ataatagaac tgtgactaat atcttaggcc cgttgagaga                     4600
gaacttggat gctctcctat ctgacttcga taaacctgca                     4640
tcgaggttcg tgggcgccat cattgggtcg gtggccttgg                     4680
gggtagcaac agctgcacaa atcacagccg ccgtggctct                     4720
```

-continued

```
caatcaagca caagagaatg cccggaatat atggcgtctc                     4760
aaggaatcga taaagaaaac caatgcggct gtgttggaat                     4800
tgaaggatgg acttgcaacg actgctatag ctttggacaa                     4840
agtgcaaaag tttatcaatg atgatattat accacagatt                     4880
aaggacattg actgccaggt agttgcaaat aaattaggcg                     4920
tctacctctc cttatactta acagagctta caactgtatt                     4960
tggttctcag atcactaatc ctgcattatc aacgctctct                     5000
taccaggcgc tgtacagctt atgtggaggg gatatgggaa                     5040
agctaactga gctgatcggt gtcaatgcaa aggatgtggg                     5080
atccctctac gaggctaacc tcataaccgg ccaaatcgtt                     5120
ggatatgacc ctgaactaca gataatcctc atacaagtat                     5160
cttacccaag tgtgtctgaa gtgacaggag tccgggctac                     5200
tgagttagtc actgtcagtg tcactacacc aaaaggagaa                     5240
gggcaggcaa ttgttccgag atatgtggca cagagtagag                     5280
tgctgacaga ggagttggat gtctcgactt gtaggtttag                     5320
caaaacaact ctttattgta ggtcgattct cacacggccc                     5360
ctaccaactt tgatcgccag ctgcctgtca gggaagtacg                     5400
acgattgtca gtacacaaca gagataggag cgctatcttc                     5440
gagattcatc acagtcaatg gtggagtcct tgcaaactgc                     5480
agagcaattg tgtgtaagtg tgtctcaccc ccgcatataa                     5520
taccacaaaa cgacattggc tccgtaacag ttattgactc                     5560
aagtatatgc aaggaagttg tcttagagag tgtgcagctt                     5600
aggttagaag gaaagctgtc atcccaatac ttctccaacg                     5640
tgacaattga cctttcccaa atcacaacgt cagggtcgct                     5680
ggatataagc agtgaaattg gtagcattaa caacacagtt                     5720
aatcgggtcg acgagttaat caaggaatcc aacgagtggc                     5760
tgaacgctgt gaacccccgc cttgtgaaca atacgagcat                     5800
catagtcctc tgtgtccttg ccgccctgat tattgtctgg                     5840
ctaatagcgc tgacagtatg cttctgttac tccgcaagat                     5880
actcagctaa gtcaaaacag atgaggggcg ctatgacagg                     5920
gatcgataat ccatatgtaa tacagagtgc aactaagatg                     5960
tagagaggtt aattaagcct aaacatgata tgatttaaga                     6000
aaaaattgga aggtgggggc gacagcccat tcaatgaagg                     6040
gtgtacactc caacttgatc ttgtgacttg atcatcatac                     6080
tcgaggcacc atggatttcc catctaggga gaacctggca                     6120
gcaggtgaca tatcggggcg gaagacttgg agattactgt                     6160
tccggatcct cacattgagc ataggtgtgg tctgtcttgc                     6200
catcaatatt gccacaattg caaaattgga tcacctggat                     6240
aacatggctt cgaacacatg gacaacaact gaggctgacc                     6280
gtgtgatatc tagcatcacg actccgctca aagtccctgt                     6320
```

| | |
|---|---|
| caaccagatt aatgacatgt ttcggattgt agcgcttgac | 6360 |
| ctacctctgc agatgacatc attacagaaa gaaataacat | 6400 |
| cccaagtcgg gttcttggct gaaagtatca acaatgtttt | 6440 |
| atccaagaat ggatctgcag gcctggttct tgttaatgac | 6480 |
| cctgaatatg caggggggat cgctgtcagc ttgtaccaag | 6520 |
| gagatgcatc tgcaggccta aatttccagc ccatttcttt | 6560 |
| aatagaacat ccaagttttg tccctggtcc tactactgct | 6600 |
| aagggctgta taaggatccc gaccttccat atgggccctt | 6640 |
| cacattggtg ttactcacat aacatcattg catcaggttg | 6680 |
| ccaggatgcg agccactcca gtatgtatat ctctctgggg | 6720 |
| gtgctgaaag catcgcagac cgggtcgcct atcttcttga | 6760 |
| caacggccag ccatctcgtg gatgacaaca tcaaccggaa | 6800 |
| gtcatgcagc atcgtagcct caaaatacgg ttgtgatatc | 6840 |
| ctatgcagta ttgtgattga aacagagaat gaggattata | 6880 |
| ggtctgatcc ggctactagc atgattatag gtaggctgtt | 6920 |
| cttcaacggg tcatacacag agagcaagat taacacaggg | 6960 |
| tccatcttca gtctattctc tgctaactac cctgcggtgg | 7000 |
| ggtcgggtat tgtagtcggg gatgaagccg cattcccaat | 7040 |
| atatggtggg gtcaagcaga acacatggtt gttcaaccag | 7080 |
| ctcaaggatt ttggttactt cacccataat gatgtgtaca | 7120 |
| agtgcaatcg gactgatata cagcaaacta tcctggatgc | 7160 |
| atacaggcca cctaaaatct caggaaggtt atgggtacaa | 7200 |
| ggcatcctat tgtgcccagt ttcactgaga cctgatcctg | 7240 |
| gctgtcgctt aaaggtgttc aataccagca atgtgatgat | 7280 |
| gggggcagaa gcgaggttga tccaagtagg ctcaaccgtg | 7320 |
| tatctatacc aacgctcatc ctcatggtgg gtggtaggac | 7360 |
| tgacttacaa attagatgtg tcagaaataa cttcacagac | 7400 |
| aggtaacaca ctcaaccatg tagaccccat tgcccataca | 7440 |
| aagttcccaa gaccatcttt caggcgagat gcgtgtgcga | 7480 |
| ggccaaacat atgccctgct gtctgtgtct ccggagttta | 7520 |
| tcaggacatt tggccgatca gtacagccac caataacagc | 7560 |
| aacattgtgt gggttggaca gtacttagaa gcattctatt | 7600 |
| ccaggaaaga cccaagaata gggatagcaa cccagtatga | 7640 |
| gtggaaagtc accaaccagc tgttcaattc gaatactgag | 7680 |
| ggagggtact caaccacaac atgcttccgg aacaccaaac | 7720 |
| gggacaaggc atattgtgta gtgatatcag agtacgctga | 7760 |
| tggggtgttc ggatcataca ggatcgttcc tcagcttata | 7800 |
| gagattagaa caaccaccgg taaatctgag tgatgcatca | 7840 |
| atcctaaatt ggaatgacca atcaaaagcc acgtagtgtc | 7880 |

```
taacagcatt gcgaagcctg gtttaagaaa aaacttgggg              7920

gcgaatgccc atcaaccatg gatcaaactc aagctgacac              7960

tataatacaa cctgaagtcc atctgaattc accacttgtt              8000

cgcgcaaaat tggttcttct atggaaattg actgggttac              8040

ctttgccgtc tgatttgaga tcatttgtac taactacaca              8080

tgcagctgat gaccaaatcg caaaaaatga gactaggatc              8120

aaggccaaaa ttaattccct aatcgataac ttaatcaaac              8160

actgcaaggc aaggcaagtg gcactttcag ggttgacacc              8200

tgtcgtacat ccaacaactc tacagtggtt gctatccatc              8240

acatgtgaac gagcagacca ccttgcaaaa gtacgcgaga              8280

aatcagttaa gcaagcaatg tcagagaagc aacacgggtt              8320

tagacatctc ttttcggcag taagtcatca gttagttgga              8360

aacgccacac tgttctgtgc acaagactct agcaccgtga              8400

atgtcgactc tccttgctca tcaggttgtg agaggctgat              8440

aatagactct attggagcct tacaaacacg atggacaaga              8480

tgtaggtggg cttggcttca cattaaacag gtaatgagat              8520

accaggtgct tcagagtcgc ctacacgctc atgccaattc              8560

tgttagcaca tggtctgagg cgtgggggtt cattgggatc              8600

acaccagata tagtccttat tgtagactat aagagcaaaa              8640

tgtttactat cctgaccttc gaaatgatgc tgatgtattc              8680

agatgtcata gagggtcgtg ataatgtggt agctgtagga              8720

agtatgtcac caaacctaca gcctgtggtg gagaggattg              8760

aggtgctgtt tgatgtagtg gacaccttgg cgaggaggat              8800

tcatgatcct atttatgatc tggttgctgc cttagaaagc              8840

atggcatacg ctgccgtcca attgcacgat gctagtgaga              8880

cacacgcagg ggaattcttt tcgttcaatt tgacagaaat              8920

agagtccact cttgccccct tgctggatcc tggccaagtc              8960

ctatcggtga tgaggactat cagttattgt tacagtgggc              9000

tatcgcctga ccaagctgca gagttgctct gtgtgatgcg              9040

cttatttgga caccctctgc tctccgcaca acaagcagcc              9080

aaaaaagtcc gggagtctat gtgtgcccct aaactgttag              9120

agcatgatgc aatactgcaa actctatctt tcttcaaggg              9160

aatcataatc aatggctaca ggaaaagtca ttctggagta              9200

tggcctgcaa ttgacccaga ttctatagtg gacgatgacc              9240

ttagacagct gtattacgag tcggcagaaa tttcacatgc              9280

tttcatgctt aagaaatatc ggtaccttag tatgattgag              9320

ttccgcaaga gcatagagtt tgacttaaat gatgacctga              9360

gcacattcct taaagacaaa gcaatctgca ggccaaaaga              9400

tcaatgggca cgcatcttcc ggaaatcatt gttcccttgc              9440

aaaacgaacc ttggcactag tatagatgtt aaaagtaatc              9480
```

-continued gactgttgat agatttttttg gagtcacatg acttcaatcc 9520
tgaggaagaa atgaagtatg tgactacgct agcatacctg 9560
gcagataatc aattctcagc atcatattca ctgaaggaga 9600
aagagatcaa gactactggc cggatcttcg ccaaaatgac 9640
caggaaaatg aggagctgtc aagtaatatt ggaatcacta 9680
ttgtccagtc acgtctgcaa attctttaag gagaacggtg 9720
tgtcaatgga acaactgtct ttgacaaaga gcttgcttgc 9760
aatgtcacag ttagcaccca ggatatcttc agttcgccag 9800
gcgacagcac gtagacagga cccaggactc agccactcta 9840
atggttgtaa tcacattgta ggagacttag gcccacacca 9880
gcaggacaga ccggcccgga agagtgtagt cgcaaccttc 9920
cttacaacag atcttcaaaa atattgcttg aattggcgat 9960
atgggagtat caagcttttc gcccaagcct taaaccagct 10000
attcggaatc gagcatgggt ttgaatggat acacctgaga 10040
ctgatgaata gcaccctgtt tgtcggggac ccattctcgc 10080
ctcctgaaag caaagtgctg agtgatcttg atgatgcgcc 10120
caattcagac atatttatcg tgtccgccag aggggggatt 10160
gaagggttat gccagaagct gtggaccatg atttcaataa 10200
gcataatcca ttgcgtggct gagaagatag gagcaagggt 10240
tgcggcgatg gttcagggag ataatcaggt aattgcaatc 10280
acgagagagc tgtataaggg agagacttac acgcagattc 10320
agccggagtt agatcgatta ggcaatgcat tttttgctga 10360
attcaaaaga cacaactatg caatgggaca taatctgaag 10400
cccaaagaga caatccaaag tcaatcattc tttgtgtatt 10440
cgaaacggat tttctgggaa gggagaattc ttagtcaagc 10480
actgaagaat gctaccaaac tatgcttcat tgcagatcac 10520
ctcggggata atactgtctc atcatgcagc aatctagcct 10560
ctacgataac ccgcttggtt gagaatgggt atgaaaagga 10600
cacagcattc attctgaata tcatctcagc aatgactcag 10640
ttgctgattg atgagcaata ttccctacaa ggagactact 10680
cagctgtgag aaaactgatt gggtcatcaa attaccgtaa 10720
tctcttagtg gcgtcgctca tgcctggtca ggttggcggc 10760
tataatttct tgaatatcag tcgcctattc acacgcaata 10800
ttggtgatcc agtaacatgc gccatagcag atctgaagtg 10840
gttcattagg agcgggttaa tcccagagtt catcctgaag 10880
aatatattac tacgagatcc cggagacgat atgtggagta 10920
ctctatgtgc tgacccttac gcattaaata tcccctacac 10960
tcagctaccc acaacatacc tgaagaagca tactcagagg 11000
gcattactat ccgattctaa taatccgctt cttgcagggg 11040

-continued

```
tgcaattgga caatcaatac attgaagagg aggagtttgc                    11080
acgattcctt ttggatcggg aatccgtgat gcctcgagtg                    11120
gcacacacaa tcatggagtc aagtatacta gggaagagaa                    11160
agaacatcca gggtttaatc gacactaccc ctacaatcat                    11200
taagactgca ctcatgaggc agcccatatc tcgtagaaag                    11240
tgtgataaaa tagttaatta ctcgattaac tacctgactg                    11280
agtgccacga ttcattattg tcctgtagga cattcgagcc                    11320
gcggaaggaa ataatatggg agtcagctat gatctcagta                    11360
gaaacttgca gtgtcacaat tgcggagttc ctgcgcgcca                    11400
ccagctggtc caacatcctg aacggtagga ctatttcggg                    11440
tgtaacatct ccagacacta tagagctgct caaggggtca                    11480
ttaattggag agaatgccca ttgtattctt tgtgagcagg                    11520
gagacgagac attcacgtgg atgcacttag ccgggcccat                    11560
ctatatacca gacccggggg tgaccgcatc caagatgaga                    11600
gtgccgtatc ttgggtcaaa gacagaggaa aggcgtacgg                    11640
catccatggc caccattaag ggcatgtctc accacctaaa                    11680
ggccgctttg cgaggagcct ctgtgatggt gtgggccttt                    11720
ggtgatactg aagaaagttg ggaacatgcc tgccttgtgg                    11760
ccaatacaag gtgcaagatt aatcttccgc agctacgcct                    11800
gctgaccccg acaccaagca gctctaacat ccaacatcga                    11840
ctaaatgatg gtatcagcgt gcaaaaattt acacctgcta                    11880
gcttatcccg agtggcgtca tttgttcaca tttgcaacga                    11920
tttccaaaag ctagagagag atggatcttc cgtagactct                    11960
aacttgatat atcagcaaat catgctgact ggtctaagta                    12000
ttatggagac acttcatcct atgcacgtct catgggtata                    12040
caacaatcag acaattcact tacataccgg aacatcgtgt                    12080
tgtcctaggg aaatagagac aagcattgtt aatcccgcta                    12120
ggggagaatt cccaacaata actctcacaa ctaacaatca                    12160
gtttctgttt gattgtaatc ccatacatga tgaggcactt                    12200
acaaaactgt cagtaagtga gttcaagttc caggagctta                    12240
atatagactc aatgcagggt tacagtgctg tgaacctgct                    12280
gagcagatgt gtggctaagc tgatagggga atgcattctg                    12320
gaagacggta tcggatcgtc aatcaagaat gaagcaatga                    12360
tatcatttga taactctatc aactggattt ctgaagcact                    12400
caatagtgac ctgcgtttgg tattcctcca gctggggcaa                    12440
gaactacttt gtgacctggc gtaccaaatg tactatctga                    12480
gggtcatcgg ctatcattcc atcgtggcat atctgcagaa                    12520
tactctagaa agaattcctg ttatccaact cgcaaacatg                    12560
gcactcacca tatcccaccc agaagtatgg aggagagtga                    12600
cagtgagcgg attcaaccaa ggttaccgga gtccctatct                    12640
```

ggccactgtc gactttatcg ccgcatgtcg tgatatcatt 12680
gtgcaaggtg cccagcatta tatggctgat ttgttgtcag 12720
gagtagagtg ccaatataca ttctttaatg ttcaagacgg 12760
cgatctgaca ccgaagatgg aacaattttt agcccggcgc 12800
atgtgcttgt ttgtattgtt aactgggacg atccgaccac 12840
tcccaatcat acgatccctt aatgcgattg agaaatgtgc 12880
aattctcact cagttcttgt attacctacc gtcagtcgac 12920
atggcagtag cagacaaggc tcgtgtgtta tatcaactgt 12960
caataaatcc gaaaatagat gctttagtct ccaaccttta 13000
tttcaccaca aggaggttgc tttcaaatat caggggagat 13040
tcttcttcac gagcgcaaat tgcattcctc tacgaggagg 13080
aagtaatcgt tgatgtgcct gcatctaatc aatttgatca 13120
gtaccatcgt gaccccatcc taagaggagg tctatttttc 13160
tctctctcct taaaaatgga aaggatgtct ctgaaccgat 13200
ttgcagtaca gaccctgcca acccaggggt ctaactcgca 13240
gggttcacga cagaccttgt ggcgtgcctc accgttagca 13280
cactgcctta aatcagtagg gcaggtaagt accagctggt 13320
acaagtatgc tgtagtgggg gcgtctgtag agaaagtcca 13360
accaacaaga tcaacaagcc tctacatcgg ggagggcagt 13400
gggagtgtca tgacattatt agagtatctg gaccctgcta 13440
caattatctt ctacaactcg ctattcagca atagcatgaa 13480
ccctccacaa aggaatttcg gactgatgcc cacacagttt 13520
caggactcag tcgtgtataa aaacatatca gcaggagttg 13560
actgcaagta cgggtttaag caagtctttc aaccattatg 13600
gcgtgatgta gatcaagaaa caaatgtggt agagacggcg 13640
ttcctaaact atgtgatgga agtagtgcca gtccactctt 13680
cgaagcgtgt cgtatgtgaa gttgagtttg acagggggat 13720
gcctgacgag atagtaataa cagggtacat acacgtgctg 13760
atggtgaccg catacagtct gcatcgagga gggcgtctaa 13800
taatcaaggt ctatcgtcac tccgaggctg tattccaatt 13840
cgtactctct gcgatagtca tgatgtttgg ggggcttgat 13880
atacaccgga actcgtacat gtcaactaac aaagaggagt 13920
acatcatcat agctgcggcg ccggaggcat taaactattc 13960
ctctgtacca gcaatattgc agagggtgaa gtctgttatt 14000
gaccagcagc ttacattaat ctctcctata gatctagaaa 14040
gattgcgcca tgagactgag tctctccgtg agaaggagaa 14080
taatctagta atatctctga cgagagggaa gtatcaactc 14120
cggccgacac agactgatat gcttctatca tacctaggtg 14160
ggagattcat caccctattc ggacagtctg ctagggattt 14200
gatggccact gatgttgctg accttgatgc taggaagatt 14240
gcattagttg atctactgat ggtggaatcc aacattattt 14280
taagtgagag cacagacttg gaccttgcac tgttgctgag 14320
cccgtttaac ttagacaaag ggcggaagat agttacccta 14360
gcaaaggcta ctacccgcca attgctgccc gtgtatatcg 14400
catcagagat aatgtgcaat cggcaggcat tcacacacct 14440
gacatcaatt atacagcgtg gtgtcataag aatagaaaac 14480
atgcttgcta caacggaatt tgtccgacag tcagttcgcc 14520
cccagttcat aaaggaggtg ataactatag cccaagtcaa 14560
ccaccttttt tcagatctat ccaaactcgt gctttctcga 14600
tctgaagtca agcaagcact taaatttgtc ggttgctgta 14640
tgaagttcag aaatgcaagc aattaaacag gattgttatt 14680
gtcaaatcac cggttactat agtcaaatta atatgtaaag 14720
ttccctcttt caagagtgat taagaaaaaa cgcgtcaaag 14760
gtggcggttt cactgatttg ctcttggaag ttgggcatcc 14800
tccagccaat atatcggtgc cgaaatcgaa agtctgacag 14840
ctgatttgga atataagcac tgcataatca ctgagttacg 14880
ttgctttgct attccatgtc tggt 14904

<210> SEQ ID NO 118
<211> LENGTH: 14967
<212> TYPE: DNA
<213> ORGANISM: Artificial sequence
<220> FEATURE:
<223> OTHER INFORMATION: APMV-2/Yucaipa cDNA in pBR322/dr

<400> SEQUENCE: 118
ggcgcgccta atacgactca ctatagggac caaacaagga 40
ataggtaagc aacgtaaatc ttagataaaa ccatagaatc 80
cgtgggggcg acatcgcctg aagccgatct cgagatcgat 120
aactccggtt aattggtctc agcgtgagga gcttatctgt 160
ctgtggcaat gtcttctgtg ttttcagaat accaggctct 200
tcaggaccaa ctggtcaagc ctgccactcg aagggctgat 240
gtggcatcga ctggattgtt gagagcggag ataccagttt 280
gtgtaacctt gtctcaggac ccaactgata gatggaacct 320
cgcatgtctc aatctgcgat ggctgataag tgagtcctct 360
actactccca tgagacaagg ggcgatcctg tcactgctga 400
gcttgcactc tgacaacatg cgagctcacg caacccttgc 440
agcgagatcc gctgatgctg ccatcactgt gcttgaggtt 480
gacgccatag acatggcgga tggcacaatc acttttaatg 520
ccagaagtgg agtatccgag aggcgcagca cacagctcat 560
ggcaatcgca aaagatctgc cccgctcttg ttccaatgac 600
tcaccattca aagatgacac tatcgaggat cgcgaccccc 640
ttgacctgtc cgagactatc gatagactgc aggggattgc 680

-continued

```
tgcccaaatc tggatagcgg ccatcaagag catgactgcc       720
ccggatactg ctgcggagtc agaaggcaag aggcttgcaa       760
agtaccaaca acaaggccgc ttggtgcgac aggtgttagt       800
gcatgatgcg gtgcgtgcgg aattcctacg tgtcatcaga       840
ggcagcctgg tcttacggca attcatggta tcagaatgta       880
agagggcagc atccatgggt agcgagacat ctaggtacta       920
tgccatggtg ggtgacatca gcctctacat caagaatgca       960
ggacttaccg ccttcttctt gacactcaga tttggtattg      1000
ggacacacta ccccactctt gccatgagtg tgttctctgg      1040
agaactgaag aagatgtcgt ccttgatcag gctgtataag      1080
tcaaaagggg aaaatgctgc atacatggca ttcctggagg      1120
atgcggacat gggaaacttt gcgcctgcta actttagtac      1160
tctctactcc tatgcaatgg gggtaggtac agtgctggaa      1200
gcatcagttg cgaaatacca gttcgctcga gagttcacca      1240
gtgagacata cttcaggctt ggggttgaga ccgcacagaa      1280
ccaacagtgc gctctagatg aaaagaccgc caaggagatg      1320
gggcttactg atgaagccag aaagcaggtg caagcattgg      1360
ctagcaacat cgagcagggg caacattcaa tgcccatgca      1400
acaacagccc acattcatga gtcagcccta ccaggatgac      1440
gatcgtgacc agccaagcac cagcagacca gagccaagac      1480
catcgcaatt gacaagccaa tcagcagcac aggacaatga      1520
tgcggcctca ttagattggt gaccgcaatc agctcagcca      1560
agccattgtt ggacgcagga cattcaaatc atacattgcc      1600
ctaagagtat taaagtgatt taagaaaaaa ggaccctggg      1640
ggcgaagttg tcccaatcca ggcaggcgct gaaaccgaat      1680
ccctccaacc tccgagcccc aggcgaccat ggagttcacc      1720
gatgatgccg aaattgctga gctgttggac ctcgggacct      1760
cagtgatcca agagctgcag cgagccgaag tcaagggccc      1800
gcaaacaacc ggaaagccca aagttccccc ggggaacact      1840
aagagcctgg ctactctctg ggagcatgag actagcaccc      1880
aagggagtgc attgggcaca cccgagaaca acacccaggc      1920
acccgatgac aacaacgcag gtgcagatac gccagcgact      1960
accgacgtcc atcgcactct ggataccata gacaccgaca      2000
caccaccgga agggagcaag cccagctcca ctaactccca      2040
acccggtgat gaccttgaca aggctctttc gaagctagag      2080
gcgcgcgcca agctcggacc agatagggcc agacaggtta      2120
aaaaggggaa ggagatcggg tcgagcacag ggacgaggga      2160
ggcagccagt caccacatgg aagggagccg acagtcggag      2200
ccaggagcgg gcagccgagc acagccacaa ggccatggcg      2240
```

-continued

```
accgggacac aggagggagt actcattcat ctctcgagat     2280

gggagactgg aagtcacaag ctggtgcaac ccagtctgct     2320

ctcccattag aagcgagccc aggagagaaa agtgcacatg     2360

tggaacttgc ccagaatcct gcattttatg caggcaaccc     2400

aactgatgca attatggggt tgacaaagaa agtcaatgat     2440

ctagagacaa aattggctga ggtattgcgt ctgttaggaa     2480

tactccccgg aataaagaat gagattagtc agctgaaagc     2520

aaccgtggct ctgatgtcaa atcagattgc ctccattcag     2560

attcttgatc ctgggaatgc cggagtcaaa tcccttaatg     2600

agatgaaagc cctgtcaaaa gcagccagca tagttgtggc     2640

aggtccagga gtccttcctc ctgaggtcac agaaggagga     2680

ctgatcgcga aagatgagct agcaaggccc atccccatcc     2720

aaccgcaacg agactccaaa cccaaagacg acccgcacac     2760

atcaccaaat gatgtccttg ctgtacgcgc tatgatcgac     2800

acccttgtgg atgatgagaa gaagagaaag agattaaacc     2840

aggcccttga caaggcaaag accaaggatg acgtcttaag     2880

ggtcaagcgg cagatataca atgcctagga gtccatttgt     2920

ctaaagaacc tccaatcata tcaccagttt aaacccacat     2960

gcttccctgc cgagaatcta gccgacacaa aaactaaatc     3000

atagtttaac aaaaaagaag tttgggggcg aagtctcaca     3040

tcatagagca cccttgcatt ctaaaatggc tcaaacaacc     3080

gtcaggctgt atatcgatga agctagtccc gacattgaac     3120

tgttgtctta cccactgata atgaaagaca caggacatgg     3160

gaccaaagag ttgcagcagc aaatcagagt tgcagagatc     3200

ggtgcattgc agggagggaa gaatgaatca gttttcatca     3240

atgcatatgg ctttgttcag caatgcaaag ttaaaccggg     3280

ggcaacccaa ttcttccagg tagatgcagc tacaaagcca     3320

gaagtggtca ctgcagggat gattataatc ggtgcagtca     3360

agggggtggc aggcatcact aagctggcag aagaggtgtt     3400

cgagctggac atctccatca agaagtccgc atcattccat     3440

gagaaggttg cggtgtcctt taatactgtg ccactatcac     3480

tcatgaattc gaccgcatgc agaaatctgg gttatgtcac     3520

aaacgctgag gaggcgatca aatgcccgag caaaatacaa     3560

gcgggtgtga cgtacaaatt taagataatg tttgtctcct     3600

tgacacgact gcataacggg aaattgtacc gtgtccccaa     3640

ggcagtgtat gctgtagagg catcagctct atataaagtg     3680

caactggaag tcgggttcaa gcttgacgtg gccaaggatc     3720

acccacacgt taagatgttg aagaaagtgg aacggaatgg     3760

tgagactctg tatcttggtt atgcatggtt ccacctgtgc     3800

aacttcaaga agacaaatgc caagggtgag tcccggacaa     3840
```

-continued

```
tctccaacct agaagggaaa gtcagagcta tggggatcaa                    3880

ggtttccttg tacgacttat gggggcctac tttggtggtg                    3920

caaatcacag gtaagaccag caagtatgca caaggtttct                    3960

tttcaaccac aggtacctgc tgcctcccag tgtcgaaggc                    4000

tgcccctgag ctggccaaac ttatgtggtc ctgcaatgca                    4040

acaatcgttg aagctgcagt gattatccaa gggagtgata                    4080

ggagggcagt cgtgacctca gaggacttgg aagtatacgg                    4120

ggcagttgca aaagagaagc aggctgcaaa aggatttcac                    4160

ccgttccgca actgacacgt ggggccgcac acctcattac                    4200

cccagaagcc cgggcaactg caaattcacg cttatataat                    4240

ccaattacca tgatctagaa ctgcaatcga tactaatcgc                    4280

tcattgatcg tattaagaaa aaacttaact acataacttc                    4320

aacattgggg gcgacagctc cagactaagt gggtggctaa                    4360

gctctgactg ataaggaatc atgaatcaag cactcgtgat                    4400

tttgttggta tctttccagc tcggcgttgc cttagataac                    4440

tcagtgttgg ctccaatagg agtagctagc gcacaggagt                    4480

ggcaactggc ggcatataca acgaccctca cagggaccat                    4520

cgcagtgaga tttatcccgg tcctgcctgg gaacctatca                    4560

acatgtgcac aggagacgct gcaggaatat aatagaactg                    4600

tgactaatat cttaggcccg ttgagagaga acttggatgc                    4640

tctcctatct gacttcgata aacctgcatc gaggttcgtg                    4680

ggcgccatca ttgggtcggt ggccttgggg gtagcaacag                    4720

ctgcacaaat cacagccgcc gtggctctca atcaagcaca                    4760

agagaatgcc cggaatatat ggcgtctcaa ggaatcgata                    4800

aagaaaacca atgcggctgt gttggaattg aaggatggac                    4840

ttgcaacgac tgctatagct ttggacaaag tgcaaaagtt                    4880

tatcaatgat gatattatac cacagattaa ggacattgac                    4920

tgccaggtag ttgcaaataa attaggcgtc tacctctcct                    4960

tatacttaac agagcttaca actgtatttg gttctcagat                    5000

cactaatcct gcattatcaa cgctctctta ccaggcgctg                    5040

tacagcttat gtggagggga tatgggaaag ctaactgagc                    5080

tgatcggtgt caatgcaaag gatgtgggat ccctctacga                    5120

ggctaacctc ataaccggcc aaatcgttgg atatgaccct                    5160

gaactacaga taatcctcat acaagtatct tacccaagtg                    5200

tgtctgaagt gacaggagtc cgggctactg agttagtcac                    5240

tgtcagtgtc actacaccaa aaggagaagg gcaggcaatt                    5280

gttccgagat atgtggcaca gagtagagtg ctgacagagg                    5320

agttggatgt ctcgacttgt aggtttagca aaacaactct                    5360

ttattgtagg tcgattctca cacggcccct accaactttg                    5400
```

-continued atcgccagct gcctgtcagg gaagtacgac gattgtcagt 5440
acacaacaga gataggagcg ctatcttcga gattcatcac 5480
agtcaatggt ggagtccttg caaactgcag agcaattgtg 5520
tgtaagtgtg tctcaccccc gcatataata ccacaaaacg 5560
acattggctc cgtaacagtt attgactcaa gtatatgcaa 5600
ggaagttgtc ttagagagtg tgcagcttag gttagaagga 5640
aagctgtcat cccaatactt ctccaacgtg acaattgacc 5680
tttcccaaat cacaacgtca gggtcgctgg atataagcag 5720
tgaaattggt agcattaaca acacagttaa tcgggtcgac 5760
gagttaatca aggaatccaa cgagtggctg aacgctgtga 5800
acccccgcct tgtgaacaat acgagcatca tagtcctctg 5840
tgtccttgcc gccctgatta ttgtctggct aatagcgctg 5880
acagtatgct tctgttactc cgcaagatac tcagctaagt 5920
caaaacagat gaggggcgct atgacaggga tcgataatcc 5960
atatgtaata cagagtgcaa ctaagatgta gagaggttaa 6000
ttaagcctaa acatgatatg atttaagaaa aaattggaag 6040
gtgggggcga cagcccattc aatgaagggt gtacactcca 6080
acttgatctt gtgacttgat catcatactc gaggcaccat 6120
ggatttccca tctagggaga acctggcagc aggtgacata 6160
tcggggcgga agacttggag attactgttc cggatcctca 6200
cattgagcat aggtgtggtc tgtcttgcca tcaatattgc 6240
cacaattgca aaattggatc acctggataa catggcttcg 6280
aacacatgga caacaactga ggctgaccgt gtgatatcta 6320
gcatcacgac tccgctcaaa gtccctgtca accagattaa 6360
tgacatgttt cggattgtag cgcttgacct acctctgcag 6400
atgacatcat tacagaaaga aataacatcc caagtcgggt 6440
tcttggctga aagtatcaac aatgttttat ccaagaatgg 6480
atctgcaggc ctggttcttg ttaatgaccc tgaatatgca 6520
ggggggatcg ctgtcagctt gtaccaagga gatgcatctg 6560
caggcctaaa tttccagccc atttctttaa tagaacatcc 6600
aagttttgtc cctggtccta ctactgctaa gggctgtata 6640
aggatcccga ccttccatat gggcccttca cattggtgtt 6680
actcacataa catcattgca tcaggttgcc aggatgcgag 6720
ccactccagt atgtatatct ctctgggggt gctgaaagca 6760
tcgcagaccg ggtcgcctat cttcttgaca acggccagcc 6800
atctcgtgga tgacaacatc aaccggaagt catgcagcat 6840
cgtagcctca aaatacggtt gtgatatcct atgcagtatt 6880
gtgattgaaa cagagaatga ggattatagg tctgatccgg 6920
ctactagcat gattataggt aggctgttct tcaacgggtc 6960
atacacagag agcaagatta acacagggtc catcttcagt 7000

-continued ctattctctg ctaactaccc tgcggtgggg tcgggtattg 7040
tagtcgggga tgaagccgca ttcccaatat atggtggggt 7080
caagcagaac acatggttgt tcaaccagct caaggatttt 7120
ggttacttca cccataatga tgtgtacaag tgcaatcgga 7160
ctgatataca gcaaactatc ctggatgcat acaggccacc 7200
taaaatctca ggaaggttat gggtacaagg catcctattg 7240
tgcccagttt cactgagacc tgatcctggc tgtcgcttaa 7280
aggtgttcaa taccagcaat gtgatgatgg gggcagaagc 7320
gaggttgatc caagtaggct caaccgtgta tctataccaa 7360
cgctcatcct catggtgggt ggtaggactg acttacaaat 7400
tagatgtgtc agaaataact tcacagacag gtaacacact 7440
caaccatgta gaccccattg cccatacaaa gttcccaaga 7480
ccatctttca ggcgagatgc gtgtgcgagg ccaaacatat 7520
gccctgctgt ctgtgtctcc ggagtttatc aggacatttg 7560
gccgatcagt acagccacca ataacagcaa cattgtgtgg 7600
gttggacagt acttagaagc attctattcc aggaaagacc 7640
caagaatagg gatagcaacc cagtatgagt ggaaagtcac 7680
caaccagctg ttcaattcga atactgaggg agggtactca 7720
accacaacat gcttccggaa caccaaacgg gacaaggcat 7760
attgtgtagt gatatcagag tacgctgatg ggtgttcgg 7800 atcatacagg atcgttcctc agcttataga gattagaaca 7840
accaccggta aatctgagtg atgcatcaat cctaaattgg 7880
aatgaccaat caaaagccac gtagtgtcta acagcattgc 7920
gaagcctggt ttaagaaaaa acttgggggc gaatgcccat 7960
caaccatgga tcaaactcaa gctgacacta taatacaacc 8000
tgaagtccat ctgaattcac cacttgttcg cgcaaaattg 8040
gttcttctat ggaaattgac tgggttacct ttgccgtctg 8080
atttgagatc atttgtacta actacacatg cagctgatga 8120
ccaaatcgca aaaaatgaga ctaggatcaa ggccaaaatt 8160
aattccctaa tcgataactt aatcaaacac tgcaaggcaa 8200
ggcaagtggc actttcaggg ttgacacctg tcgtacatcc 8240
aacaactcta cagtggttgc tatccatcac atgtgaacga 8280
gcagaccacc ttgcaaaagt acgcgagaaa tcagttaagc 8320
aagcaatgtc agagaagcaa cacgggttta gacatctctt 8360
ttcggcagta agtcatcagt tagttggaaa cgccacactg 8400
ttctgtgcac aagactctag caccgtgaat gtcgactctc 8440
cttgctcatc aggttgtgag aggctgataa tagactctat 8480
tggagcctta caaacacgat ggacaagatg taggtgggct 8520
tggcttcaca ttaaacaggt aatgagatac caggtgcttc 8560

-continued agagtcgcct acacgctcat gccaattctg ttagcacatg 8600
gtctgaggcg tgggggttca ttgggatcac accagatata 8640
gtccttattg tagactataa gagcaaaatg tttactatcc 8680
tgaccttcga aatgatgctg atgtattcag atgtcataga 8720
gggtcgtgat aatgtggtag ctgtaggaag tatgtcacca 8760
aacctacagc ctgtggtgga gaggattgag gtgctgtttg 8800
atgtagtgga caccttggcg aggaggattc atgatcctat 8840
ttatgatctg gttgctgcct tagaaagcat ggcatacgct 8880
gccgtccaat tgcacgatgc tagtgagaca cacgcagggg 8920
aattcttttc gttcaatttg acagaaatag agtccactct 8960 tgccccccttg ctggatcctg gccaagtcct atcggtgatg 9000
aggactatca gttattgtta cagtgggcta tcgcctgacc 9040
aagctgcaga gttgctctgt gtgatgcgct tatttggaca 9080
ccctctgctc tccgcacaac aagcagccaa aaaagtccgg 9120
gagtctatgt gtgcccctaa actgttagag catgatgcaa 9160
tactgcaaac tctatctttc ttcaagggaa tcataatcaa 9200
tggctacagg aaaagtcatt ctggagtatg gcctgcaatt 9240
gacccagatt ctatagtgga cgatgacctt agacagctgt 9280
attacgagtc ggcagaaatt tcacatgctt tcatgcttaa 9320
gaaatatcgg taccttagta tgattgagtt ccgcaagagc 9360
atagagtttg acttaaatga tgacctgagc acattcctta 9400
aagacaaagc aatctgcagg ccaaaagatc aatgggcacg 9440
catcttccgg aaatcattgt tcccttgcaa aacgaacctt 9480
ggcactagta tagatgttaa aagtaatcga ctgttgatag 9520
attttttgga gtcacatgac ttcaatcctg aggaagaaat 9560
gaagtatgtg actacgctag catacctggc agataatcaa 9600
ttctcagcat catattcact gaaggagaaa gagatcaaga 9640
ctactggccg gatcttcgcc aaaatgacca ggaaaatgag 9680
gagctgtcaa gtaatattgg aatcactatt gtccagtcac 9720
gtctgcaaat tctttaagga gaacggtgtg tcaatggaac 9760
aactgtcttt gacaaagagc ttgcttgcaa tgtcacagtt 9800
agcacccagg atatcttcag ttcgccaggc gacagcacgt 9840
agacaggacc caggactcag ccactctaat ggttgtaatc 9880
acattgtagg agacttaggc ccacaccagc aggacagacc 9920
ggcccggaag agtgtagtcg caaccttcct tacaacagat 9960
cttcaaaaat attgcttgaa ttggcgatat gggagtatca 10000
agcttttcgc ccaagcctta aaccagctat tcggaatcga 10040
gcatgggttt gaatggatac acctgagact gatgaatagc 10080
accctgtttg tcggggaccc attctcgcct cctgaaagca 10120
aagtgctgag tgatcttgat gatgcgccca attcagacat 10160

-continued atttatcgtg tccgccagag gggggattga agggttatgc 10200
cagaagctgt ggaccatgat ttcaataagc ataatccatt 10240
gcgtggctga gaagatagga gcaagggttg cggcgatggt 10280
tcagggagat aatcaggtaa ttgcaatcac gagagagctg 10320
tataagggag agacttacac gcagattcag ccggagttag 10360
atcgattagg caatgcattt tttgctgaat tcaaaagaca 10400
caactatgca atgggacata atctgaagcc caaagagaca 10440
atccaaagtc aatcattctt tgtgtattcg aaacggattt 10480
tctgggaagg gagaattctt agtcaagcac tgaagaatgc 10520
taccaaacta tgcttcattg cagatcacct cggggataat 10560
actgtctcat catgcagcaa tctagcctct acgataaccc 10600
gcttggttga gaatgggtat gaaaaggaca cagcattcat 10640
tctgaatatc atctcagcaa tgactcagtt gctgattgat 10680
gagcaatatt ccctacaagg agactactca gctgtgagaa 10720
aactgattgg gtcatcaaat taccgtaatc tcttagtggc 10760
gtcgctcatg cctggtcagg ttggcggcta taatttcttg 10800
aatatcagtc gcctattcac acgcaatatt ggtgatccag 10840
taacatgcgc catagcagat ctgaagtggt tcattaggag 10880
cgggttaatc ccagagttca tcctgaagaa tatattacta 10920
cgagatcccg gagacgatat gtggagtact ctatgtgctg 10960
acccttacgc attaaatatc ccctacactc agctacccac 11000
aacatacctg aagaagcata ctcagagggc attactatcc 11040
gattctaata atccgcttct tgcaggggtg caattggaca 11080
atcaatacat tgaagaggag gagtttgcac gattcctttt 11120
ggatcgggaa tccgtgatgc ctcgagtggc acacacaatc 11160
atggagtcaa gtatactagg gaagagaaag aacatccagg 11200
gtttaatcga cactacccct acaatcatta agactgcact 11240
catgaggcag cccatatctc gtagaaagtg tgataaaata 11280
gttaattact cgattaacta cctgactgag tgccacgatt 11320
cattattgtc ctgtaggaca ttcgagccgc ggaaggaaat 11360
aatatgggag tcagctatga tctcagtaga aacttgcagt 11400
gtcacaattg cggagttcct gcgcgccacc agctggtcca 11440
acatcctgaa cggtaggact atttcgggtg taacatctcc 11480
agacactata gagctgctca aggggtcatt aattggagag 11520
aatgcccatt gtattctttg tgagcaggga gacgagacat 11560
tcacgtggat gcacttagcc gggcccatct atataccaga 11600
cccgggggtg accgcatcca agatgagagt gccgtatctt 11640
gggtcaaaga cagaggaaag gcgtacggca tccatggcca 11680
ccattaaggg catgtctcac cacctaaagg ccgctttgcg 11720

-continued

```
aggagcctct gtgatggtgt gggcctttgg tgatactgaa      11760
gaaagttggg aacatgcctg ccttgtggcc aatacaaggt      11800
gcaagattaa tcttccgcag ctacgcctgc tgaccccgac      11840
accaagcagc tctaacatcc aacatcgact aaatgatggt      11880
atcagcgtgc aaaaatttac acctgctagc ttatcccgag      11920
tggcgtcatt tgttcacatt tgcaacgatt tccaaaagct      11960
agagagagat ggatcttccg tagactctaa cttgatatat      12000
cagcaaatca tgctgactgg tctaagtatt atggagacac      12040
ttcatcctat gcacgtctca tgggtataca acaatcagac      12080
aattcactta cataccggaa catcgtgttg tcctagggaa      12120
atagagacaa gcattgttaa tcccgctagg ggagaattcc      12160
caacaataac tctcacaact aacaatcagt ttctgtttga      12200
ttgtaatccc atacatgatg aggcacttac aaaactgtca      12240
gtaagtgagt tcaagttcca ggagcttaat atagactcaa      12280
tgcagggtta cagtgctgtg aacctgctga gcagatgtgt      12320
ggctaagctg ataggggaat gcattctgga agacggtatc      12360
ggatcgtcaa tcaagaatga agcaatgata tcatttgata      12400
actctatcaa ctggatttct gaagcactca atagtgacct      12440
gcgtttggta ttcctccagc tggggcaaga actactttgt      12480
gacctggcgt accaaatgta ctatctgagg gtcatcggct      12520
atcattccat cgtggcatat ctgcagaata ctctagaaag      12560
aattcctgtt atccaactcg caaacatggc actcaccata      12600
tcccacccag aagtatggag gagagtgaca gtgagcggat      12640
tcaaccaagg ttaccggagt ccctatctgg ccactgtcga      12680
ctttatcgcc gcatgtcgtg atatcattgt gcaaggtgcc      12720
cagcattata tggctgattt gttgtcagga gtagagtgcc      12760
aatatacatt ctttaatgtt caagacggcg atctgacacc      12800
gaagatggaa caatttttag cccggcgcat gtgcttgttt      12840
gtattgttaa ctgggacgat ccgaccactc ccaatcatac      12880
gatcccttaa tgcgattgag aaatgtgcaa ttctcactca      12920
gttcttgtat tacctaccgt cagtcgacat ggcagtagca      12960
gacaaggctc gtgtgttata tcaactgtca ataaatccga      13000
aaatagatgc tttagtctcc aacctttatt tcaccacaag      13040
gaggttgctt tcaaatatca ggggagattc ttcttcacga      13080
gcgcaaattg cattcctcta cgaggaggaa gtaatcgttg      13120
atgtgcctgc atctaatcaa tttgatcagt accatcgtga      13160
ccccatccta agaggaggtc tatttttctc tctctcctta      13200
aaaatggaaa ggatgtctct gaaccgattt gcagtacaga      13240
ccctgccaac ccaggggtct aactcgcagg gttcacgaca      13280
gaccttgtgg cgtgcctcac cgttagcaca ctgccttaaa      13320
```

-continued tcagtagggc aggtaagtac cagctggtac aagtatgctg 13360
tagtgggggc gtctgtagag aaagtccaac caacaagatc 13400
aacaagcctc tacatcgggg agggcagtgg gagtgtcatg 13440
acattattag agtatctgga ccctgctaca attatcttct 13480
acaactcgct attcagcaat agcatgaacc ctccacaaag 13520
gaatttcgga ctgatgccca cacagtttca ggactcagtc 13560
gtgtataaaa acatatcagc aggagttgac tgcaagtacg 13600
ggtttaagca agtctttcaa ccattatggc gtgatgtaga 13640
tcaagaaaca aatgtggtag agacggcgtt cctaaactat 13680
gtgatggaag tagtgccagt ccactcttcg aagcgtgtcg 13720
tatgtgaagt tgagtttgac agggggatgc ctgacgagat 13760
agtaataaca gggtacatac acgtgctgat ggtgaccgca 13800
tacagtctgc atcgaggagg gcgtctaata atcaaggtct 13840
atcgtcactc cgaggctgta ttccaattcg tactctctgc 13880
gatagtcatg atgtttgggg ggcttgatat acaccggaac 13920
tcgtacatgt caactaacaa agaggagtac atcatcatag 13960
ctgcggcgcc ggaggcatta aactattcct ctgtaccagc 14000
aatattgcag agggtgaagt ctgttattga ccagcagctt 14040
acattaatct ctcctataga tctagaaaga ttgcgccatg 14080
agactgagtc tctccgtgag aaggagaata atctagtaat 14120
atctctgacg agagggaagt atcaactccg gccgacacag 14160
actgatatgc ttctatcata cctaggtggg agattcatca 14200
ccctattcgg acagtctgct agggatttga tggccactga 14240
tgttgctgac cttgatgcta ggaagattgc attagttgat 14280
ctactgatgg tggaatccaa cattatttta agtgagagca 14320
cagacttgga ccttgcactg ttgctgagcc cgtttaactt 14360
agacaaaggg cggaagatag ttaccctagc aaaggctact 14400
acccgccaat tgctgcccgt gtatatcgca tcagagataa 14440
tgtgcaatcg gcaggcattc acacacctga catcaattat 14480
acagcgtggt gtcataagaa tagaaaacat gcttgctaca 14520
acggaatttg tccgacagtc agttcgcccc cagttcataa 14560
aggaggtgat aactatagcc caagtcaacc acctttttc 14600 agatctatcc aaactcgtgc tttctcgatc tgaagtcaag 14640
caagcactta aatttgtcgg ttgctgtatg aagttcagaa 14680
atgcaagcaa ttaaacagga ttgttattgt caaatcaccg 14720
gttactatag tcaaattaat atgtaaagtt ccctctttca 14760
agagtgatta agaaaaaacg cgtcaaaggt ggcggtttca 14800
ctgatttgct cttggaagtt gggcatcctc cagccaatat 14840
atcggtgccg aaatcgaaag tctgacagct gatttggaat 14880

-continued

| | |
|---|---|
| ataagcactg cataatcact gagttacgtt gctttgctat | 14920 |
| tccatgtctg gtgggtcggc atggcatctc cacctcctcg | 14960 |
| cggtccg | 14967 |

GENOMIC SEQUENCE OF AVIAN PARAMYXOVIRUS TYPE 2 AND USES THEREOF

This application claims benefit of priority from Provisional Application Ser. No. 61/218,851 filed on Jun. 19, 2009.

This invention was made with government support under grant N01A060009 awarded by the National Institutes of Health. The Government has certain rights in the invention.

INTRODUCTION

The family Paramyxoviridae is large and diverse and includes members that have been isolated from many species of avian, terrestrial, and aquatic animals around the world (Lamb and Parks, 2007 In: Knipe, D. M. et al., eds. Fields Virology, 5th ed. Lippincott William & Wilkins, Philadelphia, pp. 1449-1496; Wang and Eaton, 2001, Infect. Dis. Rev. 3, 52-69). Paramyxoviruses are pleomorphic, enveloped, cytoplasmic viruses with a non-segmented negative-strand RNA genome. Paramyxoviruses are divided into two subfamilies, Paramyxovirinae and Pneumovirinae, based on structure, genome organization, and sequence relatedness (Lamb et al., 2005, In: Fauquet, C. M. (ed.) Virus Taxonomy: The Classification and Nomenclature of Viruses. The Eighth Report of the International Committee on Taxonomy of Viruses. Elsevier Academic Press, pp. 655-668). Subfamily Paramyxovirinae comprises five genera; *Respirovirus* (including Sendai virus [SeV] and human parainfluenza virus types 1 and 3 [HPIV-1 and -3]), *Rubulavirus* (including simian virus type 5 [SV5], mumps virus [MuV], and human parainfluenza virus types 2 and 4 [HPIV-2 and -4]), *Morbillivirus* (including measles [MeV] and canine distemper [CDV] viruses), *Henipavirus* (including Hendra [HeV] and Nipah [NiV] viruses), and *Avulavirus* (comprising the nine serotypes of avian paramyxoviruses [APMV-1 to -9]). Subfamily Pneumovirinae contains two genera, *Pneumovirus* (comprising human respiratory syncytial virus [HRSV] and its animal counterparts) and *Metapneumovirus* (comprising human *metapneumovirus* [HMPV] and its avian counterpart [AMPV].

The genome lengths of members of Paramyxoviridae range from 15 to 19 kb and contain 6-10 genes arranged in tandem (Lamb and Parks, 2007). All members of Paramyxoviridae examined to date encode a major nucleocapsid protein (N) that binds the entire length of the genomic and the replicative antigenomic RNAs, a nucleocapsid phosphoprotein (P) that is a polymerase co-factor, a large protein (L) that is the major polymerase subunit and bears catalytic domains, a matrix protein (M) that lines the inner surface of the envelope, a fusion glycoprotein (F) that is a surface antigen that mediates viral penetration and syncytium formation and a major glycoprotein (G) or hemagglutinin-neuraminidase (HN) glycoprotein that is a second surface antigen and mediates attachment.

The genome termini of members of Paramyxoviridae consist of extragenic regions, called the 3'-leader and 5'-trailer: the 3'-leader region contains the genome promoter, and the trailer encodes the 3' end of the antigenome, which is the full-length positive-sense replicative intermediate, which contains the antigenome promoter. Each gene starts with a conserved gene start (GS) sequence and ends with a conserved gene end (GE) sequence. Transcription begins at the 3'-leader region and proceeds in a sequential manner by a start-stop mechanism that is guided by short, conserved GS and GE signals that flank each gene (Lamb and Parks, 2007, supra). The genes are separated by non-coding intergenic sequences (IGS) that are conserved in length and sequence among the different gene junctions for some genera (*Respirovirus, Morbillivirus*, and *Henipavirus*) and are non-conserved in sequence or length for others (*Rubulavirus, Avulavirus, Pneumovirus*, and *Metapneumovirus*). For the members of subfamily Paramyxovirinae, efficient genome replication depends on the total genome nucleotide (nt) length being an even multiple of six, known as 'rule of six' (Kolakofsky et al., 1998, J. Virol. 72, 891-899), which is thought to reflect a requirement of nucleocapsid structure. Most members of subfamily Paramyxovirinae encode three different proteins, namely P, V and W (or I, in case of genus *Rubulavirus*), from the P/V gene due to frame-shifting into alternative open reading frames (ORFs) by RNA editing. RNA editing involves the insertion of one or more G residues at a specific motif midway along the P/V gene during transcription; yielding subpopulations of P/V mRNA have frame shifts into each of the three reading frames. In the case of genus *Avulavirus*, the unedited mRNA encodes the P protein. The insertion of a single G residue at the P editing site shifts the reading frame to access a downstream ORF encoding a highly conserved cysteine motif, resulting in the V protein. The V protein of subfamily Paramyxovirinae has been implicated in the regulation of viral RNA synthesis (Horikami et al., 1996, Virology 222, 383-390; Lin et al., 2005, Virology 338, 270-280) and in counteracting host antiviral responses (Goodbourn et al., 2000, J. Gen. Virol. 81, 2341-2364). Alternatively, the insertion of two G residues shifts the reading frame to access a third, shorter internal ORF that leads to production of the W protein, whose function is not yet understood (Steward et al., 1993, J. Gen. Virol. 74, 2539-2547).

Genus *Avularis* contains all of the paramyxoviruses that have been isolated from avian species except for avian *metapneumovirus*. The APMVs have been classified into nine different serotypes based on hemagglutination inhibition (HI) and neuraminidase inhibition (NI) assays (Alexander, 2003, In: Saif, Y. M. (Ed.), Diseases of Poultry, 11th ed. Iowa State University Press, Ames, pp. 88-92). The cross-HI and -NI tests also indicated that APMV isolates could be organized into two broad subgroups; the first subgroup consisting of APMV-2 and -6 and the second subgroup consisting of APMV-1, -3, -4, -7, -8 and -9 (Lipkind and Shihmanter, 1986, Arch. Virol. 89, 89-111). Not much is known about APMV-5. The many strains of Newcastle disease virus (NDV) comprise APMV-1. Since NDV is an important cause of disease in chickens, APMV-1 is the most extensively characterized serotype of the APMVs.

APMV-2 was first isolated in 1956 in Yucaipa, Calif. from a diseased chicken that was also infected with infectious laryngotracheitis virus (Bankowski et al., 1960, Science 132, 292-293). Since then, many APMV-2 strains have been isolated from chickens, turkeys and feral birds around the world (Alexander et al., 1982, Vet. Rec. 111, 571-574; Asahara et al., 1973, Bull. Azabu Vet. Coll. 26, 67-81; Collings et al., 1975, Res. Vet. Sci. 19, 219-221; Fleury and Alexander, 1979, Avian Dis. 23, 742-744; Goodman and Hanson, 1988, Avian Dis. 32, 713-717; Lang et al., 1975, Can. Vet. J. 16, 233-237; Lipkind et al., 1979 Israel. Vet. Rec. 105, 577-578; Lipkind et al., 1982, Israel. Vet. Rec. 110, 15-16; Mbugua and Karstad, 1985, J. Wildl. Dis. 21, 52-54; Nymadawa et al., 1977, Acta Virol. 56, 345-351; Shihmanter et al., 1997, Vet. Microbiol. 58, 73-78; Weisman et al., 1984, Vet. Rec. 115, 605; Zhang et al., 2006, Avian Dis. 50, 386-390; Zhang et al., 2007. Avian Dis. 51, 137-

139). APMV-2 strain Bangor was isolated from a finch during a routine quarantine evaluation, and the biological and serological characterization suggested that strain Bangor might represent a separate serotype or as a subgroup within serotype 2 (McFerran et al., 1973, Res. Vet. Science 15, 116-118; McFerran et al., 1974, Archiv fftr die gesamte virusforshcung 46, 281-290).

Very little is known about the molecular biology and pathogenesis of serotypes 2-9. As a first step towards characterizing the molecular genetics and pathogenesis of APMV-2, the biological activities and growth characteristics of APMV-2 were investigated. The present inventors found that APMV-2 is different than NDV in several characteristics: (I) APMV-2 does not require tryporin or allantoic fluid to grow in cell culture; (II) RNA-RNA hybridization studies showed APMV-2 is genetically different than NDV; (III) APMV-2 is the only paramyxovirus serotype which causes single cell infection, and does not produce cell fusion, which is the hallmark of paramyxovirus infection; (IV) APMV-2 does not kill chicken embryos; and (V) APMV-2 does not grow in the brain of chicken. These results suggested that APMV-2 is significantly different biologically and genetically from NDV. These differences provide certain advantages over other viruses considered for use as a vaccine, as a virus vector, or as a therapeutic. For example, unlike the current NDV vaccine such as LaSota and Hitchner B1 that can cause disease due to reversion to virulence, since AMPV-2 is not an agricultural pathogen, it is not a concern for the poultry industry.

However, in order to develop a recombinant APMV-2 virus for use as a vector, vaccine, or cancer therapy, the complete genome sequence was needed. This proved to be difficult since any primer based on NDV could not be used because RNA-RNA hybridization assays suggested that the two viruses are genetically different (Subbiah et al., 2008, Virus Res. 137, 40-48). Since RNA-RNA hybridization and reverse trancriptase-PCR (RT-PCR) could not be used, different strategies had to be designed in order to sequence APMV-2. These included design and testing of consensus primers from other paramyxoviruses, design and testing of primers with gene start and gene end sequences of other paramyxoviruses and primer walking.

Herein disclosed is the complete genome of APMV-2, strain Yucaipa, as well as the complete genomic sequences of strains Bangor, England and Kenya. These sequences produce infectious recombinant APMV-2. The recombinant APMV-2 was used to express a foreign antigen, the green fluorescent protein (GFP), and can be used as a vaccine vector. Characterization of the virus in in vitro cell culture studies indicated that recombinant APMV-2 can also be used in cancer treatment.

SUMMARY OF THE INVENTION

The invention relates to an isolated genomic sequence of avian paramyxovirus type 2, strain Yucaipa, strain Bangor, strain England, and strain Kenya. The present invention also relates to isolated RNA viruses identifiable as phylogenitically corresponding or relating to the genus paramyxoviruses and components thereof. However, the AMPV-2 genomic sequences of the present invention may encompass additional variants yet to be identified, and are not limited to the strains identified herein.

The invention relates to the use of the sequence information of different strains of APMV-2 for diagnostic and therapeutic methods. The present invention relates to the differences of the genomic nucleotide sequences among the different APMV-2-isolates, and their use in the diagnostic and therapeutic methods of the invention. The sequence variation in different strains of APMV-2 reflects their distinct biology and pathophysiology, including factors such as different tissue tropisms, receptor usage and intracellular trafficking pathways. Therefore, the genetic diversity among different strains should be taken into consideration. In specific embodiments, the nucleotide sequence of a AMPV-2 that encodes for the N, P, V, M, F, HN, L, ORFs may be used to identify a virus of the invention.

The invention relates to recombinant and chimeric viruses that are derived from AMPV-2 sequences described herein. In accordance with the present invention, a recombinant virus is one derived from AMPV-2 that is encoded by endogenous or native genomic sequences or non-native genomic sequences. In accordance with the invention, a non-native sequence is one that is different from the native or endogenous genomic sequence due to one or more mutations, including, but not limited to, point mutations, rearrangements, insertions, deletions etc., to the genomic sequence that may or may not result in a phenotypic change. In accordance with the invention, a chimeric virus of the invention is a recombinant AMPV which further comprises a heterologous nucleotide sequence. In accordance with the invention, a chimeric virus may be encoded by a nucleotide sequence in which heterologous nucleotide sequences have been added to the genome at any location, i.e. and ORF, in the intergenic sequences, 3'-leader sequence, 5'-trailer sequence, or in which endogenous or native nucleotide sequences have been replaced with heterologous nucleotide sequences. In certain embodiments, a chimeric virus of the invention is derived from AMPV in which one or more of the open reading frames (ORFs) or a portion thereof is replaced by a desired sequence. In an exemplary embodiment, the ORF of the heterologous gene can be inserted in the intergenic sequence between P and M genes of AMPV-2 as described in the examples.

The present invention relates to nucleotide sequences encoding the genome of AMPV-2 or a portion thereof. The present invention relates to nucleotide sequences encoding gene products of AMPV-2. In particular, the invention relates to, but is not limited to, nucleotide sequences encoding an N protein, a P protein, a V protein, a M protein, an F protein, a HN protein, an L protein, a W protein of any of the AMPV-2 strains described herein. The present invention further relates to a cDNA or RNA that encodes the genome or a portion thereof of an AMPV-2, in addition to a nucleotide sequence which is heterologous or non-native to the viral genome. The invention further encompasses chimeric or recombinant viruses encoded by said cDNAs or RNAs.

The invention further relates to polypeptides and amino acid sequences of an N protein, a P protein, a V protein, a M protein, an F protein, a HN protein, an L protein, a W protein of AMPV-2 disclosed herein and different variants of AMPV-2. The invention further relates to antibodies against an N protein, a P protein, a V protein, a M protein, an F protein, a HN protein, an L protein, a W protein of a AMPV-2 and different variants of AMPV-2. The antibodies can be used for diagnostic and therapeutic methods. In certain embodiments, the antibodies are specific to a variant of AMPV-2. The invention further relates to vaccine formulations and immunogenic compositions comprising one or more of the following: an N protein, a P protein, a V protein, a M protein, an F protein, a HN protein, an L protein, a W protein of a AMPV-2.

The invention further relates to vaccine formulations and immunogenic compositions comprising AMPV-2, including recombinant and chimeric forms of said viruses. The invention further relates to vaccines comprising chimeric AMPV-2 wherein the chimeric AMPV-2 encodes one or more AMPV-2 proteins and wherein the chimeric AMPV-2 optionally additionally expresses one or more heterologous or non-native sequences. The present invention also relates to multivalent vaccines, including bivalent and trivalent vaccines. In particular, multivalent vaccines of the invention encompass two or more antigenic polypeptides expressed by the same or different AMPV-2 vectors. The antigenic polypeptides of the multivalent vaccines include but are not limited to, antigenic polypeptides of AMPV-2, and another desired non-AMPV-2 antigen.

The invention further relates to methods for treating a cancer in a subject. In specific embodiments, the methods for treating cancer in a subject comprise administering to the subject a composition comprising a recombinant or a chimeric AMPV-2 or a portion thereof. In more specific embodiments, the recombinant or chimeric AMPV-2 is attenuated. In a specific embodiment, the invention relates to treating cancer in a human patient comprising administering to the human patient a formulation comprising a recombinant or chimeric APMV-2, or a nucleotide sequence encoding one or more of an N protein, a P protein, an V protein, a M protein, an F protein, a HN protein, an L protein, a W protein of APMV-2 or a portion of any of an N protein, a P protein, an V protein, a M protein, an F protein, a HN protein, an L protein, a W protein of APMV-2.

The invention provides an isolated single stranded RNA virus AMPV-2, wherein strain Yucaipa genomic nucleotide sequence is described in SEQ ID NO:1, strain Bangor is described in SEQ ID NO:2, strain England is described in SEQ ID NO:3, strain Kenya is described in SEQ ID NO:4. In certain embodiments, the invention provides an isolated nucleic acid, wherein the nucleic acid has a nucleotide sequence that is at least 60% identical to SEQ ID NO:1, SEQ ID NO:2, SEQ ID NO:3 or SEQ ID NO:4, wherein sequence identity is determined over the entire length of SEQ ID NO:1, SEQ ID NO:2, SEQ ID NO:3 or SEQ ID NO:4.

In certain embodiments, the invention provides an isolated nucleic acid, wherein the nucleic acid encodes a protein comprising (i) an amino acid sequence to the N protein of a AMPV-2 Yucaipa strain (SEQ ID NO:5); (ii) an amino acid sequence to the P protein of a AMPV-2 Yucaipa strain (SEQ ID NO:6); (iii) an amino acid sequence to the V protein of a AMPV-2 Yucaipa strain (SEQ ID NO:7); (iv) an amino acid sequence to the W protein of a AMPV-2 Yucaipa strain (SEQ ID NO:8); (v) an amino acid sequence to the M protein of a AMPV-2 Yucaipa strain (SEQ ID NO:9); (vi) an amino acid sequence to the F protein of a AMPV-2 Yucaipa strain (SEQ ID NO:10); (vii) an amino acid sequence to the HN protein of a AMPV-2 Yucaipa strain (SEQ ID NO:11); (viii) an amino acid sequence to the L protein of a AMPV-2 Yucaipa strain (SEQ ID NO:12). In certain embodiments, the invention provides an isolated nucleic acid, wherein the nucleic acid encodes a protein comprising (i) an amino acid sequence to the N protein of a AMPV-2 Bangor strain (SEQ ID NO:13); (ii) an amino acid sequence to the P protein of a AMPV-2 Bangor strain (SEQ ID NO:14); (iii) an amino acid sequence to the V protein of a AMPV-2 Bangor strain (SEQ ID NO:15); (iv) an amino acid sequence to the W protein of a AMPV-2 Bangor strain (SEQ ID NO:16); (v) an amino acid sequence to the M protein of a AMPV-2 Bangor strain (SEQ ID NO:17); (vi) an amino acid sequence to the F protein of a AMPV-2 Bangor strain (SEQ ID NO:18); (vii) an amino acid sequence to the HN protein of a AMPV-2 Bangor strain (SEQ ID NO:19); (viii) an amino acid sequence to the L protein of a AMPV-2 Bangor strain (SEQ ID NO:20). In certain embodiments, the invention provides an isolated nucleic acid, wherein the nucleic acid encodes a protein comprising (i) an amino acid sequence to the N protein of a AMPV-2 England strain (SEQ ID NO:21); (ii) an amino acid sequence to the P protein of a AMPV-2 England strain (SEQ ID NO:22); (iii) an amino acid sequence to the V protein of a AMPV-2 England strain (SEQ ID NO:23); (iv) an amino acid sequence to the W protein of a AMPV-2 England strain (SEQ ID NO:24); (v) an amino acid sequence to the M protein of a AMPV-2 England strain (SEQ ID NO:25); (vi) an amino acid sequence to the F protein of a AMPV-2 England strain (SEQ ID NO:26); (vii) an amino acid sequence to the HN protein of a AMPV-2 England strain (SEQ ID NO:27); (viii) an amino acid sequence to the L protein of a AMPV-2 England strain (SEQ ID NO:28). In certain embodiments, the invention provides an isolated nucleic acid, wherein the nucleic acid encodes a protein comprising (i) an amino acid sequence to the N protein of a AMPV-2 Kenya strain (SEQ ID NO:29); (ii) an amino acid sequence to the P protein of a AMPV-2 Kenya strain (SEQ ID NO:30); (iii) an amino acid sequence to the V protein of a AMPV-2 Kenya strain (SEQ ID NO:31); (iv) an amino acid sequence to the W protein of a AMPV-2 Kenya strain (SEQ ID NO:32); (v) an amino acid sequence to the M protein of a AMPV-2 Kenya strain (SEQ ID NO:33); (vi) an amino acid sequence to the F protein of a AMPV-2 Kenya strain (SEQ ID NO:34); (vii) an amino acid sequence to the HN protein of a AMPV-2 Kenya strain (SEQ ID NO:35); (viii) an amino acid sequence to the L protein of a AMPV-2 Kenya strain (SEQ ID NO:36). In certain embodiments, the invention provides an isolated nucleic acid, wherein the nucleic acid hybridizes specifically under high stringency, medium stringency, or low stringency conditions to a nucleic acid of an APMV-2.

In certain embodiments, the invention provides a virus comprising the nucleotide sequence of SEQ ID NO: 1-4 or a fragment thereof.

In certain embodiments, the invention provides an isolated protein, wherein the protein comprises (i) an amino acid sequence to the N protein of a AMPV-2 Yucaipa strain (SEQ ID NO:37); (ii) an amino acid sequence to the P protein of a AMPV-2 Yucaipa strain (SEQ ID NO:38); (iii) an amino acid sequence to the V protein of a AMPV-2 Yucaipa strain (SEQ ID NO:39); (iv) an amino acid sequence to the W protein of a AMPV-2 Yucaipa strain (SEQ ID NO:40); (v) an amino acid sequence to the M protein of a AMPV-2 Yucaipa strain (SEQ ID NO:41); (vi) an amino acid sequence to the F protein of a AMPV-2 Yucaipa strain (SEQ ID NO:42); (vii) an amino acid sequence to the HN protein of a AMPV-2 Yucaipa strain (SEQ ID NO:43); (viii) an amino acid sequence to the L protein of a AMPV-2 Yucaipa strain (SEQ ID NO:44). In certain embodiments, the invention provides an isolated protein, wherein the protein comprises (i) an amino acid sequence to the N protein of a AMPV-2 Bangor strain (SEQ ID NO:45); (ii) an amino acid sequence to the P protein of a AMPV-2 Bangor strain (SEQ ID NO:46); (iii) an amino acid sequence to the V protein of a AMPV-2 Bangor strain (SEQ ID NO:47); (iv) an amino acid sequence to the W protein of a AMPV-2 Bangor strain (SEQ ID NO:48); (v) an amino acid sequence to the M protein of a AMPV-2 Bangor strain (SEQ ID NO:49); (vi) an amino acid sequence to the F protein of a AMPV-2 Bangor strain (SEQ ID NO:50); (vii) an amino acid sequence to the HN protein of a AMPV-2 Bangor strain (SEQ ID NO:51); (viii) an amino acid sequence to the L protein of a' AMPV-2 Bangor strain (SEQ ID NO:52). In certain embodiments, the invention provides an isolated protein, wherein the protein comprises (i) an amino acid sequence to the N protein of a AMPV-2 England strain (SEQ ID NO:53); (ii) an amino acid sequence to the P protein of a AMPV-2 England strain (SEQ ID NO:54); (iii) an amino acid sequence to the V protein of a AMPV-2 England strain (SEQ ID NO:55); (iv) an amino acid sequence to the W protein of a AMPV-2 England strain (SEQ ID NO:56); (v) an amino acid sequence to the M protein of a AMPV-2 England strain (SEQ ID NO:57); (vi) an amino acid sequence to the F protein of a AMPV-2 England strain (SEQ ID NO:58); (vii) an amino acid sequence to the HN protein of a AMPV-2 England strain (SEQ ID NO:59); (viii) an amino acid sequence to the L protein of a AMPV-2 England strain (SEQ ID NO:60). In certain embodiments, the invention provides an isolated protein, wherein the protein comprises (i) an amino acid sequence to the N protein of a AMPV-2 Kenya strain (SEQ ID NO:61); (ii) an amino acid sequence to the P protein of a AMPV-2 Kenya strain (SEQ ID NO:62); (iii) an amino acid sequence to the V protein of a AMPV-2 Kenya strain (SEQ ID NO:63); (iv) an amino acid sequence to the W protein of a AMPV-2 Kenya strain (SEQ ID NO:64); (v) an amino acid sequence to the M protein of a AMPV-2 Kenya strain (SEQ ID NO:65); (vi) an amino acid sequence to the F protein of a AMPV-2 Kenya strain (SEQ ID NO:66); (vii) an amino acid sequence to the HN protein of a AMPV-2 Kenya strain (SEQ ID NO:67); (viii) an amino acid sequence to the L protein of a AMPV-2 Kenya strain (SEQ ID NO:68). In certain embodiments, the invention provides an antibody, wherein the antibody binds specifically to any of the above-mentioned proteins.

In certain embodiments, the invention provides an isolated nucleic acid, wherein the nucleic acid hybridizes specifically under high stringency, medium stringency, or low stringency conditions to a nucleic acid of an APMV-2.

In certain embodiments, the invention provides a method for detecting an APMV-2 in a sample, wherein said method comprises contacting the sample with an antibody specific to said virus or specific to a protein from said virus.

In certain embodiments, the invention provides a method for identifying a viral isolate as a AMPV-2, wherein said method comprises contacting said isolate or a component thereof with the antibody specific to a APMV-2. In certain embodiments, the invention provides method for virologically diagnosing a AMPV-2 infection of a subject comprising determining in a sample of said subject the presence of a viral isolate or component thereof by contacting the sample with the antibody specific to a APMV-2. In certain embodiments, the invention provides a method for virologically diagnosing a APMV-2 infection of a subject, wherein said method comprises obtaining a sample from the subject and contacting the sample with an antibody specific to APMV-2 wherein if the antibody binds to the sample the subject is infected with AMPV-2.

In certain embodiments, the invention provides an infectious recombinant virus, wherein the recombinant virus comprises the genome of an AMPV-2. The recombinant virus optionally further comprises a non-native AMPV-2 sequence. In certain embodiments, the invention provides an infectious chimeric virus, wherein the chimeric virus comprises the genome of an AMPV-2 of a first strain, wherein one or more of the open reading frames, 3'-leader, 5'-trailer, intergenic sequence in the genome of the APMV-2 of the first strain have been replaced by the analogous sequence from an APMV-2 of a second strain. In certain embodiments, the invention provides an infectious chimeric virus, wherein the chimeric virus comprises the genome of a APMV-2 of a first strain, wherein one or more of open reading frames, 3'-leader sequence, 5'-trailer sequence, and/or intergenic sequence of a APMV-2 of a second strain are inserted into the genome of the APMV-2 of the first strain.

In certain embodiments, the invention provides an immunogenic composition, wherein the immunogenic composition comprises the infectious recombinant virus of the invention.

In certain embodiments, the invention provides a method for detecting a AMPV-2 in a sample, wherein the method comprises contacting the sample with a nucleic acid sequence of the invention. In certain embodiments, the invention provides a method for detecting an APMV-2 in a sample, wherein the method comprises amplifying or probing for APMV-2 related nucleic acids, processed products, or derivatives thereof. In a more specific embodiment, the invention provides polymerase chain reaction based methods for the detection of APMV-2 in a sample. In an even further embodiment, the invention provides oligonucleotide probes that can be used to specifically detect the presence of APMV-2 related nucleic acids, processed products, or derivatives thereof. In yet another embodiment, the invention provides diagnostic methods for the detection of APMV-2 antibodies in a host that is infected with the virus.

In certain embodiments, the invention provides a method for identifying a compound useful for the treatment of cancer in a subject, wherein the method comprises: (a) Administering to the subject a test compound comprising AMPV-2 virus or APMV-2 nucleic acid; and (c) determining the effect of the test compound on the cancer of the subject, wherein a test compound that reduces the extent of the cancer or that ameliorates the symptoms associated with the cancer is identified as a compound useful for the treatment of cancer.

In certain embodiments, the treatment comprises APMV-2 nucleic acid only. In certain embodiments, the invention provides a method for identifying a compound useful for the treatment of infections with APMV-2, wherein the method comprises (a) infecting a cell culture with APMV-2 (b) incubating the cell culture with a test compound; and (c) determining the effect of the test compound on the infection of the cell culture, wherein a test compound that reduces the extent of the infection is identified as a compound useful for the treatment of infections with APMV-2. In certain embodiments, the invention provides a method for diagnosing a APMV-2 infection of an animal, wherein the method comprises determining in a sample of said animal the presence of a viral isolate or component thereof by reacting said sample with a nucleic acid or an antibody reactive with a component of an APMV-2, said nucleic acid or antibody being cross-reactive with a component of APMV-2.

BRIEF DESCRIPTION OF THE DRAWINGS

FIG. 1. Plylogenetic tree of representative members of the family Paramyxoviridae. The phylogenetic tree was constructed with the complete genome sequences and using MEGA 4.1, Molecular Evolutionary Genetics Analysis software. The numbers at the node represent the bootstep values among different viruses and the numbers under the lines indicate branch length.

FIG. 2. Generation of full length cDNA clone of APMV-2/Yuc. The full length cDNA clone was constructed by assembling six subgenomic fragments into pBR322/dr/Yuc using a 73-nt long oligonucleotide linker sequence between T7 RNA polymerase promoter sequence and the hepatitis delta ribozyme sequence, which was followed by T7 terminator sequence (between the restriction enzyme sites AscI and RsrII). The ten nt mutations and their positions, that were made to create the unique restriction enzyme sites in the full length, are represented inside boxes under each enzyme.

FIG. 3. Construction of full length plasmids expressing EGFP, with and without kozak sequence. The top panel (A) shows the construction of full length plasmid, pAPMV-2/Yuc/EGFP and the bottom panel (B) shows the construction of pAPMV-2/Yuc/$_{kozak}$EGFP along with their respective EGFP cassettes. The EGFP ORF was inserted as a transcription cassette at the Pme I site (at the putative P gene 5' UTR). This cassette contained the EGFP ORF flanked by a T residue as the 5'UTR, M gene-start (M GS), followed by a T residue as the intergenic sequence (IGS), P gene-end (P GE) and Pme I enzyme site. The EGFP ORF was flanked at the downstream end by another Pme I enzyme site. In the pAPMV-2/Yuc/$_{kozak}$EGFP, the kozak sequence (GCCACC) was inserted before EGFP ORF.

FIG. 4. Comparison of growth kinetics of wild type APMV-2/Yuc and rAPMV-2/Yuc, rAPMV-2/Yuc/EGFP and rAPMV-2/Yuc/$_{kozak}$EGFP. Briefly, DF1 cells in six-well plates were infected in triplicates with wild type APMV-2/Yuc and the recombinant viruses, rAPMV-2/Yuc, rAPMV-2/Yuc/EGFP and rAPMV-2/Yuc/$_{kozak}$EGFP, at an MOI of 1 and samples were collected from the culture supernatant at 24 h interval until 120 h post-infection. Virus titers of the samples were determined by serial end-point dilution in 96-well plates seeded with DF1 cells and immunoperoxidase staining using polyclonal antibody against wild type APMV-2/Yuc, raised in chickens. Virus titres ($TCID_{50}$/ml) were calculated using Reed & Muench method (Reed & Muench, 1938).

DETAILED DESCRIPTION

The invention relates to an isolated genomic sequence of APMV-2, strains, Yucaipa, Bangor, England, and Kenya. However, now that the genomic sequence of these strains has been elucidated, it is within the skill of a person in the art to determine the sequence of other known and not yet known APMV-2 strains. Therefore, the present invention encompasses other known APMV-2 strains, and strains yet to be identified.

The invention relates to genomic nucleotide sequences of different strains of APMV-2, including Yucaipa, Bangor, England and Kenya. The invention relates to the use of the sequence information of different strains for diagnostic and therapeutic methods. The present invention relates to the differences of the genomic nucleotide sequences among the different strains, and their use in the diagnostic and therapeutic methods of the invention. In particular, the invention relates to the use of the differences among different APMV-2 strains for diagnostic and therapeutic methods. The present invention also relates to the use serological characterization of the different strains of APMV-2, alone or in combination with the sequence information of the different isolates, for diagnostic and therapeutic methods.

The present invention relates to nucleotide sequences encoding the genome of a APMV-2 or a portion thereof. The present invention relates to nucleotide sequences encoding gene products of an APMV-2. The present invention further relates to nucleic acids, including DNA and RNA, that encode the genome or a portion thereof of an APMV-2, in addition to a nucleotide sequence which is heterologous or non-native to the viral genome. The invention further encompasses recombinant or chimeric viruses encoded by said nucleotide sequences.

In accordance with the present invention, a recombinant virus is one derived from an APMV-2 that is encoded by endogenous or native genomic sequences or non-native genomic sequences. In accordance with the invention, a non-native sequence is one that is different from the native or endogenous genomic sequence due to one or more mutations, including, but not limited to, point mutations, rearrangements, insertions, deletions etc., of the genomic sequence that may or may not result in a phenotypic change. In accordance with the invention, a chimeric virus is a recombinant APMV-2 which further comprises a heterologous nucleotide sequence. In accordance with the invention, a chimeric virus may be encoded by a nucleotide sequence in which heterologous nucleotide sequences have been added to the genome or in which endogenous or native nucleotide sequences have been replaced with heterologous nucleotide sequences.

The invention further relates to vaccine formulations comprising APMV-2, including recombinant forms of said viruses. In particular, the present invention encompasses vaccine preparations comprising recombinant or chimeric forms of APMV-2 that express antigenic proteins, including proteins of APMV-2. The invention also encompasses vaccine preparations comprising recombinant forms of APMV-2 that encode antigenic sequences of another virus, or a heterologous glycoprotein of another species or strain of APMV-2, or heterologous non-native sequences encoding a desired antigen. The present invention also relates to multivalent vaccines, including bivalent and trivalent vaccines. In particular, the bivalent and trivalent vaccines of the invention encompass two or more antigenic polypeptides expressed by the same or different AMPV-2 vectors encoding desired antigenic proteins from AMPV-2 or another source.

In certain embodiments, a virus can be identified as a APMV-2 by means of sequence homology/identity of the viral proteins or nucleic acids in comparison with the amino acid sequence and nucleotide sequences of the viral isolates disclosed herein by sequence or deposit. In particular, a virus is identified as APMV-2 when the genome of the virus contains a nucleic acid sequence that has a percentage nucleic acid identity of at least 60% to a virus isolate disclosed herein. Without being bound by theory, it is generally known that viral species, especially RNA virus species, often constitute a quasi species wherein the members of a cluster of the viruses display sequence heterogeneity.

In certain embodiments of the invention, sequence homology may be determined by the ability of two sequences to hybridize under certain conditions, as set forth below. A nucleic acid which is hybridizable to a nucleic acid of an APMV-2, or to its reverse complement, or to its complement can be used in the methods of the invention to determine their sequence homology and identities to each other. In certain embodiments, the nucleic acids are hybridized under conditions of high stringency.

It is well known to the skilled artisan that hybridization conditions, such as, but not limited to, temperature, salt concentration, pH, formamide concentration (see, e.g., Sambrook et al., 1989, Chapters 9 to 11, Molecular Cloning, A Laboratory Manual, 2d Ed., Cold Spring Harbor Laboratory Press, Cold Spring Harbor, N.Y., incorporated herein by reference in its entirety). In certain embodiments, hybridization is performed in aqueous solution and the ionic strength of the solution is kept constant while the hybridization temperature is varied dependent on the degree of sequence homology between the sequences that are to be hybridized. For DNA sequences 100% identical to each other and are longer than 200 base pairs, hybridization is carried out at approximately 15-25° C. below the melting temperature (Tm) of the perfect hybrid. The melting temperature (Tm) can be calculated using the following equation (Bolton and McCarthy, 1962, Proc. Natl. Acad. Sci. USA 84:1390): Tm=81.5° C.−16.6 (log 10[Na+])+(% G+C)−0.63(% formamide)−(600/l) Wherein (Tm) is the melting temperature, [Na+] is the sodium concentration, G+C is the Guanine and Cytosine content, and l is the length of the hybrid in basepairs. The effect of mismatches between the sequences can be calculated using the formula by Bonner et al. (Bonner et al., 1973, J. Mol. Biol. 81:123-135): for every 1% of mismatching of bases in the hybrid, the melting temperature is reduced by 1-1.5° C. Thus, by determining the temperature at which two sequences hybridize, one of skill in the art can estimate how similar a sequence is to a known sequence. This can be done, e.g., by comparison of the empirically determined hybridization temperature with the hybridization temperature calculated for the know sequence to hybridize with its perfect match. Through the use of the formula by Bonner et al., the relationship between hybridization temperature and percent mismatch can be exploited to provide information about sequence similarity.

In other embodiments of the invention, hybridization is performed under moderate or low stringency conditions, such conditions are well-known to the skilled artisan (see e.g., Sambrook et al., 1989, Molecular Cloning, A Laboratory Manual, 2d Ed., Cold Spring Harbor Laboratory Press, Cold Spring Harbor, N.Y.; see also, Ausubel et al., eds., in the Current Protocols in Molecular Biology series of laboratory technique manuals, 1987-1997 Current Protocols, COPYRGT. 1994-1997 John Wiley and Sons, Inc., each of which is incorporated by reference herein in their entirety).

In certain embodiments of the invention, the different strains of APMV-2 can be distinguished from each other by way of the amino acid sequences of the different viral proteins. In other embodiments, the different strains of APMV-2 can be distinguished from each other by way of the nucleotide sequences of the different ORFs encoded by the viral genome. The invention also contemplates that a virus may have one or more ORF that are closer related to one strain and one or more ORFs that are closer phylogenetically related to another strain. Such a virus would be classified into the variant to which the majority of its ORFS are closer phylogenetically related. Non-coding sequences may also be used to determine phylogenetic relatedness.

In certain embodiments, the percentage of sequence identity is based on an alignment of the full length proteins. In other embodiments, the percentage of sequence identity is based on an alignment of contiguous amino acid sequences of the proteins, wherein the amino acid sequences can be 25 amino acids, 50 amino acids, 75 amino acids, 100 amino acids, 125 amino acids, 150 amino acids, 175 amino acids, 200 amino acids, 225 amino acids, 250 amino acids, 275 amino acids, 300 amino acids, 325 amino acids, 350 amino acids, 375 amino acids, 400 amino acids, 425 amino acids, 450 amino acids, 475 amino acids, 500 amino acids, 750 amino acids, 1000 amino acids, 1250 amino acids, 1500 amino acids, 1750 amino acids, 2000 amino acids or 2250 amino acids in length.

In certain embodiments, the APMV-2, even though it is capable of infecting an avian host, is also capable of infecting a mammalian host, such as a mammalian cultured cell. In certain embodiments, the APMV-2 is capable of infecting a mammalian host and causing proteins of the APMV-2 to be inserted into the cytoplasmic membrane of the mammalian host. In even other embodiments, the APMV-2 of the invention is capable of infecting a mammalian host and of replicating in the mammalian host. In even other embodiments, the APMV-2 of the invention is capable of infecting a mammalian host and of replicating in the mammalian host, wherein the infection and replication causes the mammalian host to produce and package new infectious APMV-2. APMV-2 is unique among paramyxoviruses in that it does not form syncytia but infects single cells. Single cell infections have several advantages. The infection can be targeted to single cell type without the risk of spreading from cell to cell. Cell fusion usually requires cleavage of the F protein by a host cell protease. If a particular cell type does not have the required protease, then the virus cannot replicate. In single cell infections, there is no cell fusion, therefore, there is no need for packaging. Hence, APMV-2 can be used to infect more cell types.

The present invention encompasses recombinant or chimeric viruses encoded by viral vectors derived from the APMV-2 genomes. In accordance with the present invention a recombinant virus is one derived from a APMV-2 that is encoded by endogenous or native genomic sequences or non-native genomic sequences. In accordance with the invention, a non-native sequence is one that is different from the native or endogenous genomic sequence due to one or more mutations, including, but not limited to, point mutations, rearrangements, insertions, deletions etc., to the genomic sequence that may or may not result in a phenotypic change. The recombinant viruses of the invention encompass those viruses encoded by viral vectors derived from the genomes of APMV-2, and may or may not, include nucleic acids that are non-native to the viral genome. In accordance with the present invention, a viral vector which is derived from the genome of a APMV-2 is one that contains a nucleic acid sequence that encodes at least a part of one ORF of a APMV-2, wherein the polypeptides encoded by the ORF have amino acid sequence identity of at least 55% (See Table 6, titled Percent amino acid percentage identity between APMV-2 strains Yucaipa, Bangor, England and Kenya for the indicated proteins) and chosen from the proteins N, P, M, F, HN, L, and W.

In accordance with the present invention, the recombinant viruses of the invention encompass those viruses encoded by viral vectors derived from the genome of an APMV-2. In particular embodiments of the invention, the viral vector is derived from the genome of an APMV-2 Yucaipa, England, Kenya or Bangor. In accordance with the present invention, these viral vectors may or may not include nucleic acids that are non-native to the viral genome.

In accordance with the invention, a chimeric virus is a recombinant APMV-2 further comprises a heterologous nucleotide sequence. A chimeric virus may be encoded by a nucleotide sequence in which heterologous nucleotide sequences have been added to the genome or in which endogenous or native nucleotide sequences have been replaced with heterologous nucleotide sequences.

In accordance with the present invention, the chimeric virus may be encoded by nucleotide sequences derived from different strains of APMV-2. In particular, the chimeric virus is encoded by nucleotide sequences that encode antigenic polypeptides derived from different strains of APMV-2.

A chimeric virus may be of particular use for the generation of recombinant vaccines protecting against two or more viruses (Tao et al., J. Virol. 72, 2955-2961; Durbin et al., 2000, J. Virol. 74, 6821-6831; Skiadopoulos et al., 1998, J. Virol. 72, 1762-1768; Teng et al., 2000, J. Virol. 74, 9317-9321). For example, it can be envisaged that an APMV-2 virus vector expressing one or more proteins of another RNA virus, e.g., RSV or a RSV vector expressing one or more proteins of APMV-2 will protect subjects vaccinated with such vector against both virus infections. A similar approach can be envisaged for PIV or other paramyxoviruses. Attenuated and replication-defective viruses may be of use for vaccination purposes with live vaccines as has been suggested for other viruses. (See, PCT WO 02/057302, at pp. 6 and 23, incorporated by reference herein).

In accordance with the present invention the heterologous sequence to be incorporated into the viral vectors encoding the recombinant or chimeric viruses of the invention include sequences obtained or derived from different strains of paramyxovirus, strains of avian pneumovirus, and other negative strand RNA viruses, including, but not limited to, RSV, PIV and influenza virus, and other viruses, including morbillivirus.

In certain embodiments of the invention, the chimeric or recombinant viruses of the invention are encoded by viral vectors derived from viral genomes wherein one or more sequences, intergenic regions, termini sequences, or portions or entire ORF have been substituted with a heterologous or non-native sequence.

In a preferred embodiment, the heterologous nucleotide sequence is inserted or added at a lower numbered position of the viral genome, for example, position 1, 2, or 3 of the viral genome. Insertion or addition of nucleic acid sequences at the lower-numbered positions of the viral genome results in stronger or higher levels of expression of the heterologous nucleotide sequence compared to insertion at higher-numbered positions due to a transcriptional gradient across the genome of the virus. Thus, inserting or adding heterologous nucleotide sequences at lower-numbered positions is the preferred embodiment of the invention if high levels of expression of the heterologous nucleotide sequence is desired. Without being bound by theory, the position of insertion or addition of the heterologous sequence affects the replication rate of the recombinant or chimeric virus. Without being bound by theory, the size of the intergenic region between the viral gene and the heterologous sequence further determines rate of replication of the virus and expression levels of the heterologous sequence.

In certain embodiments, the viral vector of the invention contains two or more different heterologous nucleotide sequences.

In accordance with the present invention, the viral vectors can be engineered to provide antigenic sequences which confer protection against infection by a virus. The viral vectors can be engineered to provide antigenic sequences which confer protection against infection or disease by another virus, including negative strand RNA virus, including influenza, RSV or PIV, including PIV3. The viral vectors may be engineered to provide one, two, three or more antigenic sequences. In accordance with the present invention the antigenic sequences may be derived from the same virus, from different strains or variants of the same type of virus, or from different viruses, including morbillivirus.

The expression products and/or recombinant or chimeric virions obtained in accordance with the invention may advantageously be utilized in vaccine formulations. The expression products and chimeric virions of the present invention may be engineered to create vaccines against a broad range of pathogens, including viral and bacterial antigens, tumor antigens, allergen antigens, and auto antigens involved in autoimmune disorders.

In certain embodiments, the expression products and recombinant or chimeric virions of the present invention may be engineered to create vaccines against a broad range of pathogens, including viral antigens, tumor antigens and auto antigens involved in autoimmune disorders. One way to achieve this goal involves modifying existing APMV-2 genes to contain foreign sequences in their respective external domains. Where the heterologous sequences are epitopes or antigens of pathogens, these chimeric viruses may be used to induce a protective immune response against the disease agent from which these determinants are derived.

Thus, the present invention relates to the use of viral vectors and recombinant or chimeric viruses to formulate vaccines against a broad range of viruses and/or antigens. The viral vectors and chimeric viruses of the present invention may be used to modulate a subject's immune system by stimulating a humoral immune response, a cellular immune response or by stimulating tolerance to an antigen. As used herein, a subject means: humans, primates, horses, cows, sheep, pigs, goats, dogs, cats, avian species and rodents.

An illustrative approach for constructing these hybrid molecules is to insert the heterologous nucleotide sequence into a DNA complement of a APMV-2 genome, so that the heterologous sequence is flanked by the viral sequences required for viral polymerase activity; i.e., the viral polymerase binding site/promoter, hereinafter referred to as the viral polymerase binding site, and a polyadenylation site. In a preferred embodiment, the heterologous coding sequence is flanked by the viral sequences that comprise the replication promoters of the 5' and 3' termini, the gene start and gene end sequences, and the packaging signals that are found in the 5' and/or the 3' termini. In an alternative approach, oligonucleotides encoding the viral polymerase binding site, e.g., the complement of the 3'-terminus or both termini of the virus genomic segment can be ligated to the heterologous coding sequence to construct the hybrid molecule. The placement of a foreign gene or segment of a foreign gene within a target sequence was formerly dictated by the presence of appropriate restriction enzyme sites within the target sequence. However, recent advances in molecular biology have lessened this problem greatly. Restriction enzyme sites can readily be placed anywhere within a target sequence through the use of site-directed mutagenesis (e.g., see, for example, the techniques described by Kunkel, 1985, Proc. Natl. Acad. Sci. U.S.A. 82; 488). Variations in polymerase chain reaction (PCR) technology, described infra, also allow for the specific insertion of sequences (i.e., restriction enzyme sites) and allow for the facile construction of hybrid molecules. Alternatively, PCR reactions could be used to prepare recombinant templates without the need of cloning. For example, PCR reactions could be used to prepare double-stranded DNA molecules containing a DNA-directed RNA polymerase promoter (e.g., bacteriophage T3, T7 or SP6) and the hybrid sequence containing the heterologous gene and the PIV polymerase binding site. RNA templates could then be transcribed directly from this recombinant DNA. In yet another embodiment, the recombinant RNA templates may be prepared by ligating RNAs specifying the negative polarity of the heterologous gene and the viral polymerase binding site using an RNA ligase.

In addition, one or more nucleotides can be added in the untranslated region to adhere to the "Rule of Six" which may be important in obtaining virus rescue. The "Rule of Six" applies to many paramyxoviruses and states that the RNA nucleotide genome must be divisible by six to be functional. The addition of nucleotides can be accomplished by techniques known in the art such as using a commercial mutagenesis kits such as the QuikChange mutagenesis kit (Stratagene). After addition of the appropriate number of nucleotides, the correct DNA fragment can then be isolated by digestion with appropriate restriction enzyme and gel purification. Sequence requirements for viral polymerase activity and constructs which may be used in accordance with the invention are described in the subsections below.

Without being bound by theory, several parameters affect the rate of replication of the recombinant virus and the level of expression of the heterologous sequence. In particular, the position of the heterologous sequence in the recombinant virus and the length of the intergenic region that flanks the heterologous sequence determine rate of replication and expression level of the heterologous sequence.

In certain embodiments, the leader and or trailer sequence of the virus are modified relative to the wild type virus. In certain more specific embodiments, the lengths of the leader and/or trailer are altered. In other embodiments, the sequence(s) of the leader and/or trailer are mutated relative to the wild type virus.

The production of a recombinant virus of the invention relies on the replication of a partial or full-length copy of the negative sense viral RNA (vRNA) genome or a complementary copy thereof (cRNA). This vRNA or cRNA can be isolated from infectious virus, produced upon in-vitro transcription, or produced in cells upon transfection of nucleic acids. Second, the production of recombinant negative strand virus relies on a functional polymerase complex. Typically, the polymerase complex of paramyxoviruses consists of N, P, L but is not necessarily limited thereto.

Polymerase complexes or components thereof can be isolated from virus particles, isolated from cells expressing one or more of the components, or produced upon transfection of specific expression vectors.

Infectious copies of APMV-2 can be obtained when the above mentioned vRNA, cRNA, or vectors expressing these RNAs are replicated by the above mentioned polymerase complex (Schnell et al., 1994, EMBO J 13: 4195-4203; Collins, et al., 1995, PNAS 92: 11563-11567; Hoffmann, et al., 2000, PNAS 97: 6108-6113; Bridgen, et al., 1996, PNAS 93: 15400-15404; Palese, et al., 1996, PNAS 93: 11354-11358; Peeters, et al., 1999, J. Virol. 73: 5001-5009; Durbin, et al., 1997, Virology 235: 323-332).

The invention provides a host cell comprising a nucleic acid or a vector according to the invention. Plasmid or viral vectors containing the polymerase components of APMV-2 are generated in prokaryotic cells for the expression of the components in relevant cell types (bacteria, insect cells, eukaryotic cells). Plasmid or viral vectors containing full-length or partial copies of the APMV-2 genome will be generated in prokaryotic cells for the expression of viral nucleic acids in-vitro or in-vivo. The latter vectors may contain other viral sequences for the generation of chimeric viruses or chimeric virus proteins, may lack parts of the viral genome for the generation of replication defective virus, and may contain mutations, deletions or insertions for the generation of attenuated viruses.

Infectious copies of APMV-2 (being wild type, attenuated, replication-defective or chimeric) can be produced upon co-expression of the polymerase components according to the state-of-the-art technologies described above.

In addition, eukaryotic cells, transiently or stably expressing one or more full-length or partial APMV-2 proteins can be used. Such cells can be made by transfection (proteins or nucleic acid vectors), infection (viral vectors) or transduction (viral vectors) and may be useful for complementation of mentioned wild type, attenuated, replication-defective or chimeric viruses.

In accordance with the present invention the viral vectors of the invention may be further engineered to express a heterologous sequence. In an embodiment of the invention, the heterologous sequence is derived from a source other than the viral vector. By way of example, and not by limitation, the heterologous sequence encodes an antigenic protein, polypeptide or peptide of a virus belonging to a different species, subgroup or variant of APMV-2 than the species, subgroup or variant from which the viral vector is derived. By way of example, and not by limitation, the heterologous sequence is not viral in origin. In accordance with this embodiment, the heterologous sequence may encode a moiety, peptide, polypeptide or protein possessing a desired biological property or activity. Such a heterologous sequence may encode a tag or marker. Such a heterologous sequence may encode a biological response modifier, examples of which include, lymphokines, interleukines, granulocyte macrophage colony stimulating factor and granulocyte colony stimulating factor.

In a preferred embodiment, heterologous gene sequences that can be expressed into the recombinant viruses of the invention include but are not limited to antigenic epitopes and glycoproteins of viruses which result in respiratory disease, such as influenza glycoproteins, in particular hemagglutinin H5, H7, respiratory syncytial virus epitopes, New Castle Disease virus epitopes, Sendai virus and infectious Laryngotracheitis virus (ILV). In a preferred embodiment, the heterologous nucleotide sequences are derived from a RSV or Ply. In yet another embodiment of the invention, heterologous gene sequences that can be engineered into the chimeric viruses of the invention include, but are not limited to, viral epitopes and glycoproteins of viruses, such as hepatitis B virus surface antigen, hepatitis A or C virus surface glycoproteins of Epstein Barr virus, glycoproteins of human papilloma virus, simian virus 5 or mumps virus, West Nile virus, Dengue virus, glycoproteins of herpes viruses, VPI of poliovirus, and sequences derived from a lentivirus, preferably, but not limited to human immunodeficiency virus (HIV) type 1 or type 2.

In yet another embodiment, heterologous gene sequences that can be engineered into chimeric viruses of the invention include, but are not limited to, Marek's Disease virus (MDV) epitopes, epitopes of infectious Bursal Disease virus (IBDV), epitopes of Chicken Anemia virus, infectious laryngotracheitis virus (ILV), Avian Influenza virus (AIV), rabies, feline leukemia virus, canine distemper virus, vesicular stomatitis virus, and swinepox virus (see Fields et al., (ed.), 1991, Fundamental Virology, Second Edition, Raven Press, New York, incorporated by reference herein in its entirety).

Other heterologous sequences of the present invention include antigens that are characteristic of autoimmune disease. These antigens will typically be derived from the cell surface, cytoplasm, nucleus, mitochondria and the like of mammalian tissues, including antigens characteristic of diabetes mellitus, multiple sclerosis, systemic lupus erythematosus, rheumatoid arthritis, pernicious anemia, Addison's disease, scleroderma, autoimmune atrophic gastritis, juvenile diabetes, and discoid lupus erythromatosus.

Antigens that are allergens generally include proteins or glycoproteins, including antigens derived from pollens, dust, molds, spores, dander, insects and foods. In addition, antigens that are characteristic of tumor antigens typically will be derived from the cell surface, cytoplasm, nucleus, organelles and the like of cells of tumor tissue. Examples include antigens characteristic of tumor proteins, including proteins encoded by mutated oncogenes; viral proteins associated with tumors; and glycoproteins. Tumors include, but are not limited to, those derived from the types of cancer: lip, nasopharynx, pharynx and oral cavity, esophagus, stomach, colon, rectum, liver, gall bladder, pancreas, larynx, lung and bronchus, melanoma of skin, breast, cervix, uterine, ovary, bladder, kidney, uterus, brain and other parts of the nervous system, thyroid, prostate, testes, Hodgkin's disease, non-Hodgkin's lymphoma, multiple myeloma and leukemia.

In yet another embodiment, heterologous gene sequences that can be engineered into the chimeric viruses include those that encode proteins with immunopotentiating activities. Examples of immunopotentiating proteins include, but are not limited to, cytokines, interferon type 1, gamma interferon, colony stimulating factors, and interleukin-1, -2, -4, -5, -6, -12.

In addition, other heterologous gene sequences that may be engineered into the chimeric viruses include antigens derived from bacteria such as bacterial surface glycoproteins, antigens derived from fungi, and antigens derived from a variety of other pathogens and parasites. Examples of heterologous gene sequences derived from bacterial pathogens include, but are not limited to, antigens derived from species of the following genera: *Salmonella, Shigella, Chlamydia, Helicobacter, Yersinia, Bordatella, Pseudomonas, Neisseria, Vibrio, Haemophilus, Mycoplasma, Streptomyces, Treponema, Coxiella, Ehrlichia, Brucella, Streptobacillus, Fusospirocheta, Spirillum, Ureaplasma, Spirochaeta, Mycoplasma, Actinomycetes, Borrelia, Bacteroides, Trichomoras, Branhamella, Pasteurella, Clostridium, Corynebacterium, Listeria, Bacillus, Erysipelothrix, Rhodococcus, Escherichia, Klebsiella, Pseudomanas, Enterobacter, Serratia, Staphylococcus, Streptococcus, Legionella, Mycobacterium, Proteus, Campylobacter, Enterococcus, Acinetobacter, Morganella, Moraxella, Citrobacter, Rickettsia, Rochlimeae*, as well as bacterial species such as: *P. aeruginosa; E. coli, P. cepacia, S. epidermis, E. faecalis, S. pneumonias, S. aureus, N. meningitidis, S. pyogenes, Pasteurella multocida, Treponema pallidum*, and *P. mirabilis.*

Examples of heterologous gene sequences derived from pathogenic fungi, include, but are not limited to, antigens derived from fungi such as *Cryptococcus neoformans; Blastomyces dermatitidis; Aiellomyces dermatitidis; Histoplasma capsulatum; Coccidioides immitis; Candida* species, including *C. albicans, C. tropicalis, C. parapsilosis, C. guilliermondii* and *C. krusei, Aspergillus* species, including *A. fumigatus, A. flavus* and *A. niger, Rhizopus* species; *Rhizomucor* species; *Cunninghammella* species; *Apophysomyces* species, including *A. saksenaea, A. mucor* and *A. absidia; Sporothrix schenckii, Paracoccidioides brasiliensis; Pseudallescheria boydii, Torulopsis glabrata; Trichophyton* species, *Microsporum* species and *Dermatophyres* species, as well as any other yeast or fungus now known or later identified to be pathogenic.

Finally, examples of heterologous gene sequences derived from parasites include, but are not limited to, antigens derived from members of the Apicomplexa phylum such as, for example, *Babesia, Toxoplasma, Plasmodium, Eimeria, Isospora, Atoxoplasma, Cystoisospora, Hammondia, Besniotia, Sarcocystis, Frenkelia, Haemoproteus, Leucocytozoon, Theileria, Perkinsus* and *Gregarina* spp.; *Pneumocystis carinii*; members of the Microspora phylum such as, for example, *Nosema, Enterocytozoon, Encephalitozoon, Septata, Mrazekia, Amblyospora, Ameson, Glugea, Pleistophora* and *Microsporidium* spp.; and members of the Ascetospora phylum such as, for example, *Haplosporidium* spp., as well as species including *Plasmodium falciparum, P. vivax, P. ovale, P. malaria; Toxoplasma gondii; Leishmania mexicana, L. tropica, L. major, L. aethiopica, L. donovani, Trypanosoma cruzi, T brucei, Schistosoma mansoni, S. haematobium, S. japonium; Trichinella spiralis; Wuchereria bancrofti; Brugia malayli; Entamoeba histolytica; Enterobius vermiculoarus; Taenia solium, T. saginata, Trichomonas vaginatis, T. hominis, T. tenax; Giardia lamblia; Cryptosporidium parvum; Pneumocytis carinii, Babesia bovis, B. divergens, B. microti, Isospora belli, L hominis; Dientamoeba fragilis; Onchocerca volvulus; Ascaris lumbricoides; Necator americanis; Ancylostoma duodenale; Strongyloides stercoralis; Capillaria philippinensis; Angiostrongylus cantonensis; Hymenolepis nana; Diphyllobothrium latum; Echinococcus granulosus, E. multilocularis; Paragonimus westermani, P. caliensis; Chlonorchis sinensis; Opisthorchis felineas, G. Viverini, Fasciola hepatica, Sarcoptes scabiei, Pediculus humanus; Phthirlus pubis*; and *Dermatobia hominis*, as well as any other parasite now known or later identified to be pathogenic.

Insertion of a foreign gene sequence into a viral vector of the invention can be accomplished by either a complete replacement of a viral coding region with a heterologous sequence or by a partial replacement or by adding the heterologous nucleotide sequence to the viral genome. Complete replacement would probably best be accomplished through the use of PCR-directed mutagenesis.

When inserting a heterologous nucleotide sequence into the virus of the invention, the intergenic region between the end of the coding sequence of the heterologous gene and the start of the coding sequence of the downstream gene can be altered to achieve a desired effect. As used herein, the term "intergenic region" refers to nucleotide sequence between the stop signal of one gene and the start codon (e.g., AUG) of the coding sequence of the next downstream open reading frame. An intergenic region may comprise a non-coding region of a gene, i.e., between the transcription start site and the start of the coding sequence (AUG) of the gene. This non-coding region occurs naturally in some viral genes. In various embodiments, the intergenic region between the heterologous nucleotide sequence and the downstream gene can be engineered, independently from each other, to be at least from 10 to at least 200 nt in length. Depending on the purpose (e.g., to have strong immunogenicity) of the inserted heterologous nucleotide sequence, the position of the insertion and the length of the intergenic region of the inserted heterologous nucleotide sequence can be determined by various indexes including, but not limited to, replication kinetics and protein or mRNA expression levels, measured by following non-limiting examples of assays: plaque assay, fluorescent-focus assay, infectious center assay, transformation assay, endpoint dilution assay, efficiency of plating, electron microscopy, hemagglutination, measurement of viral enzyme activity, viral neutralization, hemagglutination inhibition, complement fixation, immunostaining, immunoprecipitation and immunoblotting, enzyme-linked immunosorbent assay, nucleic acid detection (e.g., Southern blot analysis, Northern blot analysis, Western blot analysis), growth curve, employment of a reporter gene (e.g., using a reporter gene, such as Green Fluorescence Protein (GFP) or enhanced Green Fluorescence Protein (eGFP), integrated to the viral genome the same fashion as the interested heterologous gene to observe the protein expression), or a combination thereof. Procedures of performing these assays are well known in the art (see, e.g., Flint et al., PRINCIPLES OF VIROLOGY, MOLECULAR BIOLOGY, PATHOGENESIS, AND CONTROL, 2000, ASM Press pp 25-56, the entire text is incorporated herein by reference), and non-limiting examples are given in the Example sections, infra.

For example, expression levels can be determined by infecting cells in culture with a virus of the invention and subsequently measuring the level of protein expression by, e.g., Western blot analysis or ELISA using antibodies specific to the gene product of the heterologous sequence, or measuring the level of RNA expression by, e.g., Northern blot analysis using probes specific to the heterologous sequence. Similarly, expression levels of the heterologous sequence can be determined by infecting an animal model and measuring the level of protein expressed from the heterologous sequence of the recombinant virus of the invention in the animal model. The protein level can be measured by obtaining a tissue sample from the infected animal and then subjecting the tissue sample to Western blot analysis or ELISA, using antibodies specific to the gene product of the heterologous sequence. Further, if an animal model is used, the titer of antibodies produced by the animal against the gene product of the heterologous sequence can be determined by any technique known to the skilled artisan, including but not limited to, ELISA.

In certain embodiments, to facilitate the identification of the optimal position of the heterologous sequence in the viral genome and the optimal length of the intergenic region, the heterologous sequence encodes a reporter gene. Once the optimal parameters are determined, the reporter gene is replaced by a heterologous nucleotide sequence encoding an antigen of choice. Any reporter gene known to the skilled artisan can be used with the methods of the invention.

Other hybrid constructions may be made to express proteins on the cell surface or enable them to be released from the cell.

Bicistronic mRNA could be constructed to permit internal initiation of translation of viral sequences and allow for the expression of foreign protein coding sequences from the regular terminal initiation site. Alternatively, a bicistronic mRNA sequence may be constructed wherein the viral sequence is translated from the regular terminal open reading frame, while the foreign sequence is initiated from an internal site. Certain internal ribosome entry site (IRES) sequences may be utilized. The IRES sequences which are chosen should be short enough to not interfere with MPV packaging limitations. Thus, it is preferable that the IRES chosen for such a bicistronic approach be no more than 500 nucleotides in length. In a specific embodiment, the IRES is derived from a picornavirus and does not include any additional picornaviral sequences. Specific IRES elements include, but are not limited to the mammalian BiP IRES and the hepatitis C virus IRES.

Alternatively, a foreign protein may be expressed from a new internal transcriptional unit in which the transcriptional unit has an initiation site and polyadenylation site. In another embodiment, the foreign gene is inserted into a MPV gene such that the resulting expressed protein is a fusion protein.

The viral vectors and recombinant templates prepared as described above can be used in a variety of ways to express the heterologous gene products in appropriate host cells or to create chimeric viruses that express the heterologous gene products. In one embodiment, the recombinant cDNA can be used to transfect appropriate host cells and the resulting RNA may direct the expression of the heterologous gene product at high levels. Host cell systems which provide for high levels of expression include continuous cell lines that supply viral functions such as cell lines superinfected with AMPV-2, or cell lines engineered to complement AMPV-2 functions, etc.

In an alternate embodiment of the invention, the recombinant templates may be used to transfect cell lines that express a viral polymerase protein in order to achieve expression of the heterologous gene product. To this end, transformed cell lines that express a polymerase protein such as the L protein may be utilized as appropriate host cells. Host cells may be similarly engineered to provide other viral functions or additional functions.

In another embodiment, a helper virus may provide the RNA polymerase protein utilized by the cells in order to achieve expression of the heterologous gene product. In yet another embodiment, cells may be transfected with vectors encoding viral proteins such as the N, P, L proteins.

In order to prepare the chimeric and recombinant viruses of the invention, a cDNA encoding the genome of a recombinant or chimeric virus of the invention in the plus or minus sense may be used to transfect cells which provide viral proteins and functions required for replication and rescue. Alternatively, cells may be transfected with helper virus before, during, or after transfection by the DNA or RNA molecule coding for the recombinant virus of the invention. The synthetic recombinant plasmid DNAs and RNAs of the invention can be replicated and rescued into infectious virus particles by any number of techniques known in the art, as described, e.g., in U.S. Pat. No. 5,166,057 issued Nov. 24, 1992; in U.S. Pat. No. 5,854,037 issued Dec. 29, 1998; in European Patent Publication EP 0702085A1, published Feb. 20, 1996; in U.S. patent application Ser. No. 09/152,845; in International Patent Publications PCT WO97/12032 published Apr. 3, 1997; WO96/34625 published Nov. 7, 1996; in European Patent Publication EP-A780475; WO 99/02657 published Jan. 21, 1999; WO 98/53078 published Nov. 26, 1998; WO 98/02530 published Jan. 22, 1998; WO 99/15672 published Apr. 1, 1999; WO 98/13501 published Apr. 2, 1998; WO 97/06270 published Feb. 20, 1997; and EPO 780 47SA1 published Jun. 25, 1997, each of which is incorporated by reference herein in its entirety.

In one embodiment, of the present invention, synthetic recombinant viral RNAs may be prepared that contain the non-coding regions (leader and trailer) of the negative strand virus RNA which are essential for the recognition by viral polymerases and for packaging signals necessary to generate a mature virion. There are a number of different approaches which may be used to apply the reverse genetics approach to rescue negative strand RNA viruses. First, the recombinant RNAs are synthesized from a recombinant DNA template and reconstituted in vitro with purified viral polymerase complex to form recombinant ribonucleoproteins (RNPs) which can be used to transfect cells. In another approach, a more efficient transfection is achieved if the viral polymerase proteins are present during transcription of the synthetic RNAs either in vitro or in vivo. With this approach the synthetic RNAs may be transcribed from cDNA plasmids which are either co-transcribed in vitro with cDNA plasmids encoding the polymerase proteins, or transcribed in vivo in the presence of polymerase proteins, i.e., in cells which transiently or constitutively express the polymerase proteins.

In accordance with the present invention, any technique known to those of skill in the art may be used to achieve replication and rescue of recombinant and chimeric viruses.

It should be noted that it may be possible to construct a recombinant virus without altering virus viability. These altered viruses would then be growth competent and would not need helper functions to replicate.

In order to recombinantly generate viruses in accordance with the methods of the invention, the genetic material encoding the viral genome must be transcribed (transcription step). This step can be accomplished either in vitro (outside the host cell) or in vivo (in a host cell). The viral genome can be transcribed from the genetic material to generate either a positive sense copy of the viral genome (antigenome copy) or a negative sense copy of the viral genome (genomic copy). The next step requires replication of the viral genome and packaging of the replicated genome into viral particles (replication and packaging step). This step occurs intracellularly in a host cell which has been engineered to provide sufficient levels of viral polymerase and structural proteins necessary for viral replication and packaging.

When the transcription step occurs in vitro, it is followed by intracellular replication and packaging of the viral genome. When the transcription step occurs in vivo, transcription of the viral genome can occur prior to, concurrently or subsequently to expression of the viral genetic material encoding the viral genome can be obtained or generated from a variety of sources and using a variety of methods known to one skilled in the art. The genetic material may be isolated from the virus itself. For example, a complex of the viral RNA genome and the polymerase proteins, ribonucleoprotein complexes (RNP), may be isolated from whole virus. The viral RNA genome is then stripped of the associated proteins, e.g., viral RNA polymerase and nuclear proteins.

The genetic material encoding the viral genome can be generated using standard recombinant techniques. The genetic material may encode the full length viral genome or a portion thereof. Alternatively, the genetic material may code for a heterologous sequence flanked by the leader and/or trailer sequences of the viral genome. A full-length viral genome can be assembled from several smaller PCR fragments using techniques known in the art. The restriction sites can be used to assemble the full-length construct. In certain embodiments, PCR primers are designed such that the fragment resulting from the PCR reaction has a restriction site close to its 5' end and a restriction site close to it 3' end. The PCR product can then be digested with the respective restriction enzymes and subsequently ligated to the neighboring PCR fragments.

In order to achieve replication and packaging of the viral genome, it is important that the leader and trailer sequences retain the signals necessary for viral polymerase recognition. The leader and trailer sequences for the viral RNA genome can be optimized or varied to improve and enhance viral replication and rescue. Alternatively, the leader and trailer sequences can be modified to decrease the efficiency of viral replication and packaging, resulting in a rescued virus with an attenuated phenotype. Examples of different leader and trailer sequences, include, but are not limited to, leader and trailer sequences of a paramyxovirus. In yet another embodiment of the invention, the leader and trailer sequence is that of a combination of different virus origins. By way of example and not meant to limit the possible combination, the leader and trailer sequence can be a combination of any of the leader and trailer sequences of any strain of APMV-2 described herein. Examples of modifications to the leader and trailer sequences include varying the spacing relative to the viral promoter, varying the sequence, e.g., varying the number of G residues (typically 0 to 3), and defining the 5' or 3' end using ribozyme sequences, including, Hepatitis Delta Virus (HDV) ribozyme sequence, Hammerhead ribozyme sequences, or fragments thereof, which retain the ribozyme catalytic activity, and using restriction enzymes for run-off RNA produced in vitro.

In an alternative embodiment, the efficiency of viral replication and rescue may be enhanced if the viral genome is of hexamer length. In order to ensure that the viral genome is of the appropriate length, the 5' or 3' end may be defined using ribozyme sequences, including, Hepatitis Delta Virus (HDV) ribozyme sequence, Hammerhead ribozyme sequences, or fragments thereof, which retain the ribozyme catalytic activity, and using restriction enzymes for run-off RNA produced in vitro.

In order for the genetic material encoding the viral genome to be transcribed, the genetic material is engineered to be placed under the control of appropriate transcriptional regulatory sequences, e.g., promoter sequences recognized by a polymerase. In preferred embodiments, the promoter sequences are recognized by a T7, Sp6 or T3 polymerase. In yet another embodiment, the promoter sequences are recognized by cellular DNA dependent RNA polymerases, such as RNA polymerase I (Pol I) or RNA polymerase II (Pol II). The genetic material encoding the viral genome may be placed under the control of the transcriptional regulatory sequences, so that either a positive or negative strand copy of the viral genome is transcribed. The genetic material encoding the viral genome is recombinantly engineered to be operatively linked to the transcriptional regulatory sequences in the context of an expression vector, such as a plasmid based vector, e.g. a plasmid with a pol II promoter such as the immediate early promoter of CMV, a plasmid with a T7 promoter, or a viral based vector, e.g., pox viral vectors, including vaccinia vectors, MVA-T7, and Fowl pox vectors.

Replication and packaging of the viral genome occurs intracellularly in a host cell permissive for viral replication and packaging.

Host cells that are permissive for APMV-2 viral replication and packaging are preferred. Examples of preferred host cells include, but are not limited to, DF1, chicken embryo fibroblast, 293T, Vero, tMK, and BHK. Other examples of host cells include, but are not limited to, LLC-MK-2 cells, Hep-2 cells, LF 1043 (HEL) cells, LLC-MK2, HUT 292, FRHL-2 (rhesus), FCL-1 (green monkey), WI-38 (human), MRC-5 (human) cells, QT 6 cells, QT 35 cells and CEF cells.

In certain embodiments, conditions for the propagation of virus are optimized in order to produce a robust and high-yielding cell culture (which would be beneficial, e.g., for manufacture the virus vaccine candidates of the invention). Critical parameters can be identified, and the production process can be first optimized in small-scale experiments to determine the scalability, robustness, and reproducibility and subsequently adapted to large scale production of virus. In certain embodiments, the virus that is propagated using the methods of the invention is a recombinant or a chimeric APMV-2.

The viral constructs and methods of the present invention can be used for commercial production of viruses, e.g., for vaccine production. For commercial production of a vaccine, it is preferred that the vaccine contains only inactivated viruses or viral proteins that are completely free of infectious virus or contaminating viral nucleic acid, or alternatively, contains live attenuated vaccines that do not revert to virulence. Contamination of vaccines with adventitious agents introduced during production should also be avoided. Methods known in the art for large scale production of viruses or viral proteins can be used for commercial production of a vaccine of the invention. In one embodiment, for commercial production of a vaccine of the invention, cells are cultured in a bioreactor or fermenter. Bioreactors are available in volumes from under 1 liter to in excess of 100 liters, e.g., Cyto3 Bioreactor (Osmonics, Minnetonka, Minn.); NBS bioreactors (New Brunswick Scientific, Edison, N.J.); and laboratory and commercial scale bioreactors from B. Braun Biotech International (B. Braun Biotech, Melsungen, Germany). In another embodiment, small-scale process optimization studies are performed before the commercial production of the virus, and the optimized conditions are selected and used for the commercial production of the virus.

The recombinant viruses of the invention can be further genetically engineered to exhibit an attenuated phenotype. In particular, the recombinant viruses of the invention exhibit an attenuated phenotype in a subject to which the virus is administered as a vaccine. Attenuation can be achieved by any method known to a skilled artisan. Without being bound by theory, the attenuated phenotype of the recombinant virus can be caused, e.g., by using a virus that naturally does not replicate well in an intended host (e.g., using an APV in human), by reduced replication of the viral genome, by reduced ability of the virus to infect a host cell, or by reduced ability of the viral proteins to assemble to an infectious viral particle relative to the wild type strain of the virus.

The attenuated phenotypes of a recombinant virus of the invention can be tested by any method known to the artisan. A candidate virus can, for example, be tested for its ability to infect a host or for the rate of replication in a cell culture system. In certain embodiments, growth curves at different temperatures are used to test the attenuated phenotype of the virus. For example, an attenuated virus is able to grow at 35° C., but not at 39° C. or 40° C. In certain embodiments, different cell lines can be used to evaluate the attenuated phenotype of the virus. For example, an attenuated virus may only be able to grow in monkey cell lines but not the human cell lines, or the achievable virus titers in different cell lines are different for the attenuated virus. In certain embodiments, viral replication in the respiratory tract of a small animal model, including but not limited to, hamsters, cotton rats, mice and guinea pigs, is used to evaluate the attenuated phenotypes of the virus. In other embodiments, the immune response induced by the virus, including but not limited to, the antibody titers (e.g., assayed by plaque reduction neutralization assay or ELISA) is used to evaluate the attenuated phenotypes of the virus. In a specific embodiment, the plaque reduction neutralization assay or ELISA is carried out at a low dose. In certain embodiments, the ability of the recombinant virus to elicit pathological symptoms in an animal model can be tested. A reduced ability of the virus to elicit pathological symptoms in an animal model system is indicative of its attenuated phenotype. In a specific embodiment, the candidate viruses are tested in a monkey model for nasal infection, indicated by mucous production.

The viruses of the invention can be attenuated such that one or more of the functional characteristics of the virus are impaired. In certain embodiments, attenuation is measured in comparison to the wild type strain of the virus from which the attenuated virus is derived. In other embodiments, attenuation is determined by comparing the growth of an attenuated virus in different host systems.

In certain embodiments, the attenuated virus of the invention is capable of infecting a host, is capable of replicating in a host such that infectious viral particles are produced. In comparison to the wild type strain, however, the attenuated strain grows to lower titers or grows more slowly. Any technique known to the skilled artisan can be used to determine the growth curve of the attenuated virus and compare it to the growth curve of the wild type virus.

In certain embodiments, the attenuated virus of the invention (e.g., a chimeric APMV-2) cannot replicate in human cells as well as the wild type virus (e.g., wild type APMV-2) does. However, the attenuated virus can replicate well in a cell line that lack interferon functions, such as Vero cells.

In other embodiments, the attenuated virus of the invention is capable of infecting a host, of replicating in the host, and of causing proteins of the virus of the invention to be inserted into the cytoplasmic membrane, but the attenuated virus does not cause the host to produce new infectious viral particles. In certain embodiments, the attenuated virus infects the host, replicates in the host, and causes viral proteins to be inserted in the cytoplasmic membrane of the host with the same efficiency as the wild type virus. In other embodiments, the ability of the attenuated virus to cause viral proteins to be inserted into the cytoplasmic membrane into the host cell is reduced compared to the wild type virus. In certain embodiments, the ability of the attenuated virus to replicate in the host is reduced compared to the wild type virus. Any technique known to the skilled artisan can be used to determine whether a virus is capable of infecting a mammalian cell, of replicating within the host, and of causing viral proteins to be inserted into the cytoplasmic membrane of the host. In certain embodiments, the attenuated virus can infect a host and can cause the host to insert viral proteins in its cytoplasmic membranes, but the attenuated virus is incapable of being replicated in the host.

In certain embodiments, mutations (e.g., missense mutations) are introduced into the genome of the virus to generate a virus with an attenuated phenotype. Mutations (e.g., missense mutations) can be introduced into a gene of the recombinant virus. Mutations can be additions, substitutions, deletions, or combinations thereof. In specific embodiments, a single amino acid deletion mutation for any of the virus proteins is introduced, which can be screened for functionality in a mini-genome assay system and be evaluated for predicted functionality in the virus. In yet another embodiment, the cleavage site of the F gene, or the amino acids spanning the F protein cleavage site and adjacent upstream end of the F1 subunit, is mutated in such a way that cleavage does not occur or occurs at very low efficiency. A mutation can be, but is not limited to, a deletion of one or more amino acids, an addition of one or more amino acids, a substitution (conserved or non-conserved) of one or more amino acids or a combination thereof.

In certain embodiments, the intergenic region of the recombinant virus is altered. In one embodiment, the length of the intergenic region is altered. In another embodiment, the intergenic regions are shuffled from 5' to 3' end of the viral genome. In other embodiments, the genome position of a gene or genes of the recombinant virus is changed.

In certain embodiments, attenuation of the virus is achieved by replacing a gene of the wild type virus with the analogous gene of a virus of a different species (e.g., of RSV, PIV3 or mouse pneumovirus), of a different subgroup, or of a different variant. In certain embodiments, attenuation of the virus is achieved by replacing one or more specific domains of a protein of the wild type virus with domains derived from the corresponding protein of a virus of a different species. In certain other embodiments, attenuation of the virus is achieved by deleting one or more specific domains of a protein of the wild type virus. In a specific embodiment, the transmembrane domain of the F-protein is deleted.

In certain embodiments of the invention, the leader and/or trailer sequence of the recombinant virus of the invention can be modified or mutated to achieve an attenuated phenotype. In certain embodiments of the invention, the leader and/or trailer sequence of the recombinant virus of the invention can be replaced with the leader and/or trailer sequence of a another virus, e.g., with the leader and/or trailer sequence of RSV, PIV3, mouse pneumovirus, or with the leader and/or trailer sequence of a APMV-2 of a subgroup or variant different from the AMPV-2 from which the protein-encoding parts of the recombinant virus are derived.

When a live attenuated vaccine is used, its safety must also be considered. The vaccine must not cause disease. Any techniques known in the art that can make a vaccine safe may be used in the present invention. In addition to attenuation techniques, other techniques may be used. One non-limiting example is to use a soluble heterologous gene that cannot be incorporated into the virion membrane.

In other embodiments, small single amino acid deletions are introduced in genes involved in virus replication to generate an attenuated virus. In more specific embodiments, a small single amino acid deletion is introduced in the N, L, or the P gene. A mutation can be, e.g., a deletion or a substitution of an amino acid. An amino acid substitution can be a conserved amino acid substitution or a non-conserved amino acid substitution. Illustrative examples for conserved amino acid exchanges are amino acid substitutions that maintain structural and/or functional properties of the amino acids' side-chains, e.g., an aromatic amino acid is substituted for another aromatic amino acid, an acidic amino acid is substituted for another acidic amino acid, a basic amino acid is substituted for another basic amino acid, and an aliphatic amino acid is substituted for another aliphatic amino acid. In contrast, examples of non-conserved amino acid exchanges are amino acid substitutions that do not maintain structural and/or functional properties of the amino acids' side-chains, e.g., an aromatic amino acid is substituted for a basic, acidic, or aliphatic amino acid, an acidic amino acid is substituted for an aromatic, basic, or aliphatic amino acid, a basic amino acid is substituted for an acidic, aromatic or aliphatic amino acid, and an aliphatic amino acid is substituted for an aromatic, acidic or basic amino acid.

In certain embodiments, one nucleic acid is substituted to encode one amino acid exchange. In other embodiments, two or three nucleic acids are substituted to encode one amino acid exchange. It is preferred that two or three nucleic acids are substituted to reduce the risk of reversion to the wild type protein sequence.

In even other embodiments, the gene order in the genome of the virus is changed from the gene order of the wild type virus to generate an attenuated virus. In other embodiments, one or more gene start sites are mutated or substituted with the analogous gene start sites of another virus (e.g., RSV, PIV3, or mouse pneumovirus) or of a APMV-2 of a subgroup or a variant different from the APMV-2 from which the protein-encoding parts of the recombinant virus are derived.

In certain embodiments of the invention, attenuation is achieved by replacing one or more of the genes of a virus with the analogous gene of a different virus, different strain, or different viral isolate. In certain embodiments, one or more regions of the genome of a virus is/are replaced with the analogous region(s) from the genome of a different viral species, strain or isolate. In certain embodiments, the region is a region in a coding region of the viral genome. In other embodiments, the region is a region in a non-coding region of the viral genome. In certain embodiments, two regions of two viruses are analogous to each other if the two regions support the same or a similar function in the two viruses. In certain other embodiments, two regions of two viruses are analogous if the two regions provide the same of a similar structural element in the two viruses. In more specific embodiments, two regions are analogous if they encode analogous protein domains in the two viruses, wherein analogous protein domains are domains that have the same or a similar function and/or structure.

In certain embodiments, the region is at least 5 nucleotides (nt) in length, at least 10 nt, at least 25 nt, at least 50 nt, at least 75 nt, at least 100 nt, at least 250 nt, at least 500 nt, at least 750 nt, at least 1 kb, at least 1.5 kb, at least 2 kb, at least 2.5 kb, at least 3 kb, at least 4 kb, or at least 5 kb in length. In certain embodiments, the region is at most 5 nucleotides (nt) in length, at most 10 nt, at most 25 nt, at most 50 nt, at most 75 nt, at most 100 nt, at most 250 nt, at most 500 nt, at most 750 nt, at most I kb, at most 1.5 kb, at most 2 kb, at most 2.5 kb, at most 3 kb, at most 4 kb, or at most 5 kb in length.

A number of assays may be employed in accordance with the present invention in order to determine the rate of growth of a chimeric or recombinant virus in a cell culture system, an animal model system or in a subject. A number of assays may also be employed in accordance with the present invention in order to determine the requirements of the chimeric and recombinant viruses to achieve infection, replication and packaging of virions.

The assays described herein may be used to assay viral titre over time to determine the growth characteristics of the virus. In a specific embodiment, the viral titre is determined by obtaining a sample from the infected cells or the infected subject, preparing a serial dilution of the sample and infecting a monolayer of cells that are susceptible to infection with the virus at a dilution of the virus that allows for the titre count to be made. Normally, viral plaques are counted, but since APMV-2 does not form plaques, titre can be made, for example as described in the Examples below, by counting immunofluorescence foci formed after immunofluorescence assay or counting particles by immunoperoxidase staining of positive cells. Other methods known to a person with skill in the art can also be used. In a specific embodiment of the invention, the growth rate of a virus of the invention in a subject is estimated by the titer of antibodies against the virus in the subject. Without being bound by theory, the antibody titer in the subject reflects not only the viral titer in the subject but also the antigenicity. If the antigenicity of the virus is constant, the increase of the antibody titer in the subject can be used to determine the growth curve of the virus in the subject. In a preferred embodiment, the growth rate of the virus in animals or humans is best tested by sampling biological fluids of a host at multiple time points post-infection and measuring viral titer.

The expression of heterologous gene sequence in a cell culture system or in a subject can be determined by any technique known to the skilled artisan. In certain embodiments, the expression of the heterologous gene is measured by quantifying the level of the transcript. The level of the transcript can be measured by Northern blot analysis or by RT-PCR using probes or primers, respectively, that are specific for the transcript. The transcript can be distinguished from the genome of the virus because the virus is in the antisense orientation whereas the transcript is in the sense orientation. In certain embodiments, the expression of the heterologous gene is measured by quantifying the level of the protein product of the heterologous gene. The level of the protein can be measured by Western blot analysis using antibodies that are specific to the protein.

In a specific embodiment, the heterologous gene is tagged with a peptide tag. The peptide tag can be detected using antibodies against the peptide tag. The level of peptide tag detected is representative for the level of protein expressed from the heterologous gene. Alternatively, the protein expressed from the heterologous gene can be isolated by virtue of the peptide tag. The amount of the purified protein correlates with the expression level of the heterologous gene. Such peptide tags and methods for the isolation of proteins fused to such a peptide tag are well known in the art. A variety of peptide tags known in the art may be used in the modification of the heterologous gene, such as, but not limited to, the immunoglobulin constant regions, polyhistidine sequence (Petty, 1996, Metal-chelate affinity chromatography, in Current Protocols in Molecular Biology, volume 1-3 (1994-1998). Ed. by Ausubel, F. M., Brent, R., Kunston, R. E., Moore, D. D., Seidman, J. G., Smith, J. A. and Struhl, K. Published by John Wiley and sons, Inc., USA, Greene Publish. Assoc. & Wiley Interscience), glutathione S-transferase (GST; Smith, 1993, Methods Mol. Cell Bio. 4:220-229), the *E. coli* maltose binding protein (Guan et al., 1987, Gene 67:21-30), various cellulose binding domains (U.S. Pat. Nos. 5,496,934; 5,202,247; 5,137,819; Tomme et al., 1994, Protein Eng. 7:117-123), and the FLAG epitope (Short Protocols in Molecular Biology, 1999, Ed. Ausubel et al., John Wiley & Sons, Inc., Unit 10.11) etc. Other peptide tags are recognized by specific binding partners and thus facilitate isolation by affinity binding to the binding partner, which is preferably immobilized and/or on a solid support. As will be appreciated by those skilled in the art, many methods can be used to obtain the coding region of the above-mentioned peptide tags, including but not limited to, DNA cloning, DNA amplification, and synthetic methods. Some of the peptide tags and reagents for their detection and isolation are available commercially.

Samples from a subject can be obtained by any method known to the skilled artisan. In certain embodiments, the sample consists of nasal aspirate, throat swab, sputum or broncho-alveolar lavage.

Techniques for practicing the specific aspect of this invention will employ, unless otherwise indicated, conventional techniques of molecular biology, microbiology, and recombinant DNA manipulation and production, which are routinely practiced by one of skill in the art. See, e.g., Sambrook et al., Molecular cloning, a laboratory manual, second ed., vol. 1-3. (Cold Spring Harbor Laboratory, 1989), A Laboratory Manual, Second Edition; DNA Cloning, Volumes I and II (Glover, Ed. 1985); and Transcription and Translation (Hames & Higgins, Eds. 1984). Western blot analysis or Northern blot analysis or any other technique used for the quantification of transcription of a nucleotide sequence, the abundance of its mRNA its protein (see Short Protocols in Molecular Biology, Ausubel et al., (editors), John Wiley & Sons, Inc., 4.sup.th edition, 1999).

In certain embodiments of the invention, the presence of antibodies that bind to a component of a APMV-2 is detected. In particular the presence of antibodies directed to a protein of an APMV-2 can be detected in a subject to diagnose the presence of an APMV-2 in the subject. Any method known to the skilled artisan can be used to detect the presence of antibodies directed to a component of an APMV-2.

In another embodiment, serological tests can be conducted by contacting a sample, from a host suspected of being infected with APMV-2, with an antibody to an APMV-2 or a component thereof, and detecting the formation of a complex. In such an embodiment, the serological test can detect the presence of a host antibody response to APMV-2 exposure. The antibody that can be used in the assay of the invention to detect host antibodies or APMV-2 components can be produced using any method known in the art. Such antibodies can be engineered to detect a variety of epitopes, including, but not limited to, nucleic acids, amino acids, sugars, polynucleotides, proteins, carbohydrates, or combinations thereof. In another embodiment of the invention, serological tests can be conducted by contacting a sample from a host suspected of being infected with APMV-2, with an a component of APMV-2, and detecting the formation of a complex. Examples of such methods are well known in the art, including but are not limited to, direct immunofluorescence, ELISA, western blot, immunochromatography.

The ability of antibodies or antigen-binding fragments thereof to neutralize virus infectivity is determined by a microneutralization assay. This microneutralization assay is a modification of the procedures described by Anderson et al., (1985, J. Clin. Microbiol. 22:1050-1052, the disclosure of which is hereby incorporated by reference in its entirety). The procedure is also described in Johnson et al., 1999, J. Infectious Diseases 180:35-40, the disclosure of which is hereby incorporated by reference in its entirety. Alternatively, standard neutralization assays can be used to determine how significantly the virus is affected by an antibody.

The ability of the antibody of interest to immunoprecipitate a particular antigen can be assessed by, e.g., western blot analysis or ELISA. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al., eds., 1994, Current Protocols in Molecular Biology, Vol. 1, John Wiley & Sons, Inc., New York at pages 10, 16, 1.

The present invention relates to APMV-2. While the present invention provides the characterization of two serological subgroups of APMV-2, and the characterization of four strains of APMV-2, the invention is not limited to these subgroups and strains. The invention encompasses any yet to be identified isolates of APMV-2, including those which are characterized as belonging to the subgroups, variants and strains described herein, or belonging to a yet to be characterized subgroup, variant, or strain.

Immunoassays can be used in order to characterize the protein components that are present in a given sample. Immunoassays are an effective way to compare viral isolates using peptides components of the viruses for identification. For example, the invention provides herein a method to identify further isolates of APMV-2 as provided herein or a virus isolate phylogenetically corresponding therewith is herewith provided. Therewith, the invention provides a virus comprising a nucleic acid or functional fragment phylogenetically corresponding to a nucleic acid sequence of SEQ. ID NO:1-4, or structurally corresponding therewith.

Bioinformatics Alignment of Sequences. Two or more amino acid sequences can be compared by BLAST (Altschul, S. F. et al., 1990, J. Mol. Biol. 215:403-410) to determine their sequence homology and sequence identities to each other. Two or more nucleotide sequences can be compared by BLAST (Altschul, S. F. et al., 1990, J. Mol. Biol. 215:403-410) to determine their sequence homology and sequence identities to each other. BLAST comparisons can be performed using the Clustal W method (MacVector™). In certain specific embodiments, the alignment of two or more sequences by a computer program can be followed by manual re-adjustment.

The determination of percent identity between two sequences can be accomplished using a mathematical algorithm. A preferred, non-limiting example of a mathematical algorithm utilized for the comparison of two sequences is the algorithm of Karlin and Altschul, 1990, Proc. Natl. Acad. Sci. USA 87:2264-2268, modified as in Karlin and Altschul, 1993, Proc. Natl. Acad. Sci. USA 90:5873-5877. Such an algorithm is incorporated into the NBLAST and XBLAST programs of Altschul et al., 1990, J. Mol. Biol. 215:403-410. BLAST nucleotide comparisons can be performed with the NBLAST program. BLAST amino acid sequence comparisons can be performed with the XBLAST program. To obtain gapped alignments for comparison purposes, Gapped BLAST can be utilized as described in Altschul et al., 1997, Nucleic Acids Res. 25:3389-3402. Alternatively, PSI-Blast can be used to perform an iterated search which detects distant relationships between molecules (Altschul et al., 1997, supra). When utilizing BLAST, Gapped BLAST, and PSI-Blast programs, the default parameters of the respective programs (e.g., XBLAST and NBLAST) can be used (see http://www.ncbi.nlm.nih.gov). Another preferred, non-limiting example of a mathematical algorithm utilized for the comparison of sequences is the algorithm of Myers and Miller, 1988, CABIOS 4:11-17. Such an algorithm is incorporated into the ALIGN program (version 2.0) which is part of the GCG sequence alignment software package. When utilizing the ALIGN program for comparing amino acid sequences, a PAM120 weight residue table can be used. The gap length penalty can be set by the skilled artisan. The percent identity between two sequences can be determined using techniques similar to those described above, with or without allowing gaps. In calculating percent identity, typically only exact matches are counted.

Alternatively, a nucleic acid which is hybridizable to a nucleic acid of APMV-2, or to its reverse complement, or to its complement can be used in the methods of the invention to determine their sequence homology and identities to each other. In certain embodiments, the nucleic acids are hybridized under conditions of high stringency. By way of example and not limitation, procedures using such conditions of high stringency are as follows. Prehybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 ug/ml denatured salmon sperm DNA. Filters are hybridized for 48 h at 65 C in prehybridization mixture containing 100 ug/ml denatured salmon sperm DNA and 5-20×$10^6$ cpm of $^{32}$P-labeled probe. Washing of filters is done at 37° C. for 1 h in a solution containing 2×SSC, 0.01% PVP, 0.01% Ficoll, and 0.01% BSA. This is followed by a wash in 0.1×SSC at 50° C. for 45 min before autoradiography. Other conditions of high stringency which may be used are well known in the art. In other embodiments of the invention, hybridization is performed under moderate of low stringency conditions, such conditions are well-known to the skilled artisan (see e.g., Sambrook et al., 1989, Molecular Cloning, A Laboratory Manual, 2d Ed., Cold Spring Harbor Laboratory Press, Cold Spring Harbor, N.Y.; see also, Ausubel et al., eds., in the Current Protocols in Molecular Biology series of laboratory technique manuals, 1987-1997 Current Protocols, 1994-1997 John Wiley and Sons, Inc.).

This invention relates to the inference of phylogenetic relationships between isolates of APMV-2. Many methods or approaches are available to analyze phylogenetic relationship; these include distance, maximum likelihood, and maximum parsimony methods (Swofford, D L., et. al., Phylogenetic Inference. In Molecular Systematics. Eds. Hillis, D M, Mortiz, C, and Mable, B K. 1996. Sinauer Associates: Massachusetts, USA. pp. 407-514; Felsenstein, J., 1981, J. Mol. Evol. 17:368-376). In addition, bootstrapping techniques are an effective means of preparing and examining confidence intervals of resultant phylogenetic trees (Felsenstein, J., 1985, Evolution. 29:783-791). Any method or approach using nucleotide or peptide sequence information to compare mammalian MPV isolates can be used to establish phylogenetic relationships, including, but not limited to, distance, maximum likelihood, and maximum parsimony methods or approaches. Any method known in the art can be used to analyze the quality of phylogenetic data, including but not limited to bootstrapping. Alignment of nucleotide or peptide sequence data for use in phylogenetic approaches, include but are not limited to, manual alignment, computer pairwise alignment, and computer multiple alignment. One skilled in the art would be familiar with the preferable alignment method or phylogenetic approach to be used based upon the information required and the time allowed.

In one embodiment, nucleic acid or peptide sequence information from an isolate of APMV-2 is compared or aligned with sequences of other APMV-2 isolates. The amino acid sequence can be the amino acid sequence of the any of the proteins of APMV-2. In another embodiment, nucleic acid or peptide sequence information from an APMV-2 isolate or a number of APMV-2 isolates is compared or aligned with sequences of other viruses. In another embodiment, phylogenetic approaches are applied to sequence alignment data so that phylogenetic relationships can be inferred and/or phylogenetic trees constructed. Any method or approach that uses nucleotide or peptide sequence information to compare APMV-2 isolates can be used to infer said phylogenetic relationships, including, but not limited to, distance, maximum likelihood, and maximum parsimony methods or approaches.

Many methods and programs are known in the art and can be used in the inference of phylogenetic relationships, including, but not limited to BioEdit, ClustalW, TreeView, and NJPlot. Methods that would be used to align sequences and to generate phylogenetic trees or relationships would require the input of sequence information to be compared. Many methods or formats are known in the art and can be used to input sequence information, including, but not limited to, FASTA, NBRF, EMBL/SWISS, GDE protein, GDE nucleotide, CLUSTAL, and GCG/MSF. Methods that would be used to align sequences and to generate phylogenetic trees or relationships would require the output of results. Many methods or formats can be used in the output of information or results, including, but not limited to, CLUSTAL, NBRF/PIR, MSF, PHYLIP, and GDE. In one embodiment, ClustalW is used in conjunction with DNA maximum likelihood methods with 100 bootstraps and 3 jumbles in order to generate phylogenetic relationships.

The invention also relates to the generation of antibodies against a protein encoded by APMV-2. In particular, the invention relates to the generation of antibodies against all APMV-2 antigens. According to the invention, any protein encoded by a APMV-2, derivatives, analogs or fragments thereof, may be used as an immunogen to generate antibodies which immunospecifically bind such an immunogen. Antibodies of the invention include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), and epitope-binding fragments. The term "antibody," as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule. Examples of immunologically active portions of immunoglobulin molecules include F(ab) and F(ab')2 fragments which can be generated by treating the antibody with an enzyme such as pepsin or papain. In a specific embodiment, antibodies to a protein encoded by APMV-2 are produced. In another embodiment, antibodies to a domain a protein encoded by APMV-2 are produced.

Various procedures known in the art may be used for the production of polyclonal antibodies against a protein encoded by APMV-2, derivatives, analogs or fragments thereof. For the production of antibody, various host animals can be immunized by injection with the native protein, or a synthetic version, or derivative (e.g., fragment) thereof, including but not limited to rabbits, mice, rats, etc. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum.*

For preparation of monoclonal antibodies directed toward a protein encoded by a APMV-2, derivatives, analogs or fragments thereof, any technique which provides for the production of antibody molecules by continuous cell lines in culture may be used. For example, the hybridoma technique originally developed by Kohler and Milstein (1975, Nature 256:495-497), as well as the trioma technique, the human B-cell hybridoma technique (Kozbor et al., 1983, Immunology Today 4:72), and the EBV-hybridoma technique to produce human monoclonal antibodies (Cole et al., 1985, in Monoclonal Antibodies and Cancer Therapy, Alan R. Liss, Inc., pp. 77-96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, Proc. Natl. Acad. Sci. U.S.A. 80:2026-2030) or by transforming human B cells with EBV virus in vitro (Cole et al., 1985, in Monoclonal Antibodies and Cancer Therapy, Alan R. Liss, pp. 77-96). In fact, according to the invention, techniques developed for the production of "chimeric antibodies" (Morrison et al., 1984, Proc. Natl. Acad. Sci. U.S.A. 81:6851-6855; Neuberger et al., 1984, Nature 312:604-608; Takeda et al., 1985, Nature 314:452-454) by splicing the genes from a mouse antibody molecule specific for a protein encoded by a APMV-2, derivatives, analogs or fragments thereof together with genes from a human antibody molecule of appropriate biological activity can be used; such antibodies are within the scope of this invention.

According to the invention, techniques described for the production of single chain antibodies (U.S. Pat. No. 4,946,778) can be adapted to produce specific single chain antibodies. An additional embodiment of the invention utilizes the techniques described for the construction of Fab expression libraries (Huse et al., 1989, Science 246:1275-1281) to allow rapid and easy identification of monoclonal Fab fragments with the desired specificity for a protein encoded by a APMV-2, derivatives, analogs or fragments thereof.

Antibody fragments which contain the idiotype of the molecule can be generated by known techniques. For example, such fragments include but are not limited to: the F(ab')2 fragment which can be produced by pepsin digestion of the antibody molecule; the Fab' fragments which can be generated by reducing the disulfide bridges of the F(ab')2 fragment, the Fab fragments which can be generated by treating the antibody molecule with papain and a reducing agent, and Fv fragments.

In the production of antibodies, screening for the desired antibody can be accomplished by techniques known in the art, e.g. ELISA (enzyme-linked immunosorbent assay). For example, to select antibodies which recognize a specific domain of a protein encoded by a APMV-2, one may assay generated hybridomas for a product which binds to a fragment of a protein encoded by a APMV-2 containing such domain.

The antibodies provided by the present invention can be used for detecting APMV-2 and for therapeutic methods for the treatment of infections with APMV-2.

The invention provides methods for the identification of a compound that inhibits the ability of APMV-2 to infect a host or a host cell. In certain embodiments, the invention provides methods for the identification of a compound that reduces the ability of APMV-2 to replicate in a host or a host cell. Any technique well-known to the skilled artisan can be used to screen for a compound that would abolish or reduce the ability of a APMV-2 to infect a host and/or to replicate in a host or a host cell.

In certain embodiments, the invention provides methods for the identification of a compound that inhibits the ability of APMV-2 to infect or replicate in a host cell. In certain embodiments, a cell is contacted with a test compound and infected with APMV-2. In certain embodiments, a control culture is infected with a virus in the absence of a test compound. The cell can be contacted with a test compound before, concurrently with, or subsequent to the infection with the APMV-2. In certain embodiments, the cell is incubated with the test compound for at least 1 minute to at least 1 day. The titer of the virus can be measured at any time during the assay. In certain embodiments, a time course of viral growth in the culture is determined. If the viral growth is inhibited or reduced in the presence of the test compound, the test compound is identified as being effective in inhibiting or reducing the growth or infection of a APMV-2.

In certain embodiments, a test compound is administered to a model animal and the model animal is infected with APMV-2. In certain embodiments, a control model animal is infected with a virus without the administration of a test compound. The test compound can be administered before, concurrently with, or subsequent to the infection with the APMV-2. In a specific embodiment, the model animal can be, but is not limited to, a chicken, a cotton rat, a mouse, or a monkey. The titer of the virus in the model animal can be measured at any time during the assay. In certain embodiments, a time course of viral growth in the culture is determined. If the viral growth is inhibited or reduced in the presence of the test compound, the test compound is identified as being effective in inhibiting or reducing the growth or infection of APMV-2.

In a preferred embodiment, the invention provides a proteinaceous molecule or APMV-2-specific viral protein or functional fragment thereof encoded by a nucleic acid according to the invention. Useful proteinaceous molecules are for example derived from any of the genes or genomic fragments derivable from a virus according to the invention. Such molecules, or antigenic fragments thereof, as provided herein, are for example useful in diagnostic methods or kits and in pharmaceutical compositions such as sub-unit vaccines. Particularly useful are also those proteinaceous substances that are encoded by recombinant nucleic acid fragments that are identified for phylogenetic analyses, of course preferred are those that are within the preferred bounds and metes of ORFs useful in phylogenetic analyses, in particular for eliciting APMV-2 specific antibody or T cell responses, whether in vivo (e.g. for protective purposes or for providing diagnostic antibodies) or in vitro (e.g. by phage display technology or another technique useful for generating synthetic antibodies).

Also provided herein are antibodies, be it natural polyclonal or monoclonal, or synthetic (e.g. (phage) library-derived binding molecules) antibodies that specifically react with an antigen comprising a proteinaceous molecule or APMV-2-specific functional fragment thereof according to the invention. Such antibodies are useful in a method for identifying a viral isolate as an APMV-2 comprising reacting said viral isolate or a component thereof with an antibody as provided herein. This can for example be achieved by using purified or non-purified APMV-2 or parts thereof (proteins, peptides) using ELISA, RIA, FACS or different formats of antigen detection assays (Current Protocols in Immunology). Alternatively, infected cells or cell cultures may be used to identify viral antigens using classical immunofluorescence or immunohistochemical techniques.

A pharmaceutical composition comprising a virus, a nucleic acid, a proteinaceous molecule or fragment thereof, an antigen and/or an antibody according to the invention can for example be used in a method for the treatment or prevention of APMV-2 infection and/or a respiratory illness comprising providing an individual with a pharmaceutical composition according to the invention. The compositions of the invention can be used for the treatment of immuno-compromised individuals including cancer patients, transplant recipients and the elderly.

In certain embodiments of the invention, the vaccine of the invention comprises APMV-2 as defined herein. The invention provides vaccine formulations for the prevention and treatment of infections with APMV-2. In certain embodiments, the vaccine of the invention comprises recombinant and chimeric viruses of the invention. In certain embodiments, the virus is attenuated.

Due to the high degree of homology among the F proteins of different viral species, the vaccine formulations of the invention can be used for protection from viruses different from the one from which the heterologous nucleotide sequence encoding the F protein was derived. In a specific exemplary embodiment, a vaccine formulation contains a virus comprising a heterologous nucleotide sequence derived from an avian pneumovirus type A, and the vaccine formulation is used to protect from infection by avian pneumovirus type A and avian pneumovirus type B. The invention encompasses vaccine formulations to be administered to humans and animals which are useful to protect against APV, including APV-C and APV-D, hMPV, PIV, influenza, RSV, Sendai virus, mumps, laryngotracheitis virus, simianvirus 5, human papillomavirus, measles, mumps, as well as other viruses and pathogens and related diseases. The invention further encompasses vaccine formulations to be administered to humans and animals which are useful to protect against human *metapneumovirus* infections and avian *pneumovirus* infections and related diseases.

In one embodiment, the invention encompasses vaccine formulations which are useful against domestic animal disease causing agents including rabies virus, feline leukemia virus (FLV) and canine distemper virus. In yet another embodiment, the invention encompasses vaccine formulations which are useful to protect livestock against vesicular stomatitis virus, rabies virus, rinderpest virus, swinepox virus, and further, to protect wild animals against rabies virus.

Attenuated viruses generated by the reverse genetics approach can be used in the vaccine and pharmaceutical formulations described herein. Reverse genetics techniques can also be used to engineer additional mutations to other viral genes important for vaccine production—i.e., the epitopes of useful vaccine strain variants can be engineered into the attenuated virus. Alternatively, completely foreign epitopes, including antigens derived from other viral or non-viral pathogens can be engineered into the attenuated strain. For example, antigens of non-related viruses such as HIV (gp160, gp120, gp41) parasite antigens (e.g., malaria), bacterial or fungal antigens or tumor antigens can be engineered into the attenuated strain. Alternatively, epitopes which alter the tropism of the virus in vivo can be engineered into the chimeric attenuated viruses of the invention.

Virtually any heterologous gene sequence may be constructed into the chimeric viruses of the invention for use in vaccines. Preferably moieties and peptides that act as biological response modifiers. Preferably, epitopes that induce a protective immune response to any of a variety of pathogens, or antigens that bind neutralizing antibodies may be expressed by or as part of the chimeric viruses. For example, heterologous gene sequences that can be constructed into the chimeric viruses of the invention include, but are not limited to influenza and parainfluenza hemagglutinin neuraminidase and fusion glycoproteins such as the HN and F genes. In yet another embodiment, heterologous gene sequences that can be engineered into the chimeric viruses include those that encode proteins with immuno-modulating activities. Examples of immuno-modulating proteins include, but are not limited to, cytokines, interferon type 1, gamma interferon, colony stimulating factors, interleukin-1, -2, -4, -5, -6, -12, and antagonists of these agents.

In addition, heterologous gene sequences that can be constructed into the chimeric viruses of the invention for use in vaccines include but are not limited to sequences derived from a human immunodeficiency virus (HIV), preferably type 1 or type 2. In a preferred embodiment, an immunogenic HIV-derived peptide which may be the source of an antigen may be constructed into a chimeric PIV that may then be used to elicit a vertebrate immune response. Such HIV-derived peptides may include, but are not limited to sequences derived from the env gene (i.e., sequences encoding all or part of gp160, gp120, and/or gp41), the pol gene (i.e., sequences encoding all or part of reverse transcriptase, endonuclease, protease, and/or integrase), the gag gene (i.e., sequences encoding all or part of p7, p6, p55, p17/18, p24/25), tat, rev, nef, vif, vpu, vpr, and/or vpx.

Other heterologous sequences may be derived from hepatitis B virus surface antigen (HBsAg); hepatitis A or C virus surface antigens, the glycoproteins of Epstein Barr virus; the glycoproteins of human papillomavirus; the glycoproteins of respiratory syncytial virus, parainfluenza virus, Sendai virus, simianvirus 5 or mumps virus; the glycoproteins of influenza virus; the glycoproteins of herpesviruses; VP1 of poliovirus; antigenic determinants of non-viral pathogens such as bacteria and parasites, to name but a few. In another embodiment, all or portions of immunoglobulin genes may be expressed. For example, variable regions of anti-idiotypic immunoglobulins that mimic such epitopes may be constructed into the chimeric viruses of the invention.

Other heterologous sequences may be derived from tumor antigens, and the resulting chimeric viruses be used to generate an immune response against the tumor cells leading to tumor regression in vivo. These vaccines may be used in combination with other therapeutic regimens, including but not limited to chemotherapy, radiation therapy, surgery, bone marrow transplantation, etc. for the treatment of tumors. In accordance with the present invention, recombinant viruses may be engineered to express tumor-associated antigens (TAAs), including but not limited to, human tumor antigens recognized by T cells (Robbins and Kawakami, 1996, Curr. Opin. Immunol. 8:628-636, incorporated herein by reference in its entirety), melanocyte lineage proteins, including gp100, MART-1/MelanA, TRP-1 (gp75), tyrosinase; Tumor-specific widely shared antigens, MAGE-1, MAGE-3, BAGE, GAGE-1, GAGE-1, N-acetylglucosaminyltransferase-V, p15; Tumor-specific mutated antigens, beta-catenin, MUM-1, CDK4; Nonmelanoma antigens for breast, ovarian, cervical and pancreatic carcinoma, HER-2/neu, human papillomavirus-E6, -E7, MUC-1.

Either a live recombinant viral vaccine or an inactivated recombinant viral vaccine can be formulated. A live vaccine may be preferred because multiplication in the host leads to a prolonged stimulus of similar kind and magnitude to that occurring in natural infections, and therefore, confers substantial, long-lasting immunity. Production of such live recombinant virus vaccine formulations may be accomplished using conventional methods involving propagation of the virus in cell culture or in the allantois of the chick embryo followed by purification.

In a specific embodiment, the recombinant virus is non-pathogenic to the subject to which it is administered. In this regard, the use of genetically engineered viruses for vaccine purposes may desire the presence of attenuation characteristics in these strains. The introduction of appropriate mutations (e.g., deletions) into the templates used for transfection may provide the novel viruses with attenuation characteristics. For example, specific missense mutations which are associated with temperature sensitivity or cold adaption can be made into deletion mutations. These mutations should be more stable than the point mutations associated with cold or temperature sensitive mutants and reversion frequencies should be extremely low.

Alternatively, chimeric viruses with "suicide" characteristics may be constructed. Such viruses would go through only one or a few rounds of replication within the host. When used as a vaccine, the recombinant virus would go through limited replication cycle(s) and induce a sufficient level of immune response but it would not go further in the human host and cause disease. Recombinant viruses lacking one or more of the genes of wild type APMV-2, respectively, or possessing mutated genes as compared to the wild type strains would not be able to undergo successive rounds of replication. Defective viruses can be produced in cell lines which permanently express such a gene(s). Viruses lacking an essential gene(s) will be replicated in these cell lines but when administered to the human host will not be able to complete a round of replication. Such preparations may transcribe and translate—in this abortive cycle—a sufficient number of genes to induce an immune response. Alternatively, larger quantities of the strains could be administered, so that these preparations serve as inactivated (killed) virus vaccines. For inactivated vaccines, it is preferred that the heterologous gene product be expressed as a viral component, so that the gene product is associated with the virion. The advantage of such preparations is that they contain native proteins and do not undergo inactivation by treatment with formalin or other agents used in the manufacturing of killed virus vaccines. Alternatively, recombinant virus of the invention made from cDNA may be highly attenuated so that it replicates for only a few rounds.

In certain embodiments, the vaccine of the invention comprises an attenuated APMV-2. In another embodiment of this aspect of the invention, inactivated vaccine formulations may be prepared using conventional techniques to "kill" the chimeric viruses. Inactivated vaccines are "dead" in the sense that their infectivity has been destroyed. Ideally, the infectivity of the virus is destroyed without affecting its immunogenicity. In order to prepare inactivated vaccines, the chimeric virus may be grown in cell culture or in the allantois of the chick embryo, purified by zonal ultracentrifugation, inactivated by formaldehyde, and pooled. The resulting vaccine is usually inoculated intramuscularly.

Pharmaceutical compositions may be formulated with a suitable adjuvant in order to enhance the immunological response. Such adjuvants may include but are not limited to mineral gels, e.g., aluminum hydroxide; surface active substances such as lysolecithin, pluronic polyols, polyanions; peptides; oil emulsions; and potentially useful human adjuvants such as BCG, *Corynebacterium parvum*, ISCOMS and virosomes.

Many methods may be used to introduce the pharmaceutical formulations described above, these include but are not limited to oral, intradermal, intramuscular, intraperitoneal, intravenous, subcutaneous, percutaneous, and intranasal and inhalation routes. It may be preferable to introduce the chimeric virus vaccine formulation via the natural route of infection of the pathogen for which the vaccine is designed.

A vaccine or immunogenic formulation of the invention may be administered to a subject per se or in the form of a pharmaceutical or therapeutic composition. Pharmaceutical compositions comprising an adjuvant and an immunogenic antigen of the invention (e.g., a virus, a chimeric virus, a mutated virus) may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries which facilitate processing of the immunogenic antigen of the invention into preparations which can be used pharmaceutically. Proper formulation is, amongst others, dependent upon the route of administration chosen.

When a vaccine or immunogenic composition of the invention comprises adjuvants or is administered together with one or more adjuvants, the adjuvants that can be used include, but are not limited to, mineral salt adjuvants or mineral salt gel adjuvants, particulate adjuvants, microparticulate adjuvants, mucosal adjuvants, and immunostimulatory adjuvants. Examples of adjuvants include, but are not limited to, aluminum hydroxide, aluminum phosphate gel, Freund's Complete Adjuvant, Freund's Incomplete Adjuvant, squalene or squalane oil-in-water adjuvant formulations, biodegradable and biocompatible polyesters, polymerized liposomes, triterpenoid glycosides or saponins (e.g., QuilA and QS-21, also sold under the trademark STIMULON, ISCOPREP), N-acetyl-muramyl-L-threonyl-D-isoglutamine (Threonyl-MDP, sold under the trademark TERMURTIDE), LPS, monophosphoryl Lipid A (3D-MLA sold under the trademark MPL).

The subject to which the vaccine or an immunogenic composition of the invention is administered is preferably a mammal, most preferably a human, but can also be a non-human animal, including but not limited to, primates, cows, horses, sheep, pigs, fowl (e.g., chickens, turkeys), goats, cats, dogs, hamsters, mice and rodents.

Many methods may be used to introduce the vaccine or the immunogenic composition of the invention, including but not limited to, oral, intradermal, intramuscular, intraperitoneal, intravenous, subcutaneous, percutaneous, intranasal and inhalation routes, and via scarification (scratching through the top layers of skin, e.g., using a bifurcated needle).

For topical administration, the vaccine or immunogenic preparations of the invention may be formulated as solutions, gels, ointments, creams, suspensions, etc. as are well-known in the art.

For administration intranasally or by inhalation, the preparation for use according to the present invention can be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

For injection, the vaccine or immunogenic preparations may be formulated in aqueous solutions, preferably in physiologically compatible buffers such as Hanks's solution, Ringer's solution, or physiological saline buffer. The solution may contain formulatory agents such as suspending, stabilizing and/or dispersing agents. Alternatively, the proteins may be in powder form for constitution with a suitable vehicle, e.g., sterile pyrogen-free water, before use.

Determination of an effective amount of the vaccine or immunogenic formulation for administration is well within the capabilities of those skilled in the art, especially in light of the detailed disclosure provided herein.

An effective dose can be estimated initially from in vitro assays. For example, a dose can be formulated in animal models to achieve an induction of an immunity response using techniques that are well known in the art. One having ordinary skill in the art could readily optimize administration to all animal species based on results described herein. Dosage amount and interval may be adjusted individually. For example, when used as an immunogenic composition, a suitable dose is an amount of the composition that when administered as described above, is capable of eliciting an antibody response. When used as a vaccine, the vaccine or immunogenic formulations of the invention may be administered in about 1 to 3 doses for a 1-36 week period. Preferably, 1 or 2 doses are administered, at intervals of about 2 weeks to about 4 months, and booster vaccinations may be given periodically thereafter. Alternate protocols may be appropriate for individual animals. A suitable dose is an amount of the vaccine formulation that, when administered as described above, is capable of raising an immunity response in an immunized animal sufficient to protect the animal from an infection for at least 4 to 12 months. In general, the amount of the antigen present in a dose ranges from about 1 pg to about 100 mg per kg of host, typically from about 10 pg to about 1 mg, and preferably from about 100 pg to about 1 ug. Suitable dose range will vary with the route of injection and the size of the patient, but will typically range from about 0.1 mL to about 5 mL.

The invention provides means and methods for the diagnosis and/or detection of APMV-2, said means and methods to be employed in the detection of APMV-2, its components, and the products of its transcription, translation, expression, propagation, and metabolic processes. More specifically, this invention provides means and methods for the diagnosis of an APMV-2 infection in animals and in humans, said means and methods including but not limited to the detection of components of APMV-2, products of the life cycle of APMV-2, and products of a host's response to APMV-2 exposure or infection.

The methods that can be used to detect APMV-2 or its components, and the products of its transcription, translation, expression, propagation and metabolic processes are well known in the art and include, but are not limited to, molecular based methods, antibody based methods, and cell-based methods. Examples of molecular based methods include, but are not limited to polymerase chain reaction (PCR), reverse transcriptase PCR (RT-PCR), real time RT-PCR, nucleic acid sequence based amplification (NASBA), oligonucleotide probing, southern blot hybridization, northern blot hybridization, any method that involves the contacting of a sample with a nucleic acid that is complementary to an APMV-2 or similar or identical to an APMV-2, and any combination of these methods with each other or with those in the art. Identical or similar nucleic acids that can be used are described herein, and are also well known in the art to be able to allow one to distinguish between APMV-2 and the genomic material or related products of other viruses and organisms. Examples of antibody based methods include, but are not limited to, the contacting of an antibody with a sample suspected of containing APMV-2, direct immunofluorescence (DIF), enzyme linked immunoabsorbent assay (ELISA), western blot, immunochromatography. Examples of cell-based methods include, but are not limited to, reporter assays that are able to emit a signal when exposed to APMV-2, its components, or products thereof. In another embodiment, the reporter assay is an in vitro assay, whereby the reporter is expressed upon exposure to APMV-2, its components, or products thereof. Examples of the aforementioned methods are well-known in the art and also described herein. In a more specific embodiment, NASBA is used to amplify specific RNA or DNA from a pool of total nucleic acids.

In one embodiment, the invention provides means and methods for the diagnosis and detection of APMV-2, said means and methods including but not limited to the detection of genomic material and other nucleic acids that are associated with or complimentary to APMV-2, the detection of transcriptional and translational products of APMV-2, said products being both processed and unprocessed, and the detection of components of a host response to APMV-2 exposure or infection.

In one embodiment, the invention relates to the detection of APMV-2 through the preparation and use of oligonucleotides that are complimentary to nucleic acid sequences and transcriptional products of nucleic acid sequences that are present within the genome of APMV-2. Furthermore, the invention relates to the detection of nucleic acids, or sequences thereof, that are present in the genome of APMV-2 and its transcription products, using said oligonucleotides as primers for copying or amplification of specific regions of the APMV-2 genome and its transcripts. The regions of the APMV-2 genome and its transcripts that can be copied or amplified include but are not limited to complete and incomplete stretches of one or more of the following: the N-gene, the P-gene, the M-gene, the F-gene, the V-gene, the HN-gene, the G-gene, and the L-gene. Said methods include but are not limited to, PCR assays, RT-PCR assays, real time RT-PCR assays, primer extension or run on assays, NASBA and other methods that employ the genetic material of APMV-2 or transcripts and compliments thereof as templates for the extension of nucleic acid sequences from said oligonucleotides. In another embodiment, a combination of methods is used to detect the presence of APMV-2 in a sample. One skilled in the art would be familiar with the requirements and applicability of each assay. For example, PCR and RT-PCR would be useful for the amplification or detection of a nucleic acid. In a more specific embodiment, real time RT-PCR is used for the routine and reliable quantitation of PCR products.

In another embodiment, the invention relates to detection of APMV-2 through the preparation and use of oligonucleotides that are complimentary to nucleic acid sequences and transcriptional products of nucleic acid sequences that are present within the genome of APMV-2. Furthermore, the invention relates to the detection of nucleic acids, or sequences thereof, that are present in or complimentary to the genome of APMV-2 and its transcription products, using said oligonucleotide sequences as probes for hybridization to and detection of specific regions within or complimentary to the APMV-2 genome and its transcripts. The regions of the APMV-2 genome and its transcripts that can be detected using hybridization probes include but are not limited to complete and incomplete stretches of one or more of the following: the N-gene, the P-gene, the M-gene, the F-gene, the V-gene, the HN-gene, the W-gene, and the L-gene. Said methods include but are not limited to, Northern blots, Southern blots and other methods that employ the genetic material of APMV-2 or transcripts and compliments thereof as targets for the hybridization, annealing, or detection of sequences or stretches of sequences within or complimentary to the APMV-2 genome.

Any size oligonucleotides can be used in the methods of the invention. As described herein, such oligonucleotides are useful in a variety of methods, e.g., as primer or probes in various detection or analysis procedures. In preferred embodiments, oligonucleotide probes and primers are at least 5, at least 8, at least 10, at least 12, at least 15, at least 20, at least 25, at least 30, at least 35, at least 40, at least 45, at least 50, at least 55, at least 60, at least 70, at least 80, at least 100, at least 200, at least 300 at least 400, at least 500, at least 1000, at least 2000, at least 3000, at least 4000 or at least 5000 bases. In another more certain embodiments, oligonucleotide probes and primers comprise at least 5, at least 8, at least 10, at least 12, at least 15, at least 20, at least 25, at least 30, at least 35, at least 40, at least 45, at least 50, at least 55, at least 60, at least 70, at least 80, at least 100, at least 200, at least 300 at least 400, at least 500, at least 1000, at least 2000, at least 3000, at least 4000 or at least 5000 bases, that are at least 50%, at least 60%, at least 70%, at least 80%, at least 90%, at least 99%, at least 99.5% homologous to a target sequence, such as an APMV-2 genomic sequence or complement thereof. In a another specific embodiment, the oligonucleotide that is used as a primer or a probe is of any length, and specifically hybridizes under stringent conditions through at least 8 of its most 3' terminal bases to a target sequence. In another specific embodiment, the oligonucleotide that is used as a primer or a probe is of any length, and specifically hybridizes under stringent conditions through at least 10 of its most 3' terminal bases to a target sequence. In another specific embodiment, the oligonucleotide that is used as a primer or a probe is of any length, and specifically hybridizes under stringent conditions through at least 12 of its most 3' terminal bases to a target sequence. In another specific embodiment, the oligonucleotide that is used as a primer or a probe is of any length, and specifically hybridizes under stringent conditions through at least 15 of its most 3' terminal bases to a target sequence. In another specific embodiment, the oligonucleotide that is used as a primer or a probe is of any length, and specifically hybridizes under stringent conditions through at least 20 of its most 3' terminal bases to a target sequence. In another specific embodiment, the oligonucleotide that is used as a primer or a probe is of any length, and specifically hybridizes under stringent conditions through at least 25 of its most 3' terminal bases to a target sequence. In another embodiment, a degenerate set of oligos is used so that a specific position or nucleotide is substituted. The degeneracy can occur at any position or at any number of positions, most preferably, at least at one position, but also at least at two positions, at least at three positions, at least ten positions, in the region that hybridizes under stringent conditions to the target sequence.

One skilled in the art would be familiar with the structural requirements imposed upon oligonucleotides by the assays known in the art.

This invention also provides means and methods for diagnostic assays or test kits and for methods to detect agents of an APMV-2 infection from a variety of sources including but not limited to biological samples, e.g., body fluids. In one embodiment, this invention relates to assays, kits, protocols, and procedures that are suitable for identifying an APMV-2 nucleic acid or a compliment thereof. In another embodiment, this invention relates to assays, kits, protocols, and procedures that are suitable for identifying an APMV-2 expressed peptide or a portion thereof. In another embodiment, this invention relates to assays, kits, protocols, and procedures that are suitable for identifying components of a host immunologic response to APMV-2 exposure or infection.

In addition to diagnostic confirmation of APMV-2 infection of a host, the present invention also provides for means and methods to classify isolates of APMV-2 into distinct phylogenetic groups or subgroups. In one embodiment, this feature can be used advantageously to distinguish between the different subtypes of APMV-2, in order to design more effective and subgroup specific therapies. Variants of APMV-2 can be differentiated on the basis of nucleotide or amino acid sequences of one or more of the following: the N-gene, the P-gene, the M-gene, the F-gene, the V-gene, the HN-gene, the G-gene, and the L-gene.

In one embodiment, the diagnosis of an APMV-2 infection in a subject is made using any technique well known to one skilled in the art, e.g., immunoassays. Immunoassays which can be used to analyze immunospecific binding and cross-reactivity include, but are not limited to, competitive and non-competitive assay systems using techniques such as western blots, radioimmunoassays, ELISA (enzyme linked immunosorbent assay), sandwich immunoassays, immunoprecipitation assays, precipitin reactions, gel diffusion precipitation reactions, immunodiffusion assays, agglutination assays, complement-fixation assays, and fluorescent immunoassays, to name but a few. Such assays are routine and well known in the art (see, e.g., Ausubel et al., eds, 1994, Current Protocols in Molecular Biology, Vol. 1, John Wiley & Sons, Inc., New York, which is incorporated by reference herein in its entirety).

In a preferred embodiment, diagnosis and/or treatment of a specific viral infection is performed with reagents that are most specific for said specific virus causing said infection. This by no means however excludes the possibility that less specific, but sufficiently crossreactive reagents are used instead, for example because they are more easily available and sufficiently address the task at hand. For nucleic acid detection, instead of designing primers or probes based on heterologous nucleic acid sequences of the various viruses and thus that detect differences between the different strains of APMV-2, it suffices to design or select primers or probes based on those stretches of virus-specific nucleic acid sequences that show high homology. In general, for nucleic acid sequences, homology percentages of 90% or higher guarantee sufficient cross-reactivity to be relied upon in diagnostic tests utilizing stringent conditions of hybridisation.

The invention for example provides a method for virologically diagnosing a APMV-2 infection of an animal, comprising determining in a sample of said animal the presence of a viral isolate or component thereof by reacting said sample with a APMV-2 specific nucleic acid a or antibody according to the invention, and a method for serologically diagnosing an APMV-2 infection of a subject comprising determining in a sample of said subject the presence of an antibody specifically directed against an APMV-2 or component thereof by reacting said sample with a APMV-2-specific proteinaceous molecule or fragment thereof or an antigen according to the invention. The invention also provides a diagnostic kit for diagnosing an APMV-2 infection comprising an APMV-2, an APMV-2-specific nucleic acid, proteinaceous molecule or fragment thereof, antigen and/or an antibody according to the invention, and preferably a means for detecting said APMV-2, APMV-2-specific nucleic acid, proteinaceous molecule or fragment thereof, antigen and/or an antibody, said means for example comprising an excitable group such as a fluorophore or enzymatic detection system used in the art (examples of suitable diagnostic kit format comprise IF, ELISA, neutralization assay, RT-PCR assay). To determine whether an as yet unidentified virus component or synthetic analogue thereof such as nucleic acid, proteinaceous molecule or fragment thereof can be identified as APMV-2-specific, it suffices to analyse the nucleic acid or amino acid sequence of said component, for example for a stretch of said nucleic acid or amino acid, preferably of at least 10, more preferably at least 25, more preferably at least 40 nucleotides or amino acids (respectively), by sequence homology comparison with known APMV-2 sequences using for example phylogenetic analyses as provided herein. Depending on the degree of relationship with said APMV-2 or non-APMV-2 sequences, the component or synthetic analogue can be identified.

Methods and means provided herein are particularly useful in a diagnostic kit for diagnosing APMV-2 infection, be it by virological or serological diagnosis. Such kits or assays may for example comprise a virus, a nucleic acid, a proteinaceous molecule or fragment thereof, an antigen and/or an antibody according to the invention. Use of a virus, a nucleic acid, a proteinaceous molecule or fragment thereof, an antigen and/or an antibody according to the invention is also provided for the production of a pharmaceutical composition, for example for the treatment or prevention of APMV-2 infections and/or for the treatment or prevention of respiratory tract illnesses. Attenuation of the virus can be achieved by established methods developed for this purpose, including but not limited to the use of related viruses of other species, serial passages through laboratory animals or/and tissue/cell cultures, site directed mutagenesis of molecular clones and exchange of genes or gene fragments between related viruses.

The contents of all cited references (including literature references, issued patents, published patent applications, and co-pending patent applications) cited throughout this application are hereby expressly incorporated by reference.

Other features of the invention will become apparent in the course of the following descriptions of exemplary embodiments which are given for illustration of the invention and not intended to be limiting thereof.

The following Materials and Methods were used in the Examples that follow.

Materials and Methods

Virus and Cells

APMV-2 strain Yucaipa was obtained from the National Veterinary Services Laboratory, Ames, Iowa. The virus was grown in 9-day-old embryonated, specific pathogen-free (SPF) chicken eggs. Hemagglutination (HA) titers were determined using 0.5% chicken RBC at room temperature. Replication of the virus was evaluated in nine different cell lines: BHK21, Baby Hamster Kidney; BT, Bovine Turbinate; DF1, chicken embryo fibroblast; HEp2, human cervical carcinoma; MDCK, Madin Darby Canine Kidney; PK15, Pig Kidney; QT35, Quail fibrosarcoma; RK13, Rabbit Kidney cells; and Vero, African green monkey kidney. The DF1 and QT35 cells were grown in Dulbecco's minimum essential medium containing 10% fetal calf serum (FCS), while the other cells were grown in Eagle's minimum essential medium (MEM) containing 10% FCS, all in a 37° C. incubator with 5% $CO_2$. Each cell type was grown as a monolayer and infected with a 10-3 dilution of 210 HA units of egg-grown APMV-2 strain Yucaipa with and without 10% allantoic fluid supplementation in the medium, which provides a source of protease for cleavage of the F protein. The cells were observed daily for cytopathic effects (CPE) and HA titers were recorded every 24 h until the fifth day. A total of three passages of virus were made in each cell type. The ability of the virus to produce plaques was tested in the different cell lines under various conditions, including 1% methylcellulose, 1% low melting agar, and 0.8% noble agar with or without magnesium sulfate (25 mM) and 1% diethylaminoethyl dextran (30 ug/ml). Plaques were visualized by staining with either crystal violet or neutral red.

Viral RNA Isolation and Sequence Analysis

APMV-2 strain Yucaipa RNA was isolated from the allantoic fluid of virus-infected eggs using RNeasy kit (QIAGEN, USA) according to the manufacturer's instructions. The complete genome sequence exclusive of the termini was determined using a combination of three different strategies. First, the nucleotide sequences of the N genes of all the available rubulaviruses and avulaviruses were aligned to identify a consensus sequence that was used to design the forward primer N-451 (5'-GAAGATGATGCACCAGAAGA (SEQ ID NO:69), numbered according to the consensus sequence). A reverse primer was designed from the APMV-2 F gene sequence that was available in GenBank (accession no. AF422844) (F-127r, 5'-ACTGCGATGGTCCCTGTGAG (SEQ ID NO:70), numbered according to the Yucaipa strain F gene sequence). This yielded a part of sequence upstream of F gene. Similarly, L genes of rubulaviruses and avulaviruses were aligned to design two reverse degenerate primers in the conserved regions of L gene; L-5544r, 5'-NGGNCCRAARTGNCK-YTGNGGNGGRTT (N=A/C/G/T, R=A/G, K=G/T, Y=C/T) (SEQ ID NO:71) and L-6960r, 5'-NSWRTAR-TANCCYTTNGCNGCRTTNCCDATNGT (N=A/C/G/T, S=G/C, W=A/T, R=A/G, Y=C/T, D=G/A/T) (SEQ ID NO:72). APMV-2 L gene specific forward primers were designed from the partial sequence that was available in GenBank (accession no. AF515835). The PCR using these primers resulted in multiple bands which upon cloning and sequencing yielded different regions of L gene. Second, we designed a gene-start forward primer (5'-GGAAAACTT GGGGGCGACA, SEQ ID NO:73)) containing the presumptively conserved gene-start sequence at its 3' end (underlined) and a reverse primer (5'-TTTTTTCTTAAACCAGGCTTC, SEQ ID NO:74) with the presumptively conserved gene-end sequence at its 5' end (underlined). Reverse transcription (RT) with the gene-start forward primer and PCR with the same forward primer and the gene-end reverse primer resulted in multiple fragments which upon sequencing yielded different regions of all the viral genes. Finally, as the third strategy, most of the L gene was sequenced by primer walking originating in the partial sequence of the upstream end of L available in GenBank. Briefly, cDNA synthesized from an RT reaction with an L gene-specific forward primer was purified by ethanol precipitation and a 3' poly-C tail was added with terminal deoxynucleotidyl transferase (Invitrogen, Carlsbad, Calif.). The dC-tailed cDNA was amplified by PCR using an L gene-specific forward primer and a poly dG-containing reverse primer. The PCR-amplified products were cloned and sequenced. The sequence from one round of cloning was used to design the forward primer for the next round of RT-PCR. All the primers were purchased from Integrated DNA technologies, USA. The RT reactions were performed with the SuperScript II RT kit (Invitrogen, USA) and PCR was performed in 50 ul reactions using Takara LA taq (Takara Bio, USA), both according to the manufacturer's instructions. The general conditions for PCR were 95° C. for 5 min, 25 cycles of 95° C. for 1 min (denaturation), 56° C. for 1 min (annealing) and 72° C. for 1 min (extension), followed by 72° C. for 10 min (final extension). The PCR fragments were cloned in TOPO TA cloning kit (Invitrogen, USA). In addition, selected PCR products were purified by agarose gel electrophoresis and sequenced directly. DNA sequencing was carried out using BigDye® Terminator v3.1 cycle sequencing kit (Applied Biosystems, USA) and an ABI PRISM 3100 Avant Genetic Analyser (Applied Biosystems). Every nucleotide in the genome was sequenced at least three times and once directly from RT-PCR product without cloning, thus ensuring a consensus sequence.

Determination of the Sequences of Genometermini

The sequences of the 3' and 5' ends of the virus genome were obtained by ligation of a RNA oligonucleotide to viral RNA and cDNA, respectively, as described (Troutt et al., 1992, PNAS USA 89, 9823-9825). To determine the 3' end of viral RNA, a 5'-phosphorylated and 3' blocked RNA oligonucleotide (5' phos-CCAAAACGCCAUUUCCAC-CUUCUCUUC 3'-blocked SEQ ID NO:75), was ligated to viral RNA. Briefly, 8 ul of viral RNA (1-5 ug) and 1 ul of RNA oligonucleotide (50 pmol) were denatured at 65.0 for 5 min and snap frozen on dry ice. The ligation reaction was carried out overnight at 16° C. with 4 ul of 10×T4 RNA ligase buffer, 10 units of T4 RNA ligase (Promega, USA), 1 mM hexamine cobalt chloride, 10 ug/ml BSA, 25% (w/v) of PEG 8000 and RNase-free water to make a 40 ul reaction mixture. Ligation was terminated by heating to 65° C. for 20 min. The ligated RNA was precipitated following the protocol described in the GeneRacer kit (Invitrogen, USA), RT was carried out with an adaptor primer (5'-GAAGA-GAAGGTGGAAATGGCGTTTTGG, SEQ ID NO:76) complimentary to the RNA oligonucleotide, as described (Li et al., 2005, J. Virol. Methods 130, 154-156). PCR was performed with the same primer together with a reverse primer within N gene, N287 (5'-GGATCGCCCCTTGTCT-CAT, SEQ ID NO:77). To determine the 5' end, viral RNA was reverse transcribed using an L gene-specific primer L-5.7 (5'-AAGAGTTTGACAGGGGGATGC, SEQ ID NO:78). The cDNA was ligated to the RNA oligonucleotide following the same procedure as described above. The ligated cDNA was amplified by PCR using an L gene specific forward primer, L-5.9 (5'-GGCTTGATATACAC-CGGAACTCGT, SEQ ID NO:79), which anneals to sequence downstream of L 5.7), together with the adaptor primer. The PCR products were cloned into the TOPO TA cloning vector and sequenced, and also were directly sequenced.

Sequence and Phylogenetic Tree Analysis

Sequence compilation and prediction of ORFs were carried out using the SEQMAN and EDITSEQ programs in the LASERGENE (DNASTAR) software package. The search for homologous protein sequences in GenBank was done using the BLAST program in the same package. Phylogenetic analysis was carried out using T-Coffee (tree-based consistency objective function for alignment evaluation), a multiple sequence alignment program. The phylogenetic trees were drawn using the same program and applying the "average distance using percentage identity" method (Notredame et al., 2000, J. Mol. Biol. 302, 205-217).

Database Accession Numbers

The complete genome sequence of APMV-2 strain Yucaipa has been deposited in GenBank under accession number EU338414. Accession numbers for other sequences used in this study are given below. For some viruses, individual gene sequences were used since full-length genome sequences were unavailable. They are indicated by the abbreviated gene letter in parentheses following the GenBank accession number. Virus sequences used were as follows: AMPV, NC_007652; APMV-1 (NDV) strain Beaudette C (for the 3' leader sequence, see reference Krishnamurthy and Samal, 1998), AF064091 (N), X60599 (P/V), X04687 (M), X04719 (F), X04355 (HN), and X05399 (L); APMV-4, D14031 (HN gene); APMV-6, AY029299; CDV, AF014953; HeV, AF017149; HMPV, NC_004148; HPIV-2, X57559; HPIV-3, AB012132; HRSV, AF013254; MeV, AB016162; MuV, AB040874; MrV, D13990 (F and HN genes); NiV, AF212302; SeV, AB005795.

Example 1

Growth Characteristics of APMV-2 Strain Yucaipa

APMV-2 strain Yucaipa yielded a titer of 210 to 212 HA units in 9-day-old embryonated SPF chicken eggs 4 days post-inoculation. Nine different cell culture systems each representing a different species of origin were evaluated to determine the cell type(s) that can support the growth of APMV-2 to high titers as well as whether or not added protease is required for replication. Each of the nine cell types supported the growth of APMV-2, as determined by the observable CPE and HA activity of the infected cell culture supernatant. The HA titers were the same with and without 10% allantoic fluid supplementation of the media, and varied from $2^3$ to $2^9$ HA units among the cell types. The peak HA titers of the different cell lines tested in HA units were BHK21: $2^9$, BT: $2^4$, DF1: $2^8$, Hep2: $2^6$, MDCK: $2^4$, PK15: $2^5$, QT35: $2^7$, RK13: $2^4$, and Vero: $2^6$. The virus grew most efficiently in BHK21, QT35 and DF1 cell lines, representing hamsters, quail, and chicken, respectively. In general, there was not a strong host range restriction in vitro, and each of the cell lines was able to execute efficient cleavage of the F protein without added protease, even at low moi (10-6 dilution of 210 HA units of the virus). Virus replication in all cell types was detected even at passage 1, but the CPE was more pronounced in subsequent passages. The general CPE observed in all the cell types involved rounding of cells and detachment of dead cells. Interestingly, syncytia formation, which is the hallmark of many paramyxoviruses, was absent. The virus failed to produce plaques in any cell line despite the use of different overlay media and plaque assay conditions. Examination of infected cell culture supernatant by electron microscopy confirmed the presence of virus particles whose morphology was characteristic of family Paramyxoviridae. The viruses observed by negative staining were pleomorphic, enveloped and 150-200 nm in size.

Example 2

Determination of Complete Genome Sequence of AMPV-2 Strain Yucaipa

The genome of APMV-2 strain Yucaipa consists of 14,904 nt (SEQ ID NO: 1, GenBank accession no. EU338414) and thus is the smallest among the members of subfamily Paramyxovirinae reported to date (Wang et al., 2007, Curr. Genomics 4, 263-273). The genome length is a multiple of six, conforming to the "rule of six" common to members of subfamily Paramyxovirinae (Calain and Roux, 1993, J. Virol. 67, 4822-4830; Samal and Collins, 1996, J. Virol. 70, 5075-5082). The genome organization of Yucaipa virus is 3'-N-P/V-M-F-HN-L-5', resembling that of NDV. The percentage of the genome that encodes protein is 92.37%, the same as the average coding percentage (92%) of other members of subfamily Paramyxovirinae (Miller et al., 2003, Virology 317, 330-344). The length, position, and characteristics of the six genes and their intergenic sequences (IGS) are summarized in Table 1a and described in detail below. The 3' leader sequence of APMV-2 strain Yucaipa is 55 nt, a length that generally is conserved among almost all of the members of subfamily Paramyxovirinae (data not shown). The length of the 5' trailer sequence is 154 nt, a property that is variable among the members of Paramyxovirinae (data not shown). The first four nucleotides at the 3' end of the leader (3'-UGGU) and the 5' end of the trailer (5'-ACCA) sequences are identical in all Paramyxovirinae members. The first eight nucleotides of the leader (3'-UGGUUUGU) are conserved exactly in the avulaviruses (APMV-1 and APMV-6) and respiroviruses (BPIV-3, HPIV-3 and SeV), but are less well conserved compared with the other genera. The comparable sequences at the 5' end of the genome were somewhat less conserved but showed a similar pattern among the different genera. The sequences of the 34 nucleotides at the 3' leader and 5' trailer termini are complementary, suggestive of conserved elements in the 3' promoter regions of the genome and antigenome (data not shown). We also identified a three times repeated motif ($^{73}$UUCGGC$^{78}$, $^{79}$UAGAGC$^{84}$, $^{85}$UCUAGC$^{90}$) in the N gene and another three times repeated motif ($^{14832}$CUUUCG$^{14827}$, $^{14826}$AUUUCG$^{14821}$, $^{14820}$GCACCG$^{14815}$) in the 5' end of the genome. Thus, as seen in some paramyxoviruses, strain Yucaipa also has a bipartite promoter.

Example 3

Sequences of Transcription Gene-Start, Gene-End, and Intergenic Sequences

The conserved gene-start sequence of APMV-2 strain Yucaipa is 3'-C5GCUG(U)U(C/A) while the conserved gene-end sequence is 3'-A(U)AAUUC(G)U6 (data not shown). Thus, the first nucleotide of the mRNAs of APMV-2 strain Yucaipa (the gene-start signal) is 5'-G (mRNA-sense) compared to A, for most of the other members of Paramyxovirinae mRNA have an A residue (data not shown), which also is the nucleotide assignment at the 5' end of the genome and antigenome. Three other viruses in Paramyxovirinae that have G residue at the 5' end of their mRNAs are Menangle, Tioman and APMV-6 (Wang et al., 2003, Curr. Genomics 4, 263-273). The APMV-2 strain Yucaipa IGS vary in length between 3 and 23 nt (data not shown), whereas the IGS of other members of Paramyxovirinae are up to 45 nt in length (Wang et al., 2003, supra), and they all end with an A residue (data not shown), as observed in many paramyxoviruses (Collins et al., 1986, PNAS USA 83, 4594-4598; Crowley et al., 1988, Virology 164, 498-506; Kawano et al., 1991, Nucl. Acids Res. 19, 2739-2746; Chang et al., 2001, J. Gen. Virol. 82, 2157-2168), but otherwise there were no evident conserved IGS sequence motifs. The hexamer phasing positions of the gene-start sequences of APMV-2 strain Yucaipa are 2, 2, 2, 3, 3 and 3 (Tables 1a and 1b), which are different from those of the viruses within the genus *Avulavirus* namely, APMV-1 (2, 4, 3, 3, 2 and 5) and APMV-6 (2, 2, 2, 2, 2, 4 and 4) (Kolakofsky et al., 1998, J. Virol. 72, 891-899), while all the members of a particular genus within the family share the same pattern of hexamer phasing positions (Wang et al., 2003, supra).

TABLE 1a

Molecular features of genes and their proteins products of APMV-2 strain Yucaipa and subunit hexamer phasing position at gene start.

| Genes | Hexamer Phasing position at gene start | mRNA features (nt) Total Length | 5' UTR | ORF | 3' UTR | Intergenic sequence (nt) | Deduced protein Size (aa) | MW (Da) | pI |
|---|---|---|---|---|---|---|---|---|---|
| N | 2 | 1547 | 85 | 1374 | 88 | 7 | 457 | 50481.19 | 5.321 |
| P/V (P) | 2 | 1379 | 71 | 1200 | 108 | 7 | 399 | 42280.21 | 5.557 |
| P/V (V) | 2 | 1380 | — | — | — | — | 232 | 25134.59 | 5.508 |
| P/V (W) | 2 | 1381 | — | — | — | — | 207 | 22168.30 | 6.456 |
| M | 2 | 1280 | 42 | 1110 | 128 | 23 | 369 | 40417.07 | 9.254 |

TABLE 1a-continued

| Molecular features of genes and their proteins products of APMV-2 strain Yucaipa and subunit hexamer phasing position at gene start. | | | | | | | | | |
|---|---|---|---|---|---|---|---|---|---|
| | Hexamer Phasing position at gene | mRNA features (nt) | | | | Intergenic | Deduced protein | | |
| Genes | start | Total Length | 5' UTR | ORF | 3' UTR | sequence (nt) | Size (aa) | MW (Da) | pI |
| F | 3 | 1707 | 54 | 1611 | 42 | 9 | 536 | 57692.77 | 5.099 |
| HN | 3 | 1899 | 76 | 1743 | 80 | 3 | 580 | 63889.87 | 7.667 |
| L | 3 | 6834 | 21 | 6729 | 84 | — | 2242 | 252621.16 | 7.421 |

TABLE 1b

| Gene start, Gene end and intergenic sequences of APMV-2 strain Yucaipa | | | |
|---|---|---|---|
| Genes | Gene-End | IGS | Gene-start |
| /N | | | $C_5$GCUGUAG |
| N/P | AAAUUCU$_6$ | CCUGGGA | $C_5$GCUUCAA |
| P/M | AAAUUGU$_6$ | CUUCAAA | $C_5$GCUUCAG |
| M/F | AAAUUGU$_6$ | GAAUUGAUGUAUUGAAGUUGUAA SEQ ID NO: 80 | $C_5$GCUGUCG |
| F/HN | AAAUUCU$_6$ | AACCUUCCA | $C_5$GCUGUCG |
| HN/L | AAAUUCU$_6$ | GAA | $C_5$GCUUACG |
| L/ | UAAUUCU$_6$ | | |

Example 4

The Nucleoprotein (N) Gene

The N gene is 1547 nt long with a major ORF of 1374 nt. The encoded protein is 457 amino acids (aa) long, with a predicted molecular weight (Mr) of 50,481 kDa. The N protein of strain Yucaipa has 55.8% and 41.3% amino acid sequence identity, respectively, with that of APMV-6 and APMV-1 of genus *Avulavirus*. The extent of amino acid sequence identity with members of the other genera of subfamily Paramyxovirinae decreased in the order: rubula-viruses (36.5-41.4%), henipaviruses (28.9-29.4%), morbil-liviruses (23.7-24.2%), and respiroviruses (17.3-19.7%). An amino acid sequence motif that is highly conserved in the N proteins of members of Paramyxovirinae and is thought to be involved in N-N self assembly, F-X4-Y-X3-Φ-S-Φ-A-M-G, where X represents any amino acid residue and Φ represents an aromatic amino acid residue (Morgan, 1991), is seen within the central domain of the strain Yucaipa N protein ($^{324}$FAPANFSTLYSYAMG$^{338}$, position 324-338 of SEQ ID NO:37). In SeV and in other paramyxoviruses, residue Y260, needed for N protein binding with RNA, and residue F324, needed for correct self-assembly (Myers et al., 1997, Virology 229, 322-335), are also conserved at the same amino acid sequence number in strain Yucaipa.

Example 5

The Phosphoprotein (P) Gene and P/V/W Editing

The P gene is 1379 nt long with a major ORF of 1200 nt. The P protein is encoded by the unedited mRNA; the addition of a single G residue to the editing site would yield a predicted V protein; and the addition of 2 G residues would yield a predicted W protein, as is the case with NDV (Steward et al., 1993). The putative editing site of the strain Yucaipa P gene is 5'-AAAAAGGGG (mRNA sense) at nt position 2090-2102 in the viral RNA genome, while the P gene editing sequence of NDV and other paramyxoviruses with similar coding strategy is AAAAA(A)GGG. The P protein is 399 amino aa long, with a predicted Mr of 42.28 kDa; the V protein is 232 aa long with aMr of 25.13 kDa; the predicted W protein would be 207 aa length with a Mr of 22.16 kDa. The amino acid sequence of strain Yucaipa P protein has 28.1% and 27.5% identity, respectively, with that of APMV-1 and APMV-6 of genus *Avulavirus*. The extent of amino acid sequence identity with the proteins of members of the other genera of Paramyxovirinae decreased in the order: rubulaviruses (23-28%), morbilliviruses (15.8-16%), henipaviruses (14.9-15.4%), and respiroviruses (8.6-9.3%). The V protein has 34.2% and 34.4% amino acid sequence identity with that of APMV-1 and Porcine Rubulavirus (PoRV), respectively, and has 17 conserved residues with other paramyxoviruses including 7 cysteine residues in the C terminal portion that resemble the zinc-finger like motif found in other paramyxoviruses.

Example 6

The Matrix Protein (M) Gene

The M gene is 1280 nt long with a major ORF of 1110 nt. The encoded protein is 369 aa long, with a predicted Mr of 40.41 kDa. The matrix protein showed 42.5% and 31.2% amino acid sequence identity with those of APMV-6 and APMV-1, respectively. The extent of amino acid sequence identity with members of the other genera of Paramyxoviri-nae decreased in the order: rubulaviruses (30%), morbilli-viruses (18.5-21.8%), henipaviruses (18.2%), and respiro-viruses (16.4-18.1%).

Example 7

The Fusion Protein (F) Gene

The F gene is 1707 nt with a major ORF of 1611 nt. The F protein is 536 aa long with a predicted Mr of 57.69 kDa. Among the available paramxyxovirus sequences, the F protein of Yucaipa was most closely related (80.6%) to that of Murayama virus (MrV), a monkey paramyxovirus that is antigenically related to Yucaipa virus and for which the F and HN sequences are available (Nishikawa et al., 1977, J. Mol. Biol. 302, 205-217, GenBank accession no. D13990). In contrast, the Yucaipa virus F protein was less closely related to APMV-1 and APMV-6 (42.2% and 49.8% identity, respectively). The extent of amino acid sequence identity with members of the other genera of Paramyxovirinae decreased in the order: rubulaviruses (29.4-31.2%), henipaviruses (27.5-27.7%), morbilliviruses (21.9-26.4%), and respiroviruses (22.5-22.8%). The first 18 aa of the Yucaipa virus F protein are highly hydrophobic and are predicted to contain the signal sequence. Compared to the Yucaipa virus F gene sequence available in GenBank (accession no. AF422844), the present consensus sequence has nucleotide differences in F gene at positions 4309, 4310, 4786, 5099 and 5489 (assignments of G, C, C, C and T in our sequence compared to C, G, A, T and C in the previous sequence). This resulted in one amino acid difference at position 140, which is alanine in the present sequence and glutamic acid in the previous sequence. The alignment of the F protein cleavage sites of APMV-1, -2, -6 and MrV are shown in Table 8. The putative F protein cleavage site contained a monobasic residue but a phenylalanine at the beginning of the F1 subunit.

Example 8

The Hemagglutination-Neuraminidase Protein (HN) Gene

The HN gene is 1899 nt long with a single ORF of 1743 nt. The encoded protein is 580 aa long with predicted Mr of 63.86 kDa. The strain Yucaipa HN protein has 75% amino acid sequence identity with that of MrV and 43.6% and 36% identity with that of APMV-6 and APMV-1. There was a lower level of sequence identity with the HN proteins of rubulaviruses (29%), respiroviruses (21-23.7%), morbilliviruses (10.4-11.6%) and with the attachment protein of henipaviruses (17.6-18.2%). By aligning the HN sequence of APMV-1 and APMV-2 strain Yucaipa, the six conserved neuraminidase active sites were identified as R175, E400, R415, R505, Y533, E554 equivalent to R174, E401, R416, R498, Y526, E547 of NDV (Langedijk et al., 1997, J. Virol. 71, 6155-6167). The hexapeptide NRKSCS (position 235-240 of SEQ ID NO: 43), thought to form part of the sialic acid binding site is present at aa positions 235-240 (Mirza et al., 1994). Five potential N-linked glycosylation sites are found, at N 120, N 279, N 346, N 391, N 488, compared to six potential sites in NDV Beaudette C strain at N119, N341, N433, N481, N500 and N538. The HN protein of strain Yucaipa has all the 11 conserved cysteine residues in the region corresponding to the globular head, as also found in NDV.

The sequence that we determined for the HN gene has two differences compared to the Yucaipa virus HN gene sequence available in GenBank (accession no. AF422844). One involves position 6774 (residue T compared to residue G in the previous sequence) resulting in a histidine in our sequence compared to glutamine in the previous sequence. The second difference was found at position 7768 (T to G), which did not result in an amino acid coding change.

Example 9

The Large Polymerase Protein (L) Gene

The L gene is 6834 nt long, with a 6729 nt long ORF. The L protein is 2242 aa long with predicted Mr of 252.62 kDa. The Yucaipa L protein has 44.1% and 39.6% amino acid sequence identity with that of APMV-6 and APMV-1. The extent of amino acid sequence identity with the L proteins of members of the other general of Paramyxovirinae decreased in the order: rubulaviruses (37.5%), respiroviruses (31.2%), morbilliviruses (30.3%), and henipaviruses (25.2-25.7%). The six strongly conserved linear domains of L proteins of nonsegmented negative-strand RNA viruses (Poch et al., 1990, J. Gen. Virol. 71, 1153-1162) are also identified within the L protein of strain Yucaipa. The conserved GDNQ sequence motif within domain III concerned with L protein transcription activity (Schnell and Conzelmann, 1995, Virology 214, 522-530) was found in the L protein of strain Yucaipa at aa positions 774-777.

Example 10

Phylogenetic Analysis

Phylogenetic trees were generated from amino acid sequence alignments of the N, P, M, F, HN and L proteins of strain Yucaipa with the cognate proteins of prototype viruses of all the five genera of family Paramyxoviridae. The phylogenetic trees clearly indicate the close genetic relationship between APMV-2 strain Yucaipa and APMV-6, and strongly supporting the classification of APMV-1, APMV-2, APMV-3, APMV-4 and APMV-6 under the genus *Avulavirus* (data not shown).

Discussion

Nine serological types of avian paramyxoviruses have been isolated around the world. The disease potential and molecular features of these viruses are mostly unknown apart from APMV-1. It is important to characterize these common viruses. Here, we present the complete genome sequence of APMV-2 strain Yucaipa. APMV-2 strain Yucaipa has the shortest genome in subfamily Paramyxovirinae (14,904 nt) described to date, being 276 nt shorter than the next smallest genome, that of PoRV. The pattern of sequence relatedness clearly places APMV-2 in genus *Avulavirus*, consistent with the International Committee on Taxonomy of Viruses statement that the amino acid sequence relationships are the main criteria for grouping viruses into genera within the family Paramyxoviridae (Lamb et al., 2000, supra). This is offered with the caveat that most of the serotypes of *Avulavirus* remain to be sequenced, and so the extent of diversity within the genus is unknown. Sequence identity between Yucaipa virus and members of the other genera of subfamily Paramyxovirinae was greatest with rubulaviruses and usually (except for the L protein) was least with the respiroviruses, and was intermediate with the morbilliviruses and henipaviruses.

The classification of Yucaipa virus in *Avulavirus* also is supported by (i) the absence of a C protein, which is present in respiroviruses, morbilliviruses, and henipaviruses and is encoded by an alternative ORF in the P gene, (ii) the presence of intergenic regions of nonconserved length and sequence, as are found in avulaviruses and rubulaviruses but not in respiroviruses, morbilliviruses, or henipaviruses, and (iii) the pattern of P/V RNA editing in which the non edited mRNA encodes P and an edited version encodes V, which distinguishes avulaviruses and the other members of subfamily Pneumovirinae from rubulaviruses. Whereas most members of subfamily Paramyxovirinae initiate their mRNAs with an A residue, Yucaipa virus is predicted to use G, a feature that is shared with APMV-6 (but APMV-1), the rubulaviruses, Tioman and Menangle viruses, and HRSV and HMPV of subfamily Pneumovirinae.

The paramyxovirus F protein is synthesized as an inactive precursor (F0) and is cleaved to two biologically active disulfide bonded F1-F2 subunits by host protease (Lamb and Parks, 2007, In: Knipe, and Howley, Eds., Fields Virology, 5th ed. Lippincott Williams and Wilkins, Philadelphia, pp. 1449-1496). The F protein cleavage site is a well-characterized determinant of NDV pathogenicity in chickens.

Virulent NDV strains typically contain a polybasic cleavage site that contains the preferred recognition site for furin (R-X-K/R-R↓, SEQ ID NO:81) which is an intracellular protease that is present in most cells. This provides for efficient cleavage in a wide range of tissues, making it possible for virulent strains to spread systemically. In contrast, avirulent NDV strains typically have basic residues at the −1 and −4 positions relative to the cleavage site and depend on secretory protease (or, in cell culture, added trypsin) for cleavage. This limits the replication of avirulent strains to the respiratory and enteric tracts where the secretory protease is found. The putative cleavage site of strain Yucaipa F protein (DKPASR↓F, position 93-100 of SEQ ID NO:42) has basic residues (underlined), which is similar but not identical to the pattern of avirulent NDV strains. Conversely, the F1 subunit of Yucaipa virus begins with a phenylalanine residue, as is characteristic of virulent NDV strains, rather than a leucine reside, as seen in most avirulent NDV strains (Collins et al., 1993, Arch. Virol. 128, 363-370). We found that the Yucaipa virus replicated in a wide range of cells without the addition of exogenous protease, and the inclusion of protease did not improve the efficiency of replication. This is incongruent with the observation that the F protein cleavage site is not polybasic and does not conform to the preferred furin motif. Thus, the Yucaipa virus is an example of paramyxovirus in which efficient intracellular cleavage occurs in the absence of an apparent furin motif. As another example, whereas wild type SeV contains a single basic residue at the cleavage site (GAPQSR↓, SEQ ID NO:82) and is strictly dependent on added trypsin for infectivity in vitro, a number of experimentally derived mutants of SeV have been described that are trypsin-independent and yet have not acquired a furin site (Okada et al., 1998, Arch. Virol. 142, 2343-2352). Sequence analysis identified a number of mutations occurring upstream of the cleavage site, one being a S-to-P substitution at position −2 relative to the cleavage site and another involving the loss of an upstream glycosylation site. It may be that these mutations altered the local protein structure to make the cleavage site more accessible and thus more readily cleaved. Certain naturally occurring isolates of HPIV-3 contain glutamate at the −2 position (DPRTKR↓, SEQ ID NO:83), thus lacking a furin site, whereas other isolates possess a furin site. The two types of isolates appeared to replicate with equal efficiency in vitro and in the respiratory tract of rhesus monkeys (Coelingh and Winter, 1990, J. Virol. 64, 1329-1334). Yet another example involves NiV and HeV, in which intracellular cleavage does not depend on a furin site, and indeed does not even require a basic residue in the −1 position (Moll et al., 2004, J. Virol. 78, 9705-9712). This suggests that some paramyxovirus F proteins can be cleaved by proteases in addition to the furin- or trypsin-related ones. However, the study with the SeV mutants indicated above showed that, while a number of mutants lacking the preferred furin cleavage site were competent for efficient multicycle replication in vitro without added protease, some were restricted in their ability to form plaques and spread systemically. Similarly, the lack of a furin site might explain the inability of Yucaipa virus to form plaques and might also correlate with reduced virulence in birds.

The F and HN proteins of strain Yucaipa were more closely related to those of MrV (80.6% and 75% amino acid sequence identity (respectively) than those of any other paramyxovirus, including NDV. MrV is a paramyxovirus that was isolated in 1973 from cynomolgous monkeys experiencing mild respiratory tract disease (Nishikawa et al., 1977, Jpn. J. Med. Sci. Biol. 30, 191-204). MrV exhibited no serological relationship with mammalian paramyxoviruses, but cross-reacted with APMV-2 strain Yucaipa. The high level of sequence relatedness between the F and HN gene and proteins of Yucaipa virus and MrV (F and HN are the only sequences available for MrV) provide strong support for the interpretation that these viruses indeed are members of the same serotype, APMV-2. *Avulavirus* appears to contain at least one virus that can infect and cause disease in a non-avian host. Yucaipa virus also was shown to infect and cause disease in a non-avian host, namely guinea pigs. These observations support the previous suggestion that MrV might have evolved by adapting in monkeys after infection with APMV-2 strain Yucaipa or a similar avian AMPV-2 strain (Kusagawa et al., 1993, Virology 194, 828-832).

As a first step towards understanding the serological and genetic relationship among APMV-2 strains, we have determined the complete genome sequences of three other strains of APMV-2; Bangor, England and Kenya, isolated from a finch, a chicken and a gadwell duck, respectively, and here below describe comparison with the complete genome sequence of prototype strain Yucaipa and other paramyxoviruses. Our sequence and antigenic analyses suggested that APMV-2 strains can be classified into two genetic subgroups under a single serotype.

The following Materials and Methods were used in the Examples that follow.

Materials and Methods

Virus and Cells

APMV-2/Chicken/Yucaipa/Cal/56 (APMV-2 Yucaipa) and APMV-2/Finch/N.Ireland/Bangor/73 (APMV-2 Bangor) were received from the National Veterinary Services Laboratory, Ames, Iowa, USA and APMV-2/Chicken/England/7702/06 (APMV-2 England) and APMV-2/Gadwell/Kenya/3/80 (APMV-2 Kenya) were obtained from Veterinary Laboratories Agency, Weybridge, UK. The viruses were grown in 9-day-old embryonated, specific pathogen-free (SPF) chicken eggs. Hemagglutination (HA) titers were determined using 0.5% chicken RBC at room temperature. The ability of the viruses to replicate in cell culture was examined in two established cell lines, namely DF1 chicken fibroblast and Vero African green monkey kidney cells. Both cell lines were grown in Dulbecco's MEM containing 10% fetal bovine serum (FBS) in a 37° C. incubator with 5% $CO_2$.

Replication of Viruses in Cell Cultures

Cell monolayers (DF1 and Vero) were infected with a $10^{-3}$ dilution of $2^8$ HA units of egg-grown APMV-2 strains Yucaipa, Bangor, England and Kenya and, after 1 h of adsorption, the viral inoculum was replaced with maintenance medium containing 2% FBS with or without the supplementation of exogenous protease (10% allantoic fluid or 1 μg/ml trypsin). The cells were observed daily for cytopathic effects (CPE) and the supernatants of the infected cells were collected every 24 h until the fifth day post-infection (dpi). Virus titers were determined by serial end-point dilution on monolayers of DF1 cells in 96-well plates. The infected cells were immunostained using polyclonal antisera raised against each of the viruses in chickens. Virus titers ($TCID_{50}$/ml) were calculated using the Reed & Muench method (Reed & Muench, 1938, Amer. J. of Hyg. 27, 493-497). The ability of the viruses to produce plaques was tested in both cell lines under various conditions, including 1% methylcellulose, 1% low melting agar, or 0.8% noble agar with or without magnesium sulfate (25 mM) and 1% diethylaminoethyl dextran (30 μg/ml), and with and without allantoic fluid. The monolayers were stained with either crystal violet or neutral red in attempts to detect plaques.

Serological Analysis

Antisera against APMV-2 strains Yucaipa, Bangor, England and Kenya were prepared separately by single infection of 2-week-old chickens via the intraocular (10) and intranasal (IN) routes, mimicking natural infection. Briefly, groups of three 2-week-old chickens per group were infected with each virus ($2^8$ HAU) at separate times to avoid cross-infection. Two weeks after infection, sera were collected and stored at −20° C. HN-specific antibody titers in the serum samples were determined by HI assay using the homologous virus and chicken RBC as described previously (Alexander, 1997, supra). The cross-reactivity of the sera was determined by HI assay against heterologous APMV-2 strains. The ability of immunized chicken sera to cross-neutralize heterologous APMV-2 strains was determined by a focus reduction microneutralization assay using standard procedures (Borisevich et al., 2007, J. Virol. Methods 147, 197-205). Briefly, different dilutions of sera were mixed with a constant titer of virus ($10^3$ $TCID_{50}$/ml), incubated for 2 h at room temperature, and transferred to monolayers of DF1 cells in 96-well plates. The plates were incubated for three days at 37° C. with 5% $CO_2$. Each plate included both uninfected and infected cell controls. On the third day, the culture medium was removed and cells were fixed with methanol for 30 min and washed with PBS three times. The fixed cells were immunostained to identify virus-containing wells, and a 50% focus reduction was considered as the end point of the titration.

Pathogenicity Tests

The virulence of the APMV-2 strains was determined by two standard pathogenicity tests for APMV-1: mean death time (MDT) in 9-day-old embryonated SPF chicken eggs and intracerebral pathogenicity index (ICPI) test in 1-day-old SPF chicks (Alexander 1989, supra). Briefly, for MDT, a series of 10-fold ($10^{-6}$-$10^{-9}$) dilutions of fresh infective allantoic fluid in PBS was made and 0.1 ml of each dilution was inoculated into the allantoic cavities of five 9-day-old SPF embryonated chicken eggs (BEE eggs company, PA), which were incubated at 37° C. The eggs were candled 3 times a day for the next 7 days and the time of embryo death, if any, were recorded. The minimum lethal dose (MLD) is the highest virus dilution that kills all the embryos. The MDT is the mean time in hours for the MLD to kill all the inoculated embryos. The MDT has been used to classify APMV-1 strains into the following groups: velogenic strains (taking less than 60 h to kill); mesogenic strains (taking 60-90 h to kill); and lentogenic strains (taking more than 90 h to kill).

For ICPI, 0.05 ml (1:10 dilution) of fresh infective allantoic fluid of each virus was inoculated into groups of ten 1-day-old SPF chicks via the intracerebral route. The inoculation was done using a 27-gauge needle attached to a 1 ml stepper syringe dispenser that was set to dispense 0.05 ml of inoculum per bird. The birds were inoculated by inserting the needle up to the hub into the right or left rear quadrant of the cranium. The birds were observed for clinical symptoms and mortality once every 8 h for a period of 10 days. At each observation, the birds were scored: 0, if normal, 1, if sick and 2, if dead. The ICPI is the mean score per bird over the 10-day period. Highly virulent (velogenic) viruses give values approaching 2, and avirulent (lentogenic) viruses give values close to 0.

Virus RNA Isolation and Complete Genome Sequencing

The viral RNA was isolated from the allantoic fluid of virus-infected eggs using RNeasy kit according to the manufacturer's instructions (QIAGEN, USA, Valencia, Calif.). Each of the APMV-2 genomes, except for the 3' and 5' termini, was amplified into cDNAs using primers designed from the published APMV-2 strain Yucaipa (Table 2). All primers were commercially synthesized from Integrated DNA Technologies Inc, USA. Briefly, the first-strand cDNA was synthesized from viral RNA by Superscript II kit using random hexamers according to manufacturer's instructions (Invitrogen, Carlsbad, Calif.). PCR was performed using virus specific or consensus primers and Taq polymerase (Invitrogen). The PCR fragments were cloned into TOPO TA cloning kit (Invitrogen) and the clones were sequenced using vector primers. In addition, selected PCR products were purified by agarose gel electrophoresis and sequenced directly. The DNA sequencing was carried out using BigDye® Terminator v3.1 cycle sequencing kit (Applied Biosystems Inc, USA) in ABI 3130×l genetic analyzer. Every nt in the genome was sequenced at least three times and once directly from RT-PCR product without cloning, thus ensuring a consensus sequence. The sequences of the 3' and 5' genomic ends were determined from cDNA prepared by rapid amplification of cDNA ends (RACE) as described previously (Subbiah et al., 2008, Virus Res. 137, 40-48).

Virus Genome Sequence Alignment and Phylogenetic Analyses

Sequence compilation and prediction of ORFs were carried out using the SeqMan and EditSeq programs in the Lasergene 6 (DNASTAR, Madison, Wis.) software package. The search for matching protein sequences in GenBank was done using the blastp program of the same package. The bootstrap values in phylogenetic tree were calculated using 1000 replicas and the construction of phylogenetic trees was performed by maximum parsimony method using MEGA 4 software (Tamura et al., 2007, Mol. Biol. Evol. 1596-1599).

TABLE 2

Primers used to amplify APMV-2 genome based on previously available genome sequence of APMV-2 prototype strain Yucaipa.

| Primer name | position within APMV-2 strain Yucaipa genome, SEQ ID NO: 1 | Primer sequence |
|---|---|---|
| Gene Start forward | Gene start consensus | *NNNNNNNGGGGGCGA |
| Gene End reverse | Gene end consensus | *NNNNNNNNNNNTTTTTTCTTAA |
| N Forward | 388-415 | ACATGCGAGCTCACGCAACCCTTGCAGC |
| N Reverse | 1019-1044 | GCCTGATCAAGGACGACATCTTCTTC |
| P Forward | 1758-1781 | CGAAGTCAAGGGCCCGCAAACAAC |
| P Reverse | 2464-2484 | CTGACTAATCTCATTCTTTAT |
| M Forward | 3135-3157 | CCAAAGAGTTGCAGCAGCAAATC |
| F Forward | 5217-5242 | AGTGTCACTACACCAAAAGGAGAAGG |
| HN Forward | 6698-6719 | CCAGTATGTATATCTCTCTGGG |
| L1 Forward | 8869-8890 | ATGCTAGTGAGACACACGCAGG |

TABLE 2-continued

Primers used to amplify APMV-2 genome based on previously available genome sequence of APMV-2 prototype strain Yucaipa.

| Primer name | position within APMV-2 strain Yucaipa genome, SEQ ID NO: 1 | Primer sequence |
|---|---|---|
| L1 Reverse | 10422-10441 | GAATACACAAAGAATGATTG |
| L2 Forward | 11967-11986 | ATATATCAGCAAATCATGCT |
| L2 Reverse | 13314-13332 | CAGCATACTTGTACCAGCT |
| L3 Forward | 14170-14186 | TCACCCTATTCGGACAG |

Database Accession Numbers

The complete genome sequences of APMV-2 strains Bangor, England and Kenya were submitted to GenBank (accession number HM159995, HM159993 and HM159994, respectively). Accession numbers for other paramyxovirus sequences used in this study were: Avulaviruses: APMV-1, AF07761; APMV-2 strain Yucaipa, EU338414; APMV-3, EU403085; APMV-4KR, EU877976; APMV-4HK, FJ177514; APMV-5, GU206351.1; APMV-6TW, NC 003043; APMV-6HK, EU622637; APMV-6FE, EF569970; APMV-7, FJ231524; APMV-8DEL, FJ215863; APMV-8WAK, FJ215864; APMV-9, EU910942. Rubulaviruses: HPIV-2, NC_003443; SV5 (also known as Parainfluenza virus 5), NC_006430; MuV, NC_002200; simian virus 41 (SV41), NC_006428. Respiroviruses: HPIV-1, NC_003461; HPIV-3, NC_001906; SeV, NC_001552, BPIV-3, NC_002161. Henipaviruses: NiV, NC_002728; HeV, NC_001906. Morbilliviruses: CDV, NC_001921; MeV, Af266288; phocine distemper virus (PDV), NC_006383; rinderpest virus (RPV), NC_006296; peste des petits ruminants virus (PPRV), NC_006383; dolphin morbillivirus (DMV), NC_005283; other paramyxovirus: Atlantic salmon paramyxovirus (ASPV), EF646380; Beilong virus (BeV), NC_007803; Fer-de-Lance virus (FDLV), NC_005339; J virus (JV), NC_007454; Menangle virus (MenV), NC_007620; Mossman (MoV), NC_005339; Tupaia paramyxovirus (TpV), NC_002199*; Pneumoviruses*: HRSV, NC001781; BRSV, NC001989. *Metapneumoviruses*: AMPV, NC007652; HMPV, NC004148.

Example 11

In Vitro Growth Characteristics of APMV-2 Strains Bangor, England and Kenya

APMV-2 strains Bangor, England and Kenya yielded titers of $2^{10}$-$2^{12}$ HA units in 9-day-old embryonated SPF chickens eggs at 4 dpi. The inclusion of exogenous protease, either 10% allantoic fluid or 1 μg/ml trypsin, did not affect the efficiency of replication of these viruses in cell culture, indicating a lack of requirement of external proteases for efficient cleavage of the F protein. The viruses grew more efficiently in DF1 cells than in Vero cells (data not shown). Viral CPE involved rounding and detachment of the cells. The growth kinetics and the CPE of all the three strains were similar to those of APMV-2 prototype strain Yucaipa. None of the strains produced syncytia or formed plaques but caused single cell infections similar to that of APMV-2 strain Yucaipa (data not shown).

Example 12

Antigenic Relationship Among APMV-2 Strains

The antigenic relationship among APMV-2 strains Yucaipa, Bangor, England and Kenya was evaluated by reciprocal HI tests using strain specific convalescent sera raised by a single infection of chickens via the IN/10 route. Each of the antiserum exhibited a 2 to 16-fold difference in HI titer between the homologous and heterologous strains (Table 3). Conversely, the HI titer of antisera specifically against strains Bangor, England and Kenya were 4, 4 and 8-fold higher against the homologous strains than against the prototype strain Yucaipa. The antiserum against strain Bangor showed 2-, 2-, and 4-fold higher HI titer against strain Bangor than against strains England, Kenya, and Yucaipa. The antiserum specific for strain England showed 4-fold higher titer against strain England and Kenya than against strains Bangor and Yucaipa. The antiserum specific for strain Kenya showed 8-, 16- and 2-fold higher titers against the homologous strain Kenya than against strains Yucaipa, Bangor, and England, respectively. The ability of antisera to neutralize homologous and heterologous APMV-2 strains was assessed by a microneutralization assay in DF1 cells. The antiserum specific for strain Yucaipa showed 4-fold higher neutralization titer against homologous strain Yucaipa and strains England and Kenya than against strain Bangor. On the contrary, antisera specific for strain Bangor showed 4-fold higher neutralization titer against homologous strain Bangor than against prototype strain Yucaipa and 2-fold higher neutralization titer against homologous strain Bangor than against strains England and Kenya. The antisera specific to strains England and Kenya showed 4-fold higher neutralization titers against their homologous strains compared to those against strains Yucaipa and Bangor, while showing 2-fold difference between either of the strains (Table 3). These reactions indicated the existence of a low level of antigenic differences among APMV-2 strains. These results suggested that the strains Yucaipa, England and Kenya represented one antigenically-distinct subgroup while strain Bangor represented a second subgroup, a distinction that was not observed in most, but not every, comparison.

Example 13

The Pathogenicity of APMV-2 Strains

The pathogenicity of APMV-2 strains Bangor, England and Kenya was evaluated by MDT in 9-day-old embryonated SPF chicken eggs and ICPI test in 1-day-old chicks. The MDT and ICPI values for all the three APMV-2 strains were >168 h and 0, respectively, similar to those of APMV-2 strain Yucaipa (>168 h and 0, respectively). These results indicated that these APMV-2 strains are avirulent in chickens, similar to lentogenic NDV strains.

Example 14

Determination of the Complete Genome Sequences of APMV-2 Strains Bangor, England and Kenya We determined the complete genome sequences of APMV-2 strains Bangor, England and Kenya. A number of the initial cDNAs in this analysis was synthesized using primers derived from the published sequence of APMV-2 strain Yucaipa (Table 2). The 3' and 5' ends of each genome were determined by RACE procedures (Materials and Methods). Every nt in each complete sequence was confirmed in uncloned RT-PCR cDNA, providing a consensus sequence.

TABLE 3

Antigenic analyses of APMV-2 strains Yucaipa, Bangor, England and Kenya using antisera from chickens infected with the individual strains.

| APMV-2 antiserum | APMV-2 strains | Cross HI titer[a] | Neutralization titer[b] |
|---|---|---|---|
| strain Yucaipa | Yucaipa | 160 | 40 |
| | Bangor | 20 | 10 |
| | England | 40 | 40 |
| | Kenya | 40 | 40 |
| strain Bangor | Yucaipa | 20 | 10 |
| | Bangor | 80 | 40 |
| | England | 40 | 20 |
| | Kenya | 40 | 20 |
| strain England | Yucaipa | 40 | 20 |
| | Bangor | 40 | 20 |
| | England | 160 | 80 |
| | Kenya | 160 | 40 |
| strain Kenya | Yucaipa | 80 | 20 |
| | Bangor | 40 | 20 |
| | England | 320 | 40 |
| | Kenya | 640 | 80 |

[a]Cross HI titer is the reciprocal of the highest dilution of antisera that inhibited 4 HA units of the virus.
[b]Neutralization titer was defined as the reciprocal of highest dilution of antisera that caused 50% reduction in the number of infected wells compared to the positive control wells.

The genome of strain England is identical in length (14904 nt) to that of strain Yucaipa, whereas the genome lengths of strains Bangor (15024 nt) and Kenya (14916 nt) are slightly larger than that of strain Yucaipa (14904 nt). The nt lengths of the genomes of all three strains are multiple of six, as in the case of the previously reported sequence for strain Yucaipa. Thus all three strains conform to the rule of six, which is a characteristic of the genome of all members of subfamily Paramyxovirinae (Kolakofsky et al., 1998, supra). All three APMV-2 strains have the gene order of $^{3'}$N-P/V/W-M-F-HN-L$^{5'}$, which is the same as previously reported for strain Yucaipa.

The complete genome and predicted proteins of strain Bangor have 70.4% nt and 75.3% aggregate aa sequence identity with those of the previously sequenced strain Yucaipa, and have 69.4% and 70.8% nt and 76.15% and 76.3% aggregate aa sequence identity with strains England and Kenya, respectively. In contrast, strains England and Kenya are much more closely related to strain Yucaipa, with nt sequence identities of 94.5% and 88%, respectively, and aggregate aa sequence identities of 96.1% and 92.4%, respectively. Thus, strains Yucaipa, England and Kenya are genetically closely related, whereas strain Bangor is somewhat distinct. This is consistent with the finding noted before that strain Bangor is distinct antigenically, and provides unequivocal evidence for dimorphism within the APMV-2 serotype.

The 3'-leader sequences of APMV-2 strains consist of 55 nt, a length that is conserved among almost all the members of the subfamily Paramyxovirinae. The nt sequences of the leader regions of strains Bangor and Yucaipa shows differences at 9 out of 55 nt positions, while those of strains England and Kenya are 100% identical to strain Yucaipa (Table 4). The lengths of trailer regions of APMV-2 strains England and Kenya are 154 nt each, same as strain Yucaipa. But the length of trailer region of strain Bangor is 173 nt (Table 4). This difference accounted for most of the difference in genome length between strain Bangor versus the others. The sequence of trailer region of strains England and Kenya are 100% identical to strain Yucaipa, but the sequence of strain Bangor had only 51.3% nt identity with the other three strains. The proposed GS and GE signal sequences are highly conserved among the APMV-2 strains (Table 4). In general, the conserved GS and GE sequences of all the four strains are (mRNA-sense) 5'-GGGGGCGA(A/C)(A/T) and 5'-T(T/A)(A/T)(A/G)NAAAAA respectively. In strain Bangor, the GS and GE sequences had a number of single nt variations compared to the other three strains (Table 4).

TABLE 4

Nucleotide (nt) sequence alignment of the leader region (A) and of the 5'-terminal 60 nt of the trailer region (B) of the indicated APMV-2 strains, shown 3' to 5' in negative sense. Dots indicate identity with strain Yucaipa. Sequences are in negative-sense. Numbers indicate nt position.

(A)

APMV-2 Yucaipa-SEQ ID NO: 1
1 UGGUUUGUUCCUUAUCCAUUCGUUGCAUUUAGAAUCUAUUUUGGUAUCUUAGGCA 55
APMV-2 Bangor
1 ..............................GAC.........UU.GA..G.A... 55
APMV-2 England
1 ....................................................... 55
APMV-2 Kenya
1 ....................................................... 55

(B)

APMV-2 Yucaipa-SEQ ID NO:1
AAACCUUAUAUUCGUGACGUAUUAGUGACUCAAUGCAACGAAACGAUAAGGUACAGACCA 14904
APMV-2 Bangor
U.UG.G.GG..AUUA.GUUA...UAAA.AA..G..........G...U...A...A.... 15024
APMV-2 England
............................................................ 14904
APMV-2 Kenya
............................................................ 14916

The intergenic sequences (IGS) of APMV-2 strains vary in length from 3 to 23 nt and are exactly conserved in length between the N, P, M and F genes (Table 5). The IGS sequences of strain England are 100% identical in length and sequence to strain Yucaipa, and the IGS sequences of strain Kenya are also are identical in length and sequence to strain Yucaipa except between HN and L genes. In contrast, the IGS between the F and HN in strain Bangor is only 4 nt in length compared to 9 nt in length in the other three strains, and the IGS between HN and L is 8 nt in length in strains Bangor and Kenya compared to 3 nt in length in the other two strains. In addition, the IGS sequences of strain Bangor have less than 50% nt identity with those of strain Yucaipa.

Example 15

The Nucleocapsid Protein (N) Gene

The N gene of APMV-2 strains Bangor, England and Kenya is 1547 nt in length and encodes a N protein of 457 aa (Table 5), as is the case for strain Yucaipa. The N protein of strains Bangor, England and Kenya has 90.4%, 99.3% and 94.5% aa sequence identity, respectively, with that of strain Yucaipa (Table 6). An amino acid sequence motif that is highly conserved in the N proteins of members of subfamily Paramyxovirinae and is involved in N-N self assembly, F-X4-Y-X3-Φ-S-Φ-A-M-G, where X represents any amino acid residue and Φ represents an aromatic amino acid residue (Morgan, 1991, Virology 180, 126-134), is present within the central domain of the N protein of each the four strains and is exactly conserved among all four strains ($^{32}$FAPANFSTLYSYAMG$^{338}$, SEQ ID NO:37).

Example 16

The Phosphoprotein (P) Gene and P/V/W Editing

The P gene of APMV-2 strains Bangor, England and Kenya is 1379 nt in length and encodes a P protein of 399 aa (Table 5), as is the case for strain Yucaipa. The P protein of strains Bangor, England and Kenya has 55.8%, 87.7% and 99.5% aa sequence identity, respectively, with that of strain Yucaipa (Table 6). The P gene of all four APMV2 strains contains a putative P gene editing site (3'-UUUUUCCCC (negative-sense), located at nt position 2092-2100 in the viral RNA genome. The addition of a single G residue to the editing site would yield a predicted V protein and the addition of 2 G residues would yield a predicted W protein, as is the case with NDV (Steward et al., 1993, J. Gen. Virol. 74, 2539-2547). For all four APMV-2 strains, the predicted V protein is 232 aa in length. For all four strains, the V protein domain contains the conserved cysteine rich motif that is characteristic of most members of subfamily Paramyxovirinae (Table 7). This 52-aa motif was completely conserved among strains England, Kenya, and Yucaipa, whereas that of strain Bangor has a number of aa difference. The predicted W protein of strains England and Kenya is 207 aa in length, as also is the case for strain

TABLE 5

Molecular features of the genes and their deduced protein products for the four strains of APMV-2.

| | | Gene-start (GS) | | Gene-end (GE) | |
|---|---|---|---|---|---|
| | | Locations* | Sequences | Locations* | Sequences |
| N | Yucaipa | 56-65 | GGGGGCGACA | 1592-1602 | TTAAGAAAAAA |
| | Bangor | 56-65 | GGGGGCGACA | 1592-1602 | TTAAGAAAAAA |
| | England | 56-65 | GGGGGCGACA | 1592-1602 | TTAAGAAAAAA |
| | Kenya | 56-65 | GGGGGCGACA | 1592-1602 | TTAAGAAAAAA |
| P | Yucaipa | 1610-1619 | GGGGGCGAAG | 2978-2988 | TTAACAAAAAA |
| | Bangor | 1610-1619 | GGGGGCGAAT | 2978-2988 | TAAGAAAAAAA |
| | England | 1610-1619 | GGGGGCGAAG | 2978-2988 | TAAGAAAAAAA |
| | Kenya | 1610-1619 | GGGGGCGAAG | 2978-2988 | TTAACAAAAAA |
| P/V | Yucaipa | 1610-1619 | GGGGGCGAAG | 2978-2988 | TTAACAAAAAA |
| | Bangor | 1610-1619 | GGGGGCGAAT | 2978-2988 | TAAGAAAAAAA |
| | England | 1610-1619 | GGGGGCGAAG | 2978-2988 | TAAGAAAAAAA |
| | Kenya | 1610-1619 | GGGGGCGAAG | 2978-2988 | TTAACAAAAAA |
| P/W | Yucaipa | 1610-1619 | GGGGGCGAAG | 2978-2988 | TTAACAAAAAA |
| | Bangor | 1610-1619 | GGGGGCGAAT | 2978-2988 | TAAGAAAAAAA |
| | England | 1610-1619 | GGGGGCGAAG | 2978-2988 | TAAGAAAAAAA |
| | Kenya | 1610-1619 | GGGGGCGAAG | 2978-2988 | TTAACAAAAAA |
| M | Yucaipa | 2996-3005 | GGGGGCGAAG | 4265-4275 | TTAAGAAAAAA |
| | Bangor | 2996-3005 | GGGGGCGAAT | 4289-4299 | TTTAGAAAAAA |
| | England | 2996-3005 | GGGGGCGAAG | 4265-4275 | TTAAGAAAAAA |
| | Kenya | 2996-3005 | GGGGGCGAAG | 4265-4275 | TTAAGAAAAAA |
| F | Yucaipa | 4299-4308 | GGGGGCGACA | 5995-6005 | TTAAGAAAAAA |
| | Bangor | 4323-4332 | GGGGGCGAAA | 6072-6082 | TTAAGAAAAAA |
| | England | 4299-4308 | GGGGGCGACA | 5995-6005 | TTAAGAAAAAA |
| | Kenya | 4299-4308 | GGGGGCGACA | 5995-6005 | TTAAGAAAAAA |
| HN | Yucaipa | 6015-6024 | GGGGGCGACA | 7903-7913 | TTAAGAAAAAA |
| | Bangor | 6087-6096 | GGGGGCGAAA | 7970-7980 | TTAATAAAAAA |
| | England | 6015-6024 | GGGGGCGACA | 7903-7913 | TTAAGAAAAAA |
| | Kenya | 6015-6024 | GGGGGCGACA | 7903-7913 | TTAAGAAAAAA |

TABLE 5-continued

Molecular features of the genes and their deduced protein products for the four strains of APMV-2.

| | | Gene-start (GS) | | Gene-end (GE) | |
|---|---|---|---|---|---|
| | | Locations* | Sequences | Locations* | Sequences |
| L | Yucaipa | 7917-7926 | GGGGGCGAAT | 14740-14750 | TTAAGAAAAAA |
| | Bangor | 7989-7998 | GGGGGCGAAT | 14842-14851 | TTAAGAAAAAA |
| | England | 7917-7926 | GGGGGCGAAT | 14740-14750 | TTAAGAAAAAA |
| | Kenya | 7929-7938 | GGGGGCGAAT | 14752-14762 | TTAAGAAAAAA |

Sequence locations for strain Yucaipa are from SEQ ID NO: 1;
for strain Bangor from SEQ ID NO: 2,
for strain England from SEQ ID NO: 3,
for strain Kenya from SEQ ID NO: 4.

TABLE 6

Percent amino acid percentage identity between APMV-2 strains Yucaipa, Bangor, England and Kenya for the indicated proteins.

| Strains | Bangor | England | Kenya | Bangor | England | Kenya | Bangor | England | Kenya |
|---|---|---|---|---|---|---|---|---|---|
| | N | | | P | | | M | | |
| Yucaipa | 90.4 | 99.3 | 94.5 | 55.8 | 87.7 | 99.5 | 85.1 | 99.7 | 98.4 |
| Bangor | | 89.9 | 89.7 | | 60.8 | 55.3 | | 84.8 | 85.1 |
| England | | | 94.1 | | | 87.2 | | | 98.1 |
| Kenya | | | | | | | | | |
| | F | | | HN | | | L | | |
| Yucaipa | 79.1 | 99.8 | 98.1 | 75 | 96 | 76.2 | 66.5 | 94.2 | 87.8 |
| Bangor | | 78.9 | 77.6 | | 75.2 | 85.1 | | 67.4 | 68.2 |
| England | | | 97.9 | | | 76.4 | | | 86.1 |
| Kenya | | | | | | | | | |

TABLE 7

Amino acid sequence alignment of the C-terminal domain of the V proteins of the indicated APMV-2 strains. Conserved cysteine (C) residues are underlined; dots indicate identity with strain Yucaipa. Numbers indicate the amino acid position.

APMV-2 Yucaipa-SEQ ID NO: 39
$^{181}$HRREYSFISRDGRLEVTSWCNPVCSPIRSEPRREKCTCGTCPESCILCRQPN$^{232}$ APMV-2 Bangor-SEQ ID NO: 47
$^{181}$.......AC.......I.....I.T...A.....V.K..K..I.....C.SQ$^{232}$ APMV-2 England-SEQ ID NO: 55
$^{181}$....................................................$^{232}$ APMV-2 Kenya-SEQ ID NO: 63
$^{181}$....................................................$^{232}$ Yucaipa, while that of strain Bangor is only 153 aa in length (Table 5).

Example 17

The Matrix Protein (M) Gene

The M gene of APMV-2 strains England and Kenya is 1280 nt in length, as is the case for strain Yucaipa, whereas that of strain Bangor is 1304 nt in length (Table 5). The increased length found in strain Bangor is due to longer 5' and 3' untranslated regions. The M gene of all four strains encodes a M protein of 369 aa. The M protein of strains Bangor, England and Kenya has 85.1%, 99.7% and 98.4% aa sequence identity, respectively, with that of strain Yucaipa (Table 6).

Example 18

The Fusion Protein (F) Gene

The F gene of APMV-2 strains Yucaipa, England, and Kenya is 1707 nt in length and encodes a F protein of 536 aa (Table 5), whereas that of strain Bangor is 1760 nt in length and encodes an F protein of 544 aa. The difference in length is due increased lengths of the 3' untranslated region and ORF in strain Bangor, which are partially offset by a shorter 5' untranslated region. The F protein of strains Bangor, England and Kenya has 79.1%, 99.8% and 98.1% aa sequence identity, respectively, with that of strain Yucaipa (Table 6). In APMV-1, the cleavage sequence of the F protein has been shown to be a critical factor for viral replication and pathogenesis. For APMV-2 strains England, Kenya and Yucaipa, the aa sequences spanning the F protein cleavage site and adjacent upstream end of the F1 subunit are identical (DKPASR↓F, position 93-100 of SEQ ID NO:42) and contain dibasic aa residues (Table 8). In contrast, in strain Bangor, the sequence of the six amino acids preceding the cleavage site differ from the other strains at four positions and contains only one basic aa residue (TLPSAR↓F, position 101-108 of SEQ ID NO:59). A similar difference in the number of basic amino acids at cleavage site between strains of same serotype has been reported in APMV-6 (Xiao et al., 2010, Virus Res. 150, 61-72). However, all the APMV-2 strains contain a phenylalanine residue at the F1 amino terminal end: this also is the case in virulent APMV-1 strains, whereas avirulent APMV-1 strains have a leucine at this position (Table 8) (Lamb and Parks, 2007, supra).

TABLE 8

Alignment of the F protein cleavage site sequences of the four APMV-2 strains with those of other APMVs. Basic amino acids (R = arginine and K = lysine) are underlined and in bold. Numbers indicate amino acid position.

| | | | |
|---|---|---|---|
| APMV-2 (Yucaipa) | $^{93}$DKPASR | ↓ $F^{100}$ | SEQ ID NO: 42 |
| APMV-2 (Bangor) | $^{101}$TLPSAR | ↓ $F^{108}$ | SEQ ID NO: 50 |
| APMV-2 (England) | $^{93}$DKPASR | ↓ $F^{100}$ | SEQ ID NO: 58 |
| APMV-2 (Kenya) | $^{93}$DKPASR | ↓ $F^{100}$ | SEQ ID NO: 66 |
| APMV-1 (Avirulent) | $^{111}$GGRQGR | ↓ $L^{117}$ | SEQ ID NO: 84 |
| APMV-1 (Virulent) | $^{111}$GRRQKR | ↓ $F^{117}$ | SEQ ID NO: 85 |
| APMV-3 (Netherland) | $^{101}$ARPRGR | ↓ $L^{107}$ | SEQ ID NO: 86 |
| APMV-3 (Wisconsin) | $^{96}$PRPSGR | ↓ $L^{102}$ | SEQ ID NO: 87 |
| APMV-4 | $^{115}$ADIQPR | ↓ $F^{121}$ | SEQ ID NO: 88 |
| APMV-5 | $^{104}$GKRKKR | ↓ $F^{110}$ | SEQ ID NO: 89 |
| APMV-6 (Hong Kong) | $^{113}$PAPEPR | ↓ $L^{119}$ | SEQ ID NO: 90 |
| APMV-6 (IT4524-2) | $^{103}$SIREPR | ↓ $L^{109}$ | SEQ ID NO: 91 |
| APMV-7 | $^{101}$TLPSSR | ↓ $F^{107}$ | SEQ ID NO: 92 |
| APMV-8 | $^{98}$TYPQTR | ↓ $L^{104}$ | SEQ ID NO: 93 |
| APMV-9 | $^{105}$IREGRI | ↓ $F^{111}$ | SEQ ID NO: 94 |

Example 19

The Hemagglutinin-Neuraminidase (HN) Gene

The HN gene of APMV-2 strain England is 1899 nt long, as is the case for strain Yucaipa, while the lengths of the HN genes of strains Bangor and Kenya are 1894 nt and 1906 nt, respectively. These latter two strains have differences relative to the others and to each other in the lengths of the 5' and 3' untranslated regions and the ORFs. The lengths of HN protein of strains Yucaipa and England are 580 aa, while those of strains Bangor and Kenya are 583 and 582 aa, respectively (Table 5). The HN protein of strains Bangor, England and Kenya has 75%, 96% and 76.2% aa sequence identity, respectively, with that of strain Yucaipa (Table 6). In addition, all the four strains have the hexapeptide (NRKSCS) that forms part of the sialic acid binding site (Mirza et al., 1994, J. Virol. 68, 5093-5099).

Example 20

The Large Polymerase Protein (L) Gene

The L gene of APMV-2 strains England and Kenya is 6834 nt long, as is the case for strain Yucaipa. The L gene of strain Bangor is 6863 in length, with the difference due to a longer 3' untranslated region. The L genes of all the four strains encode an L protein of 2242 aa (Table 5). The L protein of strains Bangor, England and Kenya has 66.5%, 94.2% and 87.8% aa sequence identity, respectively, with that of strain Yucaipa (Table 6). In addition, all four strains have the conserved motif GDNQ in the L protein domain III, as seen in all non-segmented negative strand RNA viruses, which involved in L protein transcriptional activity (Schnell and Conzelmann, 1995, Virology 214, 522-530).

Example 21

Phylogenetic Analysis

A phylogenetic tree was generated from alignments of the complete nt sequences of the genomes of APMV-2 strains Yucaipa, Bangor, England and Kenya with those of the representative members of family Paramyxoviridae (FIG. 1). This shows the APMV-2 strains clustering together on a branch that is distinct from other the paramyxoviruses, as would be expected. Also, strains Yucaipa, England and Kenya are more closely related to each other than to strain Bangor.

Discussion

Avian paramyxoviruses are classified into nine serotypes based on their serological relationships in HI and NI tests (Alexander, 2003, supra). Among these serotypes, APMV-1 causes severe disease in poultry; hence, a great deal of information is available on the antigenic and genetic relationships among APMV-1 strains isolated from different parts of the world (Alexander, 1988, A Laboratory manual for the isolation and identification of avian pathogens, $3^{rd}$ ed. The American Association of Avian Pathologists, Kendall/Hunt Publishing Company, Dubuque, Iowa. pp. 114-120). Recently we and others have reported complete genome sequences for representative strains of APMV-2 to -9 (Subbiah et al., 2008, Virus Res. 137, 40-48; Kumar et al., 2008, Virus Res. 137, 189-197; Nayak et al., 2008, Virol. J. 5, 124; Samuel et al., 2010, PloS One February 17:5(2):e9269; Chang et al., 2001, J. Gen. Virol. 82, 2157-2168; Xiao et al., 2009, Virus Res. 145, 80-91; Paldurai et al., 2009, Virus Res. 142, 144-153; Samuel et al., 2009, Virus Res. 142, 10-18). However, very little information is available about the antigenic and genetic relationships among the strains within serotypes 2 through 9 (Alexander, 2003, supra). In this study we have determined the antigenic and genetic relations among APMV-2 strains Yucaipa, Bangor, England and Kenya isolated from a chicken, finch, chicken and gadwell duck, respectively. Furthermore, these strains were isolated from different parts of the world and in different years. Therefore, it was interesting to know the extent of antigenic and genetic variation among these strains. The antigenic relationships among these four strains were evaluated using cross-HI and cross-serum microneutralization assays, and genetic variation was assessed by determining and comparing complete sequences for the viral genomes and predicted proteins. This information will have implications for studies in pathogenesis, epidemiology and for the development of vaccines against APMV-2.

To evaluate the antigenic relationships among the four APMV-2 strains described in the present study, we raised chicken antisera against each strain individually by respiratory infection mimicking a natural route of infection. Since serological responses tend to broaden over time, and with repeated antigenic exposure, we limited the immunization to a single infection and collected serum samples at an early time point (14 dpi). HI assays showed that, in the majority of comparisons, antigenic relatedness was greater between stains Yucaipa, England, and Kenya versus strain Bangor. Consistent with this, the results from the microneutralization tests in cell culture suggested an antigenic dimorphism that would be consistent with the existence of two antigenic subgroups within APMV-2, with strains Yucaipa, England and Kenya belonging to one antigenic subgroup and with strain Bangor belonging to the second antigenic subgroup, as seen with APMV-3 and -6 strains (Kumar et al., 2010, Virus Res. 137, 189-197; Xiao et al., 2010, supra). It was previously suggested that strain Bangor be classified as a separate serotype or as a subtype of serotype 2 (McFerran et al., 1974, supra) based on distinct differences in neuraminidase activities (Alexander et al., 1974, Archives of Vir. 46, 291-301) and cross serum neutralization tests between strains Bangor and Yucaipa. Our data support the classification of strain Bangor as a separate subgroup within serotype 2 rather than a distinct new serotype. It will be interesting to extend this analysis to additional strains to further evaluate antigenic variability among APMV-2 strains.

The genome lengths of strains Bangor, England and Kenya are 15024, 14904 and 14916 nt, respectively, compared with 14904 for strain Yucaipa. Among the APMV-1 (NDV) strains, there are three genome sizes: (1) 15,186 nt in early (>1930s) isolated strains, 2) 15,192 nt in late (>1960s) isolated strains (due to a six nt insertion in the upstream of the N gene), and (3) 15,198 nt (12 nt insertion in the P gene ORF) (Czeglédi et al., 2006, Virus Res. 120, 36-48). These different genome sizes of NDV strains did not relate to the viral virulence, but seem to be related to the time (year) of virus isolation with the genomes becoming progressively longer (Miller et al., 2009, Infect. Genet. 10, 26-35; Czeglédi et al., 2006, supra). However, in APMV-2, the genome length does not seem to be decided by the year of isolation but rather by the host species. Strains Yucaipa and England were both isolated from chicken and have the same genome length (14904 nt). Despite the difference in the genome length, all the three strains follow the "rule of six" consistent with this rule being a requirement for virus replication and survival.

Comparison of the complete consensus sequences for the genomes of the four APMV strains showed that strain Bangor has 70.4, 69.4, and 70.8% nt and 75.3, 76.1, 76.8% aggregate aa sequence identity with strain Yucaipa, England, and Kenya, respectively. In contrast, strains England and Kenya are more closely related to strain Yucaipa, with a nt sequence identity of 94.5% and 88%, respectively, and an aggregate aa sequence identity of 96.1% and 92.4%, respectively. Also, strains England and Kenya have 86.1% nt and 89.9% aggregate aa sequence identity with each other. These results unequivocally show that strains Yucaipa, England and Kenya are closely related genetically, while strain Bangor is somewhat distinct. This is consistent with the proposed antigenic subgroups described above, and provides a molecular basis for this antigenic dimorphism.

Comparison of the aa sequence relatedness of cognate proteins between the APMV-2 strains revealed values ranging from 55.8 to 99.8% aa identity, with different proteins having different ranges of identity. In particular, the P and L proteins of strain Bangor were among the most divergent (55.3-60.8 and 66.5-68.2% aa identity, respectively), compared to the Yucaipa, England, and Kenya strains. However, the percent identity for these proteins was much higher among the latter three strains (87.2-99.5% for P and 86.1-94.2 for L), consistent with these three strains representing a subgroup separate from strain Bangor. The extent of variability in the APMV-2 P proteins is similar to that observed among APMV-6 strains (Xiao et al., 2010, supra) but differs from that of the P proteins of the two subgroups of HMPV and HRSV, which are more highly conserved (85 and 90% aa identity, respectively) (Biacchesi et al., 2003, Virology 315, 1-9). The V protein also was relatively divergent: the V protein of strain Bangor had only 56.3, 55.4 and 56.3% aa identities, respectively with that of strains Yucaipa, England, and Kenya, whereas the V proteins of strains Yucaipa and Kenya had 100% aa identity and the V protein of both these strains had 99.1% aa identity with that of strain England. In addition, it is interesting to note that the W protein of strain Bangor was smaller in length, 153 aa compared to a length of 207 aa that was conserved for the other three strains. A similar difference in W protein size between strains of same serotype has been reported in APMV-8 (Paldurai et al., 2009, supra). Since the role of W protein is not known, the functional significance of the W protein size difference remains to be studied. It is also interesting to find that the F and HN proteins of strain Bangor exhibited more divergence (77.6-79.1% and 75-85.1% aa identity, respectively) with those of strains Yucaipa, England, and Kenya, while the F and G proteins of the HMPV subgroups have 95% and 37% aa identity, respectively, and that of the HRSV subgroups have 89% and 55% aa identity, respectively (Biacchesi et al., 2003, supra). Among the Yucaipa, England, and Kenya strains, Yucaipa and England were more closely related on the nt level as well as for most of the proteins. These two strains also were from the same host, namely the chicken. This was the most evident for the HN, and L proteins, for which strains Yucaipa and England were substantially more closely related to each other than either was to strain Bangor. Curiously, however, for the P protein, strains Yucaipa and Kenya were substantially more closely related than either was to strain England.

Another difference between strain Bangor and the other three strains was observed in the fusion protein cleavage site, which plays a major role in NDV pathogenesis (Lamb and Parks, 2007, supra). Virulent NDV strains have a multiple basic aa cleavage site R-X-K/R-R↓F, SEQ ID NO:81, which is cleaved intracellularly by ubiquitous cellular furin-like proteases, and also have a phenylalanine (F) residue at the beginning of the F1 subunit, which also may play a role in facilitating cleavage (Morrison et al., 1993, Virology 193, 997-1000). The avirulent NDV strains have one or a few basic residues at the cleavage site and do not conform to the furin motif, and have a leucine (L) residue at the first position of F1 subunit. Interestingly, the putative cleavage sites of other APMV serotypes showed that the cleavage site sequences of some serotypes are not necessarily predictive of the protease activation phenotype (Samuel et al., 2010, supra). The putative F protein cleavage site (DKPASR↓F, position 93-100 of SEQ ID NO:42) of the strains England and Kenya resembled that of prototype strain Yucaipa and contained two basic residues and a phenylalanine residue at the F1 terminal end, while that of strain Bangor (TLPSAR↓F, position 101-108 of SEQ ID NO:50) contained only one basic amino acid. However, none of the sites conform to the preferred furin cleavage site (R-X-(K/R)-R↓, SEQ ID NO:81). Each of these strains replicated in a trypsin-independent manner in both of the cell lines that we tested and the addition of trypsin or allantoic fluid did not substantially increase virus replication, as we previously observed for the prototype strain Yucaipa in a comparison involving nine different cell lines (Subbiah et al., 2008, Virus Res. 137, 40-48). Thus, on the basis of cleavage site sequence, it will be difficult to predict the virulence of these strains, unlike in the case of APMV-1 strains. Our results of MDT in chicken eggs and ICPI in day-old chicks provided evidence of an avirulent phenotype for each of these strains in chickens.

In conclusion, the complete genome sequences were determined for APMV-2 strains Bangor, England and Kenya. Comparison of the nt and predicted protein aa sequences among four APMV-2 strains showed the existence of divergence between strains Yucaipa, England, Kenya versus strain Bangor, suggesting that APMV-2 contains two antigenic subgroups, as reported with the APMV-3 and -6 serotypes. This grouping based on sequence relatedness and phylogenetic tree also is consistent with the antigenic analysis. This indicated that APMV-2 strains represent two APMV-2 subgroups and we propose that the prototype strain Yucaipa and strains England and Kenya represent one subgroup while strain Bangor represents a second subgroup. It will be interesting in future to look at the antigenic and genetic analyses of other APMV-2 strains isolated from different avian species.

NDV (APMV-1) strains segregate into three pathotypes: highly virulent (velogenic) strains that cause severe respiratory and neurological diseases in chickens; moderately virulent (mesogenic) strains that cause milder disease, and nonpathogenic (lentogenic) strains that cause inapparent infection and can serve as live vaccines against NDV disease. Currently, it is not known whether there is any variation in pathogenicity among APMV-2 strains. The purpose of this study was to evaluate the pathogenicity of APMV-2 strains Yucaipa and Bangor, both of which were completely sequenced as described above (Subbiah et al., 2008, Virus Res. 137, 40-48). Initially these two viruses were considered as separate antigenic groups due to their four-fold difference in the serum cross neutralization test, but they are now grouped together as two different strains of APMV-2 (McFerran, 1974, supra). In this study, we studied infection of APMV-2 strains Yucaipa and Bangor in 9-day-old embryonated chicken eggs, 1-day-old chicks, and 4-week-old chickens and turkeys in order to investigate their tropism and pathogenicity. The 1-day-old chicks were infected intracerebrally to evaluate the potential for neurotropism. The older birds were infected by the oculonasal route and the viral tropism and replication efficiency were evaluated by quantitative virology and immunohistochemistry of a wide range of possible target organs.

The following Materials and Methods were used in the Examples that follow.

Materials and Methods

Viruses and Cells

APMV-2 strains Yucaipa (APMV-2/chicken/USA(Ca)/Yucaipa/1956) and Bangor (APMV-2/finch/N.Ireland/Bangor/1973) were obtained from National Veterinary Services Laboratory, Ames, Iowa. APMV-1 lentogenic strain LaSota and mesogenic strain Beaudette C (BC) were used for comparison purposes in pathogenicity tests and for studying virus replication in the brain of 1-day-old chicks, respectively: the former was performed in our Bio Safety Level (BSL)-2 animal facility and the latter study was performed in our BSL-3 animal facility. The viruses were grown in 9-day-old specific pathogen free (SPF) embryonated chicken eggs via allantoic route of inoculation. The allantoic fluids from infected embryonated eggs were collected 96 h post-inoculation and titer of the virus was determined by hemagglutination (HA) assay with 0.5% chicken RBC. The virus titers in the tissue samples were determined by 50% tissue culture infectivity dose ($TCID_{50}$) assay in DF1 cells (chicken embryo fibroblast cell line), calculated by the method of Reed and Muench (Reed and Muench, 1938, supra).

Mean Death Time (MDT) in 9-Day-Old Embryonated SPF Chicken Eggs

Briefly, a series of 10-fold ($10^{-6}$ to $10^{-42}$) dilutions of fresh infective allantoic fluid in sterile phosphate-buffered saline (PBS) were made and 0.1 ml of each dilution was inoculated into the allantoic cavities of five 9-day-old embryonated SPF chicken eggs, which were then incubated at 37° C. Each egg was examined three times daily for 7 days, and the times of embryo deaths were recorded. The minimum lethal dose is the highest virus dilution that caused death of all the embryos. MDT is the mean time in hours for the minimum lethal dose to kill all inoculated embryos. The MDT has been used to characterize the NDV pathotypes as follows: velogenic (less than 60 h), mesogenic (60 to 90 h), and lentogenic (more than 90 h) (Alexander, 1989, supra).

Intracerebral Pathogenicity Index (ICPI) in 1-Day-Old Chicks

Briefly, 0.05 ml of 1/10 dilution of fresh infective allantoic fluid ($2^8$ HA units) of each virus was inoculated into groups of ten 1-day-old SPF chicks via intracerebral route. The birds were observed for clinical symptoms and mortality every 8 h for a period of 8 days. At each observation, the birds were scored as follows: 0, healthy; 1, sick; and 2, dead. The ICPI is the mean score per bird per observation over the 8-day period. Highly virulent NDV (velogenic) viruses give values approaching 2 and avirulent NDV (lentogenic) viruses give values close to 0 (Alexander, 1989, supra).

Replication and Viral Growth Kinetics in Brain Tissue of 1-Day-Old Chicks

To compare the replication of APMV-2 strains Yucaipa and Bangor in chick brains, groups of twelve 1-day-old SPF chicks were inoculated with 0.05 ml of a 1/10 dilution of $2^8$ HA units of fresh infected allantoic fluid via the intracerebral route. APMV-1 strain BC was included for comparison purposes. Brain tissue samples were collected by sacrificing three birds from each group on 1, 2, 3 and 4 days post inoculation (dpi), or when any birds died of infection. The samples were snap-frozen on dry ice and homogenized. The virus titers in the tissue samples were determined by 50% tissue culture infectivity dose ($TCID_{50}$) in DF1 cells (chicken embryo fibroblast cell line) by Reed and Muench method (Reed and Muench, 1938, supra).

Pathogenicity Assessment in Chickens and Turkeys

Two groups of twelve 4-week-old SPF chickens (Charles River, Md., USA) were housed in negative pressure isolators in our BSL-2 facility and were provided with food and water ad libitum. Birds in group one were inoculated with a total volume of 0.2 ml of $2^8$ HA units of APMV-2 strain Yucaipa contained in freshly-harvested infected-egg allantoic fluid via the intranasal and intraocular routes, and the birds in group two were inoculated with the same dose of APMV-2 strain Bangor by the same routes. The inoculations were performed on separate days to avoid cross infection between the groups. Similarly two groups of twelve 4-week-old Midget White turkeys (McMurray Hatchery, Iowa, USA) were infected with the two strains of APMV-2 using the same dose and the same routes. The birds were monitored every day for clinical signs. Three birds from each group were euthanized on 2, 4 and 6 dpi by placing them directly inside a $CO_2$ chamber. The birds were swabbed orally and cloacally just before euthanasia. The following tissue samples were collected on dry ice, both for immunohistochemistry (IHC) and for virus isolation: eyelid, trachea, lung, liver, spleen, brain, colon, caecal tonsil, bursa and kidney. Serum samples were also collected. On day 14, the three remaining birds from each group were euthanized and serum samples were collected. Seroconversion was evaluated by hemagglutination inhibition (HI) assay (Alexander, 1996, supra).

Virus Detection and Quantification from Tissue Samples and Swabs

Infectious virus was detected by inoculating homogenized tissue samples in 9-day-old embryonated SPF chicken eggs and testing for HA activity of the infected allantoic fluids 4 dpi. All HA positive samples were considered as virus-positive tissue samples. The virus titers in the HA-positive tissue samples were determined by $TCID_{50}$ method in DF1 cells (Reed and Muench, 1938, supra).

The oral and cloacal swabs were collected in 1 ml of PBS containing antibiotics. The swab containing tubes were centrifuged at 1000×g for 20 min, and the supernatant was removed for virus detection. Infectious virus was detected by infecting this supernatant into 9-day-old embryonated SPF chicken eggs. Positive samples were identified by HA activity of the allantoic fluid harvested from eggs 4 dpi.

Immunohistochemistry

Sections of all the frozen tissue samples were prepared at Histoserve, Inc. (Maryland, USA). The sections were immunostained to detect viral nucleocapsid (N) protein using the following protocol. Briefly, the frozen sections were thawed and rehydrated in three changes of PBS (10 min each). The sections were fixed in ice cold acetone for 15 min at −80° C. and then washed three times with 2% BSA in PBS and blocked with the same for 1 h at room temperature. The sections were then incubated with a 1:500 dilution of the primary antibody (hyperimmune sera raised against the N protein of APMV-2 strain Yucaipa in rabbit) in PBS overnight in a humidified chamber. After three washes with 2% BSA in PBS, sections were incubated with the secondary antibody (FITC conjugated goat anti-rabbit antibody) for 30 min. After a further wash cycle, the sections were mounted with glycerol and viewed under an immunofluorescence microscope.

Preparation of Hyperimmune Antiserum Against the Viral N Protein in a Rabbit

APMV-2 strain Yucaipa virions were purified on a sucrose gradient and the virion proteins were separated on a 10% SDS-Polyacrylamide gel and negatively stained using E-Zinc™ reversible stain kit (Pierce, Rockford, Ill., USA). The N protein band was excised from the gel and destained with Tris-glycine buffer pH 8. The excised gel band was minced in a clean pestle and mixed with elution buffer (50 mM Tris-HCl buffer pH 8, 150 mM NaCl, 0.5 mM EDTA, 5 mM DTT and 0.1% SDS) and transferred to the upper chamber of a Nanosep centrifugal device (Pall Life Sciences, Ann Arbor, Mich., USA). After centrifugation two times, the eluted protein in the supernatant was quantified and 0.2 mg of protein was mixed in complete Freund's adjuvant and injected subcutaneously into a rabbit. After two weeks a booster immunization was given with 0.2 mg of protein in incomplete Freund's adjuvant and 2 weeks later the hyperimmune sera was collected. This serum was tested by western blot and was found to recognize specifically the N protein of APMV-2 strains Yucaipa and Bangor.

The lentogenic NDV strain LaSota was included in the pathogenicity test for comparison. The MDT for both of the APMV-2 strains was more than 168 h. The ICPI value was zero for both the strains. The MDT and ICPI values of NDV strain LaSota were 110 h and zero, respectively, consistent with a lentogenic virus. These results indicate that APMV-2 strains Yucaipa and Bangor are probably nonpathogenic to chickens, similar to lentogenic NDV strains.

Example 22

Virus Growth in the Chick Brain

The ability of the APMV-2 strains Yucaipa and Bangor to grow in the brains of 1-day-old chicks was evaluated in parallel with the mesogenic neurotropic NDV strain BC. This study was performed to determine whether the zero ICPI value of APMV-2 strains was due to the inability of the virus to grow intracerebrally or if there was virus multiplication without a high degree of cell destruction.

Virus replication was evaluated by inoculating 0.05 ml of a 1:10 dilution of $2^8$ HA units of each virus, strains Yucaipa, Bangor and BC, into the brains of twelve 1-day-old SPF chicks. Three birds from each group were sacrificed on 1, 2, 3 and 4 dpi and virus titers in brain tissue were assayed and expressed as $TCID_{50}$ per gram of the brain in DF1 cells (data not shown). Neither of the two APMV-2 strains produced any clinical signs nor did they kill the chicks by 4 dpi. Neither of the two APMV-2 strains was isolated from the brain homogenate of any of the chicks on 1 to 4 dpi, indicating lack of growth in neural tissue. In comparison, the chicks that were infected with NDV strain BC were either killed or sacrificed by 3 dpi and reached a titer of $2.5\times10^5$ $TCID_{50}$/g of brain on day 3.

Example 23

Experimental Infection of 4-Week-Old SPF Chickens and Turkeys

Groups of twelve 4-week-old chickens were inoculated by the intranasal and intraocular routes with $2^8$ HA units of either APMV-2 strain Yucaipa or Bangor. None of the chickens or turkeys displayed any overt clinical signs, and none of the birds died of disease. Further, there were no gross visceral pathological lesions in any of the birds at 2, 4, 6 and 14 dpi.

Example 24

Virus Detection in Tissues and Swabs

Three birds from each of the four groups were euthanized on 2, 4 and 6 dpi. The following tissue samples were collected for virus detection by inoculation in embryonated chicken eggs: eyelid, trachea, lung, liver, spleen, brain, colon, caecal tonsil, bursa and kidney. Samples that were positive for virus, as measured by HA assay of egg allantoic fluid, were analyzed for virus quantitation using the $TCID_{50}$ method in DF1 cells.

Strain Yucaipa was isolated from eyelids, respiratory tract (trachea and lungs) and alimentary tract (colon and caecal tonsils) in chickens. Although the virus was isolated from bursa in one of the chickens on 4 dpi, the titer of retrieved virus was very low (data not shown). Strain Yucaipa was not detected in the brain or heart. Strain Bangor was isolated from the same tissues, although the number of virus-positive samples was somewhat less than for strain Yucaipa. In general, the titers in virus-positive tissue samples were similar for the two viruses. In addition, strain Bangor also was detected in the brain and heart in one bird each, but the titers were very low (data not shown).

In infected turkeys, strain Yucaipa was isolated from the respiratory tract (trachea and lungs) and eyelids, but not from the alimentary tract (data not shown). The virus titers in these organs were low compared to those from infected chickens. Strain Bangor was isolated from the respiratory tract (trachea and lungs) and the alimentary tract (caecal tonsils), and the virus titers were higher than those obtained from strain Yucaipa-infected turkeys. No virus of either strain was detectable on 6 dpi from any of the tissues harvested from the infected turkeys. For both strains, the number of virus-positive samples from all days was considerably less for turkeys than for chickens.

In chickens, strain Yucaipa was detected in oral swabs on day 4 and in cloacal swabs on days 4 and 6 (data not shown). In comparison, strain Bangor was not detected in oral swabs from chickens but was detected in cloacal swabs like strain Yucaipa on days 4 and 6. In turkeys, strain Yucaipa was not detected in oral swabs but was detected in cloacal swabs on day 4 (data not shown). In comparison, strain Bangor was detected in oral swabs on day 6 and in cloacal swabs on days 4 and 6. In general, strain Yucaipa was detected less frequently in swabs from turkeys than from chickens, whereas the frequency of isolation of strain Bangor between the two species was similar. Virus detection in the swabs with either strain was most frequent in cloacal swabs, and was frequently detected on day 6.

Example 25

Immunohistochemistry

The frozen sections of all the virus-positive tissue samples and some of the viral-negative control samples were immunostained using monospecific antibodies against N protein of APMV-2 strain Yucaipa. Large amounts of viral N antigens were detected consistently in all the tissue samples that were positive by virus isolation; no viral antigen was detected in tissue samples that were negative by virus isolation. However, no viral N antigens could be detected in the brain of a chicken infected with strain Bangor that was positive by virus isolation (data not shown).

Example 26

Seroconversion

An HI assay using chicken erythrocytes was performed with the sera collected from chickens and turkeys on 0, 2, 4, 6 and 14 dpi. The HI titers of the pre-infection chickens and turkeys were 2 or less. An HI titer of greater than 8 was considered positive. All of the inoculated chickens and turkeys seroconverted from day 6 onwards. The mean HI titers in chickens for strains Yucaipa and Bangor was 1:40 and 1:40 on day 6 and 1:2560 and 1:2560 on day 14, and in turkeys was 1:40 and 1:80 on day 6 and 1:2560 and 1:5120 on day 14, respectively.

Discussion

The APMVs are frequently isolated from a wide variety of avian species around the world. Currently, nine serological types of APMVs have been recognized, of these, the disease potential of APMV-1 (NDV) is well studied, but the disease potential of APMV-2 to APMV-9 is mostly unknown. Here, we have investigated the clinical disease and pathogenesis of APMV-2 strains Yucaipa and Bangor in chicken eggs, in 1-day-old chicks inoculated intracerebrally, and in 4-week-old chickens and turkeys inoculated via a natural route of infection. In this study, 4-week-old chickens and turkeys were chosen over the other age groups because at this age they are fully susceptible to viral infections. The APMV-2 strains Yucaipa and Bangor were first characterized by standard pathogenicity tests (MDT and ICPI). Results of MDT test showed that both the APMV-2 strains did not kill any of the chicken embryos even after seven days of inoculation. ICPI values of both APMV-2 strains were zero, indicating an absence of morbidity and mortality. Similar ICPI value for APMV-2 strains Yucaipa and Bangor has been reported previously (McFerran et al, 1974, supra; Shortridge and Burrows, 1997, Vet Rec. 140, 373-374). Our MDT and ICPI values suggest that both strains are apathogenic to chickens. Since the APMV-2 strains did not kill 1-day-old chicks by intracerebral inoculation, we investigated whether the absence of neurovirulence was due to a lack of virus replication in the brain or whether replication occurred without any notable cell destruction. Our results showed that neither of the APMV-2 strains replicated detectably in the brains of the chicks. In contrast, all of the chicks that were inoculated with the mesogenic NDV strain BC died at 3 dpi, and the virus titers in the brain reached a value of $2.5\times10^5$ $TCID_{50}$/g. These results suggest that the absence of neurovirulence of APMV-2 strains was due to a lack of neurotropism rather than nonpathogenic replication.

It has been previously shown that experimental infection of 1-day-old chicks with APMV-2 strain SCWDS ID A102-1008, via the oculonasal route resulted in mild disease and that virus was isolated from trachea, lungs and gut for 7 dpi and from pancreas up to 28 dpi (Warke et al., 2008, Avian Pathol. 37, 429-434). In this study, we have evaluated the disease potential and pathogenesis of APMV-2 strains in 4-week-old SPF chickens and turkeys by the oculonasal route of infection. None of the infected birds showed any clinical signs of illness. In chickens, strain Yucaipa was isolated from tissues from both the respiratory and alimentary tracts while in turkeys the virus was isolated only from tissues from the respiratory tract and the titers of recovered virus were low. Each of the viruses was detected in oral and cloacal swabs from both chickens and turkeys, but strain Yucaipa was isolated less frequently from turkeys. Taken together, these results confirmed that strain Yucaipa replicated better in adult chickens than turkeys. On the other hand, strain Bangor was isolated from respiratory and alimentary tracts of both chickens and turkeys confirming that the virus replicated well in both the tracts in chickens and turkeys.

Visceral gross lesions were not evident in any infected birds at 2, 4, 6 and 14 dpi. Using IHC, viral N protein was detected in the same tissues that were positive by virus isolation except in a brain tissue that was positive by virus isolation but negative by IHC. It is possible that the virus load in this infected brain tissue was too low to be detected by IHC or that the tissue was contaminated with virus during collection. In contrast, staining of the tissues that were negative by virus isolation was very weak or absent. An interesting finding was the presence of large amounts of viral antigens in epithelial cells, suggesting that these cells are highly permissive to viral replication and that extensive virus replication occurred. Thus, assays for infectious virus were considerably less sensitive than IHC in detecting virus replication in the inoculated birds. Another prominent finding of our IHC study was the presence of viral antigen only in the epithelial surfaces of these organs. There was no evidence of viral antigen in the sub epithelial portion of the tissues. This suggests that these viruses have a tropism for the superficial epithelial cells. Nonetheless, the detection of viral antigen, and in some cases infectious virus, in multiple internal organs of the birds indicates that both viruses were capable of replication in multiple tissues rather than being restricted to the respiratory and alimentary tracts. Presumably, the virus reached the various internal organs through the blood stream. Nonetheless, this extensive amount of virus replication was not accompanied by disease.

These results show that APMV-2 strains are capable of infecting adult chickens and turkeys using a possible natural route of infection. Serological titers demonstrated a humoral response in all of the birds inoculated with either APMV-2 strain, a further indication of successful replication. However, our results suggest that chickens are comparatively more susceptible than turkeys to APMV-2 infection.

The fusion F protein cleavage site of NDV is a well characterized determinant of NDV pathogenicity in chickens (Millar et al., 1988, J. Gen. Virol. 69, 613-620; de Leeuw et al., 2003, supra; Panda et al., 2004, Microb. Pathog. 36, 1-10). Virulent NDV strains typically contain a polybasic cleavage site that contains the preferred recognition site for furin (R-X-K/R-R↓, SEQ ID NO:81), which is an intracellular protease that is present in most cells. This provides for efficient cleavage in a wide range of tissues, making it possible for virulent strains to spread systemically. In contrast, avirulent NDV strains typically have basic residues at the −1 and −4 positions relative to the cleavage site and depend on secretory protease (or, in cell culture, added trypsin) for cleavage. Also, whereas the first amino acid of the newly-created F1 terminus is phenylalanine for virulent NDV strains, it is leucine for avirulent NDV strains, an assignment that also reduces the efficiency of cleavage (Morrison et al., 1993, Virology 193, 997-1000). The inability to be cleaved by furin limits the replication of avirulent strains to the respiratory and enteric tracts where secretory protease is available for cleavage. The putative F protein cleavage site of APMV-2 strain Yucaipa (DKPASRIF, position 93-100 of SEQ ID NO:42) and strain Bangor (TLPSARIF, position 101-108 of SEQ ID NO:50) have one or two basic residues (underlined), which is similar but not identical to the pattern of avirulent NDV strains. Conversely, the F1 subunit of both the APMV-2 strains begins with a phenylalanine residue, as is characteristic of virulent NDV strains, rather than a leucine residue, as seen in most avirulent NDV strains (Collins et al., 1993, supra). APMV-2 strains Yucaipa and Bangor replicated in a wide range of cells in vitro without the addition of exogenous protease and the inclusion of protease did not improve the efficiency of replication. In the present study, the APMV-2 strains were detected abundantly in various internal organs, suggesting a systemic spread of the virus. These results confirm our in vitro findings that APMV-2 is capable of efficient intracellular cleavage in the absence of an apparent furin motif in F protein, and show that this confers the ability to spread systemically.

In conclusion, we have shown that adult SPF chickens and turkeys are susceptible to APMV-2 infection without causing overt signs of clinical disease. However, in commercial chickens and turkeys the disease picture could be quite different depending on management practices, environmental conditions and other concomitant infections. This study has demonstrated that APMV-2 has an affinity for epithelial linings of respiratory and intestinal tracts and lacks the ability to grow in neural tissues, but does spread systemically.

The knowledge of the complete viral genome sequence is essential for genetic manipulation through a reverse genetics system, rendering recovery of recombinant virus entirely from cloned cDNA (reviewed in Collins and Murphy, 2002, Virology 296, 204-211; Neumann et al., 2002, Rev. Med. Virol. 12, 13-30; and Conzelmann, 1998, Ann. Rev. Genet. 32, 123-162). The most successful reverse genetics system is a plasmid based approach, wherein, four plasmids—one encoding the viral anti-genome and the others encoding the viral polymerase complex (N, P and L proteins), all under the control of T7 promoter are cotransfected in permissive cells expressing T7 RNA polymerase or in cells infected with recombinant vaccinia virus expressing T7 RNA polymerase. The reverse genetics system can be applied for the genetic manipulation of viruses to study their molecular biology and pathogenesis and secondly, for development of vaccine vectors against important and emerging pathogens by engineering viruses to express foreign immunogens (Khattar et al., 2010, Vaccine 28, 3159-3170; Bukreyev et al., 2010, Virology 399, 290-298; Billeter et al., 2009, Curr. Top. Microbiol. Immunol. 329, 129-62; Buchholz et al., 2006, Expert Rev. Vaccines 5, 695-706).

This study describes the recovery of recombinant APMV-2/Yuc entirely from cloned cDNA using a reverse genetics system. The rescued recombinant virus was biologically similar to the wild-type APMV-2/Yuc. Furthermore, we have recovered recombinant viruses expressing enhanced green fluorescent protein (EGFP), with and without kozak sequence, to evaluate potential of APMV-2 as a vaccine vector. The EGFP-expressing recombinant viruses were biologically similar to the parental recombinant and wild-type virus, and stably expressed GFP for at least five consecutive passages suggesting that this system could be used to develop vaccine vectors.

The following Materials and Methods were used in the Examples that follow.

Materials and Methods

Cells and Virus

DF-1 cells (Chicken embryo fibroblast cell line) and HEp-2 cells (Human Epidermoid carcinoma tissue from the larynx) were maintained in Dulbecco's modified Eagle's medium (DMEM), supplemented with 10% fetal bovine serum (FBS). APMV-2 strain Yucaipa (APMV-2/Yuc) was obtained from the National Veterinary Services Laboratory, Ames, Iowa. The wild-type as well as the recombinant viruses were propagated in the allantoic cavity of 9-day-old embryonated specific pathogen free (SPF) chicken eggs. After 72 h of infection, the allantoic fluids were harvested and titrated by hemagglutination assay (HA) using 0.5% chicken RBC at room temperature. The recombinant modified vaccinia virus strain Ankara expressing the T7 RNA polymerase (MVA-T7, a generous gift of Bernard Moss, National Institute of Health) was grown in primary chicken embryo fibroblast cells.

Construction of Support Plasmids

For constructing the support plasmids, the cDNAs bearing the open reading frame (ORF) of nucleocapsid protein (N)

and phosphoprotein (P) were cloned into expression vector pGEM7z(+) (Promega, Win., USA) under T7 promoter between Sph I and Hind III, Eco R I and Sac I, respectively. The ORF of large polymerase protein (L) was subcloned as two fragments into pTM1 (B. Moss, et al., 1990, Nature 348:91-91) vector (possessing the encephalomyo-carditis virus internal ribosome entry site (IRES) downstream of the T7 RNA polymerase promoter and using the translation initiation codon contained in the Nco I site of the IRES) between the enzyme sites Nco I, Stu I and Sac I. The Sac I enzyme site was artificially created by G11468C mutation within L ORF without changing any amino acids. Briefly, RNA was isolated from the allantoic fluid of APMV-2/Yuc-infected eggs, 72 h post infection using RNeasy kit (QIAGEN, USA) according to the manufacturer's instructions. The cDNA fragments of ORFs of the N, P and L genes were generated by RT-PCR. All RT reactions were performed with Superscript II reverse transcriptase (Invitrogen) and gene specific primers. The primers used in the RT-PCR are listed in Table 9. The N, P and L support plasmids (pN, pP and pL) were used for the recovery of the recombinant viruses.

TABLE 9

The list of oligonucleotide primers used in the synthesis of cDNA fragments of N, P and L ORFS. The restriction enzyme sites artificially created in the primers are underlined.

| |
|---|
| N ORF |
| + 5' ACATGCATGCATGTCTTCTGTGTTTTCAGAATACCAGG 3', SEQ ID NO: 95 |
| - 5' CCCAAGCTTTCACCAATCTAATGAGGCCGCATCATTG 3', SEQ ID NO: 96 |
| P ORF |
| +5' CCGGAATTCATGGAGTTCACCGATGATGCCGAAA--TTGCTGAGCTG 3', SEQ ID NO: 97 |
| - 5' TGACGAGCTCCTAGGCATTGTATATCTG 3', SEQ ID NO: 98 |
| L ORF |
| Fragment 1: |
| + 5' CATGCCATGGATCAAACTCAAGCTGACA 3', SEQ ID NO: 99 |
| - 5' CCCCTTGAGGAGCTCTATAGTGTCTGGAGA 3', SEQ ID NO: 100 |
| Fragment 2: |
| + 5' TCTCCAGACACTATAGAGCTCCTCAAGGGG 3', SEQ ID NO: 101 |
| - 5' AAAAGGCCTTTAATTGCTTGCATTTCTGAAC--TTCATACAGC 3', SEQ ID NO: 102 |

Construction of Full Length Plasmid

The restriction enzyme profile of the complete genome sequence of APMV-2/Yuc was analyzed by SeqBuilder software (DNASTAR Lasergene 8) to facilitate cloning the full length cDNA into a low copy plasmid pBR322/dr. Plasmid pBR322/dr was a modified form of plasmid pBR322 which contained a 72-nt oligo linker between the EcoR I and Pst I sites and hepatitis delta viral 84-nt antigenome ribozyme sequence and T7 RNA polymerase transcription termination signal between the Rsr II and Fse I sites (Krishnamurthy et al., 2000, Virology 278, 168-182). A 73-nt oligo linker with unique restriction enzyme sites was synthesized and inserted between Asc I and Rsr II sites of the pBR322/dr vector to generate pBR322/dr/Yuc for cloning the full length APMV-2/Yuc. The antigenomic cDNA of APMV-2/Yuc (14,904 nt) was divided into six fragments and sequentially cloned into pBR322/dr/Yuc plasmid between the T7 promoter and Hepatitis delta ribozyme sequence. A total of five unique restriction enzyme sites were created in the full length by mutating 10 nt without changing any amino acids (FIG. 2, SEQ ID NO:117). For cloning, RNA was isolated from the allantoic fluid of APMV-2/Yuc-infected eggs at 72 h post infection, using RNeasy kit. All RT reactions were carried out using Superscript II reverse transcriptase (Invitrogen). The primers used for RT-PCR of the six fragments are listed in Table 10. The unique restriction enzyme sites in the full length were generated by the following 10 mutations: C2923A, G2924A, T2925A, G2926C, G4154C, G5971A, A5973T and T7870C in the untranslated regions (UTRs), A11321G and A11322C within L ORF without changing any amino acids. After ligation into the plasmid, each cDNA fragment was sequenced completely. The APMV-2/Yuc full length plasmid was called pAPMV-2/Yuc and had three non-viral G residues adjacent to the T7 promoter, at the 5' end of the antigenome, to enhance promoter efficiency (Biacchesi et al., 2004a, Virology 321, 247-259).

The full length cDNA clone was constructed by assembling six subgenomic fragments into pBR322/dr/Yuc using a 73-nt long oligonucleotide linker sequence between T7 RNA polymerase promoter sequence and the hepatitis delta ribozyme sequence, which was followed by T7 terminator sequence (SEQ ID NO:118; Asc1 sequence 1-8; T7 promoter sequence 9-25; 26-28, 3 nonoviral G residues; 29-14932, APMV-2 cDNA; 14933-14960, Partial HDV antigenomic ribozyme sequence, 14961-14967, RsrII sequence). The ten nt mutations and their positions, that were made to create the unique restriction enzyme sites in the full length, are represented inside boxes under each enzyme.

Construction of Full Length Plasmids Expressing EGFP, with and without Kozak Sequence The plasmid pAPMV-2/Yuc was modified by the insertion of a transcription cassette containing the ORF for enhanced green fluorescent protein (EGFP) (Clontech, Inc.). The ORF of EGFP was flanked by the Pme I enzyme site, a 10-nt putative P gene-end (TAACAAAAAA, SEQ ID NO:115), 1-nt intergenic sequence (T), 1-nt 5'UTR (T), a 10-nt putative M gene-start (GGGGGCGAAG, SEQ ID NO:115) upstream and by the Pme I enzyme site downstream. This fragment containing the ORF of EGFP was cloned between P and M genes in the full length plasmid to generate the pAPMV-2/Yuc/EGFP plasmid (FIG. 3). Additionally,

TABLE 10

Oligonucleotide primers used for construction of the full-length cDNA

| cDNA Fragment | Primers | Order of Cloning |
|---|---|---|
| I | + 5' TCATTGGCGCGCCTAATACGACTCACTATA GGGACC--AAACAAGG 3' SEQ ID NO: 103<br>- 5' CATGTGGGTTTAAACTGGTGATATG 3' SEQ ID NO: 104 | 1 |
| II | + 5' TCACCAGTTTAAACCCACATGCTTCCC TGC 3' SEQ ID NO: 105<br>- 5' GAGGTGTGCGGCCGCACGTGTC 3' SEQ ID NO: 106 | 2 |

TABLE 10-continued

Oligonucleotide primers used for construction of the full-length cDNA

| cDNA Fragment | Primers | Order of Cloning |
|---|---|---|
| III | + 5' GACACGTGCGGCCGCACACCTC 3' SEQ ID NO: 107 - 5' GTTTAGGCTTAATTAACCTCTCTACA 3' SEQ ID NO: 108 | 3 |
| IV | + 5' GAGAGGTTAATTAAGCCTAAACATGAT 3' SEQ ID NO: 109 - 5' GCTGTTAGACACTACGTGGCTTTTG 3' SEQ ID NO: 110 | 4 |
| V | + 5' CAAAAGCCACGTAGTGTCTAACAGC 3' SEQ ID NO: 111 - 5' TATTTCCTTCCGCGGCTCGAATG 3' SEQ ID NO: 112 | 5 |
| VI | + 5' CATTCGAGCCGCGGAAGGAAATA 3' SEQ ID NO: 113 - 5' ATGCCCAGGTCCGGACCGCGAGGAGGT GGAGATG--CCATGCCGACCACCAGACATG 3' SEQ ID NO: 114 | 6 |

plasmid pAPMV-2/Yuc/$_{kozak}$EGFP was constructed by inserting a 6-nt kozak sequence (GCCACC) in front of the start codon of EGFP ORF (FIG. 3). The length of the encoded rAPMV-2/Yuc/EGFP and rAPMV-2/Yuc/$_{kozak}$EGFP antigenomes, excluding the non-viral sequences, were 15,654 nt and 15,660 nt, respectively.

The EGFP ORF was inserted as a transcription cassette at the Pme I site (at the putative P gene 5' UTR). This cassette contained the EGFP ORF flanked by a T residue as the 5'UTR, M gene-start (M GS), followed by a T residue as the intergenic sequence (IGS), P gene-end (P GE) and Pme I enzyme site. The EGFP ORF was flanked at the downstream end by another Pme I enzyme site. In the pAPMV-2/Yuc/$_{kozak}$EGFP, the kozak sequence (GCCACC) was inserted before EGFP ORF.

Transfection and Recovery

The recombinant viruses were recovered from the full length plasmids as described previously (Krishnamurthy et al., 2000). Briefly, in a six well plate, HEp-2 cells (80-90% confluent) were infected with MVA-T7 at a one focus forming unit per cell and then transfected with pNP (3 μg), pP (2 μg), pL (1 μg) and pAPMV-2/Yuc (3-5 μg) or the full length plasmids containing EGFP gene. Lipofectamine (Invitrogen, USA) was used for transfection according to the manufacturer's protocol. After 6 h of transfection, the supernatant was discarded and fresh DMEM containing 0% FBS was added. The supernatant was collected after 48 h and passaged in 9-day-old embryonated SPF chicken eggs to remove residual vaccinia virus. The allantoic fluid was harvested at 3 dpi and tested for HA activity. The recovered viruses were passaged five times in 9-day-old embryonated SPF chicken eggs and RT-PCR and sequencing confirmed the recombinant viruses. The virus stocks were aliquoted and stored at −70° C. until future use.

HEp-2 cells were first infected with recombinant vaccinia virus expressing T7 polymerase and cotransfected with antigenome full-length cDNA plasmid pAPMV-2/Yuc and expression plasmids pN, pP, pL.

Identification of Genetic Markers in Recombinant Viruses by RT-PCR and Sequencing RT-PCR was performed on the RNA extracted from recombinant viruses using P gene-specific forward primer, P-2629 (5'-CTCCTGAGGTCACAGAAGGAGG-3', position 2630-2651 of SEQ ID NO:1) and M gene-specific reverse primer, M-3285 (5'CCTGCAGTGACCACTTCTG-GCTTTG-3', position 3309-3285 of SEQ ID NO:1). The RT-PCR product was digested using Pme I enzyme and sequenced to confirm the Pme I site. The same primers were used to amplify the GFP gene in the recombinant viruses and DNA sequencing confirmed the presence of the restriction enzyme site, the GFP ORF and the kozak sequence. RNA isolated from wt APMV-2/Yuc was included as a control. Furthermore, the GFP expression by the recombinant viruses was determined by monitoring the virus-infected DF1 cells under fluorescence microscope.

Immuno Staining of Infected Cells

The recombinant viruses were grown in DF1 cells and overlaid with 0.8% methyl cellulose (Sigma) in DMEM without FBS. The infected cells were incubated in 37° C. incubator. After three days of infection, the overlay was removed and the cells were fixed with methanol at room temperature for 30 min. The cells were then washed and incubated with polyclonal antisera raised against wt APMV-2/Yuc in chickens at 1:500 dilutions for 1 h followed by incubation for 45 min with goat anti-chicken IgG conjugated with horseradish peroxidase (KPL, MD, USA). The virus infected cells were detected under light microscope after staining with DAB substrate (Vector Labs, USA).

Growth Kinetics of Recombinant Viruses and Wild-Type Virus

Briefly, the DF1 cells were grown in six-well plates as monolayer (80% confluency) and infected in triplicates with the following viruses (MOI of 1); wt APMV-2/Yuc, rAPMV-2/Yuc, rAPMV-2/Yuc/EGFP and rAPMV-2/Yuc/$_{kozak}$EGFP. The supernatants were collected at 24, 48, 72, 96, and 120 h post-infection (p.i). Virus titers in the supernatants were determined by serial end-point dilution in 96-well plates seeded with DF1 cells. The infected cells were stained by immunoperoxidase staining using polyclonal antibody raised against wt APMV-2/Yuc in chickens. Virus titers ($TCID_{50}$/ml) were calculated using Reed & Muench method (Reed & Muench, 1938, supra).

Pathogenicity Tests

The virulence of the recombinant viruses was compared with the wt APMV-2/Yuc by the internationally accepted standard pathogenicity tests: mean death time (MDT) in 9-day-old embryonated SPF chicken eggs and intracerebral pathogenicity index (ICPI) in 1-day-old SPF chicks (Alexander, 1989, In: H. G. Purchase et al. Eds. A Laboratory Manual for the Isolation and Identification of Avian Pathogens, 3$^{rd}$ ed. The American Association of Avian Pathologists, Kendall/Hunt Publishing Company, Dubuque, Iowa 114-120). Briefly, for MDT, a series of 10-fold ($10^{-6}$-$10^{-9}$) dilutions of fresh infective allantoic fluid in PBS was made and 0.1 ml of each diluent was inoculated into the allantoic cavities of five 9-day-old SPF embryonated chicken eggs (BEE eggs company, PA) and the eggs were incubated at 37° C. The eggs were candled 3 times a day for the next 7 days, and the time of embryo death if any were recorded. The minimum lethal dose (MLD) is the highest virus dilution that kills all the embryos. The MDT is the mean time in hours for the MLD to kill all the inoculated embryos.

For ICPI, 0.05 ml (1:10 dilution) of fresh infective allantoic fluid of each virus was inoculated into groups of ten 1-day-old SPF chicks via the intracerebral route. The inoculation was done using a 27-gauge needle attached to a 1 ml stepper syringe dispenser that was set to dispense 0.05 ml of inoculum per bird. The birds were inoculated by inserting the needle up to the hub into the right or left rear quadrant of the cranium. The birds were observed for clinical symptoms and mortality, once every 8 h for a period of 10 days. At each observation, the birds were scored: 0 if normal, 1 if sick and 2 if dead. ICPI is the mean score per bird per observation over the 10-day period. Highly virulent (velogenic) viruses give values approaching 2 and avirulent (lentogenic) viruses give values close to 0.

Example 27

Construction of Support Plasmids Expressing N, P and L Proteins

The support plasmids, pN and pP were generated by inserting the cDNA bearing the ORF of N, P into expression vector pGEM7z(+) between Sph I and Hind III, Eco R I and Sac I, respectively, while pL was obtained by cloning the L ORF as two fragments into pTM1 vector using the enzyme sites Nco I, Stu I and Sac I. The Sac I enzyme site was artificially created by G11468C mutation within L ORF without changing any amino acids. The support plasmids were confirmed by digesting with corresponding restriction enzymes and DNA sequencing of the complete ORF, prior to using them in the recovery of the recombinant viruses (data not shown).

Example 28

Construction of the Full Length cDNA Clone of APMV-2/Yuc

In order to construct the full length cDNA of APMV-2/Yuc, pBR322/dr/Yuc, the whole APMV-2 genome was divided into six fragments and they were sequentially cloned. Each fragment represented one gene except the first fragment that included both N and P genes and fragments 5 and 6 together constituted the large L gene. A 73-nt oligo linker was synthesized to contain unique restriction enzyme sites and was inserted between Asc I and Rsr II sites of the pBR322/dr vector to clone the full length cDNA. The DNA sequence results of the entire full length cDNA confirmed ten nucleotide mutations, C2923A, G2924A, T2925A, G2926C, G4154C, G5971A, A5973T, T7870C, A11321G and A11322C which were artificially created to generate unique restriction enzyme sites and served as the genetic markers in recombinant viruses.

Example 29

Construction of Full Length Plasmids Encoding EGFP with and without Kozak Sequence The full length plasmid encoding the EGFP, pAPMV-2/Yuc/EGFP, was constructed by inserting the EGFP transcription cassette at Pme I site between P and M genes. The EGFP ORF was inserted between the genes P and M since this position is known to support stable expression of foreign genes without affecting virus replication. The EGFP cassette contained appropriate viral GS and GE signals along with the EGFP ORF, additionally, pAPMV-2/Yuc/$_{kozak}$EGFP, had a 6-nt kozak sequence in front of the EGFP ORF. The kozak sequence was introduced to determine whether the sequence can enhance the levels of GFP expression. The plasmids were sequenced to confirm the insertion of foreign cassette at the Pme I site.

Example 30

Recovery of Infectious Recombinant Viruses

The transfection of full length cDNA plasmids pAPMV-2/Yuc, pAPMV-2/Yuc/EGFP and pAPMV-2/Yuc/$_{kozak}$EGFP along with support plasmids pN, pP and pL in HEp-2 cells infected with MVA-T7, yielded infectious recombinant viruses two days after transfection. The recovered viruses were passaged in 9-day-old embryonated SPF chicken eggs to amplify the recombinant viruses (rAPMV-2/Yuc, rAPMV-2/Yuc/EGFP and rAPMV-2/Yuc/$_{kozak}$EGFP). RT-PCR of the infective allantoic fluid and DNA sequencing confirmed the presence of genetic markers and the GFP.

Example 31

In Vitro Characterization of Recombinant Viruses

The morphological characteristics of recombinant viruses were similar to wild-type virus in DF1 and Vero cells. None of the recombinants produced plaques but caused single cell infections comparable to wild-type APMV-2 and the maximum CPE was observed on 4 dpi (data not shown).

The GFP expression by the recovered viruses was confirmed by infecting DF1 cells with rAPMV-2/Yuc/EGFP and rAPMV-2/Yuc/$_{kozak}$EGFP (data not shown). Both the viruses expressed GFP and caused single cell infections as seen in wild type APMV-2/Yuc.

The recovered viruses, rAPMV-2/Yuc, rAPMV-2/EGFP, rAPMV-2/$_{kozak}$EGFP were compared with the parental wild-type virus for their in vitro growth characteristics by multiple-step growth kinetics in DF1 cells at an MOI of 1 (FIG. 4). The kinetics and the magnitude of replication of the recombinant viruses were similar to those of the wild type virus. The virus titers of the recombinant viruses expressing GFP was 1.5 log lower than those of the wild-type virus, suggesting that the insertion of foreign gene resulted in virus attenuation. The virus titer of wt APMV-2/Yuc, rAPMV-2/Yuc, rAPMV-2/EGFP and rAPMV-2/$_{kozak}$EGFP were $10^{5.25}$, $10^{4.75}$, $10^{3.25}$ and $10^3$ $TCID_{50}$/ml, respectively, on 4 dpi.

Example 32

Pathogenicity Tests

The virulence of the recombinant viruses were compared with wt APMV-2/Yuc by two internationally accepted tests namely; MDT in 9-day-old embryonated SPF chicken eggs and ICPI in 1-day-old SPF chicks. The recombinant viruses did not kill the chicken embryos even after 7 dpi and had ICPI value of zero, suggesting that the recovered recombinant viruses were avirulent, similar to the wild type APMV-2/Yuc.

Discussion

This study describes the recovery of infectious recombinant APMV-2 strain Yucaipa from the cloned cDNA by reverse genetics system for the first time. The availability of the complete genome sequence of APMV-2/Yuc assisted in generating the full length cDNA clone, required for recovery of infectious recombinant virus. In this system, recombinant vaccinia virus expressing T7 RNA polymerase (MVA-T7) was used to synthesize the antigenomic RNA from the full-length plasmid and the proteins N, P, and L from the cotransfected support plasmids, pN, pP and pL. A similar system has been used to recover other viruses (rabies virus, Schnell et al., 1994, EMBO J. 13, 4195-4203; vesicular stomatitis virus, Lawson et al., 1995, PNAS USA 92, 4477-4481; human respiratory syncytial virus, Collins et al., 1995, PNAS USA 92, 11563-11567; measles virus, Radecke et al., 1995, EMBO J. 14, 5773-5784; Sendai virus, Garcin et al., 1995, EMBO J. 6087-6094; SV5, He et al., 1997, Virology 237, 249-260; rinderpest virus, Baron and Barrett, 1997, J. Virol. 71, 1265-1271; parainfluenza virus, Hoffman and Banerjee, 1997, J. Virol. 71, 4272-4277; bovine respiratory syncytial virus, Yunus et al., 2001, Virus Genes. 23, 157-164; Newcastle disease virus, Peeters et al., 1999, J. Virol. 73, 5001-5009, and Krishnamurthy et al., 2000, Virology 278, 168-182; AMPV-A, Naylor et al., 2004, J. Gen. Virol. 85, 3219-3227, AMPV-C, Govindarajan et al., 2006, J. Virol. 12, 5790-5797). The growth characteristics of the recombinant virus, rAPMV-2/Yuc generated in this study was similar to that of the wild-type virus. The rAPMV-2/Yuc produced single cell infections in DF1 and Vero cells and was antigenically similar to wild type APMV-2/Yuc, as observed by immunoperoxidase staining of the infected cells. These results indicate the possibility of recovering a wild-type-virus-like recombinant virus entirely from cloned cDNA. One of the important applications of reverse genetics system is the development of vaccine vectors by engineering viruses to express foreign immunogens. Paramyxovirus vectors have several advantages as follows; the ability to accommodate large foreign genes without drastic reduction in virus growth (Sakai et al., 1999, FEBS Letters 456, 221-226; Haglund et al., 2000, Virology 268, 112, 121, and Huang et al., 2001, J. Gen. Virol. 82, 1729-1736, and Biacchesi et al., 2004, Virology 321, 247-259), stable expression of the inserted foreign genes even after many passages in vitro (Bukreyev et al., 1996, Virology 399, 290-298, Mebatsion et al., 1996, PNAS USA 93, 7310-7314; He et al., 1997, supra; and Biacchesi et al., 2004a, supra) and finally, the absence of homologous RNA recombination makes them safe and stable vectors (Palese et al., 1996, PNAS USA 93, 11354-11358).

Using the established reverse genetics system, rAPMV-2 expressing foreign protein, enhanced GFP, was recovered. Two full length cDNA constructs were made, one with EGFP transcript cassette alone between P and M gene while the other also had kozak sequence in front of EGFP ORF. The enhanced GFP was preferred as the foreign gene mainly because of the small size and the ease of visualization of the expressed foreign protein. The region between P and M gene in the full-length cDNA clone was chosen for insertion of EGFP because paramyxoviruses show gradient transcription pattern wherein the genes located near the 3' end of the genome are transcribed and expressed in higher quantities than those further behind, also previously it has been shown that the expression of foreign genes are better when placed near the 3' end (Sakai et al., 1999, supra; Wertz et al., 1998, PNAS USA 95, 3501-3506). The reason behind using kozak sequence in one of the construct was to see if it improved the GFP expression, as kozak sequence is known to optimize protein translation after mRNA synthesis (Kozak, 1987, Nucleic Acids Res. 15, 8125-8148; Kozak, 1990, PNAS USA 87, 8301-8305). The recovered viruses were similar to the parental virus in their growth characteristics but they were attenuated, the viral titers were 1.5 log lower than the parental virus. The attenuation following the expression of foreign genes has also been reported in other paramyxoviruses (Krishnamurthy et al., 2000, Virology 278, 168-182 and Biacchesi et al., 2004a, supra). There was not much difference in the GFP expression between rAPMV-2/Yuc/EGFP and rAPMV-2/Yuc/$_{kozak}$EGFP suggesting that the inserted kozak sequence did not affect the expression level of GFP. Both the recombinant viruses stably expressed the foreign protein for at least five serial passages in 9-day-old embryonated SPF chicken eggs and in DF1 cells.

In conclusion, a reverse genetics system was established for APMV-2 and the recovered recombinant virus showed similar morphological and in vitro growth characteristics and pathogenicity to the wild type virus. The reverse genetics system can be used as a tool to understand the APMV-2 molecular biology and pathogenesis. Furthermore, the ability to engineer recombinant APMV-2/Yuc expressing a foreign gene has been demonstrated using enhanced GFP, which has implications in the development of vectored vaccine against emerging pathogens.

Example 33

Use of APMV-2 in Tumour Therapy

We have evaluated the ability of APMV-2 to replicate in and kill human tumor cells. Five different human tumor cell lines—breast carcinoma (MCF-7), fibro sarcoma (HT 1080), gastric carcinoma (MKN-1), prostate cancer (PC3) and adeno carcinoma (HUTU 80)—were used in this study. Chicken embryo fibroblast (DF1) cells were used as a control cell line. Cells were plated at x$10^4$ cells/well in 12-well plates and infected 6 hours later at multiplication of infection (MOI) of 0, 0.01, 0.1, and 1. Cells were infected in 12-well plates for 1, 3, 5, and 7 days. At each time point, the media was removed and the cells were washed with 1 ml of PBS. The cells were subsequently lysed with 1.35% Triton X-100 at 37° C. for 30 min. to lyse the cells and release intracellular lactate dehydroganase (LDH). LDH was then quantified with a Cytotox 96 nonradioactive cytotoxicity assay (Promega, Madison, Wis., USA according to the manufacturer's instructions. Results were expressed on the surviving fraction of cells as determined by the measured absorbance of each sample relative to control uninfected cell lysate.

Our research showed that APMV-2 grew in all five cell lines. The virus effectively killed the tumor cells and a dose response was observed. In general, an MOI of 1 killed more cells than an MOI of 0.01. MKN-1 cells were more sensitive to APMV-2, in which an MOI of 1, more than 74% of the cells at 7 days post infection. In contrast, the HT 1080 cells were more resistant in which an MOI of 1 killed 30% of cells at 7 days post infection. These results suggest that APMV-2 can be used for cancer therapy.

What is claimed is:

1. An isolated nucleic acid comprising a sequence identified as SEQ ID NO:1 and contains at least one substitution chosen from C2923A, G2924A, T2925A, G2926C, G4154C, G5971A, A5973T, T7870C, A111321G and A11322C.

2. A recombinant infectious APMV-2 virus comprising the nucleic acid identified in claim 1.

3. The isolated nucleic acid according to claim 1 wherein said nucleic acid contains all ten substitutions, said nucleic acid identified in SEQ ID NO:117.

4. The isolated nucleic acid according to claim 1 wherein said nucleic acid contains all ten substitutions, said nucleic acid identified in SEQ ID NO: 118.

5. A recombinant infections APMV-2 virus comprising the nucleic acid identified in claim 4.

6. The isolated nucleic acid of claim 1 further comprising a non-APMV-2 Yucaipa sequence, said sequence encoding one or more antigens of interest wherein said antigen is a viral antigen, a tumor antigen, or an auto antigen involved in an autoimmune disorder.

7. A recombinant infectious APMV-2 virus comprising the nucleic acid sequence of claim 6.

8. An immunogenic composition comprising the recombinant APMV-2 virus of claim 7.

9. A recombinant cell which expresses infectious negative-strand APMV-2 Yucaipa RNA virus, wherein said cell is infected with the following expression vectors: (i) a plasmid genome vector, comprising, as an insert operatively linked with expression control sequences functional in said cell, a cloned DNA molecule which comprises a cDNA encoding the (+) strand full-length sequence (antigenome) of said APMV-2, wherein said cDNA comprises SEQ ID NO: 1, and (ii) one or more trans-complementation plasmid vectors comprising, under control of regulation expression sequences functional in said cell, nucleotide sequences which enable said vector(s) to collectively express the proteins necessary for the synthesis of the viral transcriptase complex of said APMV-2, and enable assembly of the infective APMV-2.

10. The cell of claim 9 wherein the complementation vectors are capable of expressing the nucleocapsid (N) the phosphoprotein (P), and the polymerase (L), or derivatives thereof as functional proteins.

11. The cell according to claim 9 wherein said cell is Vero cell or HEp-2 Cell.

12. The cell according to claim 9, wherein the cDNA in (i) comprises one or more heterologous gene, wherein said heterologous gene encodes at least one of a viral antigen, a tumor antigen, and an auto antigen involved in an autoimmune disorder.

13. A method for preparation of infectious APMV-2 from a recombinant cell according to claim 9 wherein said cell is transformed with i) a plasmid genome vector, comprising, as an insert operatively linked with expression control sequences functional in said cell, a cloned DNA molecule which comprises a cDNA encoding the (+) strand full-length sequence (antigenome) of said APMV-2, wherein said cDNA comprises SEQ ID NO: 1, and (ii) one or more trans-complementation plasmid vectors comprising, under control of regulation expression sequences functional in said cell, nucleotide sequences which enable said vector(s) to collectively express the proteins necessary for the synthesis of the viral transcriptase complex of said APMV-2 and enable assembly of the infective APMV-2, culturing said recombinant cell such that infectious APMV-2 is produced and recovering the produced infectious APMV-2.

14. A recombinant infectious APMV-2 virus comprising the nucleic acid identified in claim 3.

* * * * *